(12) United States Patent
Osaka et al.

(10) Patent No.: US 9,133,173 B2
(45) Date of Patent: Sep. 15, 2015

(54) CARBAZOLE COMPOUND, MATERIAL FOR LIGHT-EMITTING ELEMENT, ORGANIC SEMICONDUCTOR MATERIAL, LIGHT-EMITTING ELEMENT

(75) Inventors: Harue Osaka, Kanagawa (JP); Satoko Shitagaki, Kanagawa (JP); Hiromi Nowatari, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 908 days.

(21) Appl. No.: 13/271,406

(22) Filed: Oct. 12, 2011

(65) Prior Publication Data
US 2012/0091887 A1 Apr. 19, 2012

(30) Foreign Application Priority Data

Oct. 15, 2010 (JP) .................................. 2010-232850
Aug. 25, 2011 (JP) .................................. 2011-183202

(51) Int. Cl.
*H01L 51/52* (2006.01)
*C07D 409/14* (2006.01)
(Continued)

(52) U.S. Cl.
CPC ............ *C07D 405/14* (2013.01); *C07D 405/04* (2013.01); *C07D 405/10* (2013.01); *C07D 409/04* (2013.01); *C07D 409/10* (2013.01); *C07D 409/14* (2013.01); *C09K 11/06* (2013.01); *H01L 51/006* (2013.01); *H01L 51/0058* (2013.01); *C09K 2211/1007* (2013.01); *C09K 2211/1011* (2013.01);
(Continued)

(58) Field of Classification Search
CPC .. C07D 405/04; C07D 405/10; C07D 405/14; C07D 409/04; C07D 409/10; C07D 409/14; C09K 11/06; C09K 2211/1007; C09K 2211/1011; C09K 2211/1029; C09K 2211/1092; H01L 51/0054; H01L 51/0058; H01L 51/006; H01L 51/0072; H01L 51/0074; H01L 51/5012; H01L 51/5016; H01L 51/5048; H01L 51/5278; H01L 51/005; H01L 51/008; H01L 51/06; H01L 51/072; H01L 51/501
See application file for complete search history.

(56) References Cited

U.S. PATENT DOCUMENTS 7,989,644 B2   8/2011   Tanabe et al.
8,642,782 B2 * 2/2014   Suzuki et al. ................. 548/440

(Continued)

FOREIGN PATENT DOCUMENTS

EP   2 001 064 A1   12/2008
JP   2007-15933      1/2007

(Continued)

*Primary Examiner* — Dawn Garrett
(74) *Attorney, Agent, or Firm* — Husch Blackwell LLP

(57) ABSTRACT

To provide a novel carbazole compound that has an excellent carrier-transport property and can be used for a transport layer or as a host material in a light-emitting element. Further, to provide an organic semiconductor material and a material for a light-emitting element using the carbazole compound. A carbazole compound in which the 4-position of a dibenzothiophene skeleton or a dibenzofuran skeleton is substituted with the 2- or 3-position of a carbazole skeleton directly or via an arylene group can be synthesized. The carbazole compound is found to have a suitable carrier-transport property, a good film quality, and be used suitably as a material of a light-emitting element and an organic semicondcutor material. Note that nitrogen of the carbazole skeleton is substituted with any of a phenyl group, a biphenyl group, and a naphthyl group.

36 Claims, 39 Drawing Sheets

(51) Int. Cl.
*C07D 409/10* (2006.01)
*C07D 405/14* (2006.01)
*C07D 405/04* (2006.01)
*C07D 405/10* (2006.01)
*C07D 409/04* (2006.01)
*C09K 11/06* (2006.01)
*H01L 51/00* (2006.01)
*H01L 51/50* (2006.01)

(52) U.S. Cl.
CPC .............. *C09K 2211/1029* (2013.01); *C09K 2211/1092* (2013.01); *H01L 51/0054* (2013.01); *H01L 51/0072* (2013.01); *H01L 51/0074* (2013.01); *H01L 51/5012* (2013.01); *H01L 51/5016* (2013.01); *H01L 51/5048* (2013.01); *H01L 51/5278* (2013.01)

(56) References Cited

U.S. PATENT DOCUMENTS

| | | | |
|---|---|---|---|
| 8,673,459 B2 * | 3/2014 | Seo et al. | 428/690 |
| 8,735,610 B2 | 5/2014 | Tanabe et al. | |
| 8,946,984 B2 | 2/2015 | Tanabe et al. | |
| 2007/0224446 A1 | 9/2007 | Nakano et al. | |
| 2009/0015140 A1 | 1/2009 | Kawakami et al. | |
| 2009/0131673 A1 | 5/2009 | Tanabe et al. | |
| 2010/0069647 A1 | 3/2010 | Suzuki et al. | |
| 2011/0006670 A1 | 1/2011 | Katakura et al. | |
| 2011/0248217 A1 | 10/2011 | Tanabe et al. | |
| 2011/0297924 A1 * | 12/2011 | Yabunouchi et al. | 257/40 |
| 2011/0309346 A1 * | 12/2011 | Watanabe et al. | 257/40 |
| 2012/0071668 A1 | 3/2012 | Suzuki et al. | |
| 2012/0074390 A1 | 3/2012 | Seo et al. | |
| 2012/0080667 A1 * | 4/2012 | Nowatari et al. | 257/40 |
| 2012/0132896 A1 | 5/2012 | Kawata et al. | |
| 2012/0133274 A1 | 5/2012 | Kawakami et al. | |
| 2012/0289708 A1 | 11/2012 | Kawakami et al. | |
| 2013/0056720 A1 * | 3/2013 | Kim et al. | 257/40 |

FOREIGN PATENT DOCUMENTS

| | | |
|---|---|---|
| JP | 2008-545729 | 12/2008 |
| JP | 2012-049518 A | 3/2012 |
| WO | WO 2006/128800 A1 | 12/2006 |
| WO | WO 2007/111176 A1 | 10/2007 |
| WO | WO 2010/004877 A1 | 1/2010 |

* cited by examiner

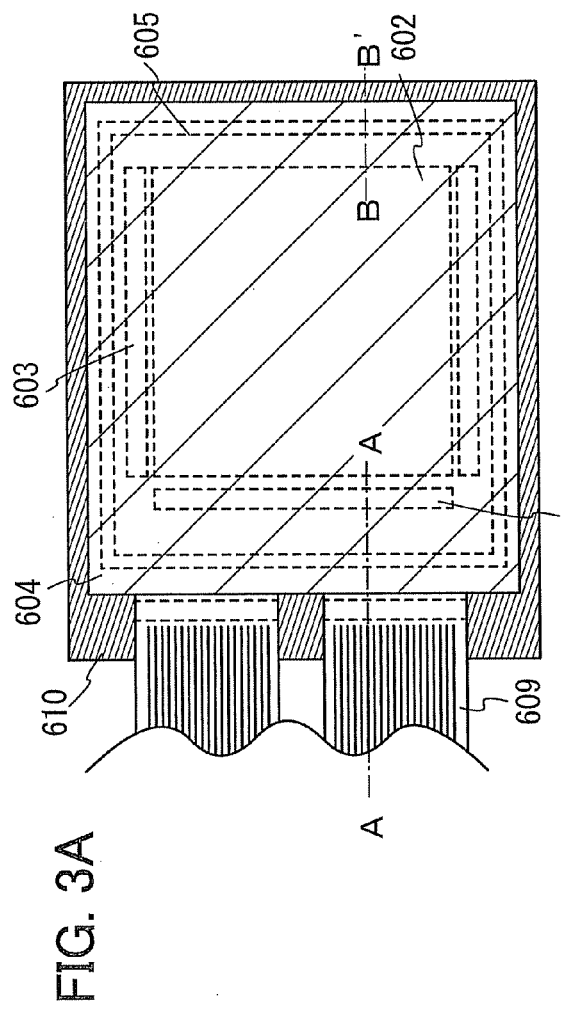
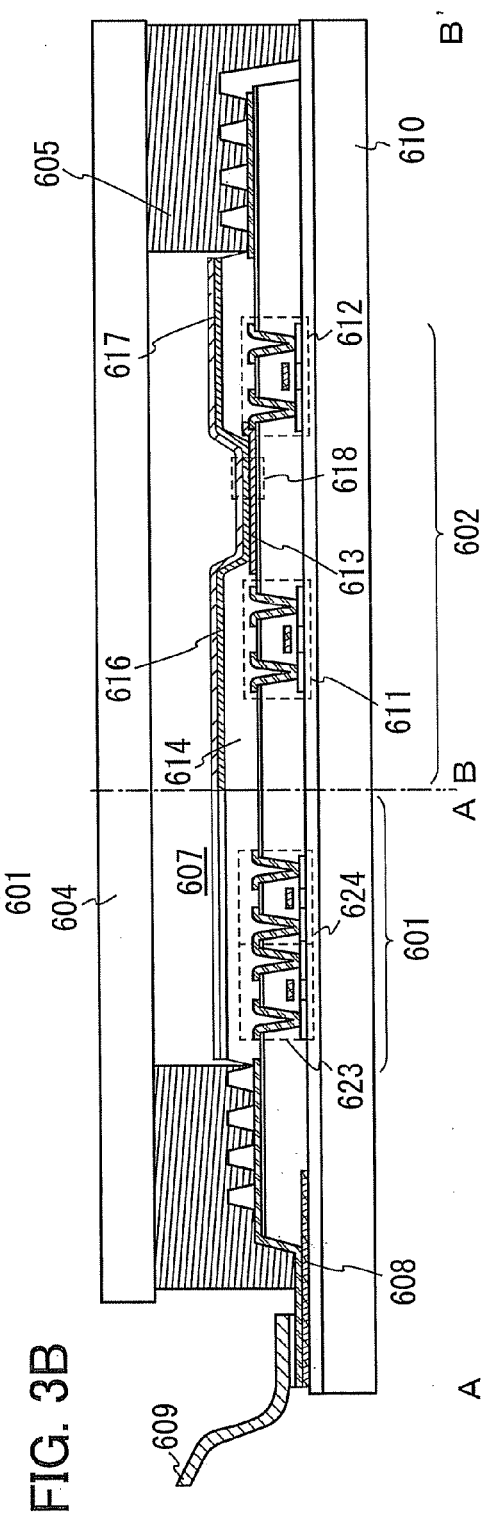
FIG. 3A
FIG. 3B

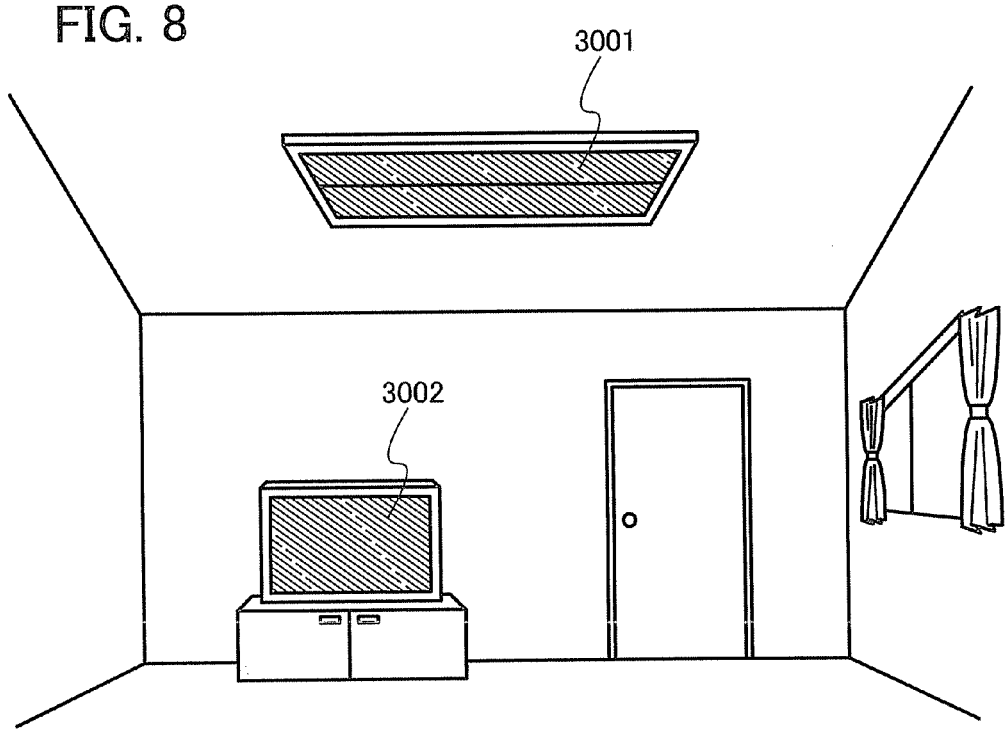

CARBAZOLE COMPOUND, MATERIAL FOR LIGHT-EMITTING ELEMENT, ORGANIC SEMICONDUCTOR MATERIAL, LIGHT-EMITTING ELEMENT

BACKGROUND OF THE INVENTION

1. Field of the Invention

The present invention relates to carbazole compounds. Further, the present invention relates to materials for light-emitting elements, organic semiconductor materials, and light-emitting elements using the carbazole compounds.

2. Description of the Related Art

A display device using a light-emitting element (organic EL element) in which an organic compound is used as a light-emitting substance has been developed rapidly as a next generation lighting device or display device because it has advantages that such a light-emitting element can be formed to be thin and lightweight, has very high response speed for input signals, and has low power consumption.

In an organic EL element, when voltage is applied between a pair of electrodes with a light-emitting layer interposed therebetween, electrons and holes injected from the electrodes are recombined to form an excited state, and when the excited state returns to a ground state, light is emitted. A wavelength of light emitted from a light-emitting substance is peculiar to the light-emitting substance; thus, by using different types of organic compounds as light-emitting substances, light-emitting elements which exhibit various wavelengths, i.e., various colors can be obtained.

For a display device which is expected to display images, such as a display, at least three colors of light having red, green, and blue wavelengths are used in order to show an image with reproduced full-color. For a lighting device, in order to obtain high color rendering property, light having wavelength components thoroughly in the visible light region is ideally obtained. Actually, two or more kinds of light having different wavelengths are mixed to be used in many lighting devices. Note that it is known that by mixing light of three colors, red, green, and blue, white light emission having high color rendering property can be obtained.

As described above, light emitted from a light-emitting substance is peculiar to the substance. However, important performances as a light-emitting element, such as lifetime or power consumption, depend not only on a light-emitting substance but also greatly on layers other than a light-emitting layer, an element structure, properties of the light-emitting substance and a host, compatibility between them, or the like. Therefore, there is no doubt that many kinds of materials for light-emitting elements are needed for the growth in this field. For these reasons, materials for light-emitting elements which have a variety of molecular structures have been proposed (for example, see Patent Document 1).

In particular, a material in contact with a light-emitting material (such as a light-emitting layer or a carrier-transport layer in contact with a light-emitting layer) should be a material having a suitable HOMO level, a suitable LUMO level, a suitable band gap between the HOMO level and the LUMO level, a suitable S1 level, and/or a suitable T1 level for efficient light emission of the light-emitting material. When a material exhibiting light with a shorter wavelength is used, a material with a low molecular weight is generally selected for keeping a small conjugation, as a material in contact with the material exhibiting light with a shorter wavelength. However, when a material with a low molecular weight is used, a structure to be selected is limited. In particular, since a T1 level is lower than an S1 level, a material in contact with a phosphorescent light-emitting material is limited. Therefore, a more preferable material has been expected to be developed.

REFERENCE

[Patent Document 1] Japanese Published Patent Application No. 2007-015933

SUMMARY OF THE INVENTION

It is an object of one embodiment of the present invention to provide a novel carbazole compound that can be used as a transport layer, a host material, or a light-emitting material in a light-emitting element.

It is an object of another embodiment of the present invention to provide a material for a light-emitting element using the novel carbazole compound.

It is an object of another embodiment of the present invention to provide an organic semiconductor material using the novel carbazole compound.

It is an object of another embodiment of the present invention to provide a light-emitting element using the novel carbazole compound.

It is an object of another embodiment of the present invention to provide a light-emitting element with high emission efficiency.

It is an object of another embodiment of the present invention to provide a light-emitting element driven with low driving voltage.

It is an object of another embodiment of the present invention to provide a light-emitting element with long lifetime.

Note that one embodiment of the present invention may achieve at least one of the above-described objects.

The present inventors synthesized a carbazole compound in which the 4-position of a dibenzothiophene skeleton or a dibenzofuran skeleton is substituted with the 2- or 3-position of a carbazole skeleton directly or via an arylene group. The present inventors have found that the carbazole compound has an appropriate carrier-transport property and a favorable film quality, and can be used suitably for a material of a light-emitting element and an organic semiconductor material. Note that nitrogen of the carbazole skeleton is substituted with any of a phenyl group, a biphenyl group, and a naphthyl group.

In other words, one embodiment of the present invention is a carbazole compound in which the 4-position of a dibenzothiophene skeleton or a dibenzofuran skeleton is substituted with the 2- or 3-position of a carbazole skeleton directly or via an arylene group and nitrogen of the carbazole skeleton is substituted with any of a phenyl group, a biphenyl group, and a naphthyl group.

Note that dibenzothiophene or dibenzofuran, or carbazole in the carbsazolyl group may or may not have a substituent.

Further, one embodiment of the present invention is a carbazole compound represented by the following general formula (G1).

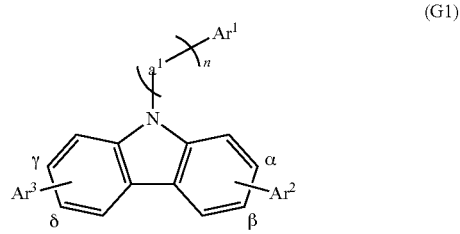

In the formula, $Ar^1$ is any of a phenyl group, a biphenyl group, and a naphthyl group; $Ar^2$ is a group represented by the following general formula (g1); and $Ar^3$ is any of hydrogen, a group represented by the following general formula (g2) and a group represented by the following general formula (g3). In addition, n is 0 or 1 and $a^1$ is a phenylene group or a biphenyldiyl group. Note that the substitution site of $Ar^2$ is a carbon atom represented by either α or β, and the substitution site of $Ar^3$ is a carbon atom represented by either γ or δ, Note that $Ar^1$ and $a^1$ may independently have a substituent, and when any of $Ar^1$ and $a^1$ has a substituent, the substituent is an alkyl group having 1 to 6 carbon atoms or an aryl group having 6 to 13 carbon atoms.

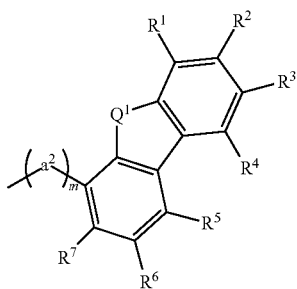

(g1)

In the formula, $R^1$ to $R^7$ are each independently any of hydrogen, an alkyl group having 1 to 6 carbon atoms, a phenyl group, a biphenyl group, and a naphthyl group. In addition, m is 0 or 1 and $a^2$ is a phenylene group or a biphenyldiyl group. In addition, $Q^1$ is sulfur or oxygen. Note that $R^1$ to $R^7$ and $a^2$ may independently have a substituent, and when any of $R^1$ to $R^7$ and $a^2$ has a substituent, the substituent is an allyl group having 1 to 6 carbon atoms or an aryl group having 6 to 13 carbon atoms.

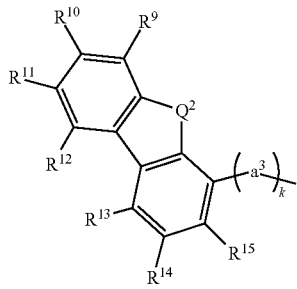

(g2)

In the formula, $R^9$ to $R^{15}$ are each independently any of hydrogen, an alkyl group having 1 to 6 carbon atoms, a phenyl group, a biphenyl group, and a naphthyl group. In addition, k is 0 or 1, and $a^3$ is a phenylene group or a biphenyldiyl group. In addition, $Q^2$ is sulfur or oxygen. Note that $R^9$ to $R^{15}$ and $a^3$ may independently have a substituent, and when any of $R^9$ to $R^{15}$ and $a^3$ has a substituent, the substituent is an alkyl group having 1 to 6 carbon atoms or an aryl group having 6 to 13 carbon atoms.

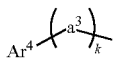

(g3)

In the formula, k is 0 or 1, and $a^3$ is a pheneylene group or a biphenyldiyl group. In addition, $Ar^4$ is any of a phenyl group, a biphenyl group, and a naphthyl group. Note that $Ar^4$ and $a^3$ may independently have a substituent, and when any of $Ar^4$ and $a^3$ has a substituent, the substituent is an alkyl group having 1 to 6 carbon atoms or an aryl group having 6 to 13 carbon atoms.

Further, another embodiment of the present invention is a carbazole compound represented by the following general formula (G1) in the above-described structure.

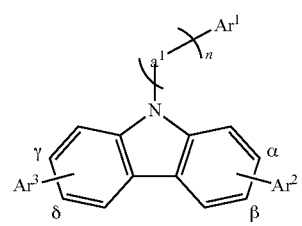

(G1)

In the formula, $Ar^1$ is any of a phenyl group, a biphenyl group, and a naphthyl group; $Ar^2$ is a group represented by the following general formula (g4); and $Ar^3$ is any of hydrogen, a group represented by the following general formula (g5) and a group represented by the following general formula (g3). In addition, n is 0 or 1, and $a^1$ is a phenylene group or a biphenyldiyl group. Note that the substitution site of $Ar^2$ is a carbon atom represented by either α or β, and the substitution site of $Ar^3$ is a carbon atom represented by either γ or δ. Note that $Ar^1$ and $a^1$ may independently have a substituent, and when any of $Ar^1$ and $a^1$ has a substituent, the substituent is an alkyl group having 1 to 6 carbon atoms or an aryl group having 6 to 13 carbon atoms.

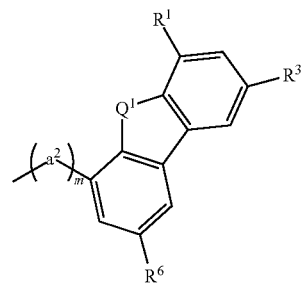

(g4)

In the formula, $R^1$, $R^3$, and $R^6$ are each independently any of hydrogen, an alkyl group having 1 to 6 carbon atoms, a phenyl group, a biphenyl group, and a naphthyl group. In addition, m is 0 or 1 and $a^2$ is a phenylene group or a biphenyldiyl group. In addition, $Q^1$ is sulfur or oxygen. Note that $R^1$, $R^3$, and $R^6$ and $a^2$ may independently have a substituent, when any of $R^1$, $R^3$, and $R^6$ and $a^2$ has a substituent, the substituent is an alkyl group having 1 to 6 carbon atoms or an aryl group having 6 to 13 carbon atoms.

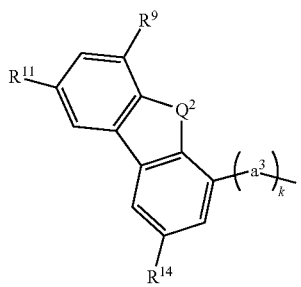

(g5)

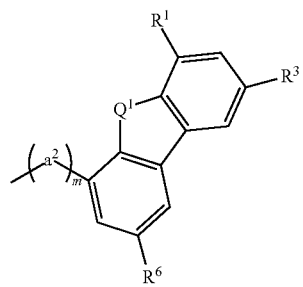

(g4)

In the formula, $R^9$, $R^{11}$, and $R^{14}$ are each independently any of hydrogen, an alkyl group having 1 to 6 carbon atoms, a phenyl group, a biphenyl group and a naphthyl group. In addition, k is 0 or 1, and $a^3$ is a phenylene group or a biphenyldiyl group. In addition, $Q^2$ is sulfur or oxygen. Note that $R^9$, $R^{11}$, and $R^{14}$, and $a^3$ may independently have a substituent, and when any of $R^9$, $R^{11}$, and $R^{14}$, and $a^3$ has a substituent, the substituent is an alkyl group having 1 to 6 carbon atoms or an aryl group having 6 to 13 carbon atoms.

In the formula, $R^1$, $R^3$, and $R^6$ are each independently any of hydrogen, an alkyl group having 1 to 6 carbon atoms, a phenyl group, a biphenyl group, and a naphthyl group. In addition, m is 0 or 1 and $a^2$ is a phenylene group or a biphenyldiyl group. In addition, $Q^1$ is sulfur or oxygen. Note that $R^1$, $R^3$, and $R^6$ and $a^2$ may independently have a substituent, when any of $R^1$, $R^3$, and $R^6$ and $a^2$ has a substituent, the substituent is an alkyl group having 1 to 6 carbon atoms or an aryl group having 6 to 13 carbon atoms.

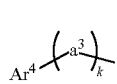

(g3)

In the formula, k is 0 or 1, and $a^3$ is a pheneylene group or a biphenyldiyl group. In addition, $Ar^4$ is any of a phenyl group, a biphenyl group, and a naphthyl group. Note that $Ar^4$ and $a^3$ may independently have a substituent, and when any of $Ar^4$ and $a^3$ has a substituent, the substituent is an alkyl group having 1 to 6 carbon atoms or an aryl group having 6 to 13 carbon atoms.

A carbazole compound of the present invention having the above-described structure can be synthesized easily, and thus is a more preferable carbazole compound.

Furthermore, another embodiment of the present invention is a carbazole compound represented by the following general formula (G1) in the above-described structure.

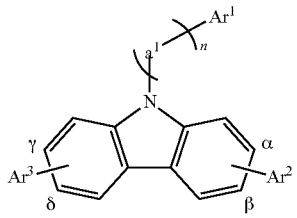

(g5)

In the formula, $R^9$, $R^{11}$, and $R^{14}$ are each independently any of hydrogen, an alkyl group having 1 to 6 carbon atoms, a phenyl group, a biphenyl group, and a naphthyl group. In addition, k is 0 or 1, and $a^3$ is a phenylene group or a biphenyldiyl group. In addition, $Q^2$ is sulfur or oxygen. Note that $R^9$, $R^{11}$, and $R^{14}$, and $a^3$ may independently have a substituent, and when any of $R^9$, $R^{11}$, and $R^{14}$, and $a^3$ has a substituent, the substituent is an alkyl group having 1 to 6 carbon atoms or an aryl group having 6 to 13 carbon atoms.

Furthermore, another embodiment of the present invention is a carbazole compound represented by the following general formula (G1) in the above-described structure.

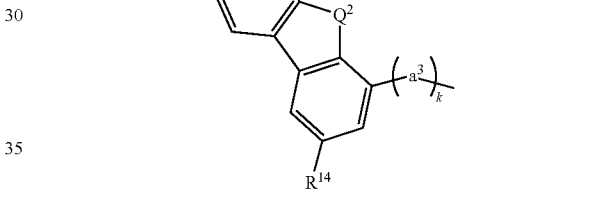

(G1)

In the formula, $Ar^1$ is any of a phenyl group, a biphenyl group, and a naphthyl group; $Ar^2$ is a group represented by the following general formula (g4); and $Ar^3$ is hydrogen or a group represented by the following general formula (g5). In addition, n is 0 or 1, and $a^1$ is a phenylene group or a biphenyldiyl group. Note that the substitution site of $Ar^2$ is a carbon atom represented by either α or β, and the substitution site of $Ar^3$ is a carbon atom represented by either γ or δ. Note that $Ar^1$ and $a^1$ may independently have a substituent, and when any of $Ar^1$ and $a^1$ has a substituent, the substituent is an alkyl group having 1 to 6 carbon atoms or an aryl group having 6 to 13 carbon atoms.

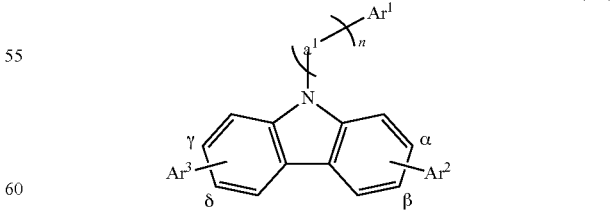

(G1)

In the formula, $Ar^1$ is any of a phenyl group, a biphenyl group, and a naphthyl group; $Ar^2$ is a group represented by the following general formula (g6); and $Ar^3$ is hydrogen or a group represented by the following general formula (g7). In addition, n is 0 or 1, and $a^1$ is a phenylene group or a biphenyldiyl group. Note that the substitution site of Ar² is a carbon atom represented by either α or β, and the substitution site of Ar³ is a carbon atom represented by either γ or δ. Note that Ar¹ and a¹ may independently have a substituent, and when any of Ar¹ and a¹ has a substituent, the substituent is an alkyl group having 1 to 6 carbon atoms or an aryl group having 6 to 13 carbon atoms.

(g6)

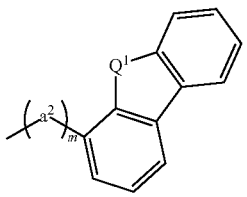

In the formula, m is 0 or 1 and a² is a phenylene group or a biphenyldiyl group. In addition, Q¹ is sulfur or oxygen. Note that a² may have a substituent, when a² has a substituent, the substituent is an alkyl group having 1 to 6 carbon atoms or an aryl group having 6 to 13 carbon atoms.

(g7)

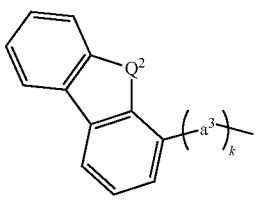

In the formula, k is 0 or 1, and a³ is a phenylene group or a biphenyldiyl group. In addition, Q² is sulfur or oxygen. Note that a³ may have a substituent, and when a³ has a substituent, the substituent is an alkyl group having 1 to 6 carbon atoms or an aryl group having 6 to 13 carbon atoms.

In addition, another embodiment of the present invention is a carbazole compound represented by the general formula (G1) in which, when Ar³ is a substituent other than hydrogen, Ar² is combined to the position α and Ar³ is combined to the position γ, or Ar² is combined to the position β and Ar³ is combined to the position δ.

In addition, another embodiment of the present invention is a carbazole compound where the groups, a¹, a², and a³, in the above-described structures are each independently any of groups represented by the following structural formulae (a-1) to (a-7).

(α-1)

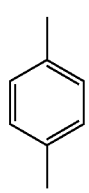

(α-2)

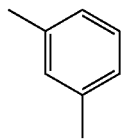

(α-3)

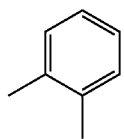

(α-4)

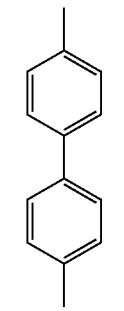

(α-5)

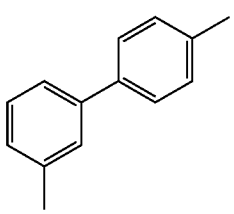

(α-6)

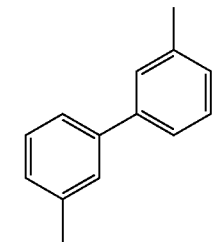

(α-7)

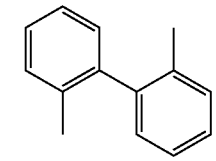

Further, another embodiment of the present invention is, a carbazole compound where the groups, R¹ to R¹⁵ in the above-described structures are each independently any of groups represented by the following structural formulae (R-1) to (R-13).

(R-1)

(R-2)

Furthermore, another embodiment of the present invention is a carbazole compound where the group, Ar⁴, in the above-described structures is any of groups represented by the following structural formulae (Ar-1) to (Ar-6).

Moreover, another embodiment of the present invention is a carbazole compound where the group, Ar¹, in the above-described structures is any of groups represented by the following structural formulae (Ar-1) to (Ar-6).

-continued (Ar-2)
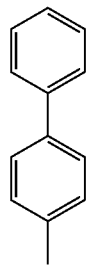

(Ar-3)
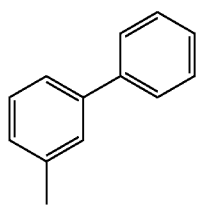

(Ar-4)
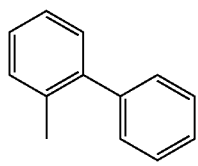

(Ar-5)
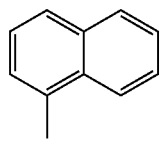

(Ar-6)
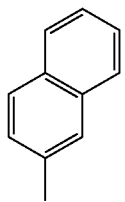

Another embodiment of the present invention is a carbazole compound in which n in the above-described structures is 0.

Another embodiment of the present invention is a carbazole compound in which the group represented by $Ar^1$ in the above-described structures is a phenyl group.

Another embodiment of the present invention is a carbazole compound in which $Q^1$ and $Q^2$ in the above-described structures are the same element.

Another embodiment of the present invention is a carbazole compound in which m and k in the above-described structures are both 0.

Further, another embodiment of the present invention is a carbazole compound represented by the following structural formula (150).

(150)
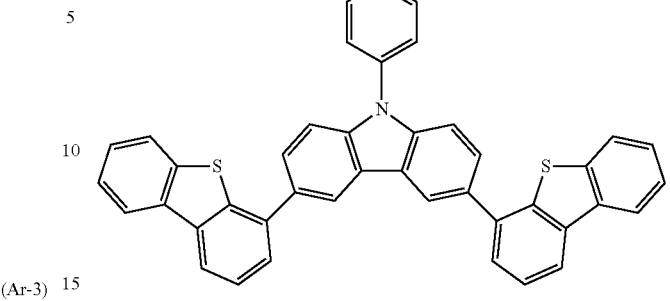

Yet another embodiment of the present invention is a carbazole compound represented by the following structural formula (154).

(154)
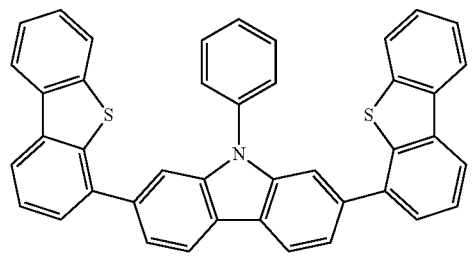

Another embodiment of the present invention is a carbazole compound in which $Ar^3$ is hydrogen and k is 1 in the above-described structures.

Yet another embodiment of the present invention is a carbazole compound represented by the following structural formula (172).

(172)
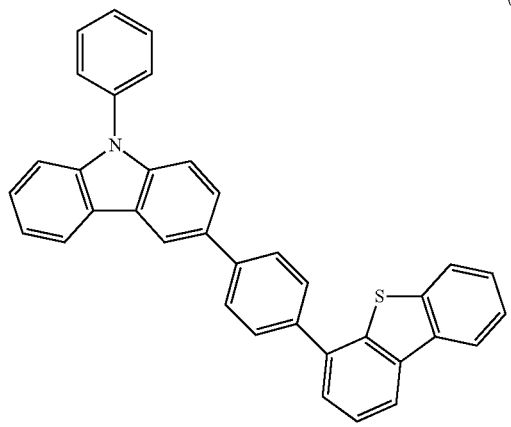

Additionally, another embodiment of the present invention is a carbazole compound represented by the following structural formula (160).

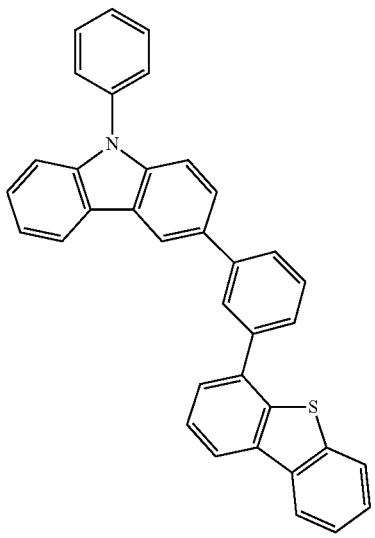

(160)

Further, one embodiment of the present invention is a light-emitting element in which a layer containing an organic compound is interposed between a pair of electrodes and a carbazole compound represented by the following general formula (G1) is contained in the layer containing an organic compound.

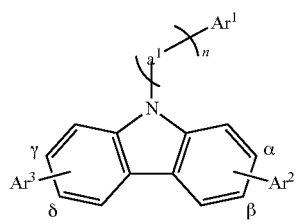

(G1)

In the formula, $Ar^1$ is any of a phenyl group, a biphenyl group, and a naphthyl group; $Ar^2$ is a group represented by the following general formula (g1'); and $Ar^3$ is any of hydrogen, a group represented by the following general formula (g2) and a group represented by the following general formula (g3). In addition, n is 0 or 1 and $a^1$ is a phenylene group or a biphenyldiyl group. Note that the substitution site of $Ar^2$ is a carbon atom represented by either α or β, and the substitution site of $Ar^3$ is a carbon atom represented by either γ or δ. Note that $Ar^1$ and $a^1$ may independently have a substituent, and when any of $Ar^1$ and $a^1$ has a substituent, the substituent is an alkyl group having 1 to 6 carbon atoms or an aryl group having 6 to 13 carbon atoms.

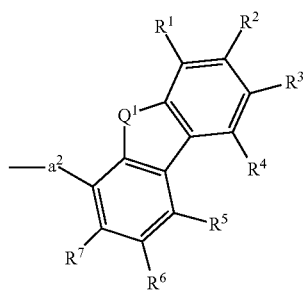

(g1')

In the formula, $R^1$ to $R^7$ are each independently hydrogen, an alkyl group having 1 to 6 carbon atoms, a phenyl group, a biphenyl group, and a naphthyl group. In addition, $a^2$ is a phenylene group or a biphenyldiyl group. In addition, $Q^1$ is sulfur or oxygen. Note that $R^1$ to $R^7$ and $a^2$ may independently have a substituent, when any of $R^1$ to $R^7$ and $a^2$ has a substituent, the substituent is an alkyl group having 1 to 6 carbon atoms or an aryl group having 6 to 13 carbon atoms.

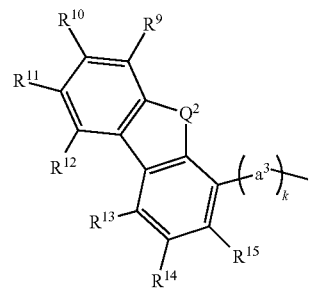

(g2)

In the formula, $R^9$ to $R^{15}$ are each independently any of hydrogen, an alkyl group having 1 to 6 carbon atoms, a phenyl group, a biphenyl group and a naphthyl group. In addition, k is 0 or 1, and $a^3$ is a phenylene group or a biphenyldiyl group. In addition, $Q^2$ is sulfur or oxygen. Note that $R^9$ to $R^{15}$ and $a^3$ may independently have a substituent, and when any of $R^9$ to $R^{15}$ and $a^3$ has a substituent, the substituent is an alkyl group having 1 to 6 carbon atoms or an aryl group having 6 to 13 carbon atoms.

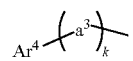

(g3)

In the formula, k is 0 or 1, and $a^3$ is a pheneylene group or a biphenyldiyl group. In addition, $Ar^4$ is any of a phenyl group, a biphenyl group, and a naphthyl group. Note that $Ar^4$ and $a^3$ may independently have a substituent, and when any of $Ar^4$ and $a^3$ has a substituent, the substituent is an alkyl group having 1 to 6 carbon atoms or an aryl group having 6 to 13 carbon atoms.

Furthermore, among the above-described carbazole compounds, a compound where m is 1 has a wide band gap and can be used suitably for a light-emitting element. In other words, another embodiment of the present invention is a light-emitting element in which a layer containing an organic compound is interposed between a pair of electrodes and a carbazole compound represented by the following general formula (G1) is contained in the layer containing an organic compound.

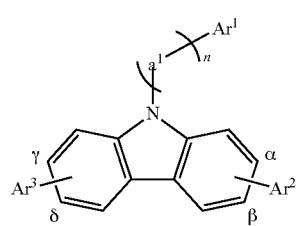

(G1)

In the formula, $Ar^1$ is any of a phenyl group, a biphenyl group, and a naphthyl group; $Ar^2$ is a group represented by the following general formula (g4'); $Ar^3$ is any of hydrogen, a group represented by the following general formula (g5) and a group represented by the following general formula (g3). In addition, n is 0 or 1 and $a^1$ is a phenylene group or a biphenyldiyl group. Note that the substitution site of $Ar^2$ is a carbon atom represented by either α or β, and the substitution site of $Ar^3$ is a carbon atom represented by either γ or δ. Note that $Ar^1$ and $a^1$ may independently have a substituent, and when any of $Ar^1$ and $a^1$ has a substituent, the substituent is an alkyl group having 1 to 6 carbon atoms or an aryl group having 6 to 13 carbon atoms.

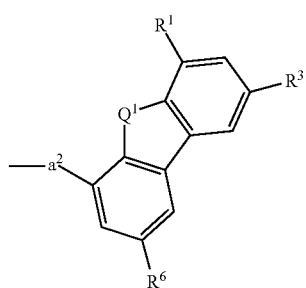

(g4')

In the formula, $R^1$, $R^3$, and $R^6$ are each independently hydrogen, an alkyl group having 1 to 6 carbon atoms, a phenyl group, a biphenyl group, and a naphthyl group. In addition, $a^2$ is a phenylene group or a biphenyldiyl group. In addition, $Q^1$ is sulfur or oxygen. Note that $R^1$, $R^3$, and $R^6$ and $a^2$ may independently have a substituent, when any of $R^1$, $R^3$, and $R^6$ and $a^2$ has a substituent, the substituent is an alkyl group having 1 to 6 carbon atoms or an aryl group having 6 to 13 carbon atoms.

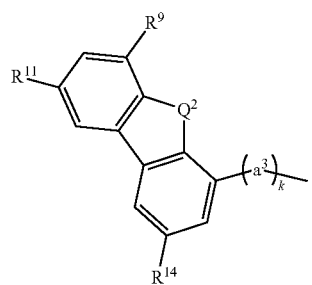

(g5)

In the formula, $R^9$, $R^{11}$, and $R^{14}$ are each independently any of hydrogen, an alkyl group having 1 to 6 carbon atoms, a phenyl group, a biphenyl group and a naphthyl group. In addition, k is 0 or 1, and $a^3$ is a phenylene group or a biphenyldiyl group. In addition, $Q^2$ is sulfur or oxygen. Note that $R^9$, $R^{11}$, and $R^{14}$, and a $a^3$ may independently have a substituent, and when any of $R^9$, $R^{11}$, and $R^{14}$, and $a^3$ has a substituent, the substituent is an alkyl group having 1 to 6 carbon atoms or an aryl group having 6 to 13 carbon atoms.

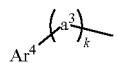

(g3)

In the formula, k is 0 or 1, and $a^3$ is a pheneylene group or a biphenyldiyl group. In addition, $Ar^4$ is any of a phenyl group, a biphenyl group, and a naphthyl group. Note that $Ar^4$ and $a^3$ may independently have a substituent, and when any of $Ar^4$ and $a^3$ has a substituent, the substituent is an alkyl group having 1 to 6 carbon atoms or an aryl group having 6 to 13 carbon atoms.

The carbazole compound of the present invention having the above-described structure can be synthesized easily, and thus a light-emitting element including a carbazole compound having a more preferable structure can be provided.

Further, another embodiment of the present invention is a light-emitting element in which a layer containing an organic compound is interposed between a pair of electrodes and a carbazole compound represented by the following general formula (G1) is contained in the layer containing an organic compound.

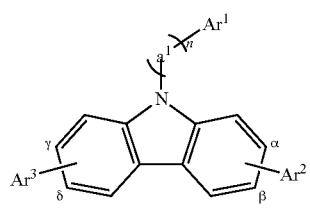

(G1)

In the formula, $Ar^1$ is any of a phenyl group, a biphenyl group, and a naphthyl group, $Ar^2$ is a group represented by the following general formula (g4'), $Ar^3$ is hydrogen or a group represented by the following general formula (g5). In addition, n is 0 or 1 and $a^1$ is a phenylene group or a biphenyldiyl group. Note that the substitution site of $Ar^2$ is a carbon atom represented by either α or β, and the substitution site of $Ar^3$ is a carbon atom represented by either γ or δ. Note that $Ar^1$ and $a^1$ may independently have a substituent, and when any of $Ar^1$ and $a^1$ has a substituent, the substituent is an alkyl group having 1 to 6 carbon atoms or an aryl group having 6 to 13 carbon atoms.

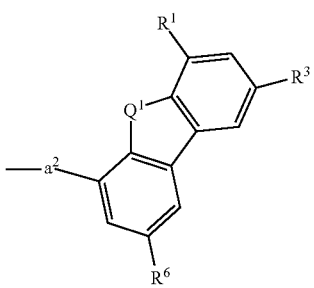

(g4')

In the formula, $R^1$, $R^3$, and $R^6$ are each independently any of hydrogen, an alkyl group having 1 to 6 carbon atoms, a phenyl group, a biphenyl group, and a naphthyl group. In addition, $a^2$ is a phenylene group or a biphenyldiyl group. In addition, $Q^1$ is sulfur or oxygen. Note that $R^1$, $R^3$, and $R^6$ and $a^2$ may independently have a substituent, when any of $R^1$, $R^3$, and $R^6$ and $a^2$ has a substituent, the substituent is an alkyl group having 1 to 6 carbon atoms or an aryl group having 6 to 13 carbon atoms.

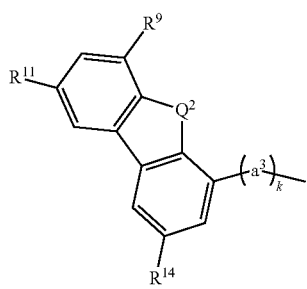

(g5)

In the formula, $R^9$, $R^{11}$, and $R^{14}$ are each independently any of hydrogen, an alkyl group having 1 to 6 carbon atoms, a phenyl group, a biphenyl group and a naphthyl group. In addition, k is 0 or 1, and $a^3$ is a phenylene group or a biphenyldiyl group. In addition, $Q^2$ is sulfur or oxygen. Note that $R^9$, $R^{11}$, and $R^{14}$, and $a^3$ may independently have a substituent, and when any of $R^9$, $R^{11}$, and $R^{14}$, and $a^3$ has a substituent, the substituent is an alkyl group having 1 to 6 carbon atoms or an aryl group having 6 to 13 carbon atoms.

Furthermore, another embodiment of the present invention is a light-emitting element in which a layer containing an organic compound is interposed between a pair of electrodes and a carbazole compound represented by the following general formula (G1) is contained in the layer containing an organic compound.

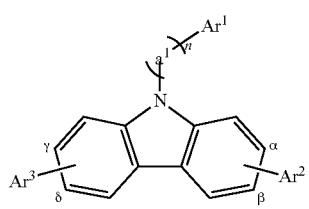

(G1)

In the formula, $Ar^1$ is any of a phenyl group, a biphenyl group, and a naphthyl group; $Ar^2$ is a group represented by the following general formula (g6'); and $Ar^3$ is hydrogen or a group represented by the following general formula (g7). In addition, n is 0 or 1 and $a^1$ is a phenylene group or a biphenyldiyl group. Note that the substitution site of $Ar^2$ is a carbon atom represented by either α or β, and the substitution site of $Ar^3$ is a carbon atom represented by either γ or δ. Note that $Ar^1$ and $a^1$ may independently have a substituent, and when any of $Ar^1$ and $a^1$ has a substituent, the substituent is an alkyl group having 1 to 6 carbon atoms or an aryl group having 6 to 13 carbon atoms.

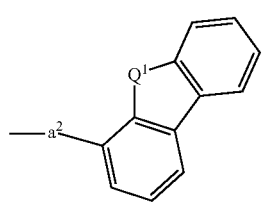

(g6')

In the formula, $a^2$ is a phenylene group or a biphenyldiyl group. In addition, $Q^1$ is sulfur or oxygen. Note that $a^2$ may have a substituent, when $a^2$ has a substituent, the substituent is an alkyl group having 1 to 6 carbon atoms or an aryl group having 6 to 13 carbon atoms.

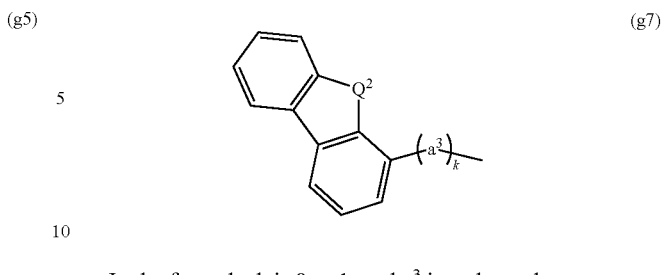

(g7)

In the formula, k is 0 or 1, and $a^3$ is a pheneylene group or a biphenyldiyl group. In addition, $Q^2$ is sulfur or oxygen. Note that $a^3$ may have a substituent, and when $a^3$ has a substituent, the substituent is an alkyl group having 1 to 6 carbon atoms or an aryl group having 6 to 13 carbon atoms.

In addition, another embodiment of the present invention is a light-emitting element including a layer containing an organic compound, and the layer containing an organic compound includes the carbazole compound represented by the general formula (G1) in which, when $Ar^3$ is a substituent other than hydrogen, $Ar^2$ is bonded at the position α and $Ar^3$ is bonded at the position γ, or $Ar^2$ is bonded at the position β and $Ar^3$ is bonded at the position δ.

In addition, another embodiment of the present invention is a light-emitting element including a layer containing an organic compound, and the layer containing an organic compound includes a carbazole compound where the groups, $a^1$, $a^2$, and $a^3$, in the above-described structures are independently any of groups represented by the following structural formulae (a-1) to (a-7).

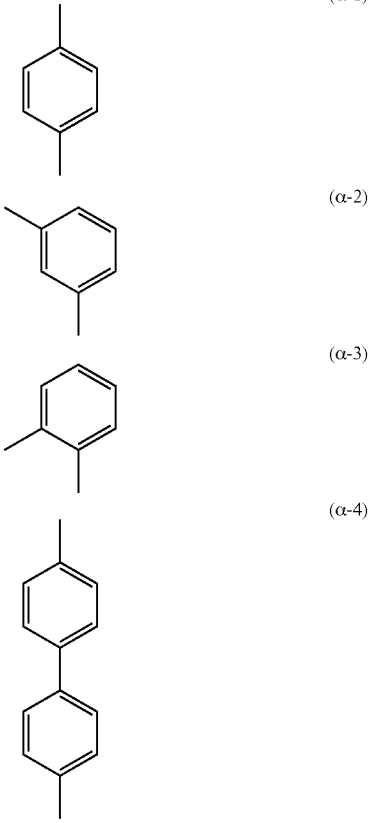

-continued

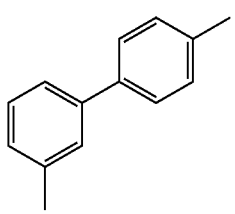
(α-5)

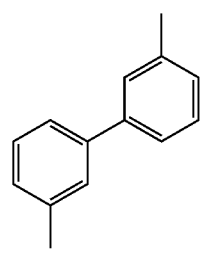
(α-6)

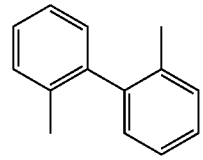
(α-7)

Further, another embodiment of the present invention is a light-emitting element including a layer containing an organic compound, and the layer containing an organic compound includes a carbazole compound where the groups, $R^1$ to $R^{15}$, in the above-described structures are independently any of groups represented by the following structural formulae (R-1) to (R-13).

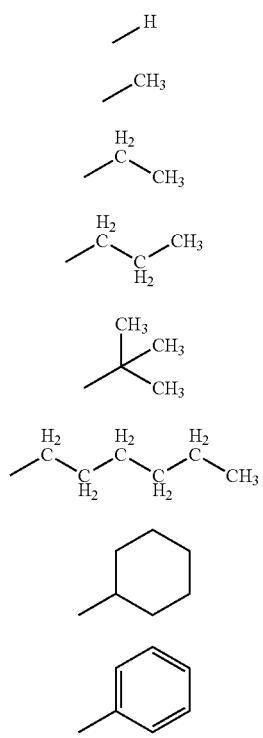

(R-1)
(R-2)
(R-3)
(R-4)
(R-5)
(R-6)
(R-7)
(R-8)

-continued

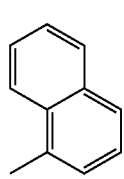
(R-9)

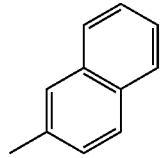
(R-10)

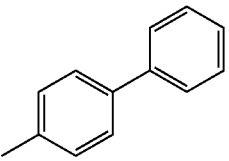
(R-11)

(R-12)

(R-13)

Furthermore, another embodiment of the present invention is a light-emitting element including a layer containing an organic compound, and the layer containing an organic compound includes a carbazole compound wherein the group, $Ar^4$, in the above-described structure is any of groups represented by the following structural formulae (Ar-1) to (Ar-6).

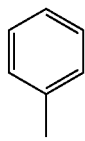
(Ar-1)

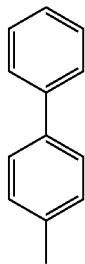
(Ar-2)

-continued (Ar-3)

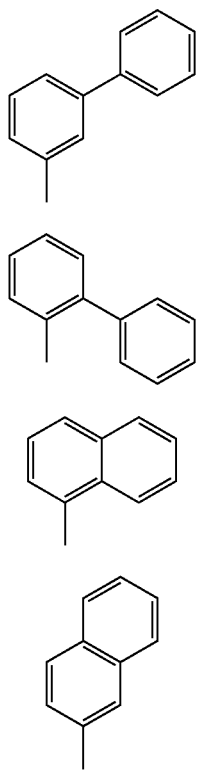

(Ar-4)

(Ar-5)

(Ar-6)

Moreover, another embodiment of the present invention is a light-emitting element including a layer containing an organic compound, and the layer containing an organic compound includes a carbazole compound where the group, Ar¹, in the above-described structures is any of groups represented by the following structural formulae (Ar-1) to (Ar-6).

(Ar-1)

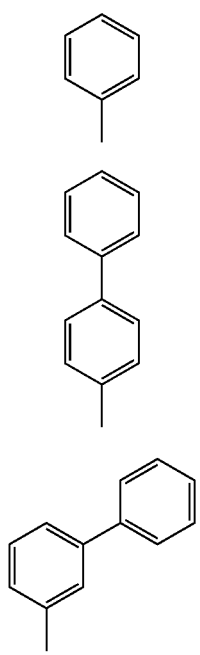

(Ar-2)

(Ar-3)

-continued (Ar-4)

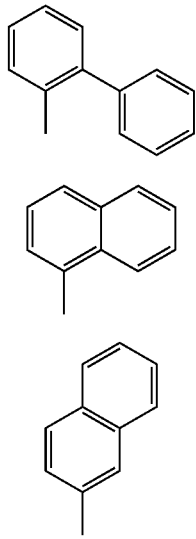

(Ar-5)

(Ar-6)

In addition, another embodiment of the present invention is a light-emitting element including a layer containing an organic compound, and the layer containing an organic compound includes a carbazole compound in which n in the above-described structures is 0.

In addition, another embodiment of the present invention is a light-emitting element including a layer containing an organic compound, and the layer containing an organic compound includes a carbazole compound in which the group Ar¹ in the above-described structures is a phenyl group.

In addition, another embodiment of the present invention is a light-emitting element including a layer containing an organic compound, and the layer containing an organic compound includes a carbazole compound in which $Q^1$ and $Q^2$ in the above-described structures are the same element.

In addition, another embodiment of the present invention is a light-emitting element including a layer containing an organic compound, and the layer containing an organic compound includes a carbazole compound in which, in the above-described structures, $Ar^3$ is hydrogen and k is 1.

Another embodiment of the present invention is a light-emitting element including a layer containing an organic compound, and the layer containing an organic compound includes a carbazole compound represented by the following structural formula (172).

(172)

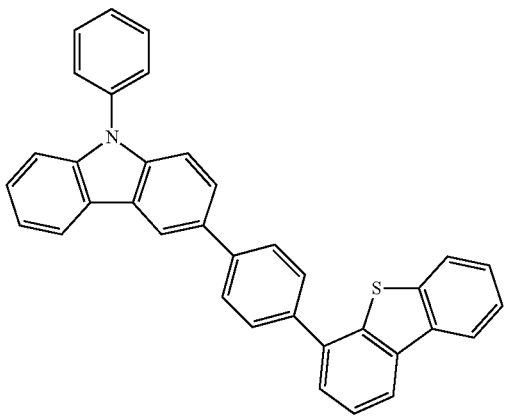

Furthermore, another embodiment of the present invention is a light-emitting element in which a carbazole compound represented by the following structural formula (160) is contained in the layer containing an organic compound.

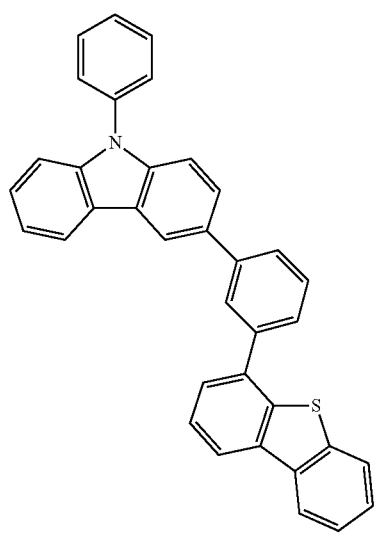

(160)

A novel carbazole compound having any of the above-described structures has a favorable carrier-transport property. In addition, the carbazole compound has a wide band gap (Bg, an energy difference between a HOMO level and a LUMO level) and/or a high T1 level (an energy difference between a ground state and a triplet excited state). For that reason, the carbazole compound can be used preferably for a transport layer or a host material in a light-emitting element. Further, the carbazole compound can be used as an organic semiconductor material.

A light-emitting element including, as a part of a functional layer in a layer containing an organic compound between electrodes, the carbazole compound having a wide band gap and/or a T1 level can be a light-emitting element with a good emission efficiency. Further, a light-emitting element including, as a part of a functional layer in a layer containing an organic compound between electrodes, the carbazole compound having a good carrier-transport property can be a light-emitting element driven with low driving voltage. Furthermore, a light-emitting element including, as a part of a functional layer in a layer containing an organic compound between electrodes, the carbazole compound can be a light-emitting element with long lifetime.

BRIEF DESCRIPTION OF THE DRAWINGS

In the accompanying drawings:
FIGS. 3A and 3B are conceptual diagrams of an active matrix light-emitting device;
FIG. 8 illustrates lighting devices.

DETAILED DESCRIPTION OF THE INVENTION

Figure 1A:
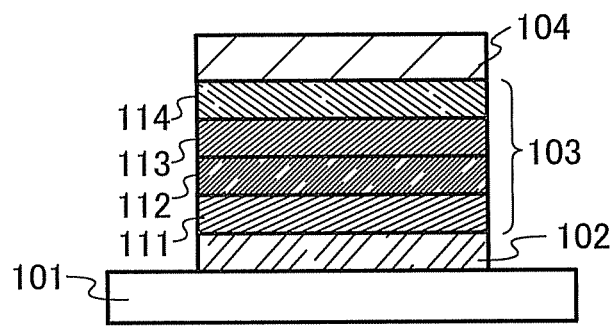
FIGS. 1A and 1B are conceptual diagrams of light-emitting elements.

Hereinafter, embodiments of the present invention are described. It is easily understood by, those skilled in the art that modes and details disclosed herein can be modified in various ways without departing from the spirit and the scope of the present invention. Therefore, the present invention is not construed as being limited to description of the embodiments.

Embodiment 1

A carbazole compound in this embodiment is a carbazole compound in which the 4-position of a dibenzothiophene skeleton or a dibenzofuran skeleton is bonded to the 2- or 3-position of a carbazole skeleton directly or via an arylene group. Note that any of a phenyl group, a biphenyl group, and a naphthyl group is bonded to nitrogen of the carbazole skeleton. The carbazole compound has a good carrier-transport property, a good film quality, a wide band gap, and/or a high T1 level. For that reason, the carbazole compound can be used suitably as a material of a light-emitting element or an organic semiconductor material.

Dibenzothiophene or dibenzofuran bonded to the carbazole may have a substituent, and when dibenzothiophene or dibenzofuran has a substituent, the substituent can be an alkyl group having 1 to 6 carbon atoms or an aryl group having 6 to 13 carbon atoms.

In addition, when the carbazole has another substituent, the substitution site is a carbon atom at 6- or 7-position of the carbazole. Examples of the substituent include an alkyl group having 1 to 6 carbon atoms, an aryl group having 6 to 13 carbon atoms, a dibenzothiophen-4-yl group, and a dibenzofuran-4-yl group. When the substituent is a dibenzothiophen-4-yl group or a dibenzofuran-4-yl group, the group may have another substituent, and the substituent can be an alkyl group having 1 to 6 carbon atoms or an aryl group having 6 to 13 carbon atoms.

In the case where the another substituent bonded to the carbon atom at the 6- or 7-position of the carbazole is a group including a dibenzothiophen-4-yl group or a dibenzofuran-4-yl group, for easier synthesis, when dibenzothiophene or dibenzofuran is bonded to the 2-position of the carbazole, the dibenzothiophen-4-yl group or the dibenzofuran-4-yl group is preferably bonded at the 7-position of the carbazole, or when dibenzothiophene or dibenzofuran is bonded to the 3-position of the carbazole, the dibenzothiophen-4-yl group or the dibenzofuran-4-yl group is preferably bonded at the 6-position of the carbazole. In other words, substituents bonded to the benzene ring of carbazole are preferably symmetrical. Note that the dibenzothiophene or dibenzofuran which is bonded to the 2- or 3-position and the substituent bonded to the 6- or 7-position are preferably of the same type for easier synthesis.

Note that the arylene group between the dibenzothiophene skeleton or the dibenzofuran skeleton and the carbazole skeleton is preferably a phenylene group or a biphenyldiyl group.

The present inventors have found that the carbazole compounds described above each have a good carrier-transport property and can be used suitably as a material of a light-emitting element. The use of the material of a light-emitting element having an excellent carrier-transport property can provide a light-emitting element capable of being driven with low voltage.

In addition, the carbazole compound described above has a wide band gap and/or a high T1 level, and thus can be used suitably as a host material or a carrier-transport material of a light-emitting element exhibiting fluorescence with a short wavelength, such as blue light or a light-emitting element exhibiting phosphorescence with a wavelength shorter than that of red light (blue, green, orange light in some cases). A light-emitting element using the carbazole compound having a wide band gap or a high T1 level can reduce loss due to excitation energy movement from an emission center substance, and thus can have high emission efficiency.

The carbazole compound as described above can be represented by the following general formula (G1).

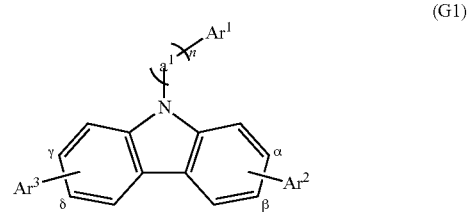

(G1)

In the formula (G1), $Ar^1$ is any of a phenyl group, a biphenyl group, and a naphthyl group. In addition, n is 0 or 1 and $a^1$ is a phenylene group or a biphenyldiyl group. Note that $Ar^1$ and $a^1$ may independently have a substituent, and when any of $Ar^1$ and $a^1$ has a substituent, the substituent is an alkyl group having 1 to 6 carbon atoms or an aryl group having 6 to 13 carbon atoms.

In the formula (G1), $Ar^2$ is a group represented by the following general formula (g1). Note that the substitution site of $Ar^2$ is a carbon atom represented by either α or β.

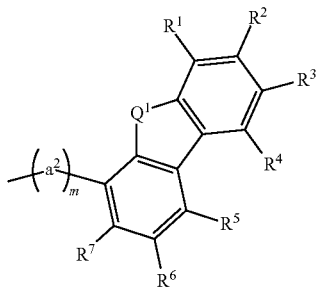

(g1)

In the formula (g1), $Q^1$ is oxygen or sulfur, and $R^1$ to $R^7$ are each independently any of hydrogen, an alkyl group having 1 to 6 carbon atoms, a phenyl group, a biphenyl group and a naphthyl group. In addition, m is 0 or 1 and $a^2$ is a phenylene group or a biphenyldiyl group. $R^1$ to $R^7$ and $a^2$ may independently have a substituent. When any of $R^1$ to $R^7$ and $a^2$ has a substituent, the substituent is an alkyl group having 1 to 6 carbon atoms or an aryl group having 6 to 13 carbon atoms.

$Ar^3$ is any of hydrogen, a group represented by the following general formula (g2), and a group represented by the following general formula (g3). Note that the substitution site of $Ar^3$ is a carbon atom represented by either γ or δ.

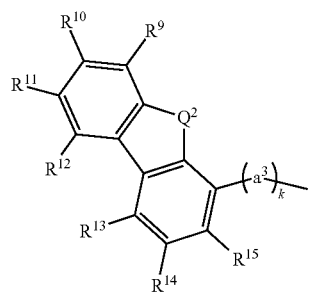

(g2)

In the formula (g2), $Q^2$ is sulfur or oxygen and $R^9$ to $R^{15}$ are each independently any of hydrogen, an alkyl group having 1 to 6 carbon atoms, a phenyl group, a biphenyl group and a naphthyl group. In addition, k is 0 or 1, and $a^3$ is a phenylene group or a biphenyldiyl group. Note that $R^9$ to $R^{15}$ and $a^3$ may independently have a substituent, and when any of $R^9$ to $R^{15}$ and $a^3$ has a substituent, the substituent is an alkyl group having 1 to 6 carbon atoms or an aryl group having 6 to 13 carbon atoms.

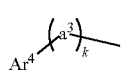

(g3)

In the formula, k is 0 or 1, and $a^3$ is a phenylene group or a biphenyldiyl group. In addition, $Ar^4$ is any of a phenyl group, a biphenyl group, and a naphthyl group. Note that $Ar^4$ and $a^3$ may independently have a substituent, and when any of $Ar^4$ and $a^3$ has a substituent, the substituent is an alkyl group having 1 to 6 carbon atoms or an aryl group having 6 to 13 carbon atoms.

Further, the carbazole compound having the above-described structure has a good carrier-transport property, especially, an excellent hole-transport property, and a light-emitting element using the carbazole compound can be a light-emitting element driven with low driving voltage.

The carbazole compound represented by the general formula (G1) is a carbazole compound in which the 4-position of the dibenzothiophene skeleton or the dibenzofuran skeleton is bonded to the 2- or 3-position of the carbazole skeleton directly or via an arylene group. Since the 4-position of the dibenzothiophene skeleton or the dibenzofuran skeleton is bonded to the carbazole skeleton, the conjugation (between dibenzothiophene or dibenzofuran and carbazole) is difficult to expand, and thus a material having a wide band gap and/or a high T1 level can be obtained. For that reason, in an organic light-emitting element, even when the material is used for a light-emitting layer or a layer in contact with the light-emitting layer, a high-efficient element can be obtained without losing generated excitation energy. Further, since the carbazole skeleton is used, a good hole-transport property can be obtained.

In this case, when the carbazole compound represented by the general formula (G1) has a substituent (including $Ar^1$ and $Ar^4$), the band gap and the T1 level of a compound in which a bond of substituent is substituted with hydrogen is preferably 2.7 eV or higher (which is larger than or equal to excitation energy of blue fluorescence, or more preferably 3.0 eV or higher) and 1.8 eV or higher (which is larger than or equal to excitation energy of red phosphorescence) respectively, in order to keep a wide band gap (Bg, an energy difference between a HOMO level and a LUMO level) or a high T1 level (an energy difference between a ground state and a triplet excited state). In this manner, the carbazole compound represented by the general formula (G1) in this embodiment can be a compound having a wide band gap and a high T1 level. Therefore, it is thought that when the carbazole compound of this embodiment is used as a layer adjacent to the light-emitting layer or a host material of the light-emitting layer, a light-emitting element can efficiently emit light without loss of excitation energy from a light-emitting substance with high excitation energy. Further, when the carbazole compound of this embodiment is used as a light-emitting substance, light with a short wavelength (bluish purple to blue) can be emitted.

Moreover, specifically, when the carbzoel compound represented by the general formula (G1) has a substituent (including $Ar^1$ and $Ar^4$), the substituent is preferably an alkyl group having 1 to 6 carbon atoms, a phenyl group, a biphenyl group, or a naphthyl group. The aryl group like those may have a substituent, and such an aryl group is preferably an alkyl group having 1 to 6 carbon atoms or a phenyl group, a biphenyl group, or a naphthyl group, for the above-described reason. In other words, more preferably, the substituent described above consists of an alkyl group having 1 to 6 carbon atoms or a phenyl group.

In addition, when the carbazole compound represented by the general formula (G1) has a substituent (including $Ar^1$ and $Ar^4$), it is preferred that the substituent is a condensed ring such as a naphthyl group because a more favorable carrier-transport property is obtained.

In addition, when the carbazole compound represented by the general formula (G1) has a substituent, it is preferred that the substituent is an alkyl group in view of solubility in an organic solvent or the like, improvement in film quality due to enhancement in stereostructure of a material.

Further, when the carbazole compound represented by the general formula (G1) has a substituent, it is also preferred that the substituent is an aryl group in view of improvement in film quality due to enhancement in stereostructure of a material.

In addition, when Ar³ and Ar² both have a dibenzothiophene skeleton or a dibenzofuran skeleton, a² and a³ are preferably 0. In other words, the 4-position of the dibenzothiophene skeleton or the dibenzofuran skeleton is directly bonded to the carbazole skeleton. The compound in this case can be used for a phosphorescent element with a higher T1 level.

In addition, when Ar² and Ar³ both have a dibenzothiophene skeleton or a dibenzofuran skeleton, Ar² and Ar³ are preferably bonded to the 3-position and the 6-position of the carbazole skeleton respectively. In other words, Ar² and Ar³ are bonded to the β position and the δ position of the carbazole compound represented by the general formula (G1). The compound in this case can be used for a phosphorescent element with a higher T1 level.

Note that when Ar³ is a substituent other than hydrogen, it is preferred that Ar³ and Ar² are the same group in view of easy synthesis.

When Ar³ is hydrogen, m in the above-described structural formula (g1) is preferably 1. In other words, when arylene as a² is interposed, the molecular weight becomes large and the structure is more sterical, and thus thermophysical property (such as Tg) or film quality is improved, which is preferable.

In addition, when Ar³ is hydrogen, the conjugation does not expand from the substituent Ar² to Ar³ via the carbazole skeleton, and thus a material having a wider band gap and/or a higher T1 level is obtained, which is preferable.

When the group represented by the above general formula (g1) has substituents (R¹ to R⁷), the substitution sites of the substituents are preferably sites represented by R¹, R³, and R⁶ for a material cost reduction owing to availability of the material and to easiness of the synthesis. From the same point of view, it is more preferred that R¹ to R⁷ are all hydrogen.

Also when the group represented by (g2) is used as Ar³, the substitution site of the substituent is preferably a site represented by R⁹, R¹¹, or R¹⁵, and more preferably, R⁹ to R¹⁵ are all hydrogen.

In addition, when Ar⁴ in the structural formula (g3) is a naphthyl group, k is preferably 1, in order to keep the wide band gap (Bg, an energy difference between a HOMO level and a LUMO level) and/or the high T1 level (an energy difference between a ground state and a triplet excited state). In other words, when arylene as a³ is interposed, the conjugation is difficult to expand from a naphthyl group to carbazole.

In the general formulae (g1) and (g2), as an alkyl group having 1 to 6 carbon atoms and an aryl group having 6 to 13 carbon atoms which are applicable as R¹ to R¹⁵, groups represented by the following structural formulae (R-1) to (R-13) can be used.

(R-1)

(R-2)

(R-3)

(R-4)

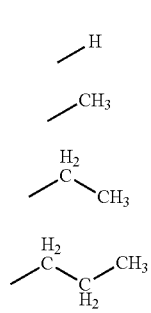

-continued

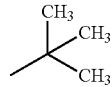
(R-5)

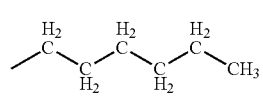
(R-6)

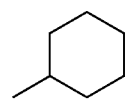
(R-7)

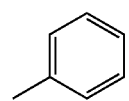
(R-8)

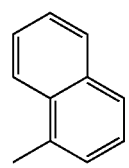
(R-9)

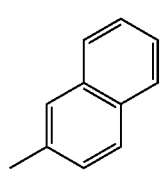
(R-10)

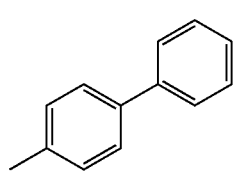
(R-11)

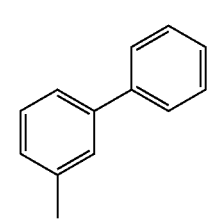
(R-12)

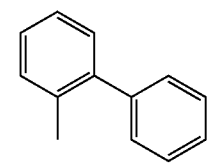
(R-13)

In the general formula (G1), specific examples of groups applicable as Ar¹ and Ar⁴ are groups represented by the following structural formulae (Ar-1) to (Ar-6). Note that Ar¹ and Ar⁴ are not necessarily the same, and can be independently selected.

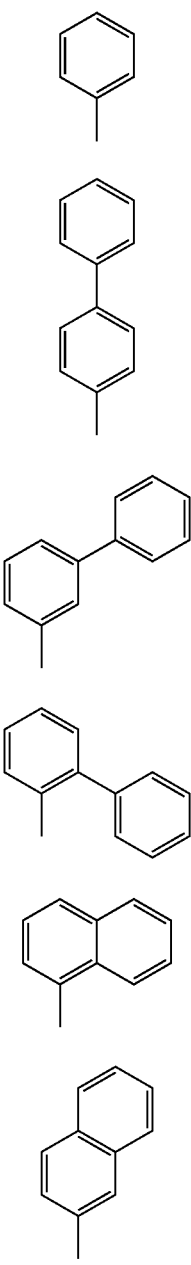

(Ar-1)

(Ar-2)

(Ar-3)

(Ar-4)

(Ar-5)

(Ar-6)

In the above-described general formulae (G1), (g1) and (g2), specific examples of the groups, $a^1$, $a^2$, and $a^3$, are groups represented by the following structural formulae (a-1) to (a-7). Note that $a^1$, $a^2$, and $a^3$ are not necessarily the same, and can be independently selected.

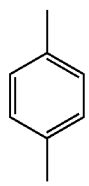

(α-1)

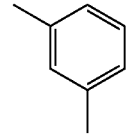

(α-2)

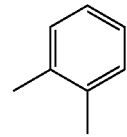

(α-3)

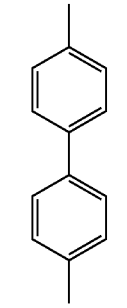

(α-4)

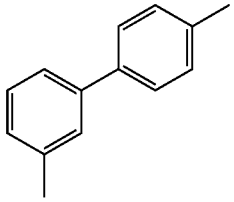

(α-5)

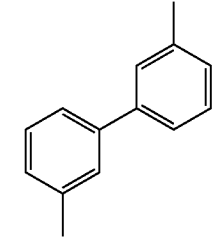

(α-6)

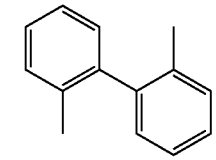

(α-7)

In this case, the carbazole compound including an arylene group represented by the structural formula (a-1) or (a-4) is bonded at the para position, and thus can reduce driving voltage more when used for a light-emitting element, which is preferable.

Further, the carbazole compound including an arylene group represented by the structural formula (a-2), (a-3), (a-5), (a-6), or (a-7) is bonded at the meta position or the ortho position, and thus can widen the band gap, which is preferable. Therefore, a more highly efficient light-emitting element can be obtained. In addition, the structure is more sterical, which is also preferable.

Further, the carbazole compound including an arylene group represented by the structural formula (a-1), (a-2) or (a-3) is bonded at a phenylene group, and the carbazole compound including an arylene group represented by the structural formula (a-6) or (a-7) is bonded at the meta-position or the ortho-position in a biphenyldiyl group, a high T1 level can be kept, which is preferable.

In this case, the carbazole compound including an arylene group represented by the structural formula (a-1) or (a-4) is bonded at the para-position and thus can reduce driving voltage when it is used for a light-emitting element, which is preferable.

The carbazole compound including an arylene group represented by the structural formula (a-2), (a-3), (a-5), (a-6), or (a-7) is bonded at the meta position or the ortho position, and thus can widen the band gap, which is preferable. Therefore, a more highly efficient light-emitting element can be obtained. In addition, the structure is more sterical, which is also preferable.

Further, the carbazole compound including an arylene group represented by the structural formula (a-1), (a-2) or (a-3) is bonded at a phenylene group, and the carbazole compound including an arylene group represented by the structural formula (a-6) or (a-7) is bonded at the meta-position or the ortho-position in a biphenyldiyl group, a high T1 level can be kept, which is preferable.

Specific examples of the carbazole compound represented by the general formula (G1) include substances represented by the following structural formulae (100) to (120), (130) to (141), (150) to (157), (160) to (177), (180), (181), (190) to (193), (200) to (209), and (220) to (223).

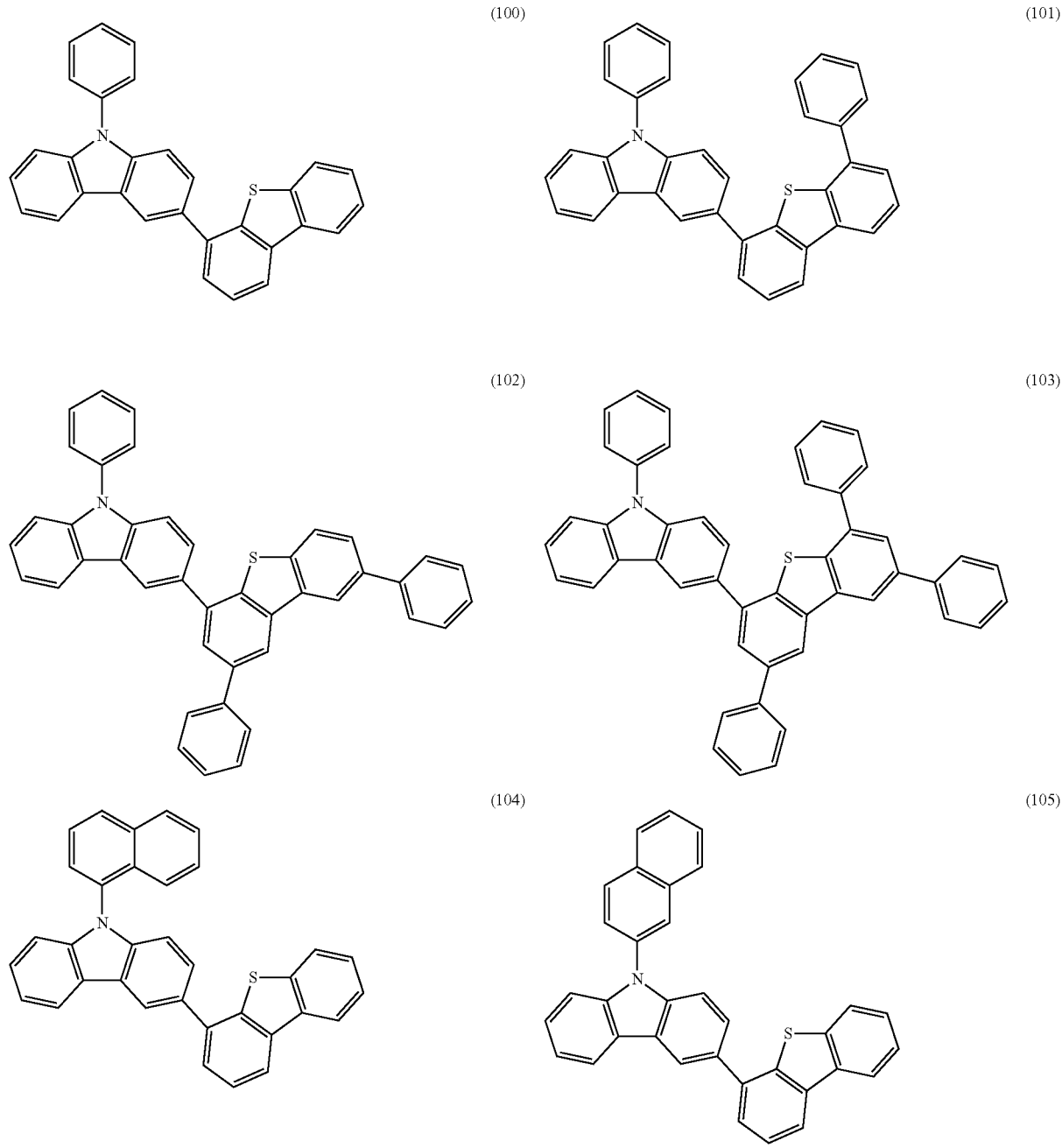

-continued
(106)
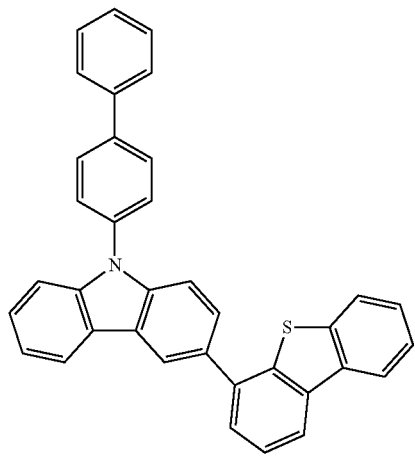
(107)
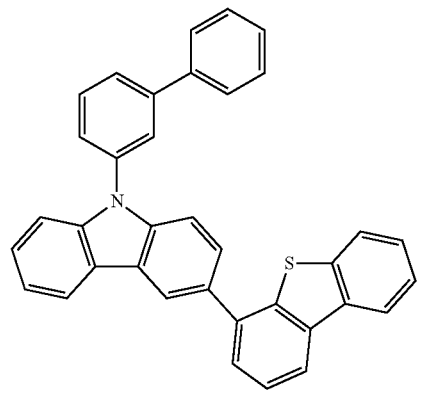
(108)
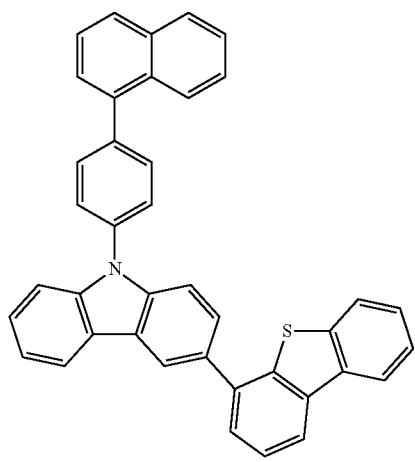
(109)
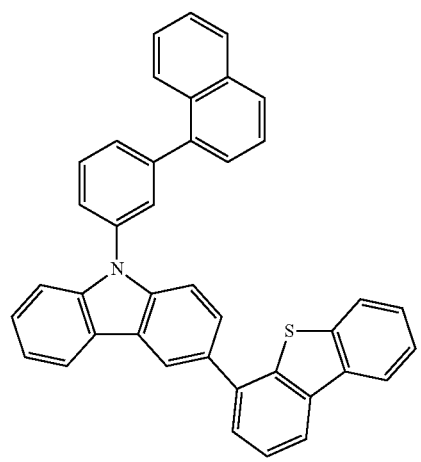
(110)
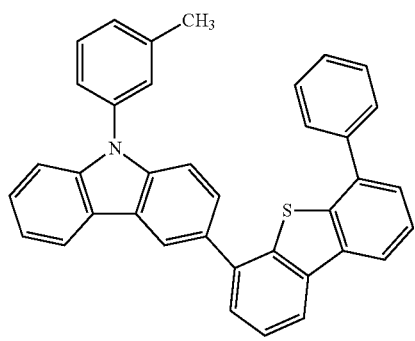
(111)
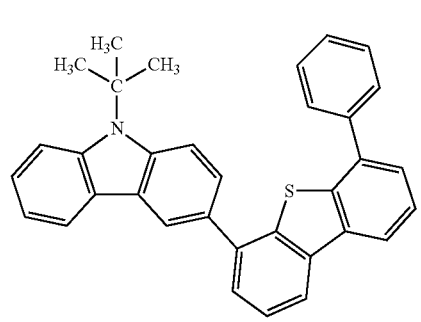

(112)
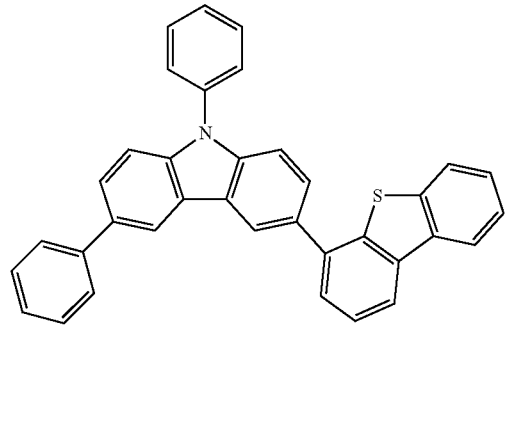
(113)
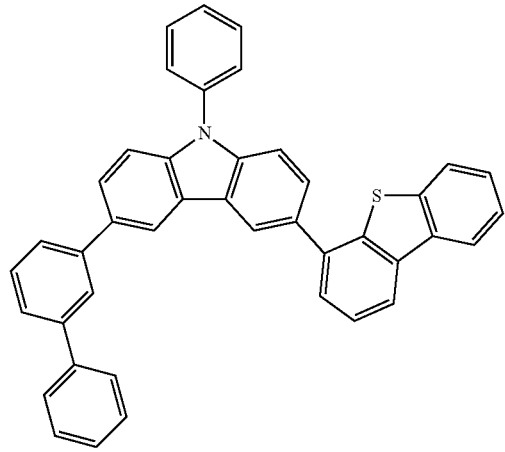
(114)
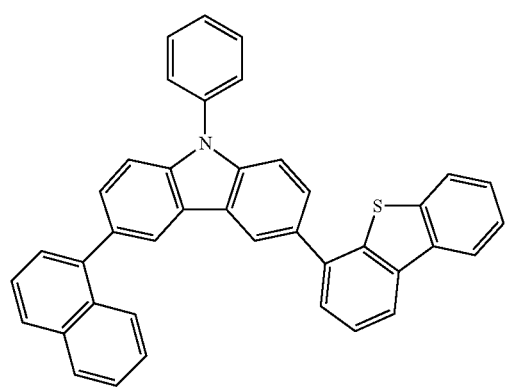
(115)
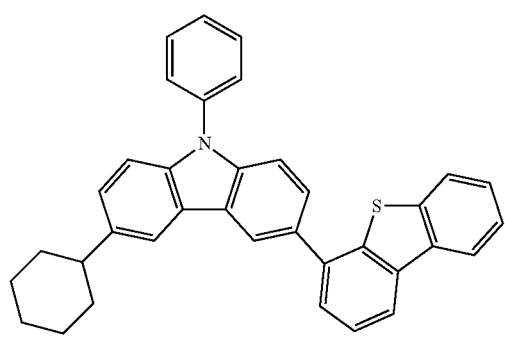
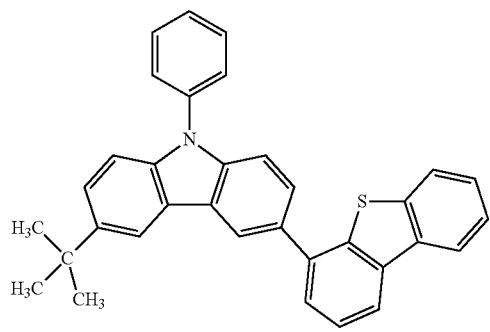
(117)
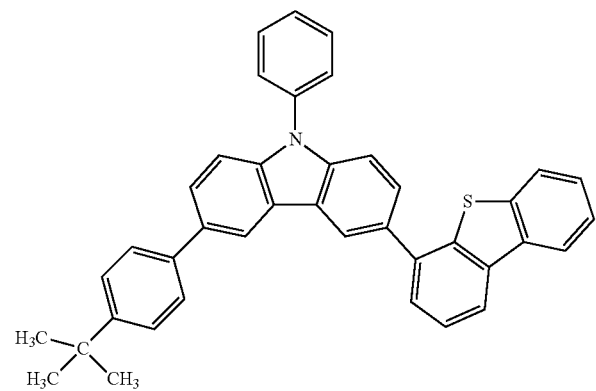

-continued
(118)
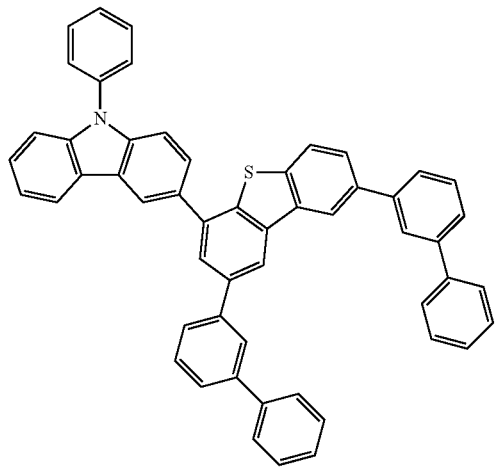
(119)
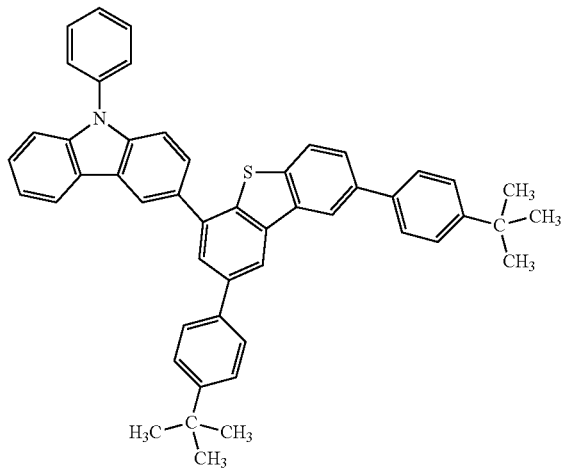
(120)
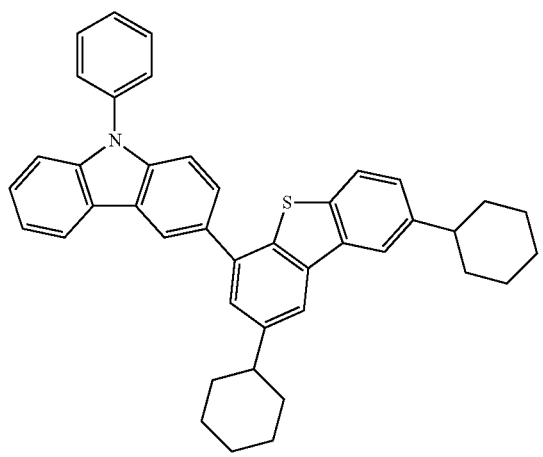
(130)
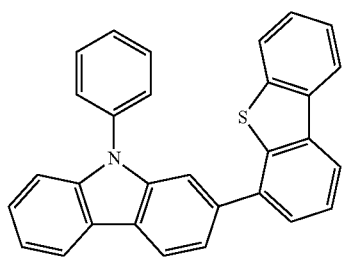
(131)
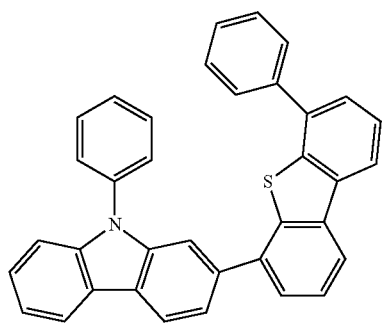
(132)
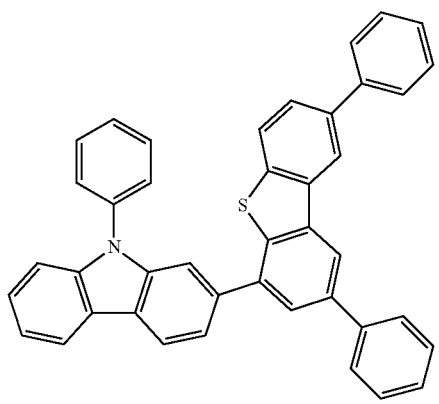

-continued
(133)
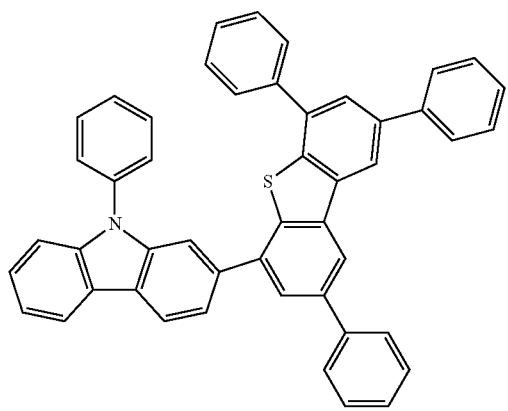
(134)
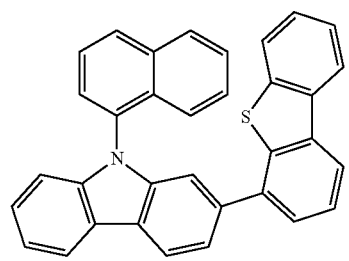
(135)
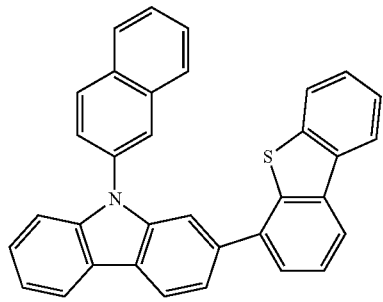
(136)
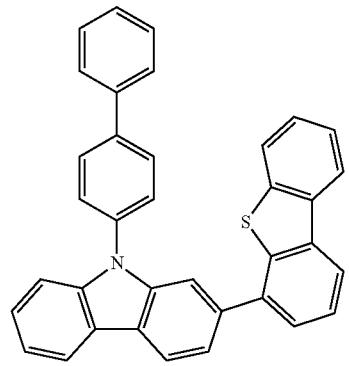
(137)
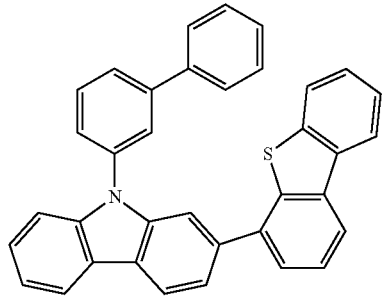
(138)
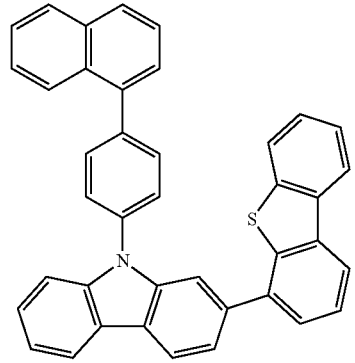
(139)
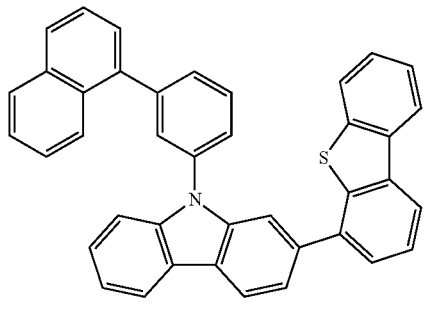
(140)
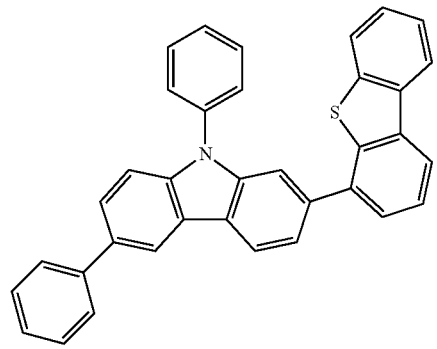

(141)
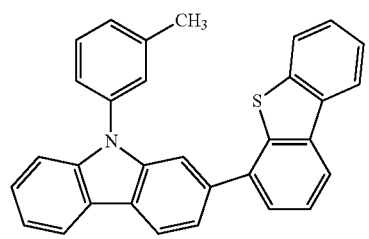
(150)
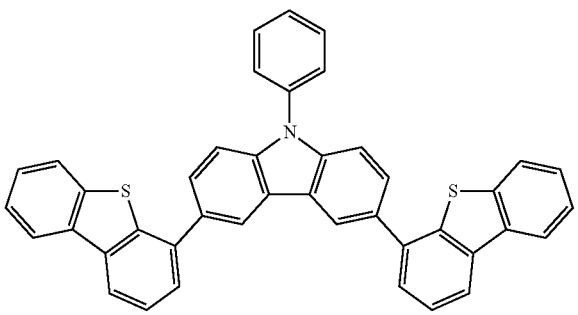
(151)
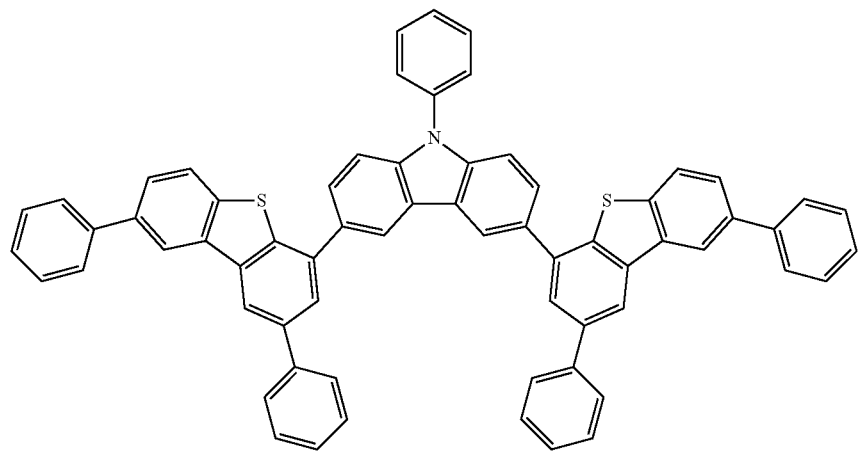
(152)
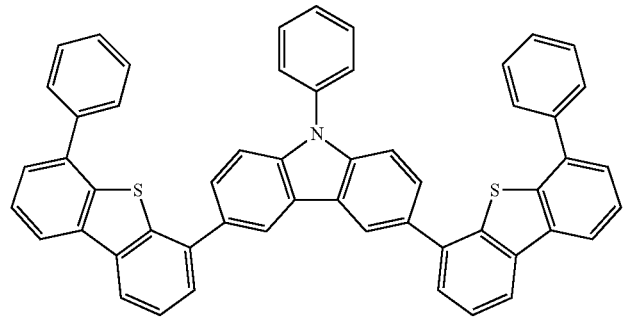
(153)
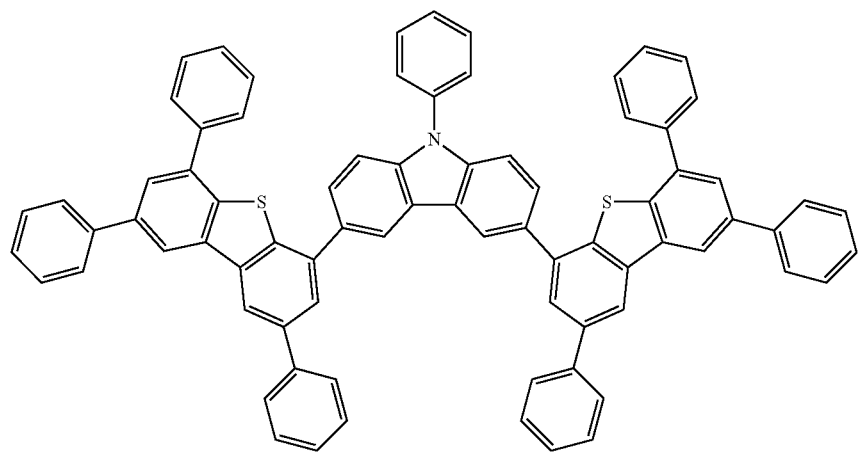

-continued
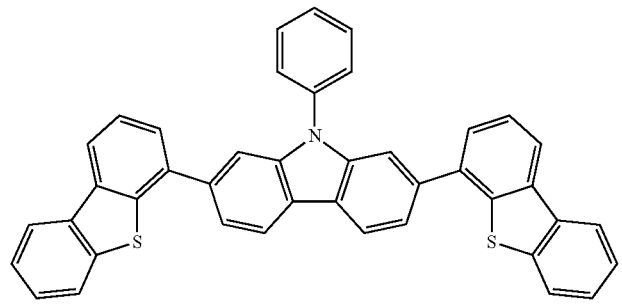
(154)
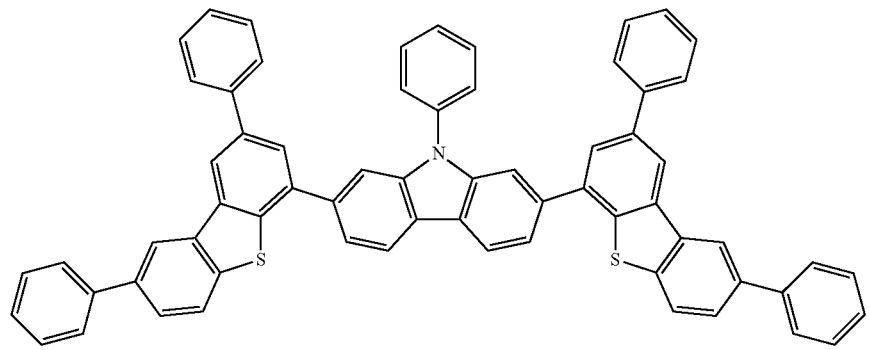
(156)
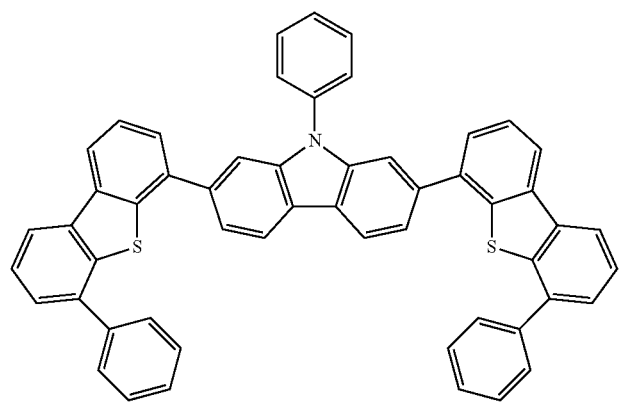
(155)
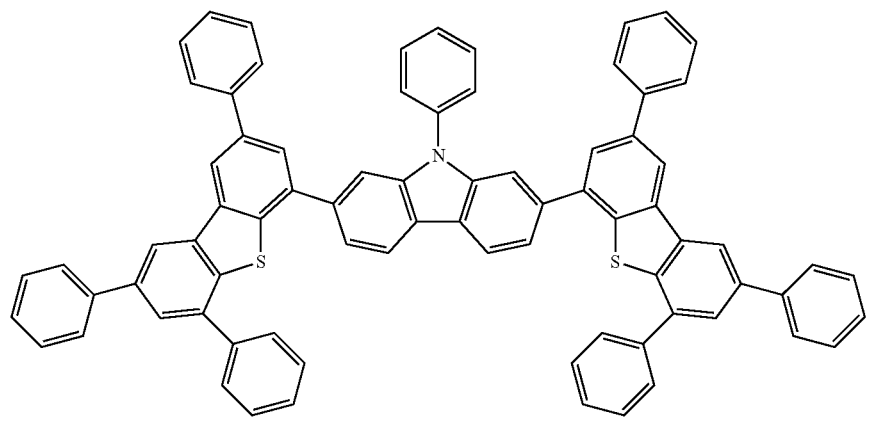
(157)

-continued
(160)
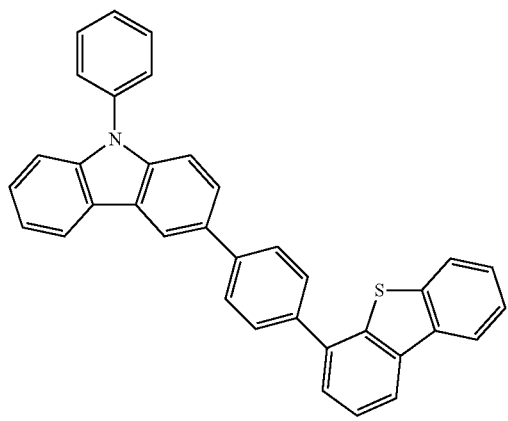
(161)
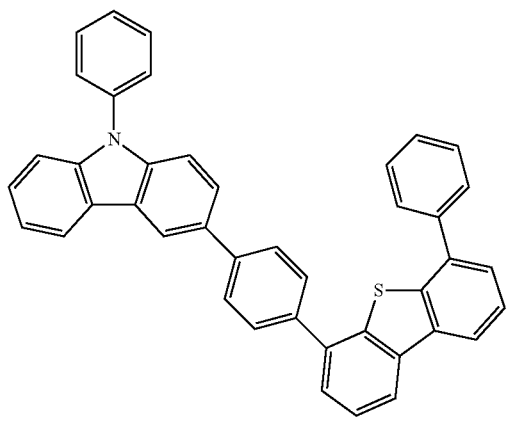
(162)
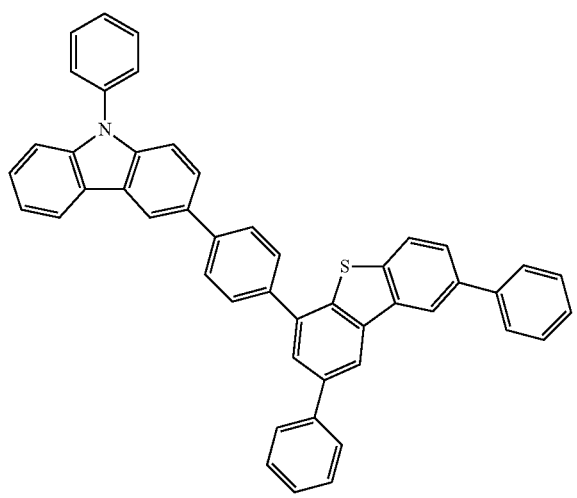
(163)
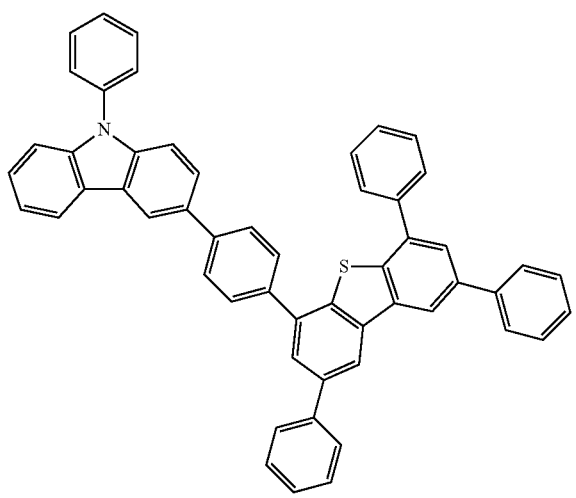
(164)
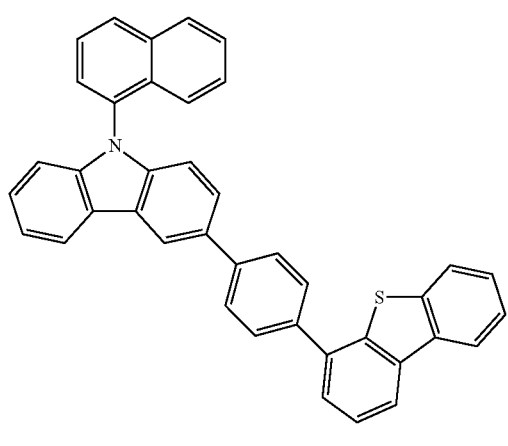
(105)
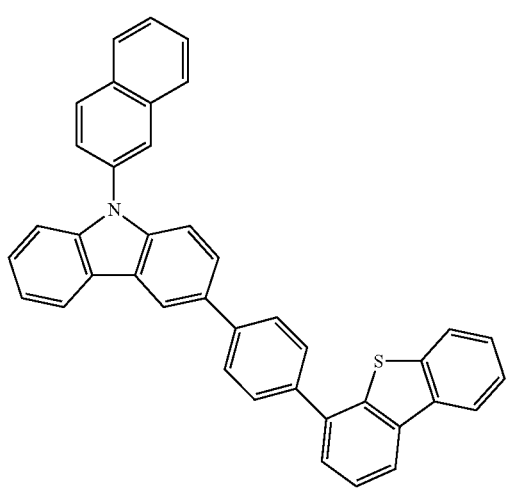

-continued
(166)
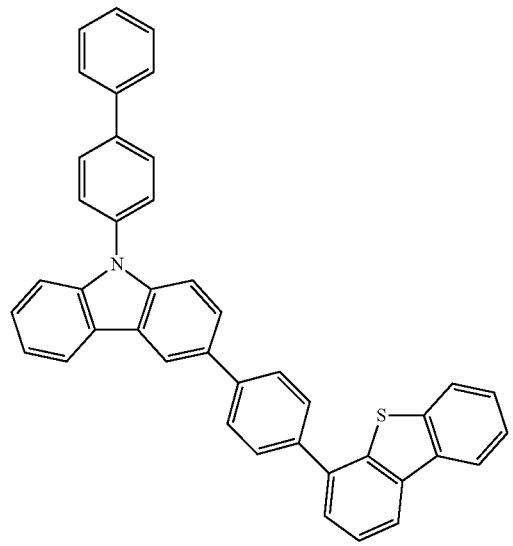
(167)
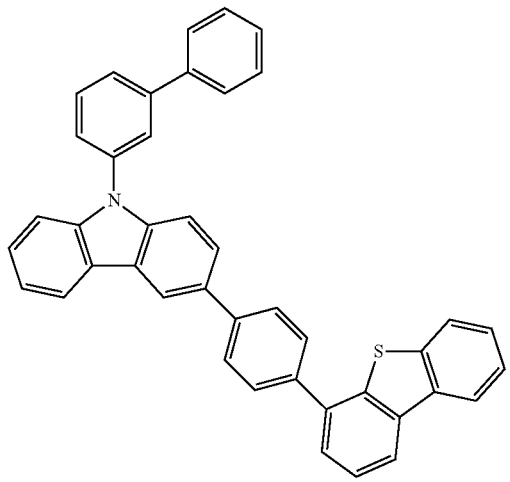
(168)
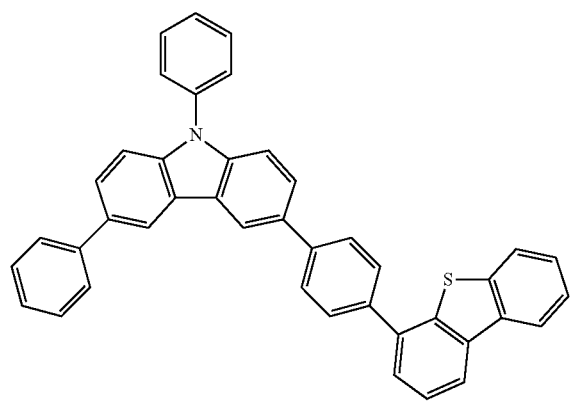
(169)
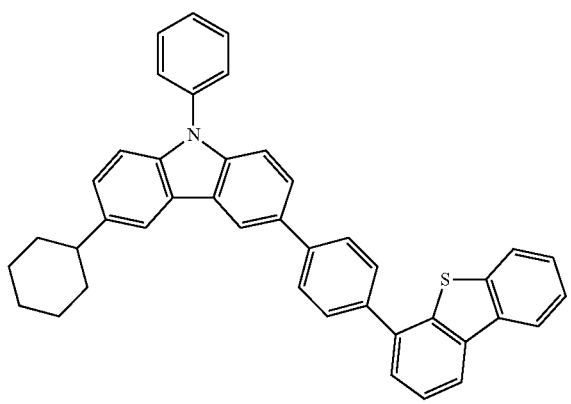
(170)
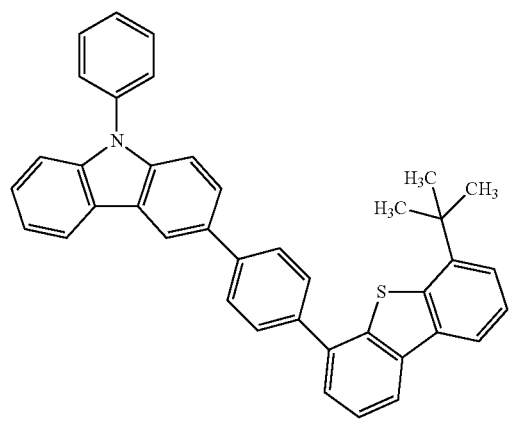
(171)
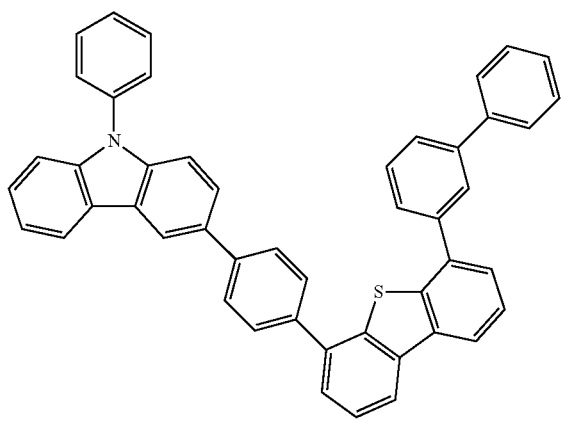

-continued
(172)
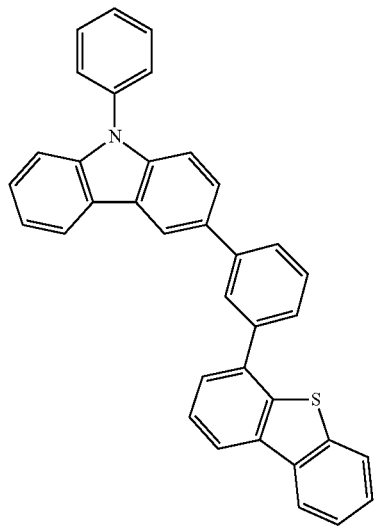
(173)
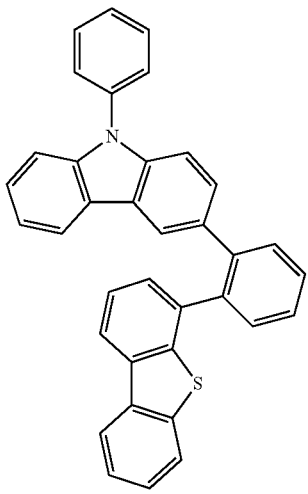
(174)
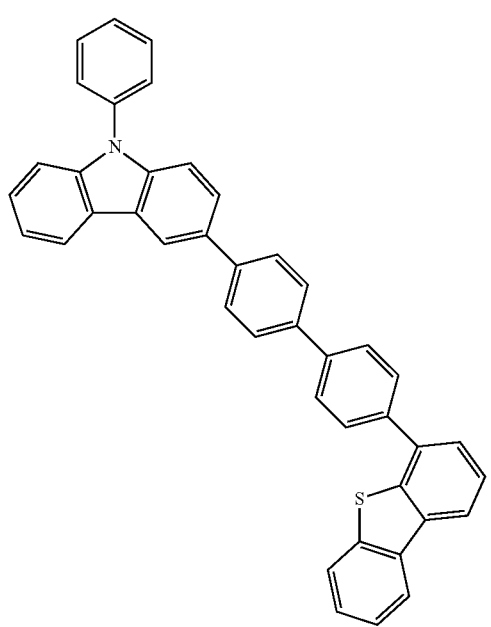
(175)
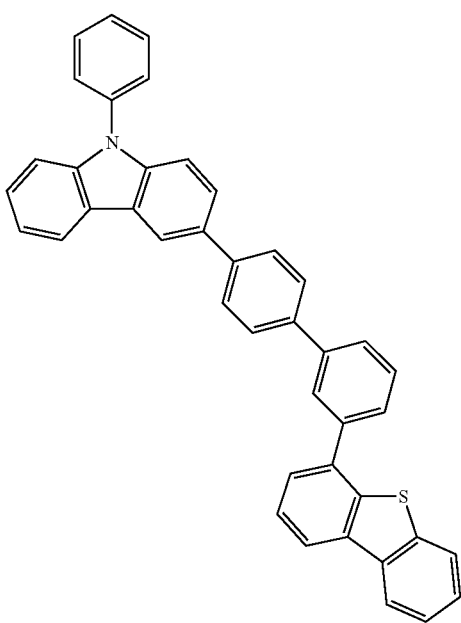

-continued
(176)
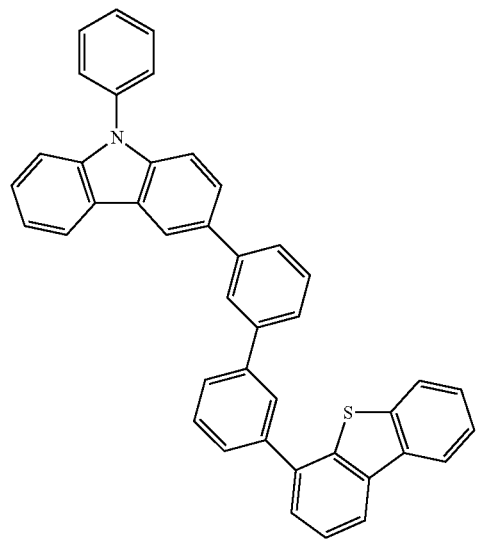
(177)
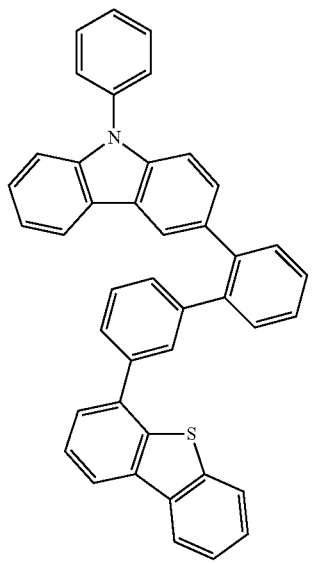
(180)
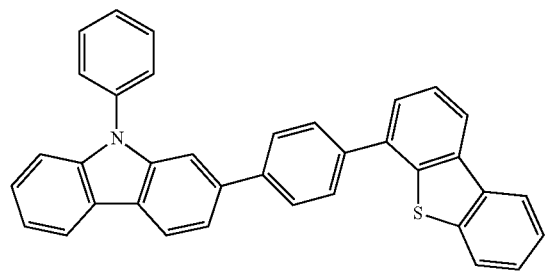
(181)
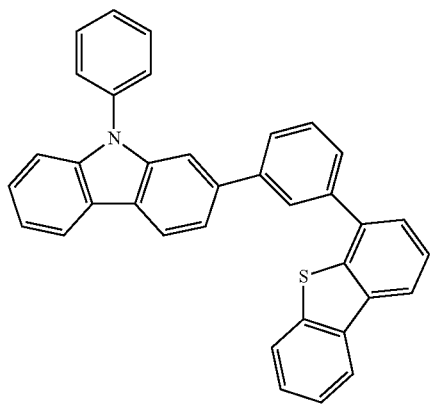
(190)
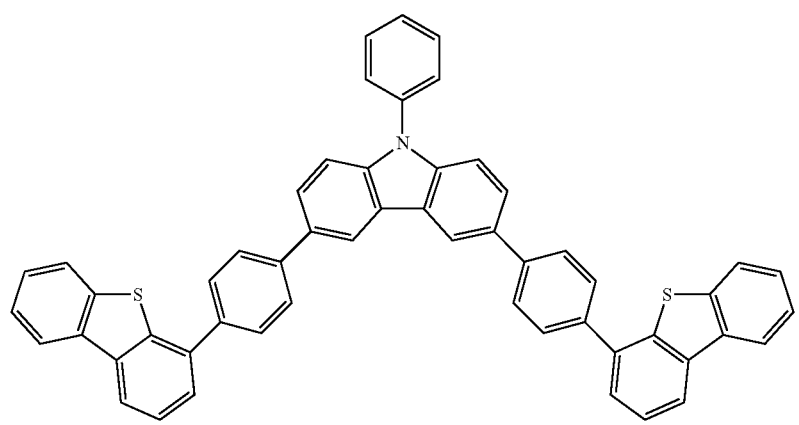

-continued
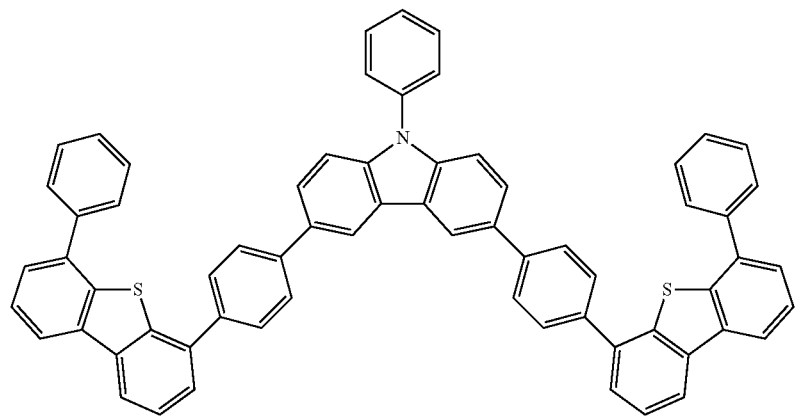
(191)
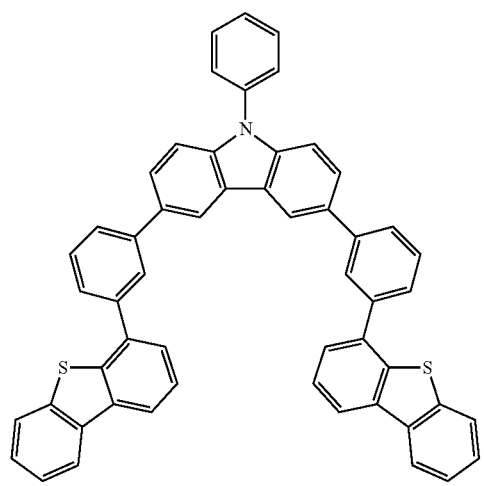
(192)
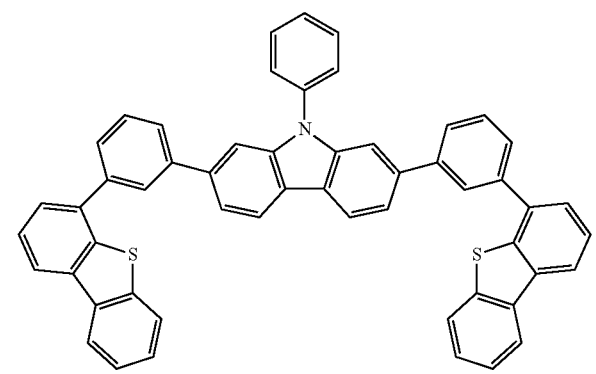
(193)
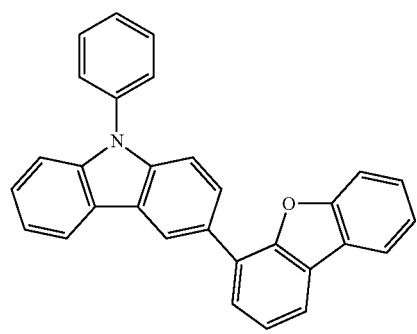
(200)
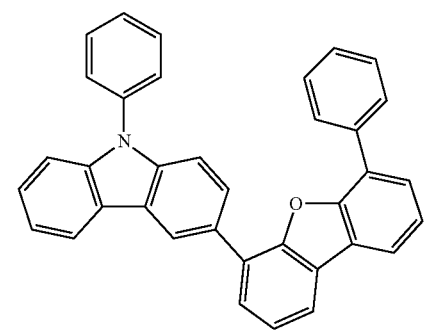
(201)

-continued
(202) 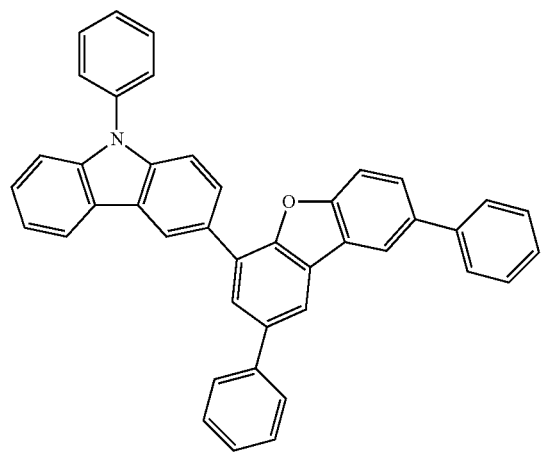
(203) 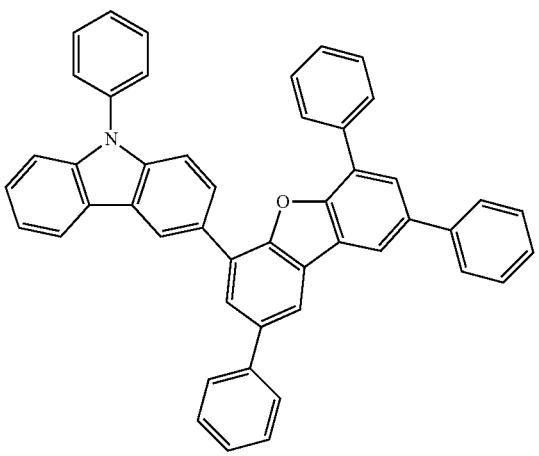
(204) 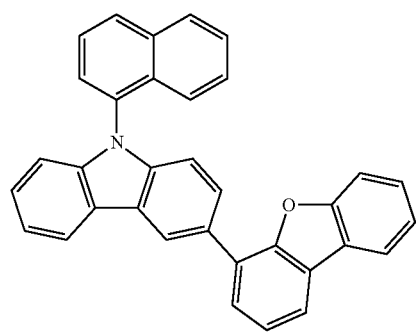
(205) 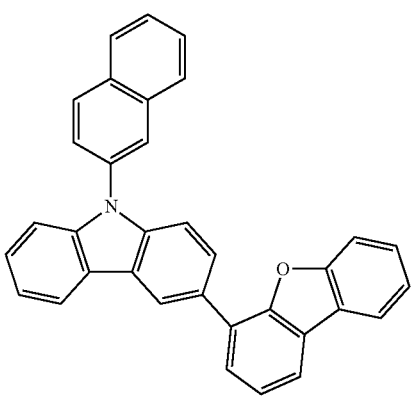
(206) 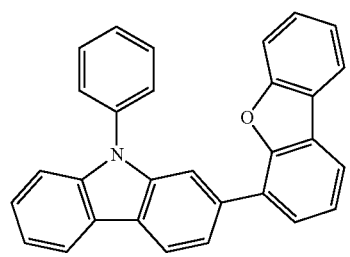
(207) 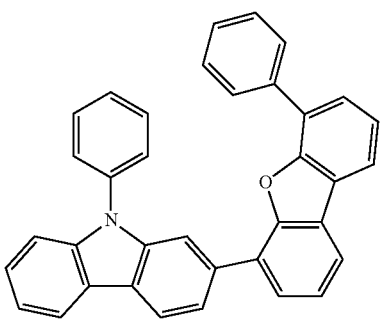
(208) 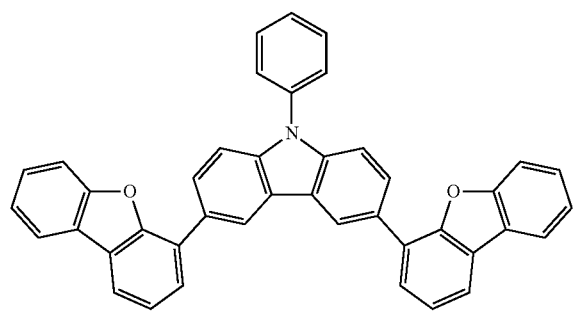
(209) 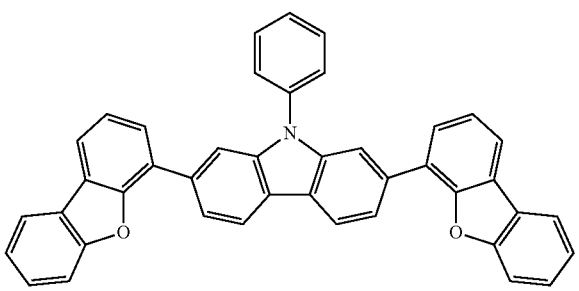

-continued (220)
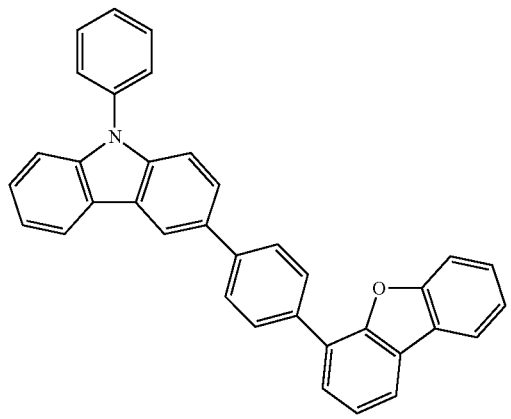

(221)
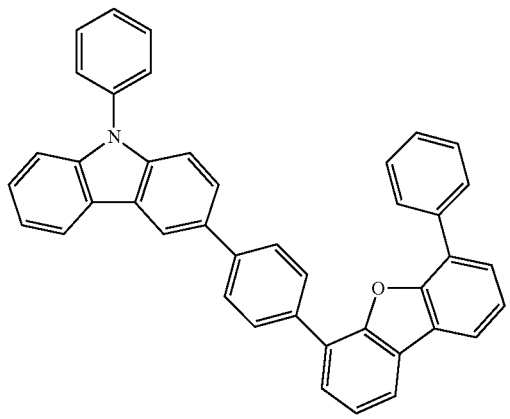

(222)
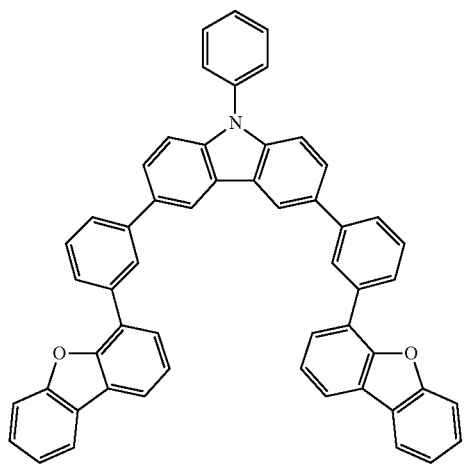

(223)
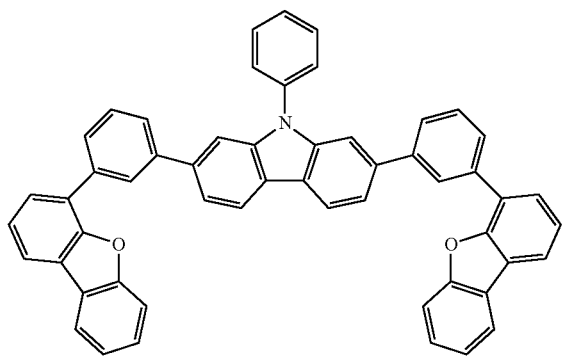

The carbazole compounds described above are each suitable as a carrier-transport material or a host material owing to its excellent carrier-transport property, and thus a light-emitting element driven with low driving voltage can also be provided.

Embodiment 2

As a synthesis method of the carbazole compound described in Embodiment 1, a variety of reactions can be applied. For example, by synthesis reactions represented by the following synthesis method 1 to synthesis method 4, a carbazole compound can be synthesized. Note that for the symbols ($\alpha^1$, $Ar^1$, $Ar^2$, $Ar^3$, n, $\alpha$, $\beta$, $\gamma$, $\delta$), which are not described here, the description of the general formula (G1) described above can be referred to.

[Synthesis Method 1]

First, as shown in the reaction scheme (S-1), a carbazole compound (a1) and an aryl halide compound (a2) are coupled with each other, so that the carbazole compound (G1) described in Embodiment 1 can be synthesized.

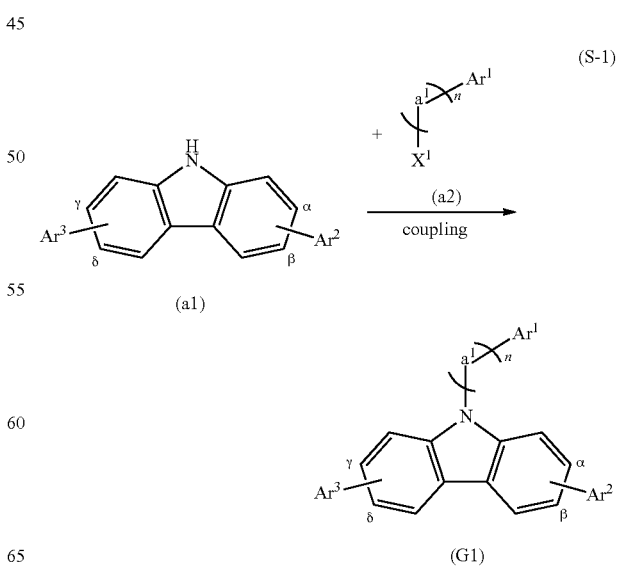

Further, $X^1$ is a halogen. $X^1$ preferably is bromine, more preferably iodine, because they have high reactivity.

Note that a variety of reaction conditions can be employed for the coupling reaction between an aryl compound having a halogen group and the 9-position of the carbazole in the reaction scheme (S-1). As an example of the reaction conditions, a synthesis method using a metal catalyst in the presence of a base can be employed.

The case of using the Buchwald-Hartwig reaction in the reaction scheme (S-1) will be described. A palladium catalyst can be used as the metal catalyst, and a mixture of a palladium complex and a ligand thereof can be used as the palladium catalyst. As examples of the palladium catalyst, bis(dibenzylideneacetone)palladium(0), palladium(II) acetate, and the like can be given. As the ligand, tri(tert-butyl)phosphine, tri(n-hexyl)phosphine, tricyclohexylphosphine, 1,1-bis(diphenylphosphino)ferrocene (abbreviated as DPPF), and the like can be given. As a substance which can be used as the base, an organic base such as sodium tert-butoxide, an inorganic base such as potassium carbonate, and the like can be given. In addition, this reaction is preferably performed in a solution, and toluene, xylene, benzene, and the like can be given as a solvent that can be used in the reaction. However, the catalyst, ligand, base, and solvent which can be used are not limited thereto. In addition, this reaction is preferably performed under an inert atmosphere of nitrogen, argon, or the like.

A case where an Ullmann reaction is performed in the synthesis scheme (S-1) is also shown. A copper catalyst can be used as the metal catalyst, and copper, copper(I) iodide and copper(II) acetate can be given as the copper catalyst. As a substance that can be used as the base, an inorganic base such as potassium carbonate can be given. The reaction is preferably performed in a solution, and 1,3-dimethyl-3,4,5,6-tetrahydro-2(1H)-pyrimidinone (DMPU), toluene, xylene, benzene, and the like can be given as a solvent that can be used in this reaction. However, the catalyst, base, and solvent which can be used are not limited thereto. In addition, this reaction is preferably performed under an inert atmosphere of nitrogen, argon, or the like.

Note that a solvent having a high boiling point such as DMPU or xylene is preferably used because, in an Ullmann reaction, a target substance can be obtained in a shorter time and at a higher yield when the reaction temperature is 100° C. or higher. In addition, DMPU is more preferable because the reaction temperature is more preferably 150° C. or higher.

Note that the reaction, in which the carbazole compound (a1) is obtained as the result from the chemical combination of the substituent $Ar^2$ and the substituent $Ar^3$ with the carbazole skeleton, can be performed in a manner similar to the reaction scheme (S-2) below. For the details, the following description can be referred to.

Further, a synthesis method 2 of the carbazole compound described in Embodiment 1, which is different from the synthesis method 1, will be described below.

[Synthesis Method 2]

As shown in the reaction scheme (S-2), a carbazole halide compound (a3), an arylboron compound (a4), and an arylboron compound (a5) are coupled, so that the carbazole compound represented by the general formula (G1) can be synthesized.

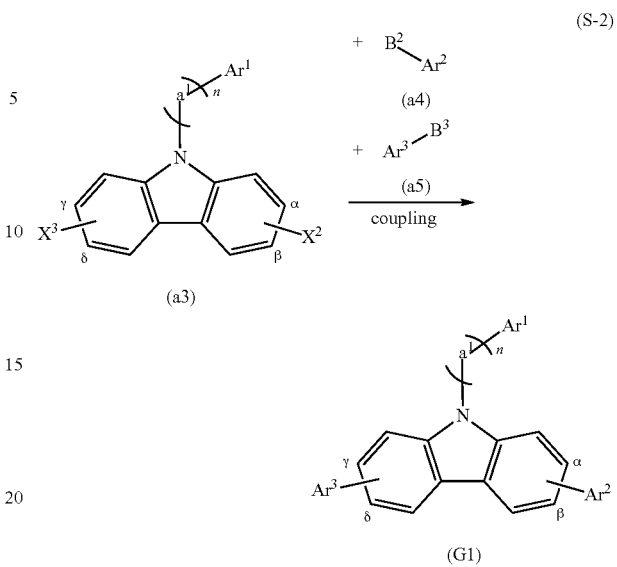

Further, $X^2$ is a halogen. $X^3$ is hydrogen when $Ar^3$ is hydrogen, while $X^3$ is halogen when $Ar^3$ is an aryl group. When $X^2$ and $X^3$ are each a halogen, $X^2$ and $X^3$ are preferably bromine, more preferably iodine, which have high reactivity. $B^1$ and $B^2$ are each independently boronic acid or dialkoxyboron. In addition, when $A^3$ is hydrogen, the arylboron compound (a5) is not necessarily added.

Note that there are a variety of reaction conditions for the coupling reaction in the synthesis scheme (S-2). As an example, a synthesis method using a metal catalyst in the presence of a base can be employed.

A case where a Suzuki-Miyaura reaction is performed in the synthesis scheme (S-2) is described. A palladium catalyst can be used as the metal catalyst, and a mixture of a palladium complex and a ligand thereof can be used as the palladium catalyst. As the palladium complex, palladium(II) acetate, tetrakis(triphenylphosphine)palladium(0), bis(triphenylphosphine)palladium(II)dichloride, and the like are given. As the ligand, tri(ortho-tolyl)phosphine, triphenylphosphine, tricyclohexylphosphine, and the like can be given. In addition, as a substance used as the base, an organic base such as sodium tert-butoxide, an inorganic base such as potassium carbonate, and the like can be given. The reaction is preferably performed in a solution, and as the solvent which can be used, a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of ethers such as ethyleneglycoldimethylether and water; and the like can be given. However, the catalyst, base, and solvent which can be used are not limited thereto. In the synthesis scheme (S-2), instead of the arylboron compound (a2), a compound such as aryl aluminum, aryl zirconium, aryl zinc, or aryl tin may be used. In addition, the reaction is preferably performed under an inert atmosphere of nitrogen, argon, or the like.

In addition, in the reaction scheme (S-2) (when $Ar^3$ is an aryl group), the arylboron compound (a4) and the arylboron compound (a5) are coupled with the carbazole halide compound (a3) at the same time. In this case, for higher yield, the others ($Ar^2$ and $Ar^3$) than the reactive groups of the arylboron compound (a4) and the arylboron compound (a5) are preferably the same compound (more preferably, the compound (a4) with two or more equivalents with respect to the compound (a3) may be added).

In addition, in the reaction scheme (S-2), the halogen group of the compound (a3) is reacted with the boron compound group of the compound (a5) or the compound (a4); however, the carbazole compound represented by the general formula (G1) can be obtained by coupling of a boron compound as the compound (a3) with or a halide as the compound (a5) or the compound (a4) (the reactive groups $X^2$ and $B^2$ are reversed, and the reactive groups $X^3$ and $B^3$ are reversed).

Further, a synthesis method 3 of the carbazole compound described in Embodiment 1, which is different from the synthesis methods 1 and 2, will be described below.

[Synthesis Method 3]

As shown in the reaction scheme (S-3), a carbazole halide compound (a6) and an arylboron compound (a4) are coupled, so that the carbazole compound represented by the general formula (G1) can be synthesized.

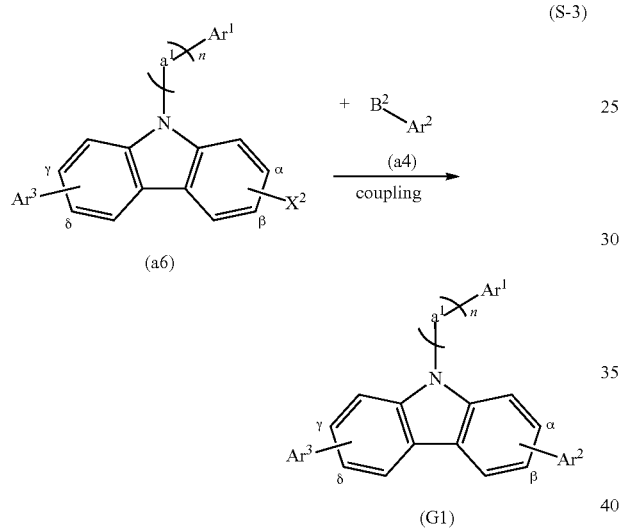

Further, $X^2$ is a halogen. $X^2$ is preferably bromine, more preferably iodine, which have high reactivity. $B^2$ is a boronic acid or dialkoxyboron.

Note that there are a variety of reaction conditions for the coupling reaction in the synthesis scheme (S-3). As an example, a synthesis method using a metal catalyst in the presence of a base can be employed. Specifically, since the synthesis scheme (S-3) can be performed in a manner similar to the reaction scheme (S-2), the above description can be referred to.

The reaction scheme (S-3) is an effective synthesis method for a case where $Ar^2$ and $Ar^3$ are different substituents. In the reaction scheme (S-3), $Ar^2$ is coupled with the carbazole compound (a6) combined with $Ar^3$; however, $Ar^3$ may be coupled with the carbazole compound (a6) combined with $Ar^2$.

Furthermore, a synthesis method 4 of the carbazole compound described in Embodiment 1, which is different from the synthesis methods 1, 2, and 3, will be described below.

[Synthesis Method 4]

As showing in the reaction scheme (S-4), a carbazole halide compound (a7), an arylboron compound (a8), and an arylboron compound (a9) are coupled, so that the carbazole compound represented by the general formula (G1) can be synthesized.

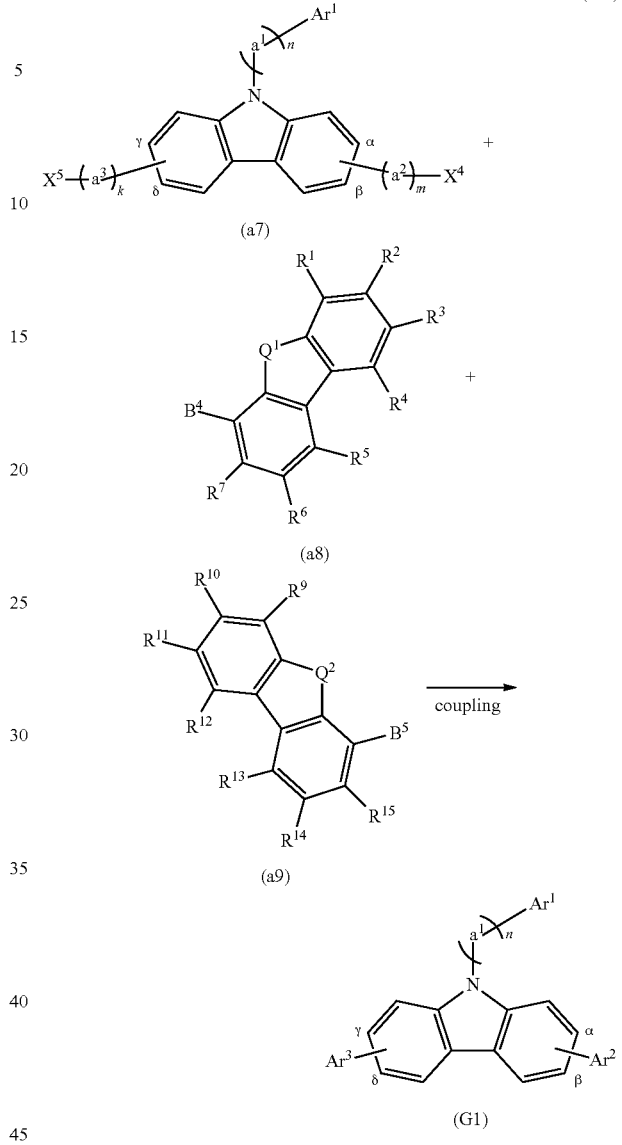

Note that $X^4$ is a halogen. $X^5$ is hydrogen when $Ar^3$ is hydrogen, while $X^5$ is a halogen when $Ar^3$ is an aryl group. $X^4$ and $X^5$ are halogens, preferably bromine, more preferably iodine, which have high reactivity. $B^4$ and $B^5$ are each independently a boronic acid or dialkoxyboron. In addition, when $Ar^3$ is hydrogen, k is 0, and the arylboron compound (a8) is not necessarily added.

Note that there are a variety of reaction conditions for the coupling reaction in the synthesis scheme (S-4). As an example, a synthesis method using a metal catalyst in the presence of a base can be employed. Specifically, since the synthesis scheme.

(S-4) can be performed in a manner similar to the reaction scheme (S-2) or (S-3), the above description can be referred to.

In addition, in the reaction scheme (S-4) (when $Ar^3$ is an aryl group), the arylboron compound (a8) and the arylboron compound (a9) are coupled with the carbazole halide compound (a7) at the same time. In this case, for higher yield, the others (Ar2 and Ar3) than the arylboron compound (a8) and the arylboron compound (a9) are preferably the same compound (more preferably, the compound (a8) with two or more equivalents with respect to the compound (a7) may be added).

In addition, in the reaction scheme (S-4), the halogen group of the compound (a7) is reacted with the boron compound group of the compound (a8) and the compound (a9); however, the carbazole compound represented by the general formula (G1) can be obtained by coupling of a boron compound as the compound (a7) and a halide as the compound (a8) and the compound (a9) (the reactive groups $X^4$ and $B^4$ are reversed, and the reactive groups $X^5$ and $B^5$ are reversed).

Embodiment 3

This embodiment shows an example in which the carbazole compound of Embodiment 1 is used for an active layer of a vertical transistor (SIT), which is a kind of an organic semiconductor element.

Figure 2:
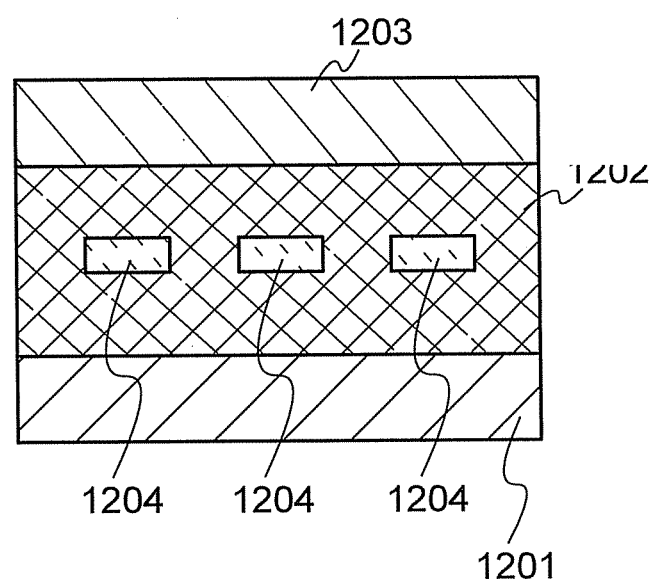
FIG. 2 is a conceptual diagram of an organic semiconductor element.

The element has a structure in which a thin-film active layer 1202 containing any one of the carbazole compounds described in Embodiment 1 is interposed between a source electrode 1201 and a drain electrode 1203, and gate electrodes 1204 are embedded in the thin-film active layer 1202, as illustrated in FIG. 2. The gate electrodes 1204 are each electrically connected to a unit to apply a gate voltage, and the source electrode 1201 and the drain electrode 1203 are electrically connected to a unit to control a voltage between the source and the drain.

In such an element structure, when a voltage is applied between the source and the drain without a gate voltage applied, a current flows (an ON state). Then, when a gate voltage is applied at this time, a depletion layer is generated in the periphery of the gate electrodes 1204, and thus a current does not flow (an OFF state). With such a mechanism, the element operates as a transistor.

In a vertical transistor, a material which has both a carrier-transport property and favorable film quality is required for an active layer like in a light-emitting element. Any of the carbazole compounds described in Embodiment 1 can be suitably used because it sufficiently meets these requirements Embodiment 4

In this embodiment, one embodiment of a light-emitting element using any of the carbazole compounds described in Embodiment 1 is described below with reference to FIG. 1A.

A light-emitting element of this embodiment has a plurality of layers between a pair of electrodes. In this embodiment, the light-emitting element includes a first electrode 102, a second electrode 104, and a layer 103 containing an organic compound provided between the first electrode 102 and the second electrode 104. In addition, in description of this embodiment, the first electrode 102 serves as an anode and the second electrode 104 serves as a cathode. In other words, when voltage is applied to the first electrode 102 and the second electrode 104 such that the potential of the first electrode 102 is higher than that of the second electrode 104, light emission can be obtained.

A substrate 101 is used as a support of the light-emitting element. As the substrate 101, glass, plastic or the like can be used, for example. Note that materials other than glass or plastic can be used as long as they can function as a support of a light-emitting element. When light is emitted through the substrate 101, a substrate having a refractive index (refractive index: 1.7 or higher) which is larger than or equal to the refractive index of the layer containing an organic compound is preferably used, so that the light-extraction efficiency can be improved. The glass substrate may be a high-refractive index glass substrate having 1.7 or higher of refractive index.

The first electrode 102 is preferably formed of a metal, an alloy, a conductive compound, a mixture of these, or the like having a high work function (specifically, a work function of 4.0 eV or higher). Specifically, for example, indium tin oxide (ITO), indium tin oxide containing silicon or silicon oxide, indium zinc oxide (IZO), indium oxide containing tungsten oxide and zinc oxide (IWZO), and the like can be given. Films of these conductive metal oxides are usually formed by sputtering; however, a sol-gel method or the like may also be used. For example, indium zinc oxide (IZO) can be formed by a sputtering method using indium oxide into which zinc oxide of 1 to 20 wt % is added, as a target. Moreover, indium oxide including tungsten oxide and zinc oxide (IWZO) can be formed by a sputtering method using a target in which 0.5 to 5 wt % of tungsten oxide and 0.1 to 1 wt % of zinc oxide with respect to indium oxide are included. Besides, gold (Au), platinum (Pt), nickel (Ni), tungsten (W), chromium (Cr), molybdenum (Mo), iron (Fe), cobalt (Co), copper (Cu), palladium (Pd), graphene, nitride of a metal material (e.g., titanium nitride), and the like can be given.

There are no particular limitations on the stacked-layer structure of the layer 103 containing an organic compound. The layer 103 containing an organic compound may be configured by combining appropriately a layer containing a substance with a high electron-transport property (also referred to as an electron-transport layer), a layer containing a substance with a high hole-transport property (also referred to as a hole-transport layer), a layer containing a substance with a high electron-injection property (also referred to as an electron-injection layer or an electron-injection buffer layer), a layer containing a substance with a high hole-injection property (also referred to as a hole-injection layer or a hole-injection buffer layer), a layer containing a substance with a bipolar property (a substance with a high transport property of electrons and holes), and the like. For example, a hole-injection layer, a hole-transport layer, a light-emitting layer, an electron-transport layer, an electron-injection layer, and the like can be combined as appropriate for the stacked-layer structure of the layer 103 containing an organic compound. In this embodiment, the layer 103 containing an organic compound has a hole-injection layer 111, a hole-transport layer 112, a light-emitting layer 113, and an electron-transport layer 114 which are stacked in this order over the first electrode 102 (anode). Specific materials to form each of the layers will be given below.

The hole-injection layer 111 is a layer containing a substance with a high hole-injection property. Molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviated as $H_2Pc$) or copper phthalocyanine (abbreviated as CuPc); an aromatic amine compound such as 4,4'-bis[N-(4-diphenylaminophenyl)-N-phenylamino]biphenyl (abbreviated as DPAB) or N,N'-bis[4-[bis(3-methylphenyl)amino]phenyl]-N,N'-diphenyl-[1,1'-biphenyl]-4,4'-diamine (abbreviated as DNTPD); a high molecule compound such as poly(ethylenedioxythiophene)/poly(styrenesulfonic acid) (PEDOT/PSS), or the like.

Alternatively, the hole-injection layer 111 can be formed using a composite material in which a substance with an acceptor property is mixed into a substance with a high hole-transport property. An acceptor substance may be a substance having an electron-accepting property to the substance having a high hole-transport property. Note that when the composite material in which an acceptor substance is contained in a substance having a high hole-transport property is used, a material for forming the electrode can be selected regardless of its work function. In other words, besides a material having a high work function, a material having a low work function can also be used for the first electrode 102. As the acceptor substance, 7,7,8,8-tetracyano-2,3,5,6-tetrafluoroquinodimethane (abbreviated as $F_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron accepting properties. In particular, molybdenum oxide is preferable as the acceptor substance used for the composite material because molybdenum oxide can be easily treated due to its stability in the air and low hygroscopic property.

As the substance having high hole-transport properties used for the composite material, any of various organic compounds such as an aromatic amine compound, a carbazole compound, aromatic hydrocarbon, heterocyclic compound, and a high-molecular compound (such as an oligomer, a dendrimer, or a polymer) can be used. The organic compound used for the composite material is preferably an organic compound having a high hole-transport property. Specifically, a substance having a hole mobility of $10^{-6}$ cm$^2$/Vs or higher is preferably used. However, other substances that have a hole-transport property higher than an electron-transport property may be used. An organic compound which can be used as a substance having a high hole-transport property for the composite material is specifically given below.

As aromatic amine compounds, for example, there are N,N'-di(p-tolyl)-N,N'-diphenyl-p-phenylenediamine (abbreviated as DTDPPA), 4,4'-bis[N-(4-diphenylaminophenyl)-N-phenylamino]biphenyl (abbreviated as DPAB), N,N'-bis[4-[bis(3-methylphenyl)amino]phenyl]-N,N'-diphenyl-[1,1'-biphenyl]-4,4'-diamine (abbreviated as DNTPD), 1,3,5-tris[N-(4-diphenylaminophenyl)-N-phenylamino]benzene (abbreviated as DPA3B), and the like.

As the carbazole compound which can be used for the composite material, specifically, the following can be given: 3-[N-(9-phenylcarbazol-3-yl)-N-phenylamino]-9-phenylcarbazole (abbreviated as PCzPCA1), 3,6-bis[N-(9-phenylcarbazol-3-yl)-N-phenylamino]-9-phenylcarbazole (abbreviated as PCzPCA2), 3-[N-(1-naphthyl)-N-(9-phenylcarbazol-3-yl)amino]-9-phenylcarbazole (abbreviated as PCzPCN1), and the like.

In addition, examples of the carbazole compound which can be used for the composite material include 4,4'-di(N-carbazolyl)biphenyl (abbreviated as CBP), 1,3,5-tris[4-(N-carbazolyl)phenyl]benzene (abbreviated as TCPB), 9-[4-(10-phenyl-9-anthryl)phenyl]-9H-carbazole (abbreviated as CzPA), 1,4-bis[4-(N-carbazolyl)phenyl]-2,3,5,6-tetraphenylbenzene, and the like.

Examples of the aromatic hydrocarbon which can be used for the composite material include 2-tert-butyl-9,10-di(2-naphthyl)anthracene (abbreviated as t-BuDNA); 2-tert-butyl-9,10-di(1-naphthyl)anthracene; 9,10-bis(3,5-diphenylphenyl)anthracene (abbreviated as DPPA); 2-tert-butyl-9,10-bis(4-phenylphenyl)anthracene (abbreviated as t-BuDBA); 9,10-di(2-naphthyl)anthracene (abbreviated as DNA); 9,10-diphenylanthracene (abbreviated as DPAnth); 2-tert-butylanthracene (abbreviated as t-BuAnth); 9,10-bis(4-methyl-1-naphthyl)anthracene (abbreviated as DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene, and 2,5,8,11-tetra(tert-butyl)perylene. Besides those, pentacene, coronene, or the like can also be used. Like these, the aromatic hydrocarbon which has a hole mobility of $1\times10^{-6}$ cm$^2$/Vs or higher and which has 14 to 42 carbon atoms is particularly preferable.

The aromatic hydrocarbon which can be used for the composite material may have a vinyl skeleton. As the aromatic hydrocarbon having a vinyl group, the following are given for example: 4,4'-bis(2,2-diphenylvinyl)biphenyl (abbreviated as DPVBi); 9,10-bis[4-(2,2-diphenylvinyl)phenyl]anthracene (abbreviated as DPVPA); and the like.

In addition, a heterocyclic compound which can be used for the composite material is a heterocyclic compound including a dibenzothiophene skeleton or a dibenzofuran skeleton. Examples of the heterocyclic compound include 4-[3-(triphenylen-2-yl)phenyl]dibenzothiophene (abbreviated as mDBTPTp-II), 4-[4-(9-phenylanthracene-10-yl)phenyl]dibenzothiophene (abbreviated as mDBTPA-II), 1,3,5-tri(dibenzothiophen-4-yl)-benzene (abbreviated as DBT3P-II), and the like.

Moreover, a high molecular compound such as poly(N-vinylcarbazole) (abbreviated as PVK), poly(4-vinyltriphenylamine) (abbreviated as PVTPA), poly[N-(4-{N'-[4-(4-diphenylamino)phenyl]phenyl-N-phenylamino}phenyl)methacrylamide] (abbreviated as PTPDMA), or poly[N,N'-bis(4-butylphenyl)-N,N'-bis(phenyl)benzidine (abbreviated as poly-TPD) can also be used.

Note that the carbazole compounds described in Embodiment 1 can also be used as the organic compound in the composite material. Any one of the carbazole compounds described in Embodiment 1 is preferably contained in the hole-transport layer of the light-emitting element of this embodiment because in this case, injection of holes from the hole-injection layer to the hole-transport layer can be smoothly performed, and thus, the driving voltage can be reduced. For the same reason, in the case where any one of the carbazole compounds described in Embodiment 1 is used as an organic compound in the composite material, it is more preferable that the carbazole compound and the carbazole compound used for the hole-transport layer be the same substance.

The carbazole compound in this embodiment absorbs almost no light in the visible region (about 380 to 750 nm), and thus when it is used for a thin film, high visible-light-transmittance can be obtained. Further, the carbazole compound in this embodiment hardly absorbs light in the visible region, even when it is used as the composite material. Therefore, the carbazole compound of this embodiment hardly absorbs emission energy even when used in a light-emitting element, which allows the light-emitting element to have a high external quantum yield.

The hole-transport layer 112 is a layer that contains a substance with a high hole-transport property. In this embodiment, the carbazole compound described in Embodiment 1 is used as the hole-transport layer 112. Since the carbazole compound described in Embodiment 1 has a good hole-transport property, the light-emitting element described in this embodiment can be a light-emitting element driven with low driving voltage. In addition, since the carbazole compounds described in Embodiment 1 have a wide band gap and a high T1 level, when any one of them is used as the hole-transport layer 112 adjacent to the light-emitting layer 113, even if a light-emitting region in the light-emitting layer 113 exists near the hole-transport layer 112, light extinction due to energy movement can be suppressed and thus a high emission efficiency light-emitting element can be obtained.

The light-emitting layer 113 is a layer containing a light-emitting substance. The light-emitting layer 113 may be formed using a film containing only a light-emitting substance or a film in which an emission center substance is dispersed in a host material.

There is no particular limitation on a material that can be used as the light-emitting substance or the emission center substance in the light-emitting layer 113, and light emitted from the material may be either fluorescence or phosphorescence. The following can be given as examples of the light-emitting substance or the emission center substance. Examples of a fluorescent substance include N,N'-bis[4-(9-phenyl-9H-fluoren-9-yl)phenyl]-N,N'-diphenyl-pyrene-1,6-diamine (abbreviated as 1,6FLPAPrn), N,N'-bis[4-(9H-carbazol-9-yl)phenyl]-N,N'-diphenylstilbene-4,4'-diamine (abbreviated as YGA2S), 4-(9H-carbazol-9-yl)-4'-(10-phenyl-9-anthryl)triphenylamine (abbreviated as YGAPA), 4-(9H-carbazol-9-yl)-4'-(9,10-diphenyl-2-anthryl)triphenylamine (abbreviated as 2YGAPPA), N,9-diphenyl-N-[4-(10-phenyl-9-anthryl)phenyl]-9H-carbazol-3-amine (abbreviated as PCAPA), perylene, 2,5,8,11-tetra-tert-butylperylene (abbreviated as TBP), 4-(10-phenyl-9-anthryl)-4'-(9-phenyl-9H-carbazol-3-yl)triphenylamine (abbreviated as PCBAPA), N,N''-(2-tert-butylanthracene-9,10-diyldi-4,1-phenylene)bis[N,N,N'-triphenyl-1,4-phenylenediamine](abbreviated as DPABPA), N,9-diphenyl-N-[4-(9,10-diphenyl-2-anthryl)phenyl]-9H-carbazol-3-amine (abbreviated as 2PCAPPA), N-[4-(9,10-diphenyl-2-anthryl)phenyl]-N,N,N'-triphenyl-1,4-phenylenediamine (abbreviated as 2DPAPPA), N,N,N',N',N'',N''',N''''-octaphenyldibenzo[g,p]chrysene-2,7,10,15-tetraamine (abbreviated as DBC1), coumarin 30, N-(9,10-diphenyl-2-anthryl)-N,9-diphenyl-9H-carbazol-3-amine (abbreviated as 2PCAPA), N-[9,10-bis(1,1'-biphenyl-2-yl)-2-anthryl]-N,9-diphenyl-9H-carbazol-3-amine (abbreviated as 2PCABPhA), N-(9,10-diphenyl-2-anthryl)-N,N',N'-triphenyl-1,4-phenylenediamine (abbreviated as 2DPAPA), N-[9,10-bis(1,1'-biphenyl-2-yl)-2-anthryl]-N,N',N'-triphenyl-1,4-phenylenediamine (abbreviated as 2DPABPhA), 9,10-bis(1,1'-biphenyl-2-yl)-N-[4-(9H-carbazol-9-yl)phenyl]-N-phenylanthracen-2-amine (abbreviated as 2YGABPhA), N,N,9-triphenylanthracen-9-amine (abbreviated as DPhAPhA), coumarin 545T, N,N'-diphenylquinacridone (abbreviated as DPQd), rubrene, 5,12-bis(1,1'-biphenyl-4-yl)-6,11-diphenyltetracene (abbreviated as BPT), 2-(2-{2-[4-(dimethylamino)phenyl]ethenyl}-6-methyl-4H-pyran-4-ylidene)propanedinitrile (abbreviated as DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviated as DCM2), N,N,N',N'-tetrakis(4-methylphenyl)tetracene-5,11-diamine (abbreviated as p-mPhTD), 7,14-diphenyl-N,N,N',N'-tetrakis(4-methylphenyl)acenaphtho[1,2-a]fluoranthene-3,10-diamine (abbreviated as p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviated as DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviated as DCJTB), 2-(2,6-bis{2-[4-(dimethylamino)phenyl]ethenyl}-4H-pyran-4-ylidene)propanedinitrile (abbreviated as BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviated as BisDCJTM). Examples of phosphorescent substances include bis[2-(3',5'-bistrifluoromethylphenyl)pyridinato-N,$C^{2'}$]iridium(III)picolinate (abbreviated as Ir(CF$_3$ppy)$_2$(pic)), bis[2-(4',6'-difluorophenyl)pyridinato-N,$C^{2'}$]iridium(III) acetylacetonate (abbreviated as FIracac), tris(2-phenylpyridinato)iridium (III) (abbreviated as Ir(ppy)$_3$), bis(2-phenylpyridinato)iridium(III) acetylacetonate (abbreviated as Ir(ppy)$_2$(acac)), tris (acetylacetonato)(monophenanthroline)terbium(III) (abbreviated as Tb(acac)$_3$(Phen)), bis(benzo[h]quinolinato) iridium(III) acetylacetonate (abbreviated as Ir(bzq)$_2$(acac)), bis(2,4-diphenyl-1,3-oxazolato-N,$C^{2'}$)iridium(III) acetylacetonate (abbreviated as Ir(dpo)$_2$(acac)), bis[2-4'-(perfluorophenylphenyl)pyridinato-N,$C^{2'}$]iridium(III) acetylacetonate (abbreviated as Ir(p-PF-ph)$_2$(acac)), bis(2-phenylbenzothiazolato-N,$C^{2'}$)iridium(III)acetylacetonate (abbreviated as Ir(bt)$_2$(acac)), bis[2-(2'-benzo[4,5-α]thienyl) pyridinato-N,$C^{3'}$]iridium(acetylacetonate) (abbreviated as Ir(btp)$_2$(acac)), bis(1-phenylisoquinolinato-N,$C^{2'}$)iridium (III) acetylacetonate (abbreviated as Ir(piq)$_2$(acac)), (acetylacetonato)bis[2,3-bis(4-fluorophenyl)quinoxalinato]iridium(III) (abbreviated as Ir(Fdpq)$_2$(acac)), (acetylacetonato) bis(2,3,5-triphenylpyrazinato)iridium(III) (abbreviated as Ir(tppr)$_2$(acac)), 2,3,7,8,12,13,17,18-octaethyl-21H,23H-porphyrin platinum(II) (abbreviated as PtOEP), tris(1,3-diphenyl-1,3-propanedionato)(monophenanthroline)europium(III) (abbreviated as Eu(DBM)$_3$(Phen)), and tris[1-(2-thenoyl)-3,3,3-trifluoroacetonato](monophenanthroline) europium(III) (abbreviated as Eu(TTA)$_3$(Phen)).

In addition, since the carbazole compound described in this embodiment exhibits a fluorescent property, it can emit light with a short wavelength. Therefore, when the carbazole compound in this embodiment is used as a light-emitting material, bluish purple to blue light emission can be obtained.

In addition, there are no particular limitations on materials that can be used as the host material in the light-emitting layer 113. Metal complexes, heterocyclic compounds, and aromatic amine compounds described below can be used, for example. As metal complexes, the following can be given: tris(8-quinolinolato)aluminum(III) (abbreviated as Alq); tris (4-methyl-8-quinolinolato)aluminum(III) (abbreviated as Almq$_3$); bis(10-hydroxybenzo[h]quinolinato)beryllium(II) (abbreviated as BeBq$_2$); bis(2-methyl-8-quinolinolato)(4-phenylphenolato)aluminum(III) (abbreviated as BAlq); bis (8-quinolinolato)zinc(II) (abbreviated as Znq); bis[2-(2-benzoxazolyl)phenolato]zinc(II) (abbreviated as ZnPBO); bis[2-(2-benzothiazolyl)phenolato]zinc(II) (abbreviated as ZnBTZ); and the like. As heterocyclic compounds, the following can be given: 2-(4-biphenylyl)-5-(4-tert-butylphenyl)-1,3,4-oxadiazole (abbreviated as PBD); 1,3-bis[5-(p-tert-butylphenyl)-1,3,4-oxadiazol-2-yl]benzene (abbreviated as OXD-7); 3-(4-biphenylyl)-4-phenyl-5-(4-tert-butylphenyl)-1,2,4-triazole (abbreviated as TAZ); 2,2',2''-(1,3,5-benzenetriyl)tris(1-phenyl-1H-benzimidazole) (abbreviated as TPBI); bathophenanthroline (abbreviated as BPhen); bathocuproine (abbreviated as BCP); 9-[4-(5-phenyl-1,3,4-oxadiazol-2-yl)phenyl]-9H-carbazole (abbreviated as CO11); and the like. As aromatic amine compounds, the following can be given: 4,4'-bis[N-(1-naphthyl)-N-phenylamino]biphenyl (abbreviated as NPB or α-NPD); N,N'-bis(3-methylphenyl)-N,N'-diphenyl-[1,1'-biphenyl]-4,4'-diamine (abbreviated as TPD); 4,4'-bis[N-(spiro-9,9'-bifluoren-2-yl)-N-phenylamino]biphenyl (abbreviated as BSPB); and the like. In addition, condensed polycyclic aromatic compounds such as anthracene derivatives, phenanthrene derivatives, pyrene derivatives, chrysene derivatives, and dibenzo[g,p]chrysene derivatives are given. Specific examples of the condensed polycyclic aromatic compound include 9,10-diphenylanthracene (abbreviated as DPAnth), N,N'-diphenyl-9-[4-(10- phenyl-9-anthryl)phenyl]-9H-carbazol-3-amine (abbreviated as CzA1PA), 4-(10-phenyl-9-anthryl)triphenylamine (abbreviated as DPhPA), 4-(9H-carbazol-9-yl)-4'-(10-phenyl-9-anthryl)triphenylamine (abbreviated as YGAPA), N,9-diphenyl-N-[4-(10-phenyl-9-anthryl)phenyl]-9H-carbazol-3-amine (abbreviated as PCAPA), N,9-diphenyl-N-{4-[4-(10-phenyl-9-anthryl)phenyl]phenyl}-9H-carbazol-3-amine (abbreviated as PCAPBA), N,9-diphenyl-N-(9,10-diphenyl-2-anthryl)-9H-carbazol-3-amine (abbreviated as 2PCAPA), 6,12-dimethoxy-5,11-diphenylchrysene, N,N,N',N',N'',N'',N''',N'''-octaphenyldibenzo[g,p]chrysene-2,7,10,15-tetramine (abbreviated as DBC1), 9-[4-(10-phenyl-9-anthryl)phenyl]-9H-carbazole (abbreviated as CzPA), 3,6-diphenyl-9-[4-(10-phenyl-9-anthryl)phenyl]-9H-carbazole (abbreviated as DPCzPA), 9,10-bis(3,5-diphenylphenyl)anthracene (abbreviated as DPPA), 9,10-di(2-naphthyl)anthracene (abbreviated as DNA), 2-tert-butyl-9,10-di(2-naphthyl)anthracene (abbreviated as t-BuDNA), 9,9'-bianthryl (abbreviated as BANT), 9,9'-(stilbene-3,3'-diyl)diphenanthrene (abbreviated as DPNS), 9,9'-(stilbene-4,4'-diyl)diphenanthrene (abbreviated as DPNS2), 3,3',3''-(benzene-1,3,5-triyl)tripyrene (abbreviated as TPB3), and the like. From these substances and known substances, one or plural kinds of substance(s) having a band gap wider than the band gap of the emission center substance (i.e., a substance having an S1 level higher than the S1 level of the emission center substance) may be selected. Moreover, in the case where the emission center substance emits phosphorescence, a substance having a T1 level (energy difference between a ground state and a triplet excitation state) which is higher than that of the emission center substance may be selected as the host material.

Note that light-emitting layer 113 may have plural layers of two or more layers. For example, in the case where the light-emitting layer 113 is formed by stacking a first light-emitting layer and a light-emitting second layer in that order from the hole-transport layer side, for example, the first light-emitting layer is formed using a substance with a hole-transport property as the host material and the second light-emitting layer is formed using a substance with an electron-transport property as the host material.

The light-emitting layer having the above-described structure may be fowled by any known method. For example, when the light-emitting layer 113 is formed using a plurality of materials, e.g., a structure in which an emission center substance is dispersed in the host material, a co-evaporation method in vacuum, a method such as an inkjet method, a spin coating method, or a dip coating method using a mixed solution can be selected.

The electron-transport layer 114 is a layer containing a substance with a high electron-transport property. For example, a layer containing a metal complex having a quinoline skeleton or a benzoquinoline skeleton, such as tris(8-quinolinolato)aluminum (abbreviated as Alq), tris(4-methyl-8-quinolinolato)aluminum (abbreviated as Almq$_3$), bis(10-hydroxybenzo[h]-quinolinato)beryllium (abbreviated as BeBq$_2$), or bis(2-methyl-8-quinolinolato)(4-phenylphenolato)aluminum (abbreviated as BAlq), or the like can be used. Alternatively, a metal complex having an oxazole-based or thiazole-based ligand, such as bis[2-(2-hydroxyphenyl)benzoxazolato]zinc (abbreviated as Zn(BOX)$_2$) or bis[2-(2-hydroxyphenyl)benzothiazolato]zinc (abbreviated as Zn(BTZ)$_2$), or the like can be used. Besides the metal complexes, 2-(4-biphenylyl)-5-(4-tert-butylphenyl)-1,3,4-oxadiazole (abbreviated as PBD), 1,3-bis[5-(p-tert-butylphenyl)-1,3,4-oxadiazol-2-yl]benzene (abbreviated as OXD-7), 3-(4-biphenylyl)-4-phenyl-5-(4-tert-butylphenyl)-1,2,4-triazole (abbreviated as TAZ), bathophenanthroline (abbreviated as BPhen), bathocuproine (abbreviated as BCP), or the like can also be used. The substances mentioned here are mainly ones that have an electron mobility of $10^{-6}$ cm$^2$/V·s or higher. The electron-transport layer may be formed of other materials than those described above as long as the materials have electron-transport properties higher than hole-transport properties.

Further, the electron-transport layer may be formed by not only a single layer but also a stacked-layer structure in which two or more layers made from the above mentioned substances are stacked.

Further, a layer for controlling transport of electron carriers may be provided between the electron-transport layer and the light-emitting layer. Specifically, the layer for controlling transport of electron carriers is a layer formed by adding a small amount of substance having a high electron-trapping property to the material having a high electron-transport property as described above, so that carrier balance can be adjusted. Such a structure is very effective in suppressing a problem (such as shortening of element lifetime) caused when electrons pass through the light-emitting layer.

In addition, an electron-injection layer may be provided between the electron-transport layer and the second electrode 104, in contact with the second electrode 104. As the electron-injection layer, an alkali metal, an alkaline earth metal, or a compound thereof such as lithium fluoride (LiF), cesium fluoride (CsF), or calcium fluoride (CaF$_2$) may be used. For example, a layer of a substance having an electron-transport property containing an alkali metal, an alkaline earth metal, or a compound thereof, such as Alq which contains magnesium (Mg), may be used. By using a layer of a substance having an electron-transport property containing an alkali metal or an alkaline earth metal as the electron-injection layer, electron injection from the second electrode 104 is performed efficiently, which is preferable.

The second electrode 104 can be formed of a metal, an alloy, an electrically conductive compound, or a mixture of these, having a low work function (specifically, a work function of 3.8 eV or lower). As a typical example of such a cathode material, an element belonging to Group 1 or 2 in the periodic table, i.e., an alkali metal such as lithium (Li) or cesium (Cs), or an alkaline earth metal such as magnesium (Mg), calcium (Ca), or strontium (Sr); an alloy containing any of these (such as MgAg or AlLi); a rare earth metal such as europium (Eu) or ytterbium (Yb); an alloy containing such a rare earth metal; or the like can be used. However, when the electron-injection layer is provided between the second electrode 104 and the electron-transport layer, the second electrode 104 can be formed from any of a variety of conductive materials such as Al, Ag, ITO, or indium oxide-tin oxide including silicon or silicon oxide regardless of its work function. Films of these conductive materials can be formed by a sputtering method, an inkjet method, a spin coating method, or the like.

Further, any of a variety of methods can be employed for forming the layer 103 containing an organic compound regardless of a dry process or a wet process. For example, a vacuum evaporation method, an inkjet method, a spin coating method or the like may be used. A different formation method may be employed for each electrode or each layer.

The electrode may be formed by a wet method using sol-gel method, or by a wet method using a paste of a metal material. Alternatively, the electrode may be formed by a dry method such as a sputtering method or a vacuum evaporation method.

In the light-emitting element having the above-described structure, current flows in accordance with a potential difference made between the first electrode 102 and the second electrode 104, a hole and an electron are recombined in the light-emitting layer 113, which contains a substance having a high light-emitting property, and light is emitted.

The emitted light is extracted out through one or both of the first electrode 102 and the second electrode 104. Therefore, either or both of the first electrode 102 and the second electrode 104 are light-transmissive electrodes. When only the first electrode 102 is an electrode having a light-transmitting property, light is extracted from the substrate side through the first electrode 102. Meanwhile, when only the second electrode 104 has a light-transmitting property, light is extracted from the side opposite to the substrate side through the second electrode 104. In a case where each of the first electrode 102 and the second electrode 104 has a light-transmitting property, light is extracted from both of the substrate side and the side opposite to the substrate through the first electrode 102 and the second electrode 104.

The structure of the layers provided between the first electrode 102 and the second electrode 104 is not limited to the above-described structure. However, a structure in which a light-emitting region for recombination of holes and electrons is positioned away from the first electrode 102 and the second electrode 104 so as to prevent quenching due to the proximity of the light-emitting region and a metal used for electrodes and carrier-injection layers is preferable. The order of stacking the layers is not limited to the above-described structure, and the following order, which is in a reverse order from that in FIG. 1A, may be employed: the second electrode, the electron-injection layer, the electron-transport layer, the light-emitting layer, the hole-transport layer, the hole-injection layer, and the first electrode from the substrate side.

In addition, in order to suppress energy transfer from an exciton which is generated in the light-emitting layer, the hole-transport layer or the electron-transport layer in direct contact with the light-emitting layer, particularly a carrier-transport layer in contact with a side closer to a light-emitting region in the light-emitting layer 113 is preferably formed with a substance having a band gap wider than the band gap of the light-emitting substance contained in the light-emitting layer or the band gap of the emission center substance contained in the light-emitting layer.

In the light-emitting element in this embodiment, since any one of the carbazole compounds having a wide band gap described in Embodiment 1 is used as the hole-transport layer, even when the light-emitting substance or the emission center substance is a substance having a wide band gap and exhibiting blue fluorescence or a substance exhibiting phosphorescence (with a wavelength shorter than red light, in some cases, blue, green, orange light) from a T1 level (energy difference between a ground state and a triplet excitation state), a light-emitting element that emits light efficiently and has a good emission efficiency can be obtained. Accordingly, a light-emitting element having lower power consumption can be provided. In addition, a light-emitting element that emits light with high color purity can be provided. Further, since the carbazole compounds described in Embodiment 1 are excellent in a carrier-transport property, a light-emitting element driven with low driving voltage can be provided.

In addition, as for the hole-transport layer or the electron-transport layer in direct contact with the light-emitting layer, in particular, the carrier-transport layer on the side closer to the light-emitting region in the light-emitting layer 113, the HOMO levels of the hole-transport layer and the light-emitting layer are preferably close to each other or the LUMO levels of the light-emitting layer and the electron-transport layer are preferably close to each other so that carriers can be injected into the light-emitting layer efficiently. Preferably, the difference between the LUMO levels or the difference between the HOMO levels is 0.5 eV or less, more preferably 0.2 eV or less. In this case, an element driven with lower driving voltage can be obtained. On the contrary, preferably, when the LUMO level of the hole-transport layer is shallower than that of the light-emitting layer and the HOMO level of the electron-transport layer is deeper than that of the light-emitting layer, carriers hardly go out of the light-emitting layer and an element with higher emission efficiency can be obtained. The difference between LUMO levels or the difference between the HOMO levels is preferably 0.2 eV or more.

In other words, when the hole-transport layer has a HOMO level close to that of the light-emitting layer, and a LUMO level or a T1 level higher than that of the light-emitting layer, the driving voltage can be more lowered, and a high emission efficiency can be obtained.

The carbazole compound in this embodiment has a relatively deeper HOMO level, has a good hole-injection property to the light-emitting layer having a deep HOMO level similarly, and has a high LUMO level and/or a high T1 level, and thus can exhibit high emission efficiency.

In this embodiment, the light-emitting element is formed over a substrate made of glass, plastic or the like. A plurality of such light-emitting elements is formed over one substrate, and thereby a passive matrix light emitting device is formed. In addition, for example, a thin film transistor (TFT) may be formed over a substrate formed of glass, plastic, or the like, and a light-emitting element may be formed over an electrode electrically connected to the TFT. In this way, an active matrix light-emitting device in which the TFT controls the drive of the light-emitting element can be manufactured. It is to be noted that there is no particular limitation on the structure of the TFT. Either a staggered TFT or an inverted staggered TFT may be employed. In addition, crystallinity of a semiconductor used for the TFT is not particularly limited either; an amorphous semiconductor or a crystalline semiconductor may be used. In addition, a driver circuit formed over a TFT substrate may be constructed from both n-channel and p-channel TFTs or from one of n-channel and p-channel TFTs.

Embodiment 5

In this embodiment, a light-emitting element having a structure different from that described in Embodiment 4 is described.

Described is a structure in which light is emitted from an emission center substance having a light-emitting property by forming the light-emitting layer 113 described in Embodiment 4 in such a manner that the emission center substance is dispersed into any one of the carbazole compounds described in Embodiment 1, i.e., a structure in which any one of the carbazole compounds described in Embodiment 1 is used as a host material of the light-emitting layer 113.

The carbazole compounds described in Embodiment 1 each have a wide band gap (S1 level) or a high T1 level (energy difference between a ground state and a triplet excited state), and thus can make another emission center substance excite and emit light effectively; therefore, the carbazole compounds described in Embodiment 1 can be suitably used as the host material and light emission that originates from the emission center substance can be obtained. Thus, a light-emitting element having high emission efficiency with small energy loss can be provided. In addition, a light-emitting element that can easily provide light emission of a desired color that originates from the emission center substance can be provided. Accordingly, a light-emitting element capable of easily emitting light with high color purity can be provided. Further, the carbazole compounds described in Embodiment 1 also have an excellent carrier-transport property; therefore, a light-emitting element driven with low driving voltage can also be provided.

Here, there is no particular limitation on the emission center substance dispersed into any one of the carbazole compounds described in Embodiment 1, which is used as a host material, and any of various materials can be used. Specifically, it is possible to use 4-(dicyanomethylene)-2-methyl-6-(p-dimethylaminostyryl)-4H-pyran (abbreviated as DCM1), 4-(dicyanomethylene)-2-methyl-6-(julolidin-4-yl-vinyl)-4H-pyran (abbreviated as DCM2), N,N-dimethylquinacridone (abbreviated as DMQd), 9,10-diphenylanthracene (abbreviated as DPA), 5,12-diphenyltetracene (abbreviated as DPT), coumarin 6, perylene, rubrene, N,N'-bis[4-(9-phenyl-9H-fluoren-9-yl)phenyl]-N,N'-diphenylpyrene-1,6-diamine (abbreviated as 1,6FLPAPm), or another known fluorescent substance that emits fluorescence. Alternatively, it is possible to use bis(2-phenylbenzothiazolato-N,$C^{2'}$)iridium(III)acetylacetonate (abbreviated as Ir(bt)$_2$(acac)), tris(2-phenylquinolinato-N,$C^{2'}$)iridium(III) (abbreviated as Ir(pq)$_3$), bis(2-phenylquinolinato-N,$C^{2'}$)iridium(III)(acetylacetonate) (abbreviated as Ir(pq)$_2$(acac)), bis[2-(2'-benzo[4,5-α]thienyl)pyridinato-N, $C^{3'}$]iridium(III)acetylacetonate (abbreviated as Ir(btp)$_2$(acac)), bis(1-phenylisoquinolinato-N,$C^{2'}$)iridium(III)acetylacetonate (abbreviated as Ir(piq)$_2$(acac)), (acetylacetonato)bis[2,3-bis(4-fluorophenyl)quinoxalinato] iridium(III) (abbreviated as Ir(Fdpq)$_2$(acac)), tris(2-phenylpyridinato-N,$C^{2'}$)iridium(III) (abbreviated as Ir(ppy)$_3$), or 2,3,7,8,12,13,17,18-octaethyl-21H,23H-porphine platinum (II) (abbreviated as PtOEP), or another known phosphorescent substance that emits phosphorescence. Among the above-described substances, the substances described as emission center substances in Embodiment 4, or known substances, a substance that has a narrower band gap or a lower T1 level than any one of the carbazole compounds described in Embodiment 1, which is used as the host material, is selected as the emission center substance.

Further, another organic compound may be dispersed at the same time in the light-emitting layer, together with any one of the carbazole compounds described in Embodiment 1 and the emission center substance dispersed into the carbazole compound. In this case, a substance that improves carrier balance of the light-emitting layer is preferably used, such as the above-described substances having a high electron-transport property.

In addition, to the layers other than the light-emitting layer 113, the structure described in Embodiment 4 can be applied as appropriate. Further, the hole-transport layer 112 can be formed using any of the materials given as the substances having a high hole-transport property which can be used in the composite material in Embodiment 4. Besides, the hole-transport layer 112 can be formed using a substance having a high hole-transport property such as the following aromatic amine compounds: 4,4'-bis[N-(1-naphthyl)-N-phenylamino] biphenyl (abbreviated as NPB), N,N'-bis(3-methylphenyl)-N,N'-diphenyl-[1,1'-biphenyl]-4,4'-diamine (abbreviated as TPD), 4,4',4"-tris(N,N-diphenylamino)triphenylamine (abbreviated as TDATA), 4,4',4"-tris[N-(3-methylphenyl)-N-phenylamino]triphenylamine (abbreviated as MTDATA), or 4,4'-bis[N-(spiro-9,9'-bifluoren-2-yl)-N-phenylamino]biphenyl (abbreviated as BSPB); or the like. Needless to say, the carbazole compounds described in Embodiment 1 can also be used. The substances mentioned here mainly have a hole mobility of $10^{-6}$ cm$^2$/Vs or higher. However, another substance whose hole-transport property is higher than the electron-transport property may also be used. Note that the layer containing a substance having a high hole-transport property is not limited to a single layer, and two or more layers containing the above-described substances may be stacked.

Alternatively, a high molecular compound such as poly(N-vinylcarbazole) (abbreviated as PVK) or poly(4-vinyltriphenylamine) (abbreviated as PVTPA) can be used for the hole-transport layer 112.

Embodiment 6

In this embodiment, an embodiment of a light-emitting element with a structure in which a plurality of light-emitting units are stacked (hereinafter this type of light-emitting element is also referred to as a stacked element) is described with reference to FIG. 1B. This light-emitting element includes a plurality of light-emitting units between a first electrode and a second electrode. Each light-emitting unit can have a structure similar to that of the layer 103 containing an organic compound described in Embodiment 4 or 5. That is, the light-emitting element described in Embodiment 4 or 5 includes a single light-emitting unit; the light-emitting element in this embodiment includes a plurality of light-emitting units.

Figure 1B:
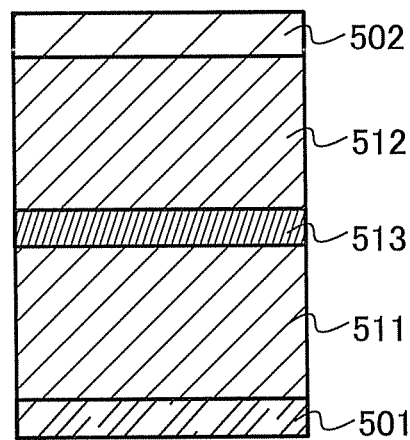

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 correspond to the first electrode 102 and the second electrode 104 in Embodiment 4, respectively, and electrodes similar to those described in Embodiment 4 can be applied to the first electrode 501 and the second electrode 502. Further, the first light-emitting unit 511 and the second light-emitting unit 512 may have the same structure or different structures.

The charge generation layer 513 contains a composite material of an organic compound and a metal oxide. This composite material of an organic compound and a metal oxide is one described in Embodiment 4 and contains an organic compound and a metal oxide such as vanadium oxide, molybdenum oxide, or tungsten oxide. As the organic compound, any of various compounds such as an aromatic amine compound, a carbazole compound, aromatic hydrocarbon, and a high molecular compound (e.g., oligomer, dendrimer, or polymer) can be used. As the organic compound, an organic compound having a hole-transport property and a hole mobility of $10^{-6}$ cm$^2$/Vs or higher is preferably used. However, another substance whose hole-transport property is higher than the electron-transport property may also be used. The composite of an organic compound and a metal oxide has excellent carrier-injection property and carrier-transport property, and hence, low-voltage driving and low-current driving can be achieved.

The charge generation layer 513 may be formed by combining a layer containing the composite material of an organic compound and a metal oxide with a layer containing another material. For example, the layer containing the composite material of an organic compound and a metal oxide may be combined with a layer containing a compound of a substance selected from substances having an electron-donating property and a compound having a high electron-transport property. Moreover, the layer containing the composite material of an organic compound and a metal oxide may be combined with a transparent conductive film.

The charge generation layer 513 interposed between the first light-emitting unit 511 and the second light-emitting unit 512 may have any structure as long as electrons can be injected to a light-emitting unit on one side and holes can be injected to a light-emitting unit on the other side when a voltage is applied between the first electrode 501 and the second electrode 502. For example, in FIG. 1B, any layer can be employed as the charge generation layer 513 as long as the layer injects electrons into the first light-emitting unit 511 and holes into the second light-emitting unit 512 when a voltage is applied such that the potential of the first electrode is higher than that of the second electrode.

Although the light-emitting element having two light-emitting units is described in this embodiment, the present invention can be similarly applied to a light-emitting element in which three or more light-emitting units are stacked. A plurality of light-emitting units which are partitioned by the charge generation layer are arranged between a pair of electrodes, as in the light-emitting element of this embodiment, whereby emission of light in a high luminance region can be realized while current density is kept low. Thus, since the current density can be low, a long lifetime element can be realized. When the light-emitting element is applied for a lighting device, voltage drop due to resistance of an electrode material can be reduced, thereby achieving homogeneous light emission in a large area. Moreover, the light-emitting device can be driven with low driving voltage and consume less power.

By making emission colors of the light-emitting units different from each other, light with a desired color can be obtained from the whole light-emitting element. For example, in a light-emitting element including two light-emitting units, the emission colors of the first light-emitting unit and the second light-emitting unit are made complementary, so that the light-emitting element which emits white light as the whole element can be obtained. Note that the word "complementary" means color relationship in which an achromatic color is obtained when colors are mixed. In other words, when light emitted from a light-emitting element and another light emitted from another light-emitting element, which are complementary to each other, are mixed, white light emission can be obtained. The same can be applied to a light-emitting element including three light-emitting units. For example, when the first light-emitting unit emits red light, the second light-emitting unit emits green light, and the third light-emitting unit emits blue light, white light can be emitted from the whole light-emitting element.

Since the light-emitting element of this embodiment contains any one of the carbazole compounds described in Embodiment 1, the light-emitting element can exhibit high emission efficiency. In addition, the light-emitting element can be driven with low driving voltage. Further, the light-emitting element can have a long lifetime. In addition, the light-emitting unit containing the carbazole compound can provide light that originates from the emission center substance with high color purity; therefore, it is easy to adjust the color of light emitted from the whole light-emitting element.

Note that this embodiment can be combined with any of the other embodiments as appropriate.

Embodiment 7

In this embodiment, a light-emitting device including a light-emitting element containing any one of the carbazole compounds described in Embodiment 1 is described.

In this embodiment, the light-emitting device including a light-emitting element containing any one of the carbazole compounds described in Embodiment 1 is described with reference to FIGS. 3A and 3B. Note that FIG. 3A is a top view of the light-emitting device and FIG. 3B is a cross-sectional view of FIG. 3A taken along the lines A-A' and B-B'. The light-emitting device includes a driver circuit portion (source-side driver circuit) 601, a pixel portion 602, and a driver circuit portion (gate-side driver circuit) 603, which are illustrated with dotted lines, for controlling light emission of the light-emitting element. Moreover, a reference numeral 604 denotes a sealing substrate; 605, a sealing material; and 607, a space surrounded by the sealing material 605.

Reference numeral 608 denotes a wiring for transmitting signals to be inputted into the source-side driver circuit 601 and the gate-side driver circuit 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, the cross-sectional structure is described with reference to FIG. 3B. Although the driving circuit portion and the pixel portion are formed over an element substrate 610, the source-side driver circuit 601 as a part of the driving circuit portion and one of the pixels in the pixel portion 602 are illustrated here.

In the source-side driver circuit 601, a CMOS circuit is formed in which an n-channel TFT 623 and a p-channel TFT 624 are combined. Such a driver circuit may be formed with various circuits such as a CMOS circuit, a PMOS circuit, or an NMOS circuit. Although this embodiment shows a driver-integrated type where the driver circuit is formed over the substrate, the present invention is not limited to this, and the driver circuit may be formed outside the substrate, not over the substrate.

The pixel portion 602 is formed with a plurality of pixels including a switching TFT 611, a current controlling TFT 612, and a first electrode 613 electrically connected to a drain of the current controlling TFT. An insulator 614 is formed so as to cover the end portions of the first electrode 613. Here, the insulator 614 is formed using a positive type photosensitive acrylic resin film.

In order to improve the coverage, the insulator 614 is formed to have a curved surface with curvature at its upper or lower end portion. For example, in the case of using positive photosensitive acrylic for the insulator 614, only the upper end portion of the insulator 614 preferably has a curved surface with a radius of curvature (0.2 μm to 3 μm). As the insulator 614, either a negative type which becomes insoluble in etchant by irradiation with light or a positive type which becomes soluble in etchant by irradiation with light can be used.

A layer 616 containing an organic compound and a second electrode 617 are formed over the first electrode 613. As a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like can be used. Alternatively, a stack of a titanium nitride film and a film containing aluminum as its main component, a stack of three layers of a titanium nitride film, a film containing aluminum as its main component, and a titanium nitride film, or the like can be used. Note that when a stacked structure is employed, the first electrode 613 has low resistance as a wiring, forms a favorable ohmic contact, and can function as an anode.

In addition, the layer 616 containing an organic compound is formed by any of a variety of methods such as an evaporation method using an evaporation mask, an inkjet method, and a spin coating method. The layer 616 containing an organic compound contains any one of the carbazole compounds described in Embodiment 1. Further, the layer 616 containing an organic compound may be formed using another material such as a low molecular compound or a high molecular compound (including oligomer and dendrimer).

As a material used for the second electrode 617, which is formed over the layer 616 containing an organic compound and functions as a cathode, a material having a low work function (e.g., Al, Mg, Li, Ca, or an alloy or compound thereof, such as MgAg, MgIn, or AM) is preferably used. In the case where light generated in the layer 616 containing an organic compound passes through the second electrode 617, the second electrode 617 is preferably formed using a stack of a thin metal film and a transparent conductive film (ITO, indium oxide containing zinc oxide at 2 wt % to 20 wt %, indium tin oxide containing silicon, zinc oxide (ZnO), or the like).

Note that the light-emitting element includes the first electrode 613, the layer 616 containing an organic compound, and the second electrode 617. The light-emitting element has any of the structures described in Embodiments 4 to 6. The pixel portion includes a plurality of light-emitting elements, and the light-emitting device of this embodiment may include both the light-emitting element with any of the structures described in Embodiments 4 to 6 and the light-emitting element with a structure other than those.

Further, a light-emitting element 618 is provided in the space 607 surrounded by the element substrate 610, the sealing substrate 604, and the sealing material 605, by adhering the sealing substrate 604 and the element substrate 610 to each other using the sealing material 605. The space 607 may be filled with filler, and may be filled with an inert gas (such as nitrogen or argon), the sealing material 605, or the like.

An epoxy based resin is preferably used for the sealing material 605. It is desirable that such a material do not transmit moisture or oxygen as much as possible. As a material for the sealing substrate 604, a plastic substrate formed of FRP (fiberglass-reinforced plastics), PVF (polyvinyl fluoride), polyester, acrylic, or the like can be used besides a glass substrate or a quartz substrate.

In this manner, the light-emitting device manufactured using the light-emitting element containing any one of the carbazole compounds described in Embodiment 1 can be obtained.

Since the light-emitting device in this embodiment uses the light-emitting element containing any one of the carbazole compounds described in Embodiment 1, the light-emitting device can have favorable characteristics. Specifically, since the carbazole compounds described in Embodiment 1 each have a wide band gap and/or a high T1 level and can suppress energy transfer from a light-emitting substance, a light-emitting element having high emission efficiency can be provided; thus, a light-emitting device having less power consumption can be provided. In addition, since a light-emitting element driven with low driving voltage can be provided, a light-emitting device driven with low driving voltage can be provided. Further, since the light-emitting element using any one of the carbazole compounds described in Embodiment 1 has a long lifetime, a light-emitting device having high reliability can be provided.

Figure 4A:
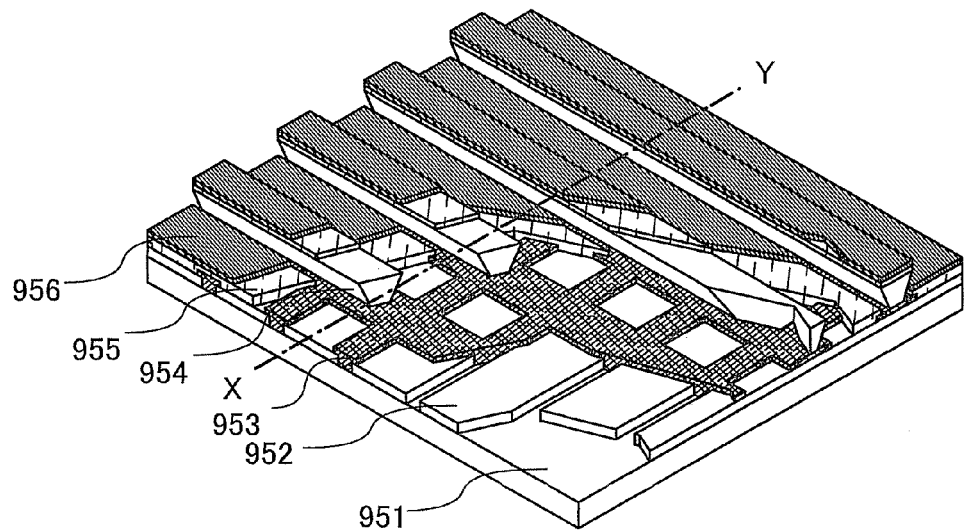
FIGS. 4A and 4B are conceptual diagrams of a passive matrix light-emitting device.
Figure 4B:
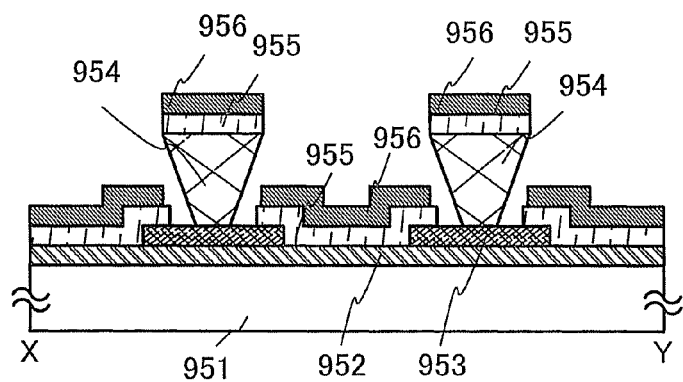

Although an active matrix light-emitting device is described in this embodiment as described above, a passive matrix light-emitting device may be alternatively manufactured. FIGS. 4A and 4B illustrate a passive matrix light-emitting device manufactured according to the present invention. FIG. 4A is a perspective view of the light-emitting device, and FIG. 4B is a cross-sectional view taken along line X-Y in FIG. 4A. In FIGS. 4A and 4B, an electrode 952 and an electrode 956 are provided over a substrate 951, and a layer 955 containing an organic compound is provided between the electrodes 952 and 956. An end portion of the electrode 952 is covered with an insulating layer 953. A partition wall layer 954 is provided over the insulating layer 953. The sidewalls of the partition wall layer 954 are aslope such that the distance between both sidewalls is gradually narrowed toward the surface of the substrate. That is, a cross section taken along the direction of the short side of the partition wall layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). By providing the partition wall layer 954 in this manner, defects of the light-emitting element due to static charge and the like can be prevented. The passive matrix light-emitting device can also be driven with low power consumption by including the light-emitting element according to any of Embodiments 4 to 6 which contains any one of the carbazole compounds described in Embodiment 1 and is operated with low driving voltage. In addition, the light-emitting device can be driven with low power consumption by including the light-emitting element according to any of Embodiments 4 to 6 which contains any one of the carbazole compounds described in Embodiment 1 and accordingly has high emission efficiency. Further, the light-emitting device can have high reliability by including the light-emitting element according to any of Embodiments 4 to 6 which contains any one of the carbazole compounds described in Embodiment 1.

Embodiment 8

In this embodiment, electronic devices of the present invention which include, as parts thereof, the light-emitting device described in Embodiment 7 are described. Since the light-emitting device described in Embodiment 7 includes a light-emitting element containing any one of the carbazole compounds described in Embodiment 1, the light-emitting element consumes less power, and thus electronic devices in this embodiment can have display portions with lower power consumption. In addition, the driving voltage of such electronic devices can be lowered. Further, such electronic devices can have high reliability.

Examples of the electronic devices to which the light-emitting device is applied include television sets (also referred to as televisions or television receivers), monitors of computers or the like, cameras such as digital cameras or digital video cameras, digital photo frames, mobile phones (also referred to as cellular phones or mobile phone sets), portable (or handheld) game consoles, portable information terminals, audio reproducing devices, large-sized game machines such as pachinko machines, and the like. Specific examples of these electronic devices are described below.

Figure 5A:
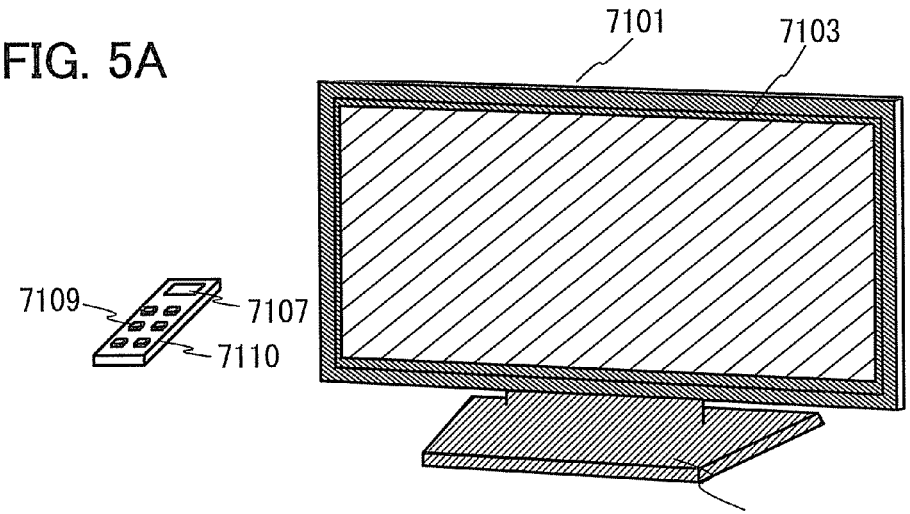
FIGS. 5A to 5D each illustrate an electronic device.

FIG. 5A illustrates an example of a television device. In the television device, a display portion 7103 is incorporated in a housing 7101. In addition, here, the housing 7101 is supported by a stand 7105. The display portion 7103 can display an image, and in the display portion 7103, light-emitting elements similar to any of those described in Embodiments 4 to 6 are disposed in matrix. Since each of light-emitting elements includes any one of the carbazole compounds described in Embodiment 1, it has good emission efficiency. In addition, the light-emitting element can be driven with low driving voltage. Further, the light-emitting element has high reliability. Therefore, this television device having the display portion 7103 which includes the light-emitting elements consumes less power. In addition, the television device can be driven with low driving voltage. Further, the television device has high reliability.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the display device is connected to a communication network with or without wires via the modem, one-way (from a sender to a receiver) or two-way (between a sender and a receiver or between receivers) information communication can be performed.

Figure 5B:
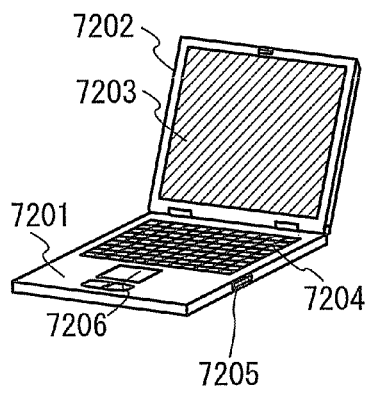

FIG. 5B illustrates a computer having a main body 7201, a housing 7202, a display portion 7203, a keyboard 7204, an external connecting port 7205, a pointing device 7206, and the like. The computer is configured such that in the display portion 7203, light-emitting elements similar to any of those described in Embodiments 4 to 6 are disposed in matrix. Since each of light-emitting elements includes any one of the carbazole compounds described in Embodiment 1, it has good emission efficiency. In addition, the light-emitting element can be driven with low driving voltage. Further, the light-emitting element has high reliability. Therefore, this computer having the display portion 7203 which includes the light-emitting elements consumes less power. In addition, the computer device can be driven with low driving voltage. Further, the computer has high reliability.

Figure 5C:
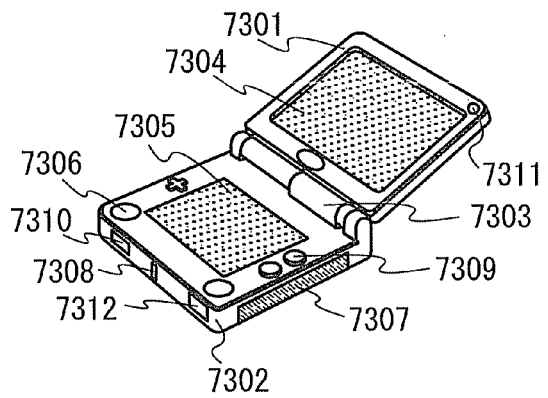

FIG. 5C illustrates a handheld game console having housings 7301 and 7302, which are connected with a joint portion 7303 so that the handheld game console can be opened or folded. The housing 7301 includes the display portion 7304 in which light-emitting elements similar to any of those described in Embodiments 4 to 6 are disposed in matrix, and the housing 7302 includes the display portion 7305. In addition, the handheld game console illustrated in FIG. 5C further includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. Needless to say, the structure of the handheld game console is not limited to the above structure as long as, for at least either the display portion 7304 or the display portion 7305, or both of them, a display portion in which light-emitting elements similar to any of those described in Embodiments 4 to 6 are disposed in matrix may be used. The handheld game console may include other accessory equipment as appropriate. The handheld game console illustrated in FIG. 5C has a function of reading out a program or data stored in a storage medium to display it on the display portion, and a function of sharing information with another handheld game console by wireless communication. The handheld game console illustrated in FIG. 5C can have a variety of functions without limitation to the above. The handheld game console having the display portion 7304 can consume less power, since the light-emitting elements used in the display portion 7304 each include any one of the carbazole compounds described in Embodiment 1 and have good emission efficiency. In addition, since the light-emitting elements used in the display portion 7304 each include any one of the carbazole compounds described in Embodiment 1 and thus can be driven with low driving voltage, the handheld game console can also be driven with low driving voltage. Further, since the light-emitting elements used in the display portion 7304 each include any one of the carbazole compounds described in Embodiment 1 and thus have high reliability, the handheld game console also has high reliability.

Figure 5D:
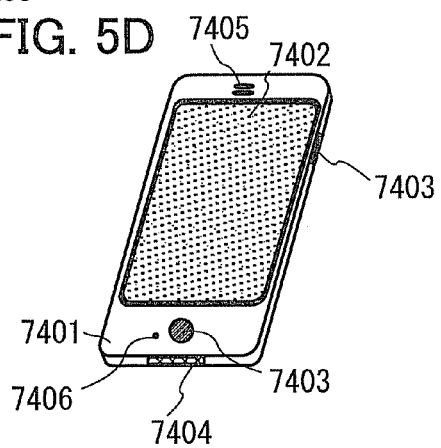

FIG. 5D illustrates an example of a mobile phone. The mobile phone is provided with a display portion 7402 incorporated in a housing 7401, operation buttons 7403, an external connection port 7404, a speaker 7405, a microphone 7406, and the like. The mobile phone 7400 includes the display portion 7402 in which light-emitting elements similar to any of those described in Embodiments 4 to 6 are disposed in matrix. Since each of light-emitting elements includes any one of the carbazole compound described in Embodiment 1, it has good emission efficiency. In addition, the light-emitting element can be driven with low driving voltage. Further, the light-emitting element has high reliability. Therefore, this mobile phone having the display portion 7402 which includes the light-emitting elements consumes less power. In addition, the mobile phone can be driven with low driving voltage. Further, the mobile phone has high reliability.

When the display portion 7402 of the mobile phone illustrated in FIG. 5D is touched with a finger or the like, data can be input into the mobile phone. In this case, operations such as calling or texting can be performed by touch on the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of calling or texting, a text input mode mainly for inputting text is selected for the display portion 7402 so that text displayed on a screen can be inputted. In that case, it is preferable to display a keyboard or number buttons on almost area of the screen of the display portion 7402.

When a detection device which includes a sensor for detecting inclination, such as a gyroscope or an acceleration sensor, is provided inside the mobile phone, the direction of the mobile phone (whether the mobile phone is placed horizontally or vertically) is determined so that display on the screen of the display portion 7402 can be automatically switched.

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a backlight or a sensing light source which emits a near-infrared light in the display portion, an image of a finger vein, a palm vein, or the like can be taken.

Note that the structure described in this embodiment can be combined with any of the structures described in Embodiments 1 to 3 as appropriate.

As described above, the light-emitting device including a light-emitting element containing any one of the carbazole compounds described in Embodiment 1, which has been described in any of Embodiments 4 to 6, can have a wider range of application fields, and thus the light-emitting device can be applied to a variety of fields of electronic devices. Electronic devices which consume less power can be provided by using any one of the carbazole compounds described in Embodiment 1. Further, electronic devices driven with low driving voltage can be provided. Furthermore, electronic devices with high reliability can be provided.

The light-emitting device described in Embodiment 7 can also be used as a lighting device. One embodiment in which the light-emitting device described in Embodiment 7 is used as a lighting device is described with reference to FIG. 6.

Figure 6:
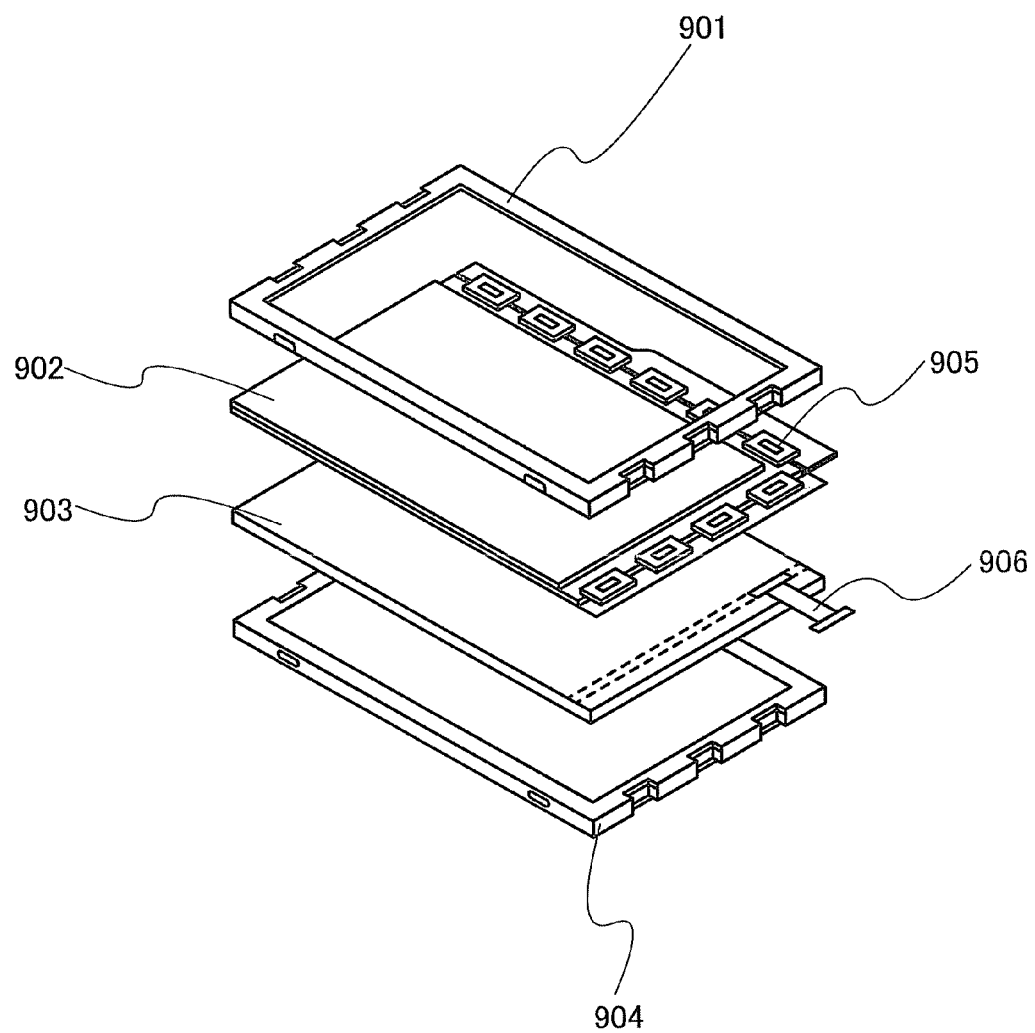
FIG. 6 illustrates an electronic device.

FIG. 6 illustrates an example of a liquid crystal display device using the light-emitting device described in Embodiment 7 as a backlight. The liquid crystal display device illustrated in FIG. 6 includes a housing 901, a liquid crystal layer 902, a backlight 903, and a housing 904. The liquid crystal layer 902 is connected to a driver IC 905. The light-emitting device of Embodiment 7 is used as the backlight 903, to which current is supplied through a terminal 906.

With the use of the light-emitting device described in Embodiment 7 as the backlight of the liquid crystal display device, the backlight consumes less power. Further, the light-emitting device described in Embodiment 7 is a lighting device with plane light emission and can have a large area. Therefore, the backlight can have a large area, and a liquid crystal display device having a large area can be obtained. Furthermore, since the light-emitting device described in Embodiment 7 is thin, it is also possible to reduce the thickness of a display device.

Figure 7:
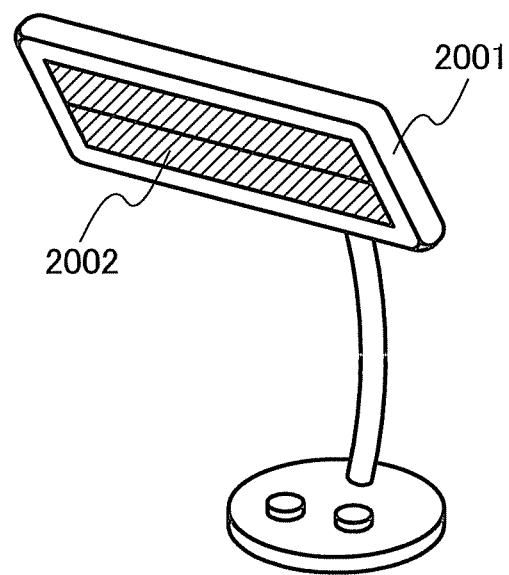
FIG. 7 illustrates a lighting device.

FIG. 7 illustrates an example in which the light-emitting device described in Embodiment 7 is used as a table lamp which is a lighting device. The table lamp illustrated in FIG. 7 includes a housing 2001 and a light source 2002, and the light-emitting device described in Embodiment 7 is used as the light source 2002.

FIG. 8 illustrates an example in which the light-emitting device described in Embodiment 7 is used as an indoor lighting device 3001. Since the light-emitting device described in Embodiment 7 consumes less power, a lighting device that consumes less power can be obtained. Further, since the light-emitting device described in Embodiment 7 can have a large area, the light-emitting device can be used as a large-area lighting device. Further, since the light-emitting device described in Embodiment 7 is thin, the light-emitting device can be used for a lighting device having reduced thickness.

Figure 48:
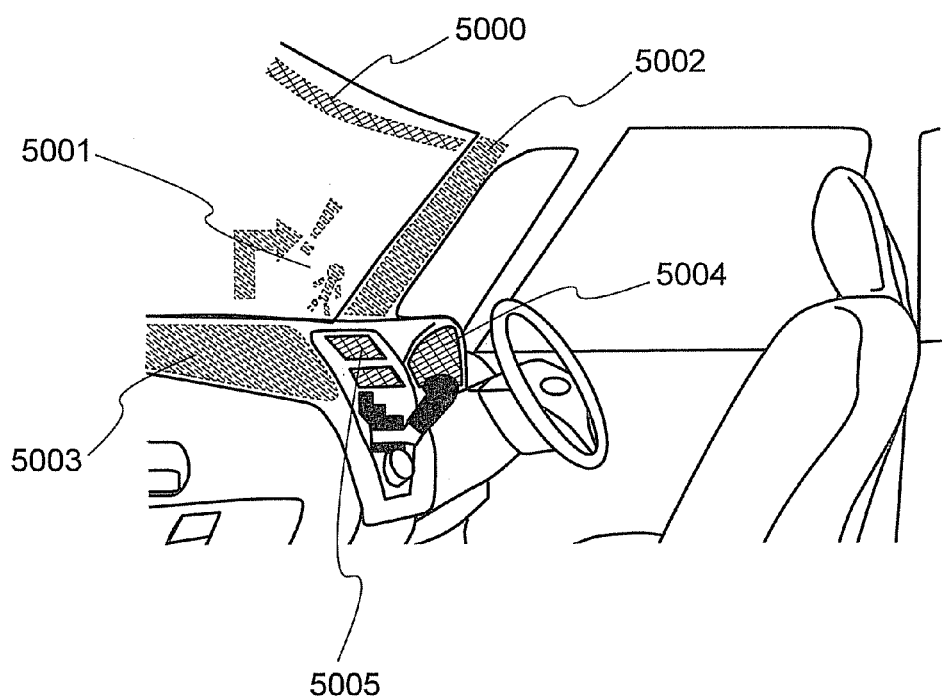
FIG. 48 is a diagram illustrating car-mounted display devices and lighting devices.

The light-emitting element described in Embodiment 7 can be used for a windshield or a dashboard on a car. FIG. 48 illustrates one embodiment in which the light-emitting device described in Embodiment 7 is used for a windshield or a dashboard on a car. Displays 5000 to 5005 each include the light-emitting device described in Embodiment 7.

The display 5000 and the display 5001 are light-emitting devices provided in the windshield on the car, which are described in Embodiment 7. The light-emitting devices described in Embodiment 7 can be so-called see-through display devices, through which the opposite side can be seen, because a first electrode and a second electrode are formed using light-transmitting materials. Such see-through display devices can be provided even in the windshield on the car, without hindering the vision. In addition, for example, when a transistor for driving the light-emitting element is provided, a transistor having a light-transmitting property, such as an organic transistor using an organic semiconductor material or a transistor using an oxide semiconductor, is preferably used.

The display 5002 is a display device provided in a pillar portion. The display 5002 can compensate for the view hindered by the pillar portion by showing an image taken by an imaging unit provided in the car body. Similarly, the display 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see, makes it possible for the driver to confirm safety easily and comfortably.

The display 5004 and the display 5005 can provide a variety of kinds of information such as information of navigation, speedometer, tachometer, mileage (travel distance), fuel meter, gearshift indicator, and air condition. The content or layout of the display can be changed freely by a user as appropriate. Further, such information can be shown in the displays 5000 to 5003. Note that the displays 5000 to 5005 can be used as lighting devices by light emission on the entire areas of the displays 5000 to 5005.

Since the light-emitting device described in Embodiment 7 includes any one of the carbazole compounds described in Embodiment 1, it can be driven with low driving voltage or reduce power consumption. When a number of large screens are provided, load to a battery can be reduced, which provides comfortable driving.

Example 1

Synthesis Example 1

In this example is described a method of synthesizing 3,6-di-(dibenzothiophen-4-yl)-9-phenyl-9H-carbazole (abbreviated as DBT2PC-II), which is one of the carbazole compounds described in Embodiment 1. A structure of DBT2PC-II is shown in the following structural formula (150).

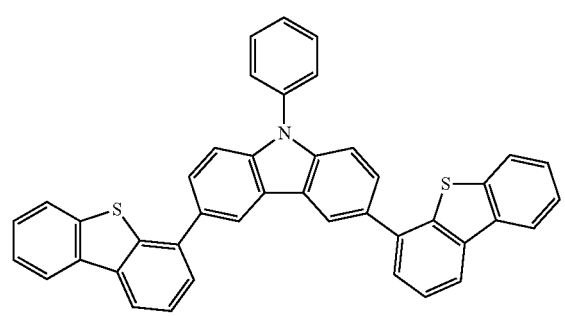

(150)

Step 1: Synthesis of 3,6-di-(dibenzothiophen-4-yl)-9-phenyl-9H-carbazole (abbreviated as DBT2PC-II)

To a 200-mL three-neck flask were added 2.0 g (5.0 mmol) of 3,6-dibromo-9-phenyl-9H-carbazole, 3.2 g (11 mmol) of dibenzothiophene-4-boronic acid, 10 mg (0.1 mmol) of palladium(II) acetate, 30 mg (0.1 mmol) of tri(ortho-tolyl)phosphine, 50 mL of toluene, 5 mL of ethanol, and 7.5 mL of a 2 mol/L aqueous potassium carbonate solution. This mixture was degassed while being stirred under reduced pressure, and then heated and stirred at 90° C. for 6 hours in a nitrogen atmosphere to be reacted. After the reaction, this reaction mixture solution was cooled to room temperature, and then filtered to give a residue while being washed with water, ethanol, toluene, and hexane in this order. The residue was purified by silica gel column chromatography (a developing solvent in which the toluene/hexane ratio was 1:3). The fraction thus obtained was concentrated, acetone and ethanol were added thereto, and the mixture was irradiated with ultrasonic waves. Then, recrystallization gave 1.4 g of a white powder in 47% yield. The synthesis scheme of Step 1 is shown in (A-1).

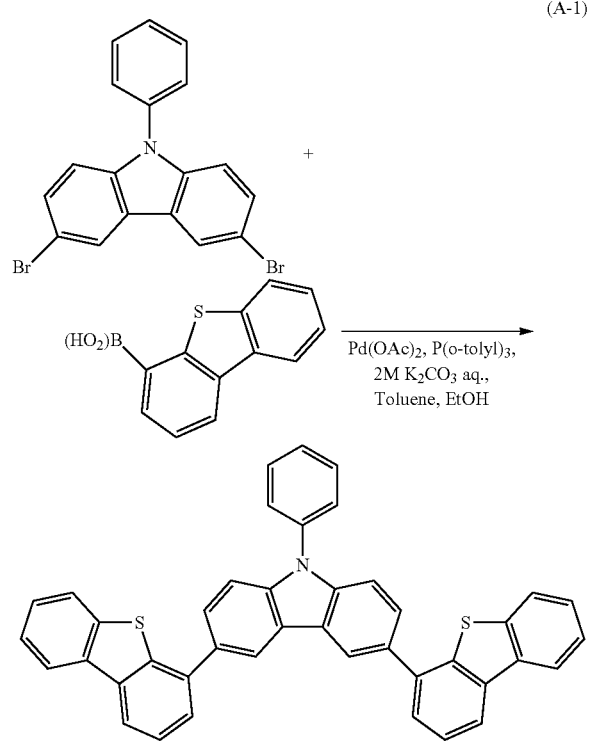

(A-1)

The obtained white powder was subjected to nuclear magnetic resonance (NMR) spectroscopy. The measurement data are shown below.

$^1$H NMR (CDCl$_3$, 300 MHz): δ=7.44-7.70 (m, 15H), 7.82-7.86 (m, 4H), 8.15-8.22 (m, 4H), 8.57 (d, J=1.5 Hz, 2H)

Figure 9A:
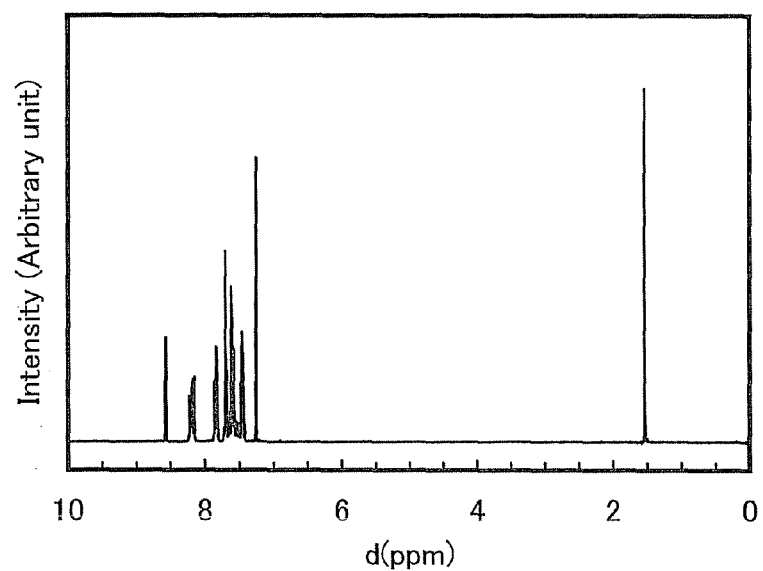
FIGS. 9A and 9B are $^1$H NMR charts of DBT2PC-II.
Figure 9B:
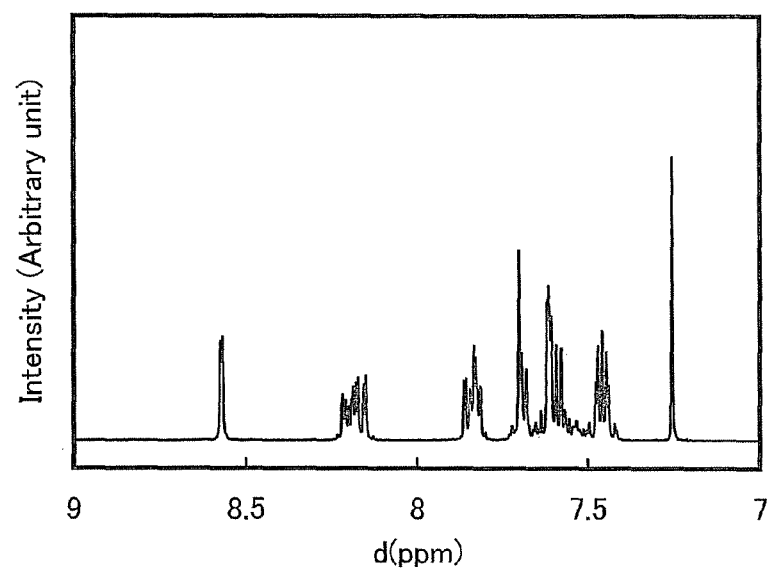

In addition, a $^1$H-NMR chart is shown in FIGS. 9A and 913. Note that FIG. 9B is a chart showing an enlarged part in the range of 7 ppm to 9 ppm of FIG. 9A. The measurement results showed that DBT2PC-II, which is the carbazole compound represented by the structural formula (150), was obtained. Note that the Rf values of DBT2PC-II and 3,6-dibromo-9-phenyl-9H-carbazole were respectively 0.41 and 0.51, which were found by silica gel thin layer chromatography (TLC) (a developing solvent in which the ethyl acetate/hexane ratio was 1:10).

Figure 10A:
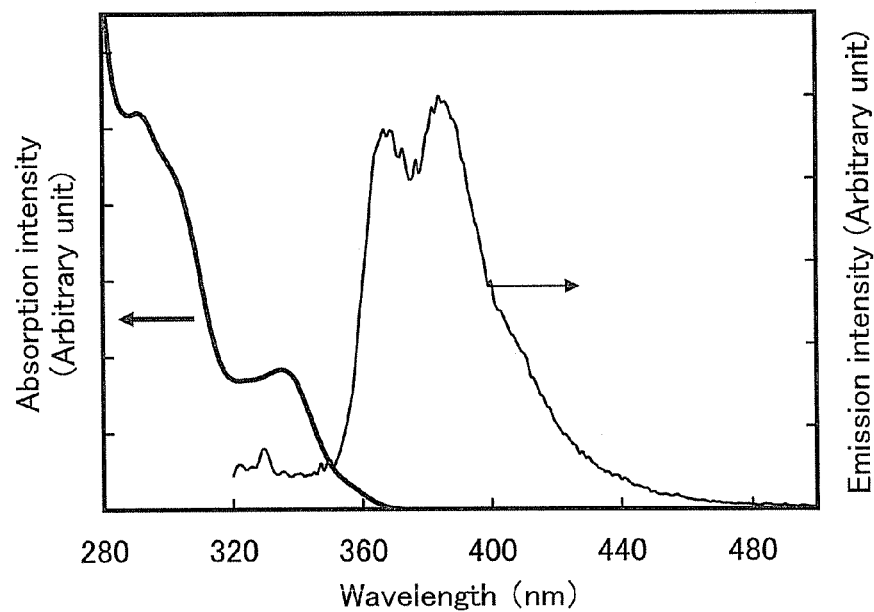
FIGS. 10A and 10B show an absorption spectrum and an emission spectrum of DBT2PC-II.
Figure 10B:
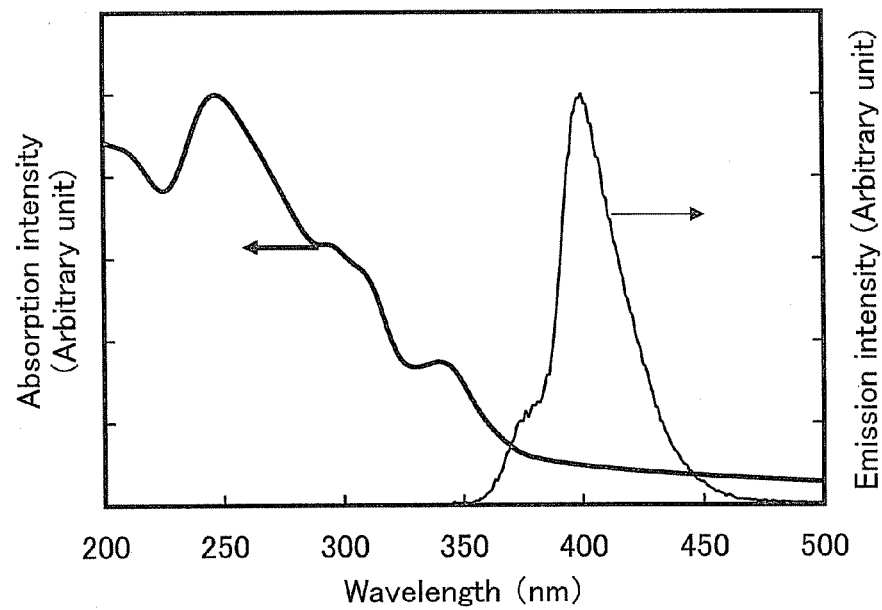

Next, an absorption spectrum and an emission spectrum of DBT2PC-II in a toluene solution of DBT2PC-II are shown in FIG. 10A, and an absorption spectrum and an emission spectrum of a thin film of DBT2PC-II are shown in FIG. 10B. The measurement of the spectra was performed using an ultraviolet-visible spectrophotometer (V-550, manufactured by JASCO Corporation). The spectra of the toluene solution were measured with a toluene solution of DBT2PC-II put in a quartz cell. The spectra of the thin film were measured with a sample prepared by evaporation of DBT2PC-II on a quartz substrate. Note that as the absorption spectrum of the toluene solution, the absorption spectrum obtained by subtraction of the absorption spectra of quartz and toluene from the measured spectra is shown in the graph, and as the absorption spectrum of the thin film, the absorption spectrum obtained by subtraction of that of quartz from the measured spectra is shown in the graph.

FIGS. 10A and 10B show that the maximum absorption wavelength of DBT2PC-II in the toluene solution of DBT2PC-II was around 332 nm, the maximum emission wavelengths thereof were around 368 nm and 385 nm (at an excitation wavelength of 300 nm), the maximum absorption wavelength of the thin film of DBT2PC-II were around 340 nm, and the maximum emission wavelengths thereof were around 380 nm and 400 nm (at an excitation wavelength of 341 nm).

The absorption spectra reveal that DBT2PC-II described in this example is a material that shows almost no absorption in the visible region. Further, the emission spectra reveal that the light emission is bluish purple.

Further, the glass transition temperature (Tg) of DBT2PC-II was examined with a differential scanning calorimeter (DSC). According to the measurement result, it was found that the glass transition temperature and the melting point were 153° C. and 265° C. respectively. In this manner, DBT2PC-II had a high glass transition temperature and favorable heat resistance.

Further, the ionization potential of DBT2PC-II in a thin film state was measured by a photoelectron spectrometer (AC-2, manufactured by Riken Keiki, Co., Ltd.) in air. The obtained value of the ionization potential was converted to a negative value, so that the HOMO level of DBT2PC-II was −5.72 eV. From the data of the absorption spectra of the thin film in FIGS. 10A and 10B, the absorption edge of DBT2PC-II, which was obtained from Tauc plot with an assumption of direct transition, was 3.40 eV. Therefore, the optical band gap of DBT2PC-II in the solid state was estimated at 3.40 eV; from the values of the HOMO level obtained above and this band gap, the LUMO level of DBT2PC-II was estimated at −2.32 eV. It was thus found that DBT2PC-II had a wide band gap of 3.40 eV in the solid state. It is also found that DBT2PC-II had a relatively deep HOMO level.

Further, thermophysical properties of DBT2PC-II were measured with a differential scanning calorimeter (DSC, manufactured by PerkinElmer, Inc., Pyris 1). First, a sample was heated from −10° C. up to 350° C. at a temperature rising rate of 40° C./min, and then it was cooled down to −10° C. at 40° C./min. After that, the sample was heated up to 290° C. at a temperature rising rate of 10° C./min, and thus a DSC chart was obtained. As can be seen from the DSC chart, a peak indicating the glass transition temperature of DBT2PC-II was observed, which showed the glass transition temperature (Tg) was 153° C. Thus, it was found that DBT2PC-II has a high glass transition point. Therefore, it was confirmed that DBT2PC-II of this synthesis example had high heat resistance.

Example 2

Synthesis Example 2

In this example is described a method of synthesizing 2,7-di-(dibenzothiophen-4-yl)-9-phenyl-9H-carbazole (abbreviated as 2,7DBT2PC-II), which is one of the carbazole compounds described in Embodiment 1. A structure of 2,7DBT2PC-II is illustrated in the following structural formula (154).

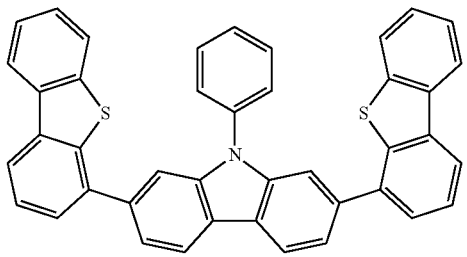
(154)

Step 1: Synthesis of 2,7-di-(dibenzothiophen-4-yl)-9H-carbazole

In a 200-mL three-neck flask were mixed 3.3 g (10 mmol) of 2,7-dibromo-9H-carbazole, 6.0 g (21 mmol) of dibenzofuran-4-boronic acid, 11 mg (0.1 mmol) of palladium(II) acetate, 30 mg (0.1 mmol) of tris(ortho-tolyl)phosphine, 50 mL of toluene, 5 mL of ethanol, and 7.5 mL of a 2 mol/L aqueous potassium carbonate solution. This mixture was degassed while being stirred under reduced pressure, and then heated and stirred at 90° C. for 4.5 hours in a nitrogen atmosphere to be reacted. After the reaction, this reaction mixture solution was cooled to room temperature, and then filtered to give a residue. This residue was heated and stirred in a mixed solution of ethanol/water, and was filtered to give 4.9 g of a white powder in 92% yield. The synthesis scheme of Step 1 is shown in (B-1).

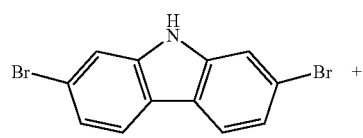
(B-1)

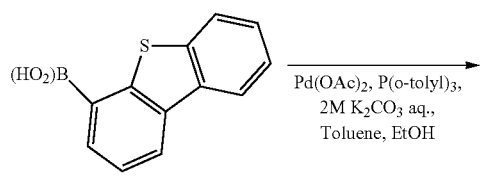

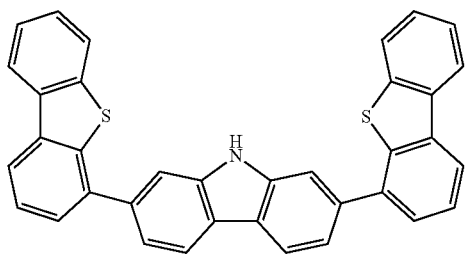

Step 2: Synthesis of 2,7-di-(dibenzothiophen-4-yl)-9-phenyl-9H-carbazole (abbreviated as 2,7DBT2PC-II)

In a 200-mL three-neck flask were mixed 0.7 g (4.3 mmol) of iodobenzene, 1.7 g (3.2 mmol) of 2,7-di-(dibenzothiophen-4-yl)-9H-carbazole, 0.6 g (5.5 mmol) of sodium tert-butoxide, and 36 mg (0.1 mmol) of bis(dibenzylideneacetone)palladium(0), and the air in the flask was replaced with nitrogen. Then, 5 mL of dehydrated xylene was added to this mixture. After the mixture was degassed while being stirred under reduced pressure, 0.7 mL (0.3 mmol) of tri(tert-butyl)phosphine (10 wt % hexane solution) was added to the mixture. This mixture was stirred under a nitrogen atmosphere at 120° C. for 5 hours to be reacted. After the reaction, 300 mL of toluene was added to this reaction mixture solution, and this suspension was filtered through Florisil and Celite. The resulting filtrate was concentrated, followed by purification using silica gel column chromatography (the developing solvent was toluene). The fraction thus obtained was concentrated, acetone and methanol were added thereto, and the mixture was irradiated with ultrasonic waves. Then, recrystallization gave 1.9 g of a white powder in 93% yield. A reaction scheme of the above synthesis method is shown in the following (B-2).

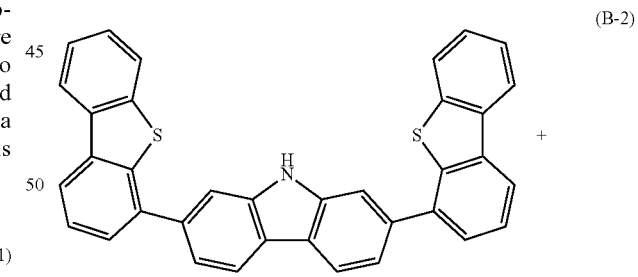
(B-2)

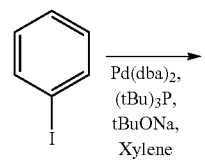

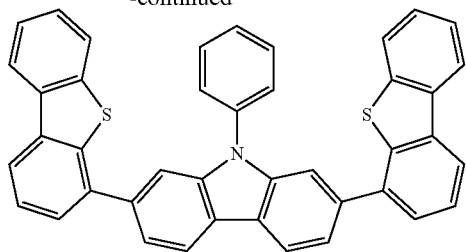

The obtained white powder was subjected to nuclear magnetic resonance (NMR) spectroscopy. The measurement data are shown below.

$^1$H NMR (CDCl$_3$, 300 MHz): δ (ppm)=7.39-7.50 (m, 5H), 7.53-7.62 (m, 6H), 7.70-7.74 (m, 4H), 7.81-7.87 (m, 4H), 8.12-8.21 (m, 4H), 8.32 (d, J=8.1 Hz, 2H)

Figure 11A:
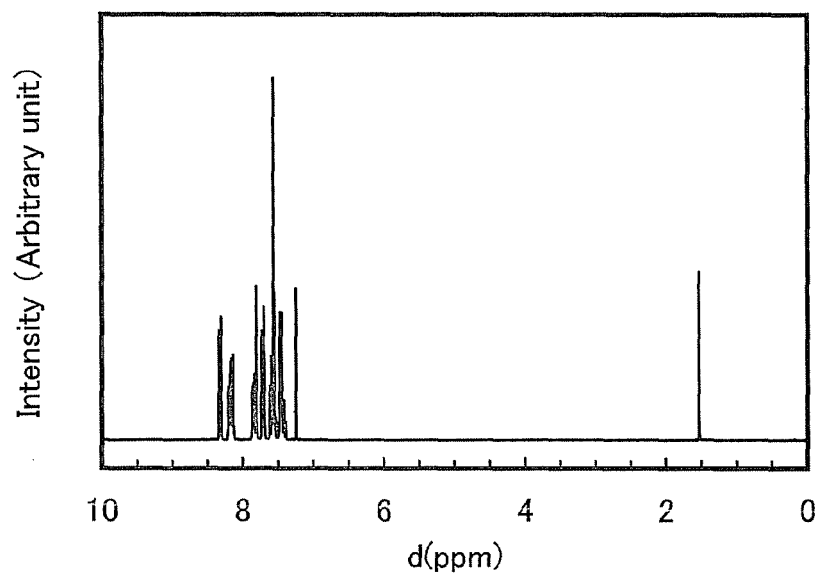
FIGS. 11A and 11B are $^1$H NMR charts of 2,7DBT2PC-II.
Figure 11B:
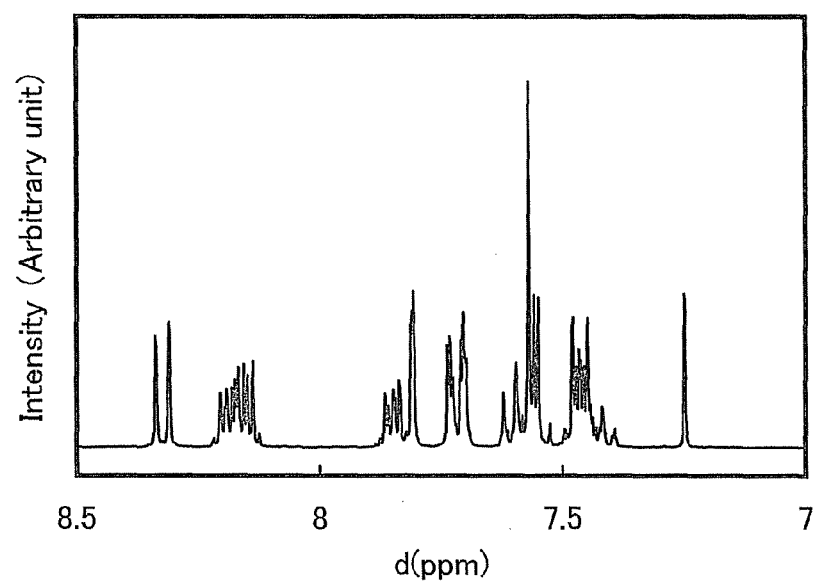

In addition, $^1$H-NMR charts are shown in FIGS. 11A and 11B. The measurement results showed that 2,7DBT2PC-II, which is the carbazole compound represented by the above structural formula (154), was obtained. Note that the Rf values of 2,7DBT2PC-II and 2,7-di-(dibenzothiophen-4-yl)-9H-carbazole were respectively 0.41 and 0.22, which were found by silica gel thin layer chromatography (TLC) (a developing solvent in which the ethyl acetate/hexane ratio was 1:5).

Figure 12A:
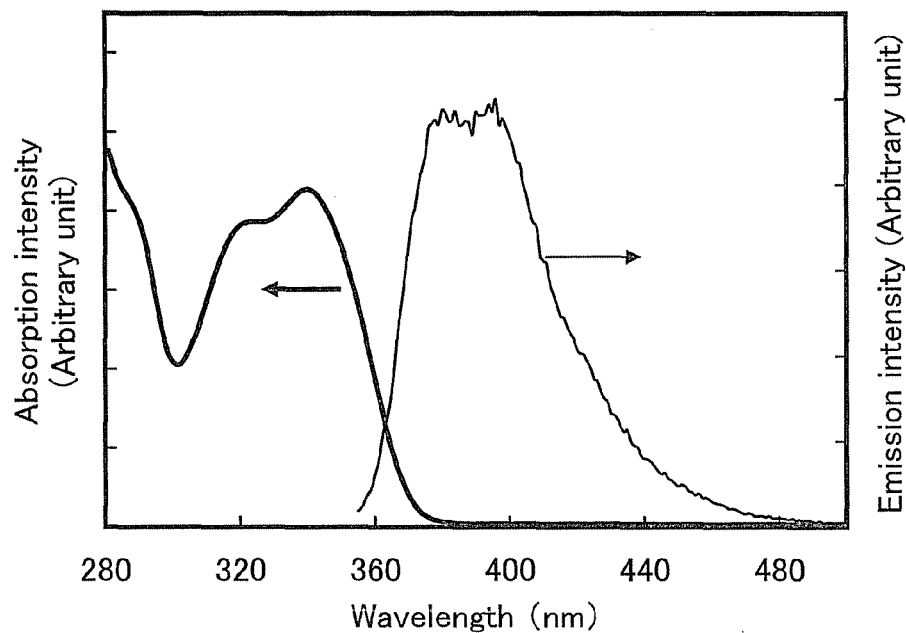
FIGS. 12A and 12B show an absorption spectrum and an emission spectrum of 2,7DBT2PC-II.
Figure 12B:
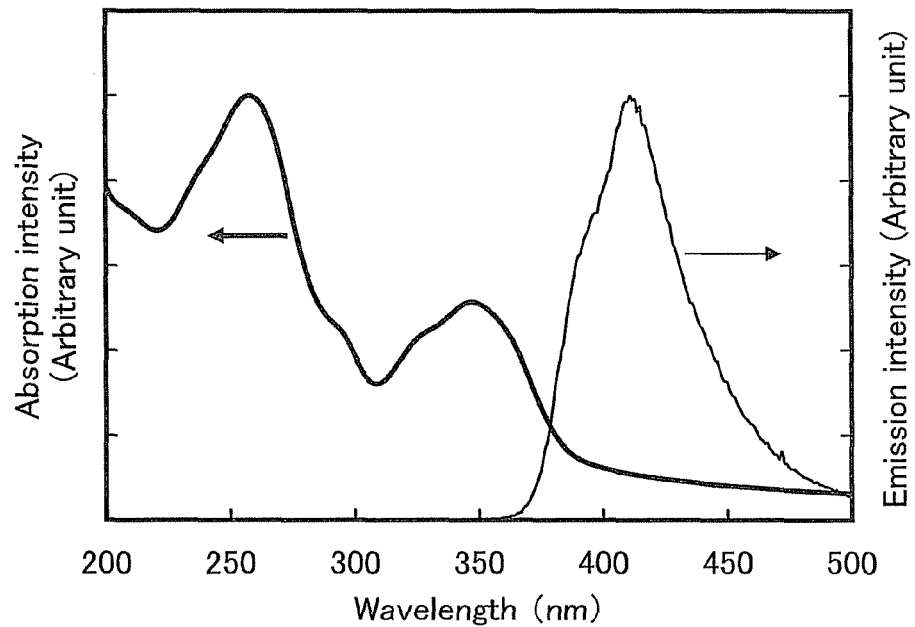

Next, an absorption spectrum and an emission spectrum of 2,7DBT2PC-II in a toluene solution of 2,7DBT2PC-II are shown in FIG. 12A, and an absorption spectrum and an emission spectrum of a thin film of 2,7DBT2PC-II are shown in FIG. 12B. The measurement of the spectra was performed using an ultraviolet-visible spectrophotometer (V-550, manufactured by JASCO Corporation). The spectra of the toluene solution were measured with a toluene solution of 2,7DBT2PC-II put in a quartz cell. The spectra of the thin film were measured with a sample prepared by evaporation of 2,7DBT2PC-II on a quartz substrate. Note that as the absorption spectrum of the toluene solution, the absorption spectrum obtained by subtraction of the absorption spectra of quartz and toluene from the measured spectra is shown in the graph, and as the absorption spectrum of the thin film, the absorption spectrum obtained by subtraction of that of quartz from the measured spectra is shown in the graph.

FIGS. 12A and 12B show that the maximum absorption wavelength of 2,7DBT2PC-II in the toluene solution of 2,7DBT2PC-II was around 339 nm, the maximum emission wavelengths thereof were around 381 nm and 395 nm (at an excitation wavelength of 345 nm), the maximum absorption wavelength of the thin film of 2,7DBT2PC-II was around 347 nm, and the maximum emission wavelengths thereof were around 298 nm and 411 nm (at an excitation wavelength of 347 nm).

The absorption spectra reveal that 2,7DBT2PC-II described in this example is a material that shows almost no absorption in the visible region. Further, the emission spectra reveal that the light emission is bluish purple.

Further, the glass transition temperature (Tg) of 2,7DBT2PC-II was examined with a differential scanning calorimeter (DSC). According to the measurement results, it was found that the glass transition temperature was 146° C. In this manner, 2,7DBT2PC-II had a high glass transition temperature and favorable heat resistance.

Further, the ionization potential of 2,7DBT2PC-II in a thin film state was measured by a photoelectron spectrometer (AC-2, manufactured by Riken Keiki, Co., Ltd.) in air. The obtained value of the ionization potential was converted to a negative value, so that the HOMO level of 2,7DBT2PC-II was −5.79 eV. From the data of the absorption spectra of the thin film in FIGS. 12A and 12B, the absorption edge of 2,7DBT2PC-II, which was obtained from Tauc plot with an assumption of direct transition, was 3.25 eV. Therefore, the optical band gap of 2,7DBT2PC-II in the solid state was estimated at 3.25 eV; from the values of the HOMO level obtained above and this band gap, the LUMO level of 2,7DBT2PC-II was estimated at −2.54 eV. It was thus found that 2,7DBT2PC-II had a wide band gap of 3.25 eV in the solid state. It is also found that 2,7DBT2PC-II had a relatively deep HOMO level.

Further, thermophysical properties of 2,7DBT2PC-II were measured with a differential scanning calorimeter (DSC, manufactured by PerkinElmer, Inc., Pyris 1). First, a sample was heated from −10° C. up to 350° C. at a temperature rising rate of 40° C./min, and then it was cooled down to −10° C. at 40° C./min. After that, the sample was heated up to 290° C. at a temperature rising rate of 10° C./min, and thus a DSC chart was obtained. As can be seen from the DSC chart, a peak indicating the glass transition temperature of 2,7DBT2PC-II was observed, which showed the glass transition temperature (Tg) was 146° C. Thus, 2,7DBT2PC-II has a high glass transition point. Therefore, it was confirmed that 2,7DBT2PC-II of this synthesis example had high heat resistance.

Example 3

Synthesis Example 3

In this example is described a method of synthesizing 3-[4-(dibenzothiophen-4-yl)-phenyl]-9-phenyl-9H-carbazole (abbreviated as DBTPPC-II), which is one of the carbazole compounds described in Embodiment 1. A structure of DBTPPC-II is shown in the following structural formula (172).

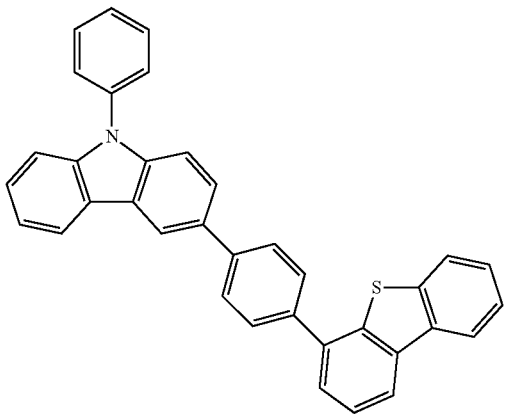

(172)

Synthesis Method of 3-[4-(dibenzothiophen-4-yl)-phenyl]-9-phenyl-9H-carbazole (abbreviated as DBTPPC-II)

To a 100-mL three-neck flask were added 2.4 g (6.0 mmol) of 3-(4-bromophenyl)-9-phenyl-9H-carbazole, 1.7 g (6.0 mmol) of dibenzothiophene-4-boronic acid, 13 mg (0.1 mmol) of palladium(II) acetate, 36 mg (0.1 mmol) of tri (ortho-tolyl)phosphine, 20 mL of toluene, 3 mL of ethanol, and 5 mL of a 2 mol/L aqueous potassium carbonate solution. This mixture was degassed while being stirred under reduced pressure, and then heated and stirred at 90° C. for 4 hours in a nitrogen atmosphere to be reacted.

After the reaction, 200 mL of toluene was added to this reaction mixture solution, and the organic layer of the mixture solution was filtered through Florisil (produced by Wako Pure Chemical Industries, Ltd., Catalog No. 540-00135), alumina (produced by Merck & Co., Inc., neutral), and Celite (produced by Wako Pure Chemical Industries, Ltd., Catalog No. 531-16855). The obtained filtrate was washed with water, and magnesium sulfate was added thereto so that moisture was adsorbed. This suspension was filtered to obtain a filtrate. The obtained filtrate was concentrated, and purified by silica gel column chromatography. At this time, a mixed solvent of toluene and hexane (toluene: hexane=1:4) was used as a developing solvent for the chromatography. The fraction thus obtained was concentrated, acetone and methanol were added thereto, and the mixture was irradiated with ultrasonic waves. Then, recrystallization gave 2.3 g of a white powder in 77% yield. A reaction scheme of the above synthesis method is shown in the following (C-1).

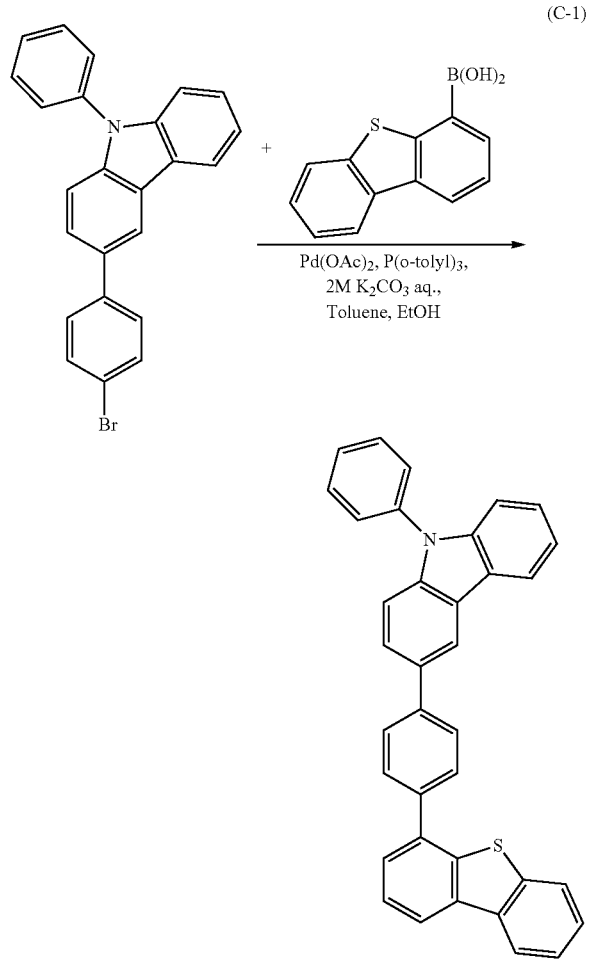

(C-1)

The Rf values of the white powder obtained through the above reaction and 3-(4-bromophenyl)-9-phenyl-9H-carbazole were respectively 0.40 and 0.60, which were found by silica gel thin layer chromatography (TLC) (a developing solvent in which the ethyl acetate/hexane ratio was 1:10).

Figure 13A:
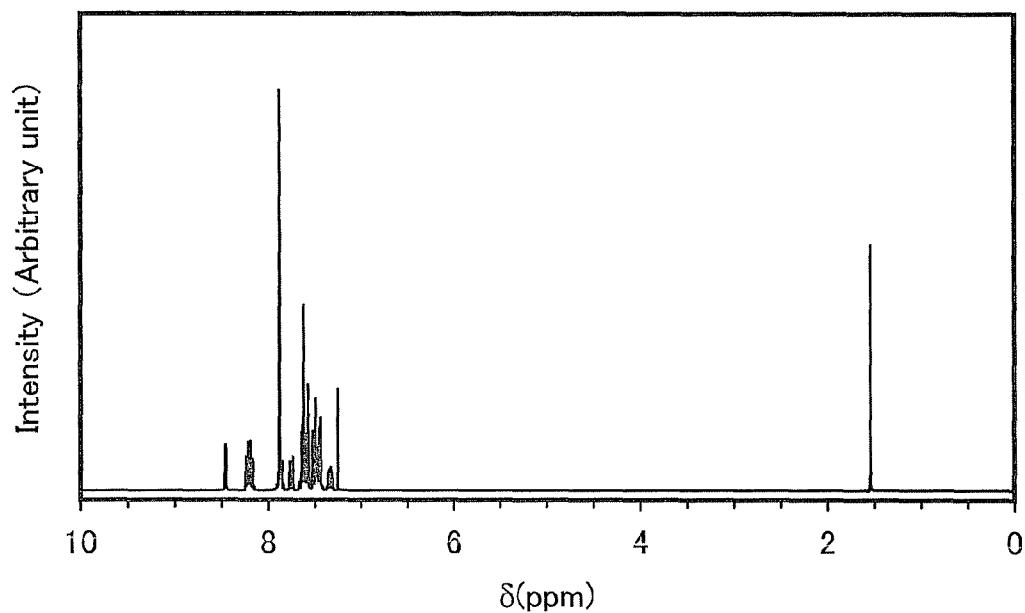
FIGS. 13A and 13B are $^1$H NMR charts of DBTPPC-II.
Figure 13B:
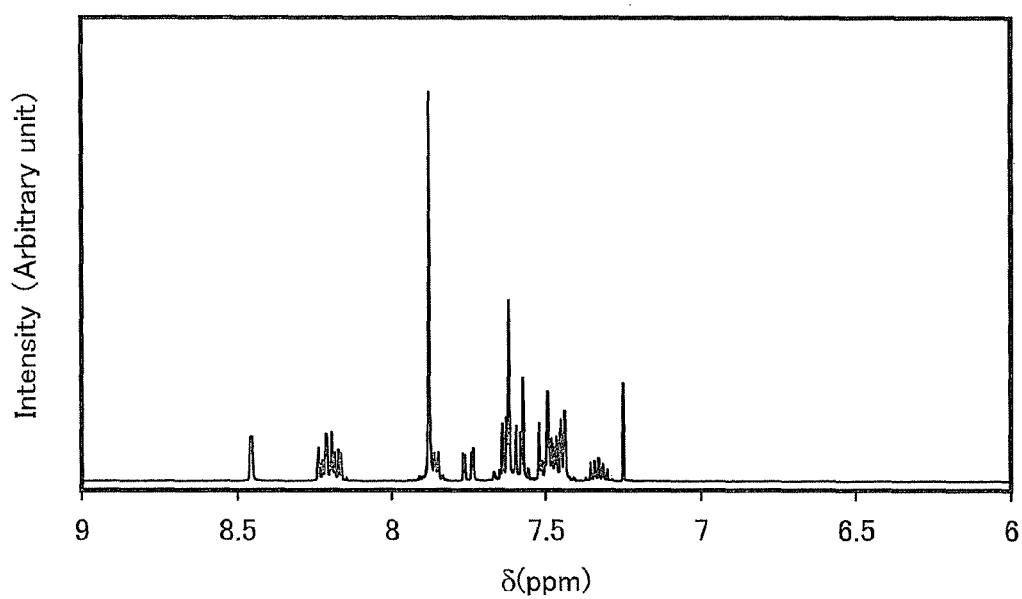

The white powder obtained by the above-described reaction was subjected to nuclear magnetic resonance (NMR) spectroscopy. The measurement data are shown below. $^1$H NMR charts are shown in FIGS. 13A and 13B. Note that FIG. 13B is an enlarged chart of FIG. 13A. The measurement results showed that the white powder obtained in the reaction was DBTPPC-II represented by the above structural formula (172) of the target substance.

$^1$H NMR (CDCl$_3$, 300 MHz): δ(ppm)=7.30-7.36 (m, 1H), 7.44-7.52 (m, 6H), 7.55-7.67 (m, 6H), 7.75 (dd, J=8.7 Hz, 1.5 Hz, 1H), 7.85-7.88 (m, 5H), 8.16-8.24 (m, 3H), 8.46 (d, J=1.5 Hz, 1H).

Figure 14A:
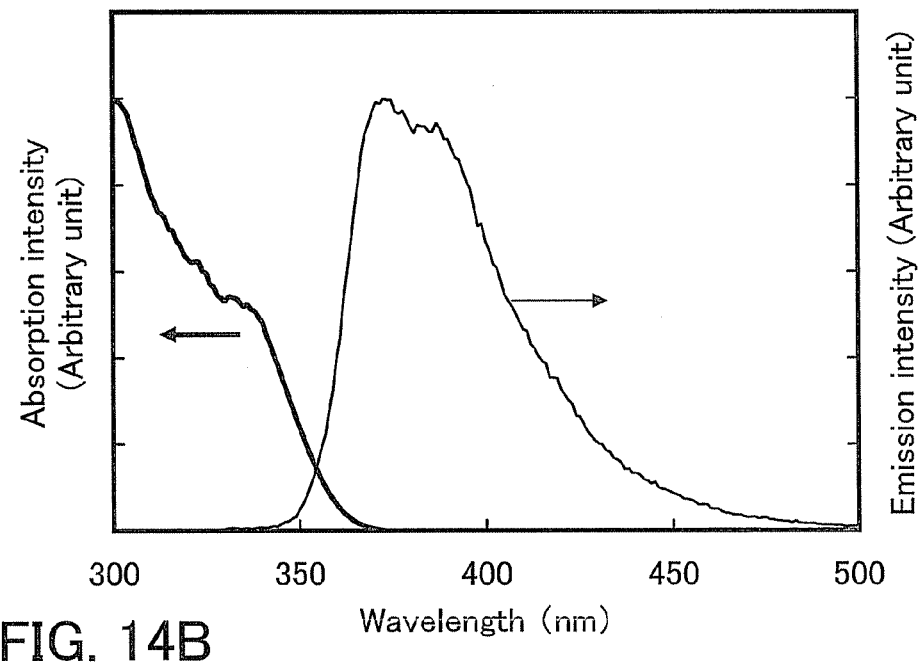
FIGS. 14A and 14B show an absorption spectrum and an emission spectrum of DBTPPC-II.
Figure 14B:
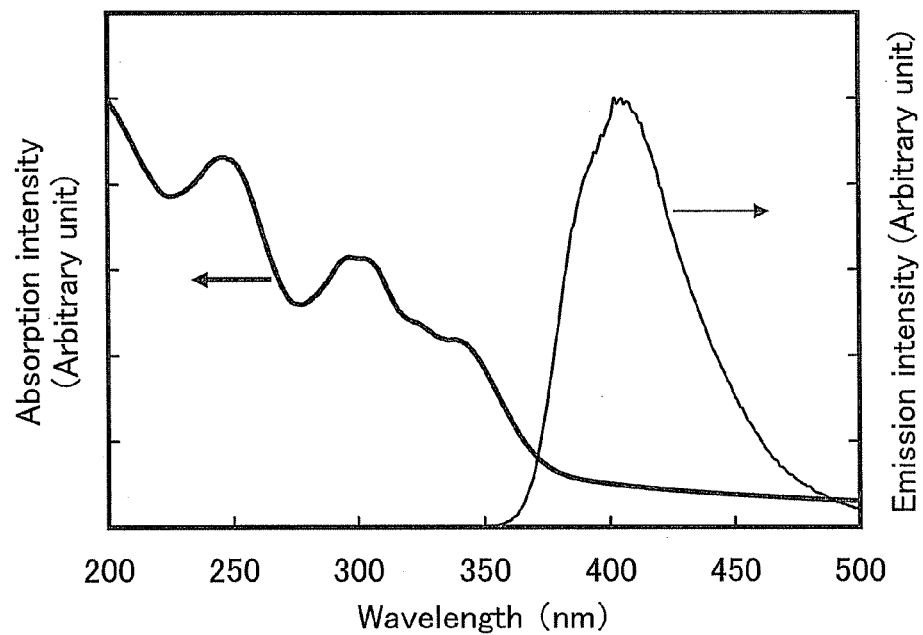

Next, an absorption spectrum and an emission spectrum of DBTPPC-II in a toluene solution of DBTPPC-II are shown in FIG. 14A, and an absorption spectrum and an emission spectrum of a thin film of DBTPPC-II are shown in FIG. 14B. The measurement of the spectra was performed using an ultraviolet-visible spectrophotometer (V-550, manufactured by JASCO Corporation). The spectra of the toluene solution were measured with a toluene solution of DBTPPC-II put in a quartz cell. The spectra of the thin film were measured with a sample prepared by evaporation of DBTPPC-II on a quartz substrate. Note that as the absorption spectrum of the toluene solution, the absorption spectrum obtained by subtraction of the absorption spectra of quartz and toluene from the measured spectra is shown in the graph, and as the absorption spectrum of the thin film, the absorption spectrum obtained by subtraction of that of quartz from the measured spectra is shown in the graph.

FIGS. 14A and 14B show that the maximum absorption wavelength of DBTPPC-II in the toluene solution of DBTPPC-II was around 334 nm, the maximum emission wavelengths thereof were around 373 nm and 386 nm (at an excitation wavelength of 320 nm), the maximum absorption wavelength of the thin film of DBTPPC-II was around 339 nm, and the maximum emission wavelengths thereof were around 405 nm (at an excitation wavelength of 346 nm).

The absorption spectra reveal that DBTPPC-II described in this example is a material that shows almost no absorption in the visible region. Further, the emission spectra reveal that the light emission is bluish purple.

Further, the glass transition temperature (Tg) of DBTPPC-II was examined with a differential scanning calorimeter (DSC). According to the measurement results, it was found that the glass transition temperature and the melting point were 107° C. and 212° C. respectively. In this manner, it is found that DBTPPC-II had a high glass transition temperature and favorable heat resistance.

Further, the ionization potential of DBTPPC-II in a thin film state was measured by a photoelectron spectrometer (AC-2, manufactured by Riken Keiki, Co., Ltd.) in air. The obtained value of the ionization potential was converted to a negative value, so that the HOMO level of DBTPPC-II was −5.71 eV. From the data of the absorption spectra of the thin film in FIGS. 14A and 14B, the absorption edge of DBTPPC-II, which was obtained from Tauc plot with an assumption of direct transition, was 3.37 eV. Therefore, the optical band gap of DBTPPC-II in the solid state was estimated at 3.37 eV; from the values of the HOMO level obtained above and this band gap, the LUMO level of DBTPPC-II was estimated at −2.34 eV. It was thus found that DBTPPC-II had a wide energy gap of 3.37 eV in the solid state. It is also found that DBTPPC-II had a relatively deep HOMO level.

Further, thermophysical properties of DBTPPC-II were measured with a differential scanning calorimeter (DSC, manufactured by PerkinElmer, Inc., Pyris 1). First, a sample was heated from −10° C. up to 350° C. at a temperature rising rate of 40° C./min, and then it was cooled down to −10° C. at 40° C./min. After that, the sample was heated up to 290° C. at a temperature rising rate of 10° C./min, and thus a DSC chart was obtained. As can be seen from the DSC chart, a peak indicating the glass transition temperature of DBTPPC-II was observed, which showed the glass transition temperature (Tg) was 107° C. Thus, DBTPPC-II has a high glass transition point. Therefore, it was confirmed that DBTPPC-II of this synthesis example had high heat resistance.

Example 4

Synthesis Example 4

In this example is described a method of synthesizing 3-[3-(dibenzothiophen-4-yl)-phenyl]-9-phenyl-9H-carbazole (abbreviated as mDBTPPC-II), which is one of the carbazole compounds described in Embodiment 1. A structure of mDBTPPC-II is shown in the following structural formula (160).

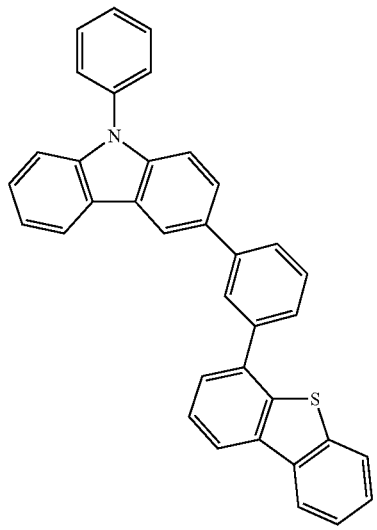

(160)

Synthesis Method of 3-[3-(dibenzothiophen-4-yl)-phenyl]-9-phenyl-9H-carbazole (abbreviated as mDBTPPC-II)

To a 100-mL three-neck flask were added 2.4 g (6.0 mmol) of 3-(3-bromophenyl)-9-phenyl-9H-carbazole, 1.7 g (6.0 mmol) of dibenzothiophene-4-boronic acid, 13 mg (0.1 mmol) of palladium(II) acetate, 36 mg (0.1 mmol) of tri(ortho-tolyl)phosphine, 20 mL of toluene, 3 mL of ethanol, and 5 mL of a 2 mol/L aqueous potassium carbonate solution. This mixture was degassed while being stirred under reduced pressure, and then heated and stirred at 90° C. for 6 hours in a nitrogen atmosphere to be reacted.

After the reaction, 200 mL of toluene was added to this reaction mixture solution, and an organic layer of the mixture solution was filtered through Florisil (produced by Wako Pure Chemical Industries, Ltd., Catalog No. 540-00135), alumina (produced by Merck & Co., Inc., neutral), and Celite (produced by Wako Pure Chemical Industries, Ltd., Catalog No. 531-16855). The obtained filtrate was washed with water, and magnesium sulfate was added thereto so that moisture was adsorbed. This suspension was filtrated to obtain a filtrate. The obtained filtrate was concentrated, and purified by silica gel column chromatography. A mixed solvent of toluene and hexane (toluene: hexane=1:4) was used as a developing solvent for the chromatography. The obtained fraction was concentrated, and acetone and hexane were added thereto. The mixture was irradiated with ultrasonic waves and then recrystallized to give 2.6 g of white powder in 87% yield. The reaction scheme of the synthesis method is shown in the following (D-1).

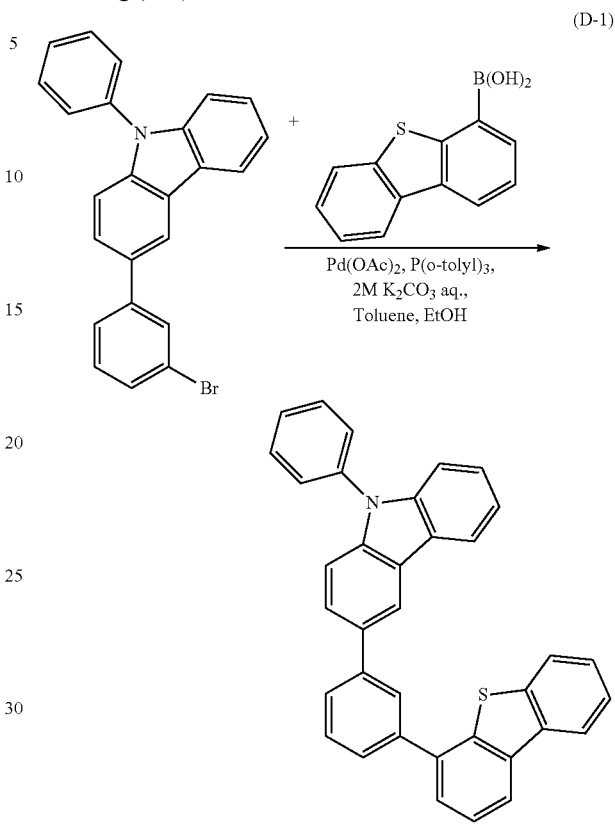

(D-1)

The Rf values of the white powder obtained through the above reaction and 3-(3-bromophenyl)-9-phenyl-9H-carbazole were respectively 0.38 and 0.54, which were found by silica gel thin layer chromatography (TLC) (a developing solvent in which the ethyl acetate/hexane ratio was 1:10).

Figure 15A:
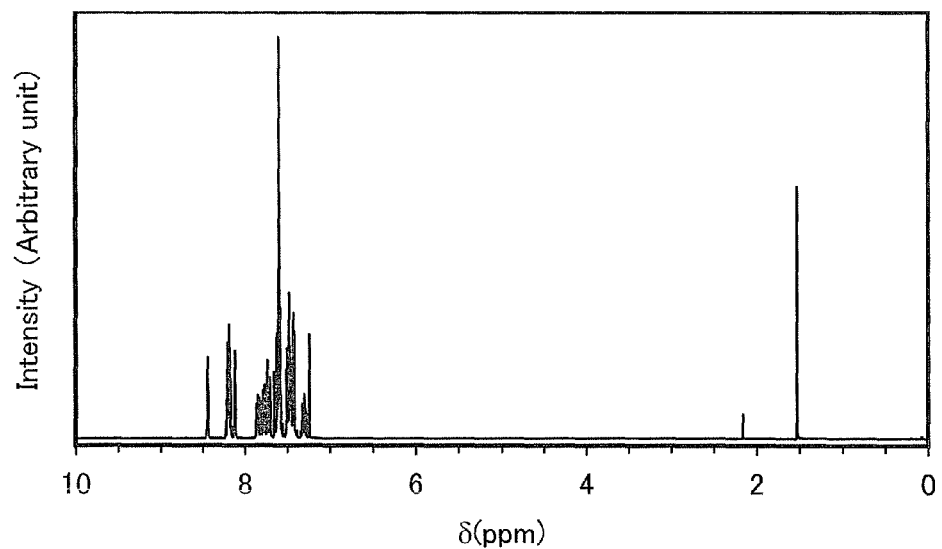
FIGS. 15A and 15B are $^1$H NMR charts of mDBTPPC-II.
Figure 15B:
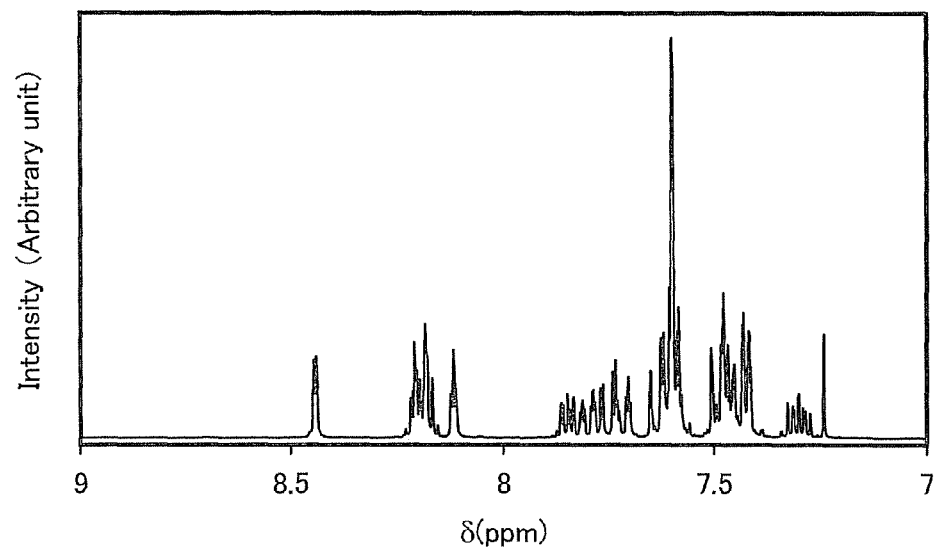

The white powder obtained by the above-described step 1 was subjected to nuclear magnetic resonance (NMR) spectroscopy. The measurement data are shown below. Also, $^1$H NMR charts are shown in FIGS. 15A and 15B. Note that FIG. 15B is an enlarged chart of FIG. 15A. By the measurement result, it was confirmed that the white powder obtained by the step 1 was mDBTPPC-II, which is represented by the above structural formula (160).

$^1$H NMR (CDCl$_3$, 300 MHz): δ (ppm)=7.27-7.33 (m, 1H), 7.41-7.51 (m, 6H), 7.58-7.65 (m, 7H), 7.70-7.86 (m, 4H), 8.12 (t, J=1.5 Hz, 1H), 8.17-8.22 (m, 3H), 8.44 (d, J=1.8 Hz, 1H).

Figure 16A:
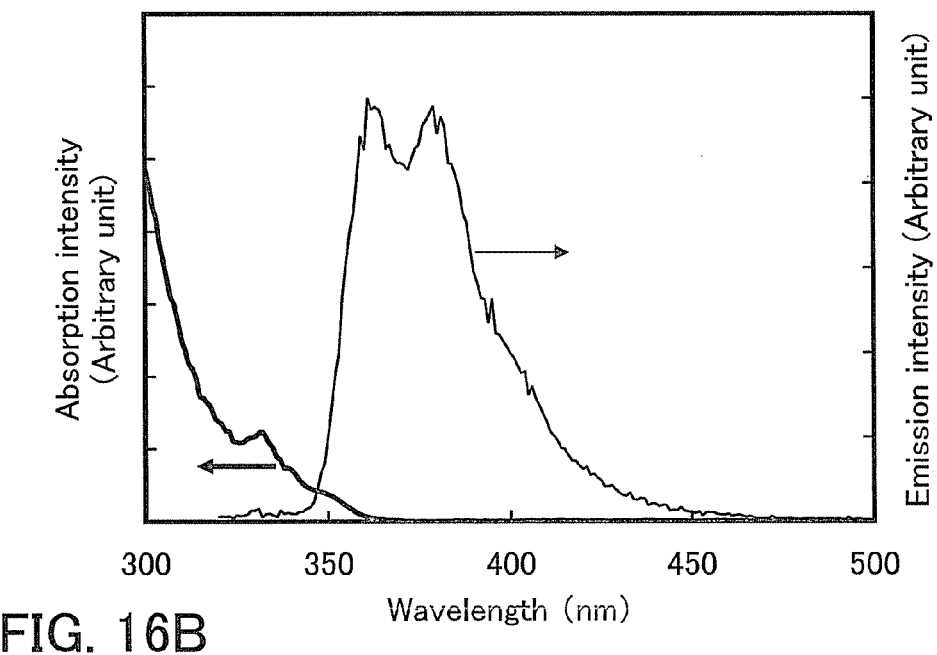
FIGS. 16A and 16B show an absorption spectrum and an emission spectrum of mDBTPPC-II.
Figure 16B:
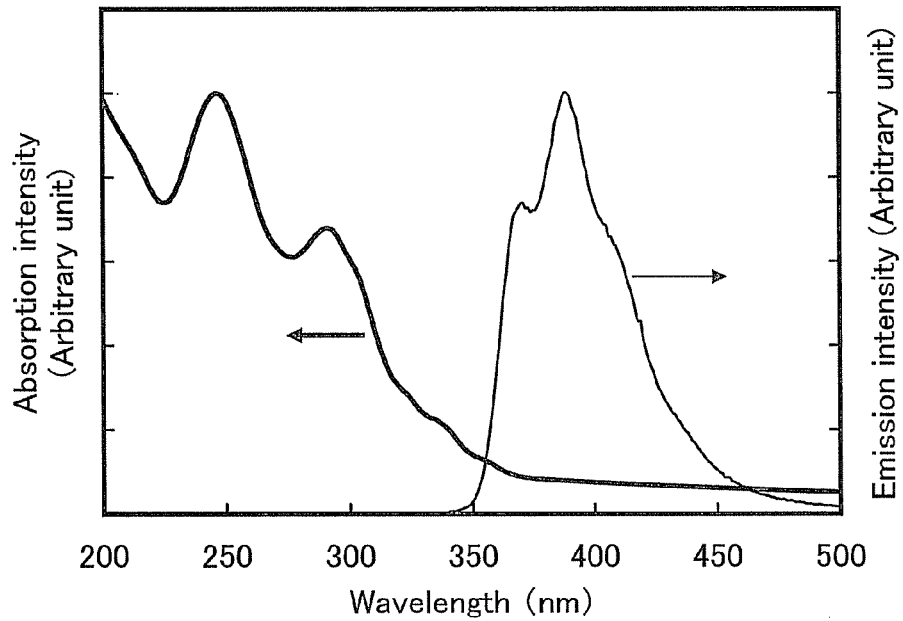

Next, an absorption spectrum and an emission spectrum of mDBTPPC-II in a toluene solution of mDBTPPC-II are shown in FIG. 16A, and an absorption spectrum and an emission spectrum of a thin film of mDBTPPC-II are shown in FIG. 16B. The measurement of the spectra was performed using an ultraviolet-visible spectrophotometer (V-550, manufactured by JASCO Corporation). The spectra of the toluene solution were measured with a toluene solution of mDBTPPC-II put in a quartz cell. The spectra of the thin film were measured with a sample prepared by evaporation of mDBTPPC-II on a quartz substrate. Note that as the absorption spectrum of the toluene solution, the absorption spectrum obtained by subtraction of the absorption spectra of quartz and toluene from the measured spectra is shown in the graph, and as the absorption spectrum of the thin film, the absorption spectrum obtained by subtraction of that of quartz from the measured spectra is shown in the graph.

FIGS. 16A and 16B show that the maximum absorption wavelength of mDBTPPC-II in the toluene solution of mDBTPPC-II was around 330 nm, the maximum emission wavelengths thereof were around 363 nm and 379 nm (at an excitation wavelength of 300 nm), the maximum absorption wavelength of the thin film of mDBTPPC-II was around 353 nm, and the maximum emission wavelengths thereof were around 389 nm and 374 nm (at an excitation wavelength of 336 nm).

The absorption spectra reveal that mDBTPPC-II described in this example is a material that shows almost no absorption in the visible region. Further, the emission spectra reveal that the light emission is bluish purple.

Further, the ionization potential of mDBTPPC-II in a thin film state was measured by a photoelectron spectrometer (AC-2, manufactured by Riken Keiki, Co., Ltd.) in air. The obtained value of the ionization potential was converted to a negative value, so that the HOMO level of mDBTPPC-II was −5.64 eV. From the data of the absorption spectra of the thin film in FIGS. 16A and 16B, the absorption edge of mDBTPPC-II, which was obtained from Tauc plot with an assumption of direct transition, was 3.31 eV. Therefore, the optical band gap of mDBTPPC-II in the solid state was estimated at 3.31 eV; from the values of the HOMO level obtained above and this band gap, the LUMO level of mDBTPPC-II was estimated at −2.33 eV. It was thus found that mDBTPPC-II had a wide band gap of 3.31 eV in the solid state. It is also found that mDBTPPC-II had a relatively deep HOMO level.

Further, thermophysical properties of mDBTPPC-II were measured with a differential scanning calorimeter (DSC, manufactured by PerkinElmer, Inc., Pyris 1). First, a sample was heated from −10° C. up to 350° C. at a temperature rising rate of 40° C./min, and then it was cooled down to −10° C. at 40° C./min. After that, the sample was heated up to 290° C. at a temperature rising rate of 10° C./min, and thus a DSC chart was obtained. As can be seen from the DSC chart, a peak indicating the glass transition temperature of mDBTPPC-II was not observed. Thus, it was found that mDBTPPC-II had a high glass transition point. Therefore, it was confirmed that mDBTPPC-II of this synthesis example had high heat resistance.

Example 5

In this example described is a light-emitting element in which 3,6-di-(dibenzothiophen-4-yl)-9-phenyl-9H-carbazole (abbreviated as DBT2PC-II, the structural formula (150)), which is one of the carbazole carbazole compounds described in Embodiment 1, is used as a material for a hole-transport layer adjacent to a light-emitting layer using an emission center substance that emits blue fluorescence.

The molecular structures of organic compounds used in this example are represented by the following structural formulae (i), (ii), (iii), and (150).

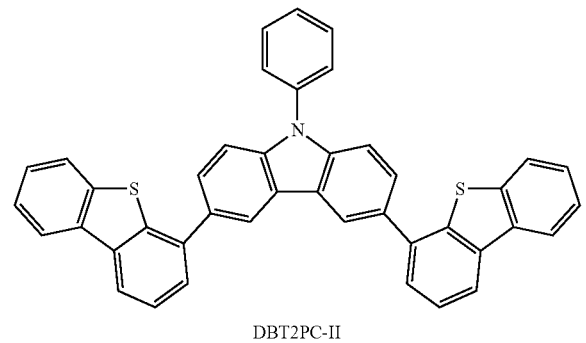

(150)

DBT2PC-II

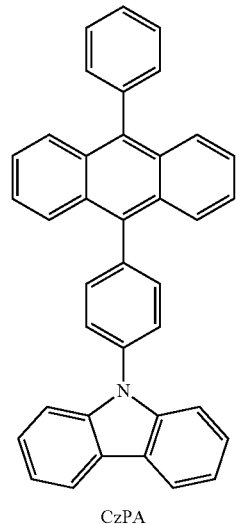

(i)

CzPA

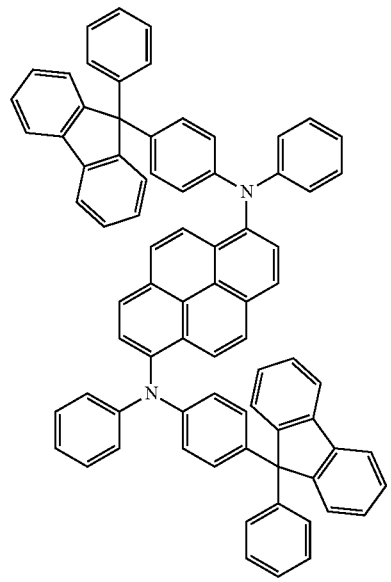

(ii)

1,6FLPAPrn

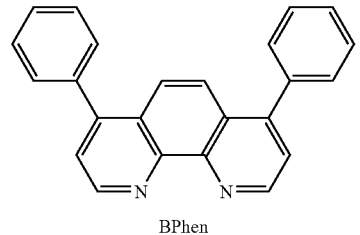

(iii)

BPhen

In FIG. 1A, the element structure in which an electron-injection layer is provided between the electron-transport layer 114 and the second electrode 104 was employed. The structure of the light-emitting element 1 is shown below.

TABLE 1

| | First electrode | Hole injection layer | Hole transport layer | Light emitting layer | Electron transport layer | | Electron injection layer | Second electrode |
|---|---|---|---|---|---|---|---|---|
| Light emitting element 1 | ITSO 110 nm | DBT2PC-II:MoOx (=4:2) 50 nm | DBT2PC-II 10 nm | CzPA:1,6FLAPrn (=1:0.05) 30 nm | CzPA 10 nm | BPhen 15 nm | LiF 1 nm | Al 200 nm |

[Fabrication of Light-Emitting Element 1]

First, a glass substrate 101 over which indium tin oxide containing silicon (ITSO) with a thickness of 110 nm had been formed as a first electrode 102 was prepared. The surface of the ITSO film excluding an area of 2 mm×2 mm was provided with a polyimide film in the peripheral portion of the area, and thereby the area of 2 mm×2 mm was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate 101 was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of DBT2PC-II represented by the structural formula (150), which is one of the carbazole compounds described in Embodiment 1, and molybdenum(VI) oxide such that the ratio of DBT2PC-II:molybdenum(VI) oxide was 2:1 (mass ratio). The thickness thereof was 50 nm. Note that a co-evaporation method is an evaporation method in which a plurality of different substances are concurrently vaporized from respective different evaporation sources.

Next, DBT2PC-II was evaporated to a thickness of 10 nm, so that the hole-transport layer 112 was formed.

Further, the light-emitting layer 113 was formed on the hole-transport layer 112 in such a way that 9-[4-(10-phenyl-9-anthryl)phenyl]-9H-carbazole (abbreviated as CzPA) represented by the structural formula (I) and N,N'-bis[4-(9-phenyl-9H-fluoren-9-yl)phenyl]-N,N'-diphenyl-pyrene-1,6-diamine (abbreviated as 1,6FLPAPm) represented by the structural formula (II) were evaporated to form a 30-nm-thick film such that the ratio of CzPA to 1,6FLPAPm was 1:0.05 (mass ratio).

Next, on the light-emitting layer 113, CzPA represented by the structural formula (I) was evaporated to a thickness of 10 nm, and then bathophenanthroline (abbreviated as BPhen) represented by the structural formula (iii) was evaporated to a thickness of 15 nm, so that the electron-transport layer 114 was formed. Further, lithium fluoride was evaporated to a thickness of 1 nm on the electron-transport layer 114, so that the electron-injection layer was formed. Finally, a film of aluminum was formed in 200 nm thick as the second electrode 104 serving as a cathode, whereby the light-emitting element 1 was fabricated. Note that in the above-described evaporation process, evaporation was all performed by a resistance heating method.

[Operation Characteristics of Light-Emitting Element 1]

After the light-emitting element 1 obtained as described above was sealed in a glove box under a nitrogen atmosphere so as not to be exposed to the air, operation characteristics of the light-emitting element was measured. Note that the measurement was carried out at room temperature (in an atmosphere kept at 25° C.).

Figure 17:
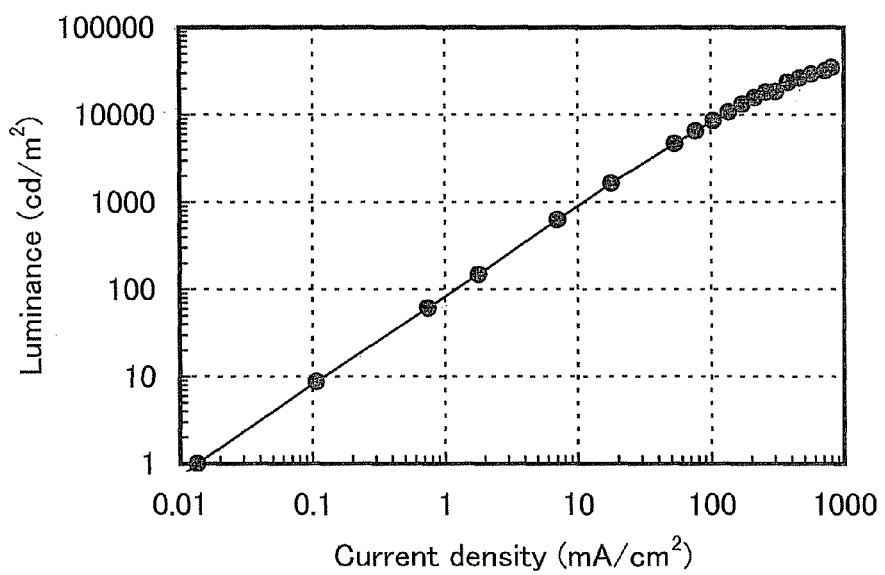
FIG. 17 shows luminance versus current density characteristics of a light-emitting element 1.
Figure 18:
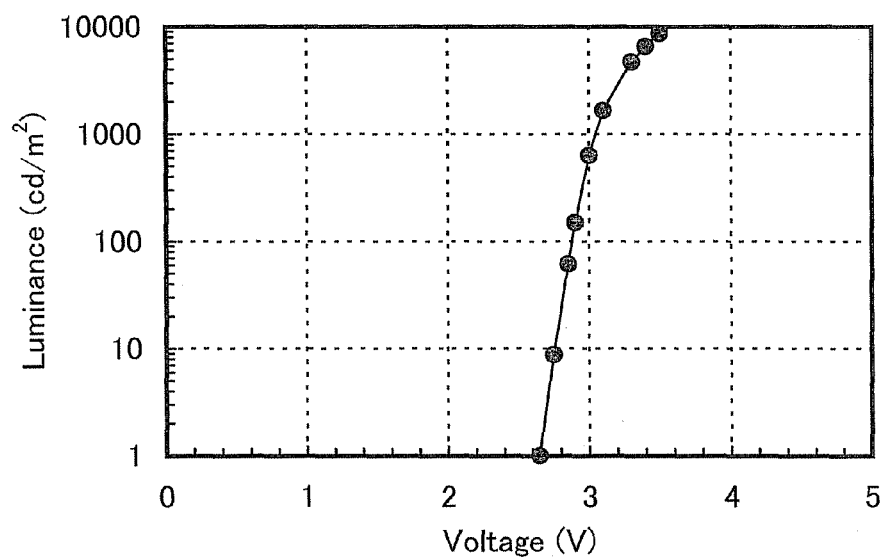
FIG. 18 shows luminance versus voltage characteristics of the light-emitting element 1.
Figure 19:
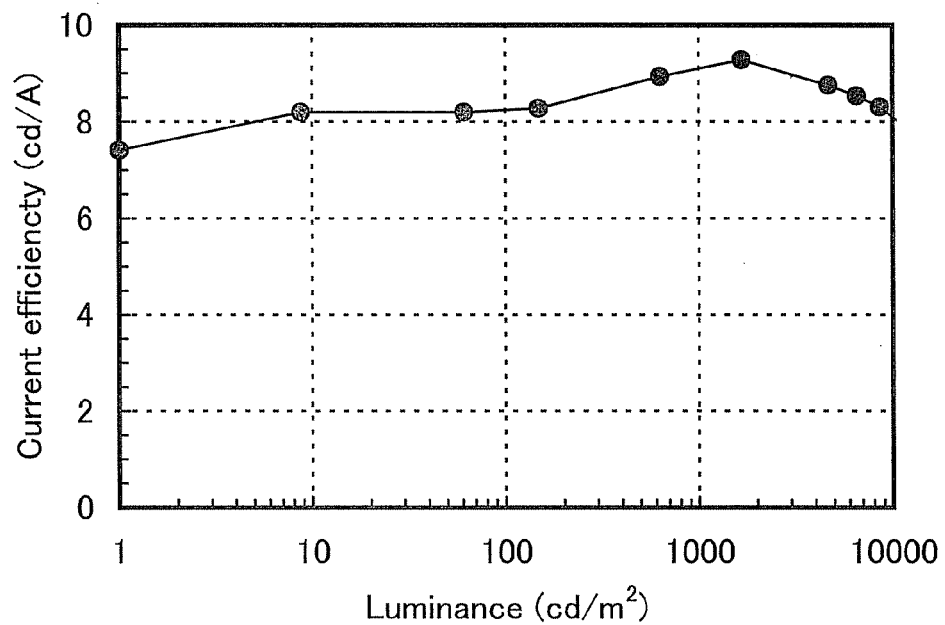
FIG. 19 shows current efficiency versus luminance characteristics of the light-emitting element 1.

FIG. 17 shows luminance versus current density characteristics of the light-emitting element 1, FIG. 18 shows luminance versus voltage characteristics thereof, and FIG. 19 shows current efficiency versus luminance characteristics thereof. In FIG. 17, the vertical axis represents luminance (cd/m$^2$), and the horizontal axis represents current density (mA/cm$^2$). In FIG. 18, the vertical axis represents luminance (cd/m$^2$), and the horizontal axis represents voltage (V). In FIG. 19, the vertical axis represents current efficiency (cd/A), and the horizontal axis represents luminance (cd/m$^2$).

FIG. 19 reveals that the light-emitting element, in which the carbazole compound described in Embodiment 1 is used as a material for the hole-transport layer in contact with the light-emitting layer for emitting blue fluorescence, has favorable luminance versus emission efficiency characteristics and high emission efficiency. This is because the carbazole compound described in Embodiment 1 has a wide band gap, and thus transfer of excitation energy can be suppressed despite the adjacency to a light-emitting substance that emits blue fluorescence and has a wide band gap. In addition, FIG. 17 reveals that the light-emitting element, in which the carbazole compound described in Embodiment 1 is used as a material for the hole-transport layer adjacent to the light-emitting layer for emitting blue fluorescence, has favorable luminance versus voltage characteristics and can be driven with low voltage. This indicates that the carbazole compound described in Embodiment 1 has a superior carrier-transport property.

In addition, it was found that the hole-injection layer formed by co-evaporation of the carbazole compound described in Embodiment 1 and molybdenum oxide exhibited a good hole-injection property. This reveals that the composite material using the carbazole compound described in Embodiment 1 has a superior carrier-injection property.

Characteristics around 1000 cd/m$^2$ of the light-emitting element 1 are shown below.

TABLE 2

| | Voltage (V) | Current (mA) | Chromaticity x | Chromaticity y | Y (Luminance (cd/m$^2$)) | Current Efficiency (cd/A) | Power Efficiency (lm/W) | Quantum Efficiency (%) |
|---|---|---|---|---|---|---|---|---|
| Light emitting element1 | 3.0 | 0.28 | 0.15 | 0.21 | 630 | 8.9 | 9.4 | 6.2 |

Figure 20:
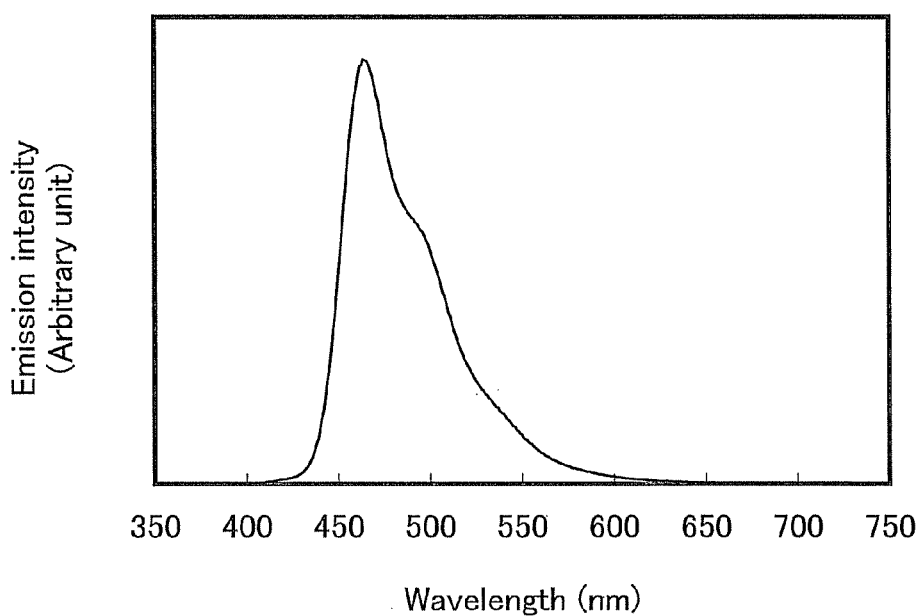
FIG. 20 shows an emission spectrum of the light-emitting element 1.

Further, FIG. 20 shows an emission spectrum when a current of 1 mA flowed to the light-emitting element 1 fabricated. In FIG. 20, the vertical axis represents emission intensity and the horizontal axis represents emission wavelength (nm). The emission intensity is shown as a value relative to the maximum emission intensity assumed to be 1. FIG. 20 reveals that the light-emitting element 1 emits blue light originating from 1,6FLPAPrn, which is the emission center substance.

Example 6

In this example described is a light-emitting element in which 2,7-di-(dibenzothiophen-4-yl)-9-phenyl-9H-carbazole (abbreviated as 2,7DBT2PC-II, a structural formula (154)), which is one of the carbazole compounds represented by the general formula (G1), is used as a material for a hole-transport layer adjacent to a light-emitting layer using an emission center substance that emits blue fluorescence.

The molecular structures of organic compounds used in this example are represented by the following structural formulae (i), (ii), (iii), (iv), and (154).

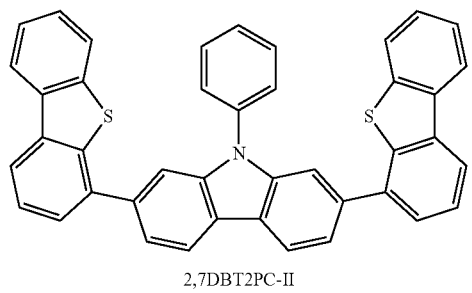

(154)

2,7DBT2PC-II

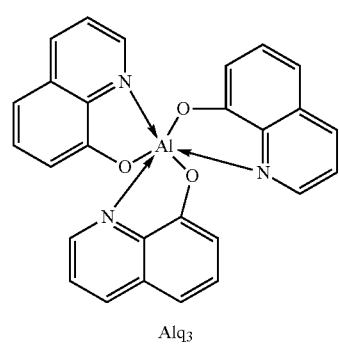

(iv)

Alq₃

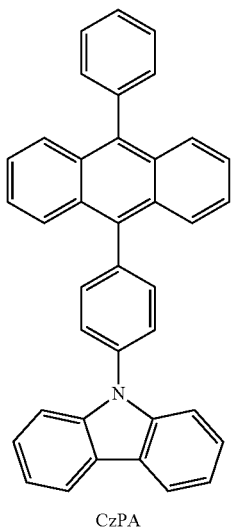

(i)

CzPA

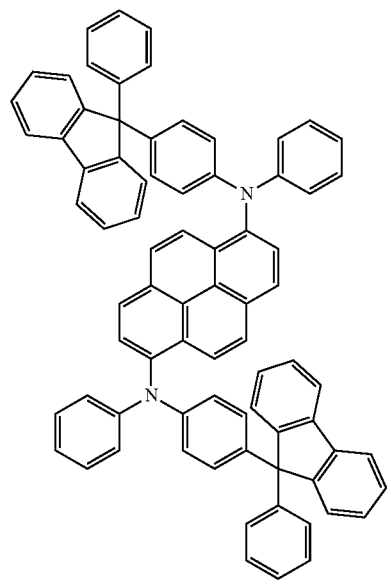

(ii)

1,6FLPAPrn

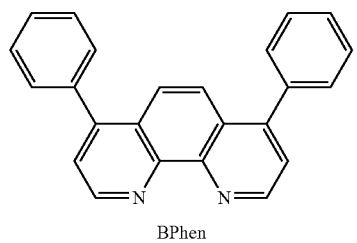

(iii)

BPhen

In FIG. 1A, the element structure in which an electron-injection layer is provided between the electron-transport layer 114 and the second electrode 104 was employed. The element structure of the light-emitting element 2 is shown below.

TABLE 3

| | First electrode | Hole injection layer | Hole transport layer | Light emitting layer | Electron transport layer | | Electron injection layer | Second electrode |
|---|---|---|---|---|---|---|---|---|
| Light emitting element 2 | ITSO 110 nm | 2,7DBT2PC-II:MoOx (=4:2) 50 nm | 2,7DBT2PC-II 10 nm | CzPA:1,6FLAPrn (=1:0.05) 30 nm | Alq 10 nm | BPhen 15 nm | LiF 1 nm | Al 200 nm |

[Fabrication of Light-Emitting Element 2]

First, a glass substrate 101 over which indium tin oxide containing silicon (ITSO) with a thickness of 110 nm had been formed as a first electrode 102 was prepared. The surface of the ITSO film excluding an area of 2 mm×2 mm was provided with a polyimide film in the peripheral portion of the area, and thereby the area of 2 mm×2 mm was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate 101 was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 2,7DBT2PC-II represented by the structural formula (154), which is one of the carbazole compounds described in Embodiment 1, and molybdenum(VI) oxide such that the ratio of 2,7DBT2PC-II:molybdenum(VI) oxide was 2:1 (mass ratio). The thickness thereof was 50 nm. Note that a co-evaporation method is an evaporation method in which a plurality of different substances are concurrently vaporized from respective different evaporation sources.

Next, 2,7DBT2PC-II was evaporated to a thickness of 10 nm, so that the hole-transport layer 112 was formed.

Further, the light-emitting layer 113 was formed on the hole-transport layer 112 in such a way that 9-[4-(10-phenyl-9-anthryl)phenyl]-9H-carbazole (abbreviated as CzPA) represented by the structural formula (i) and N,N'-bis[4-(9-phenyl-9H-fluoren-9-yl)phenyl]-N,N'-diphenyl-pyrene-1,6-diamine (abbreviated as 1,6FLPAPrn) represented by the structural formula (ii) were evaporated to form a 30-nm-thick film such that the ratio of CzPA to 1,6FLPAPrn was 1:0.05 (mass ratio).

Next, on the light-emitting layer 113, Alq represented by the structural formula (Iv) was evaporated to a thickness of 10 nm, and then bathophenanthroline (abbreviated as BPhen) represented by the structural formula (iii) was evaporated to a thickness of 15 nm, so that the electron-transport layer 114 was formed. Further, lithium fluoride was evaporated to a thickness of 1 nm on the electron-transport layer 114, so that the electron-injection layer was formed. Finally, aluminum was evaporated to a thickness of 200 nm as the second electrode 104 serving as a cathode, whereby a light-emitting element 2 was fabricated. Note that in the above-described evaporation process, evaporation was all performed by a resistance heating method.

[Operation Characteristics of Light-Emitting Element 2]

After the light-emitting element 2 obtained as described above was sealed in a glove box under a nitrogen atmosphere so as not to be exposed to the air, operation characteristics of the light-emitting element was measured. Note that the measurement was carried out at room temperature (in an atmosphere kept at 25° C.).

Figure 21:
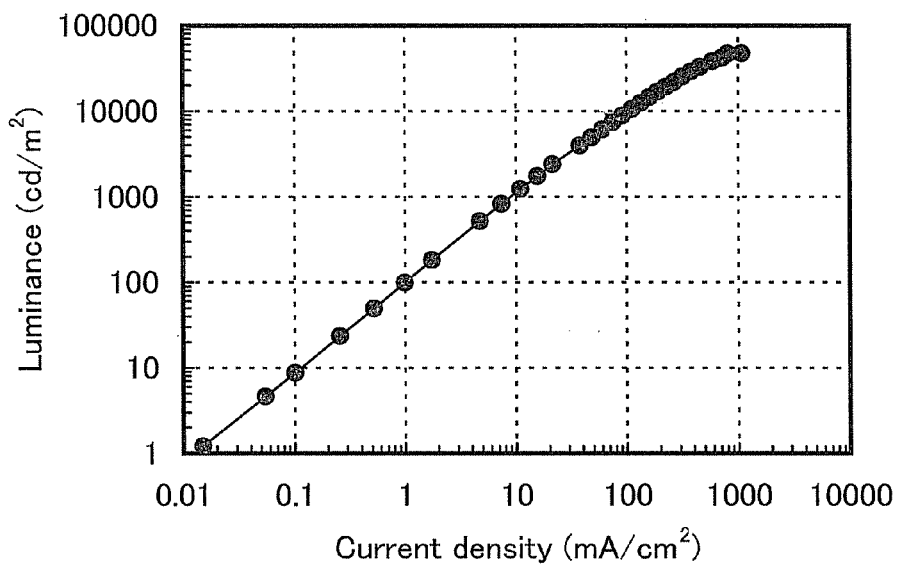
FIG. 21 shows luminance versus current density characteristics of a light-emitting element 2.
Figure 22:
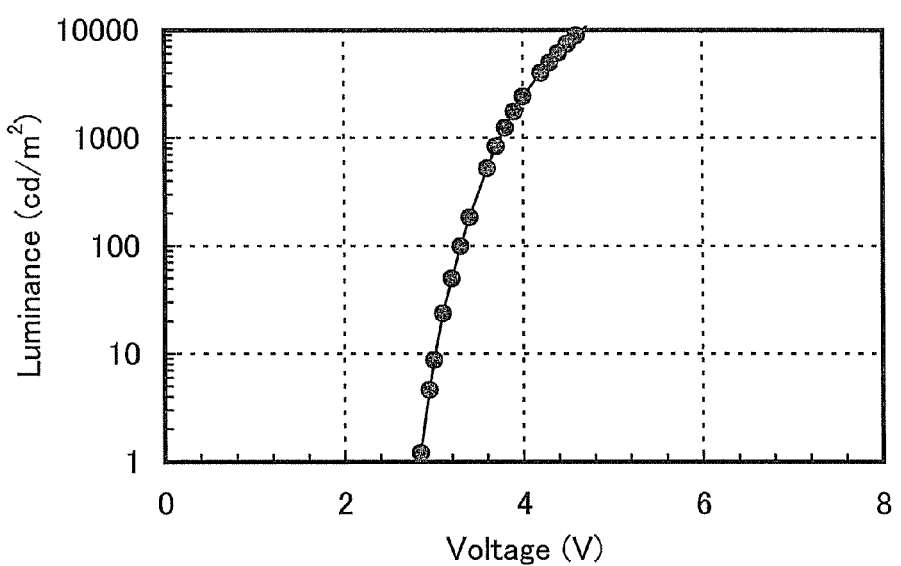
FIG. 22 shows luminance versus voltage characteristics of the light-emitting element 2.
Figure 23:
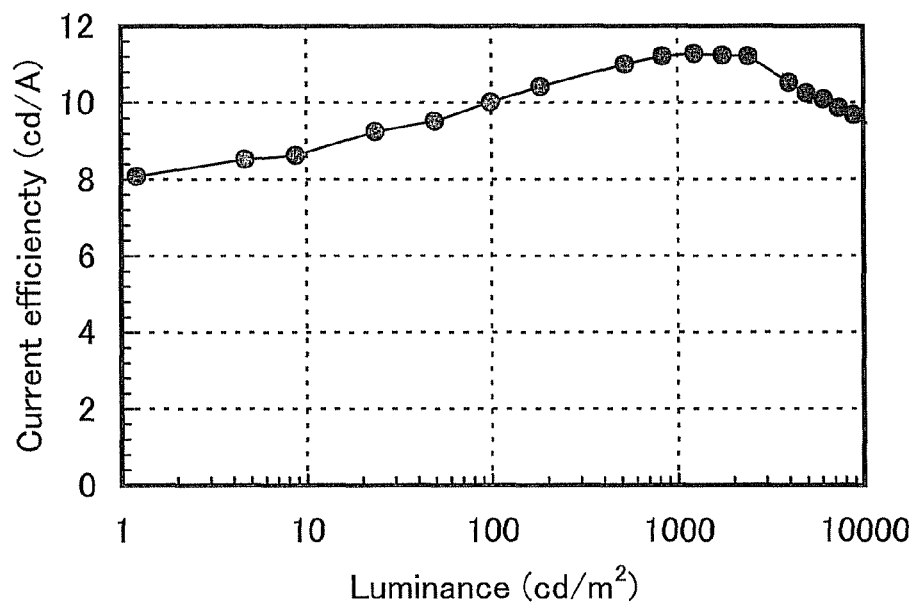
FIG. 23 shows current efficiency versus luminance characteristics of the light-emitting element 2.

FIG. 21 shows luminance versus current density characteristics of the light-emitting element 2, FIG. 22 shows luminance versus voltage characteristics thereof, and FIG. 23 shows current efficiency versus luminance characteristics thereof. In FIG. 21, the vertical axis represents luminance (cd/m$^2$), and the horizontal axis represents current density (mA/cm$^2$). In FIG. 22, the vertical axis represents luminance (cd/m$^2$), and the horizontal axis represents voltage (V). In FIG. 23, the vertical axis represents current efficiency (cd/A), and the horizontal axis represents luminance (cd/m$^2$).

FIG. 23 reveals that the light-emitting element, in which the carbazole compound represented by the general formula (G1) is used as a material for the hole-transport layer in contact with the light-emitting layer for emitting blue fluorescence, has favorable luminance versus emission efficiency characteristics and high emission efficiency. This is because the carbazole compound represented by the general formula (G1) has a wide band gap, and thus transfer of excitation energy can be suppressed despite the adjacency to a light-emitting substance that emits blue fluorescence and has a wide band gap. In addition, FIG. 21 shows that the light-emitting element, in which the carbazole compound represented by the general formula (G1) is used as a material for the hole-transport layer adjacent to the light-emitting layer for emitting blue fluorescence, has favorable luminance versus voltage characteristics and can be driven with low voltage. This reveals that the carbazole compound represented by the general formula (G1) has an excellent carrier-transport property.

In addition, it was found that the hole-injection layer formed by co-evaporation of the carbazole compound described in Embodiment 1 and molybdenum oxide exhibited a good hole-injection property. This reveals that the composite material using the carbazole compound described in Embodiment 1 has a superior carrier-injection property.

Characteristics around 1000 cd/m$^2$ of the light-emitting element 2 are shown below.

TABLE 4

| | Voltage (V) | Current (mA) | Chromaticity x | Chromaticity y | Y (Luminance (cd/m$^2$)) | Current Efficiency (cd/A) | Power Efficiency (lm/W) | Quantum Efficiency (%) |
|---|---|---|---|---|---|---|---|---|
| Light emitting element 2 | 3.7 | 0.30 | 0.15 | 0.22 | 830 | 11 | 10 | 7.5 |

Figure 24:
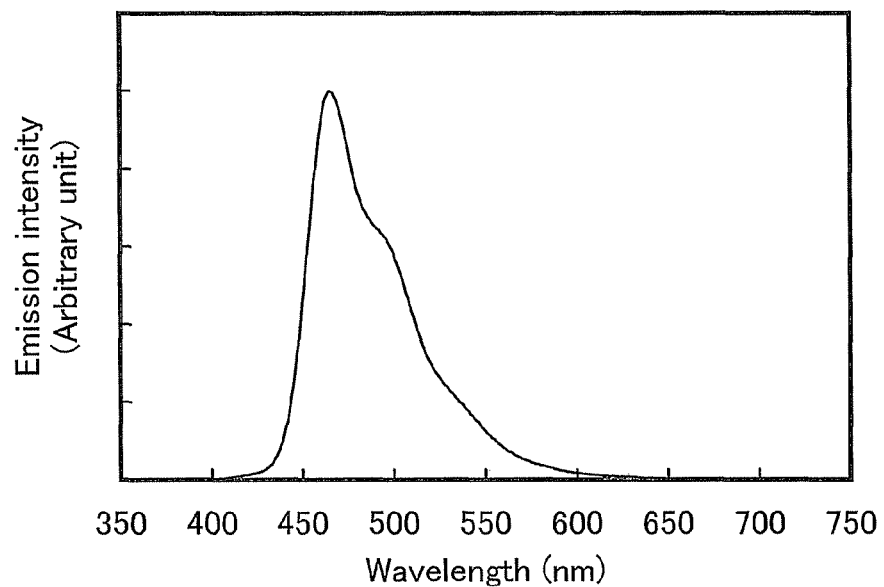
FIG. 24 shows an emission spectrum of the light-emitting element 2.

Further, FIG. 24 shows an emission spectrum when a current of 1 mA flowed to the light-emitting element 2 fabricated. In FIG. 24, the vertical axis represents emission intensity and the horizontal axis represents emission wavelength (nm). The emission intensity is shown as a value relative to the maximum emission intensity assumed to be 1. FIG. 24 reveals that the light-emitting element 2 emits blue light originating from 1,6FLPAPm, which is the emission center substance.

Example 7

In this example described are a light-emitting element 3 in which 3-[4-(dibenzothiophen-4-yl)-phenyl]-9-phenyl-9H-carbazole (abbreviated as DBTPPC-II), which is represented by the structural formula (172)), which is one of the carbazole compounds represented by the general formula (G1), is used as a material for a hole-transport layer adjacent to a light-emitting layer using an emission center substance that emits green phosphorescence, and similarly, a light-emitting element 4 in which 3-[3-(dibenzothiophen-4-yl)-phenyl]-9-phenyl-9H-carbazole (abbreviated as mDBTPPC-II), which is represented by the structural formula (160)), which is one of the carbazole compounds represented by the general formula (G1), is used as a material for a hole-transport layer adjacent to a light-emitting layer using an emission center substance that emits green phosphorescence.

Note that the molecular structures of organic compounds used in this example are shown in the following structural formulae (iii), (iv), (v), (vi), (172), and (160).

(172)

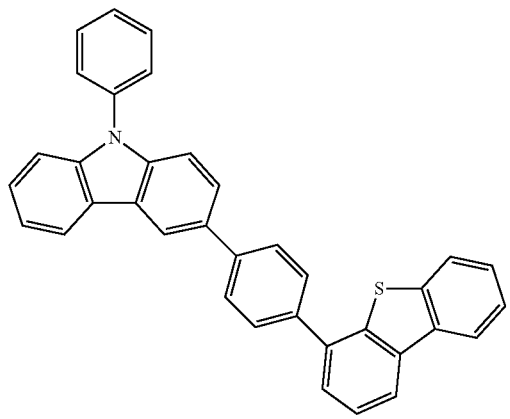

(160)

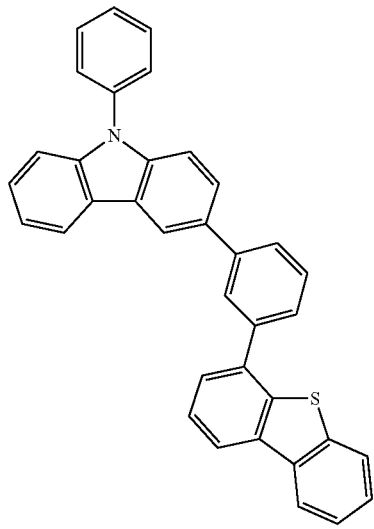

-continued (iv)

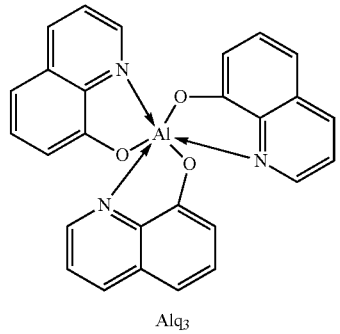

Alq₃

(v)

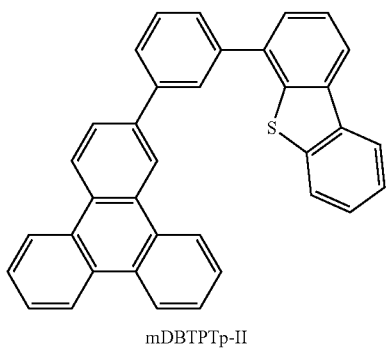

mDBTPTp-II (iii)

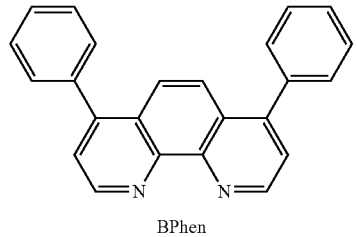

BPhen (vi)

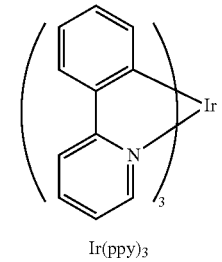

Ir(ppy)₃

In FIG. 1A, the element structure in which an electron-injection layer is provided between the electron-transport layer 114 and the second electrode 104 was employed. The element structures of the light-emitting elements 3 and 4 are shown below.

TABLE 5

| | First electrode | Hole injection layer | Hole transport layer | Light emitting layer | | Electron transport layer | Electron injection layer | Second electrode |
|---|---|---|---|---|---|---|---|---|
| Light emitting element 3 | ITSO 110 nm | DBTPPC-II:MoOx (=4:2) 50 nm | DBTPPC-II 10 nm | mDBTPTp-II:Ir(ppy)3 (=1:0.08) 10 nm | mDBTPTp-II:Ir(ppy)3 (=1:0.04) 30 nm | mDBTBIm-II 10 nm | BPhen 15 nm / LiF 1 nm | Al 200 nm |

TABLE 6

| | First electrode | Hole injection layer | Hole transport layer | Light emitting layer | | Electron transport layer | Electron injection layer | Second electrode |
|---|---|---|---|---|---|---|---|---|
| Light emitting element 4 | ITSO 110 nm | mDBTPPC-II:MoOx (=4:2) 50 nm | mDBTPPC-II 10 nm | mDBTPTp-II:Ir(ppy)3 (=1:0.08) 10 nm | mDBTPTp-II:Ir(ppy)3 (=1:0.04) 30 nm | mDBTBIm-II 10 nm | BPhen 15 nm / LiF 1 nm | Al 200 nm |

[Fabrication of Light-Emitting Element 3 and Light-Emitting Element 4]

First, a glass substrate 101 over which indium tin oxide containing silicon (ITSO) with a thickness of 110 nm had been formed as a first electrode 102 was prepared. The surface of the ITSO film excluding an area of 2 mm×2 mm was provided with a polyimide film in the peripheral portion of the area, and thereby the area of 2 mm×2 mm was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate 101 was fixed on a holder provided in the vacuum evaporation apparatus such that the surface of the substrate 101 provided with ITSO faced downward.

After the pressure in the vacuum evaporation apparatus was reduced to $10^{-4}$ Pa, as for the light-emitting element 3, a hole-injection layer 111 was formed by co-evaporation of DBTPPC-II, the carbazole compound represented by the above structural formula (172), which is described in Embodiment 1, and molybdenum(VI) oxide such that the ratio of DBTPPC-II:molybdenum(VI) oxide was 2:1 (mass ratio). As for the light-emitting element 4, after the pressure in the vacuum evaporation apparatus was reduced to $10^{-4}$ Pa, a hole-injection layer 111 was formed by co-evaporation of mDBTPPC-II, the carbazole compound represented by the above structural formula (160), which is described in Embodiment 1, and molybdenum(VI) oxide such that the ratio of mDBTPPC-II:molybdenum(VI) oxide was 2:1 (mass ratio). The thicknesses thereof were both 50 nm. Note that a co-evaporation method is an evaporation method in which a plurality of different substances are concurrently vaporized from respective different evaporation sources.

Next, DBTPPC-II was evaporated to a thickness of 10 nm, so that a hole-transport layer 112 was formed in the light-emitting element 3, while mDBTPPC-II was evaporated to a thickness of 10 nm, so that a hole-transport layer 112 was formed in the light-emitting element 4.

Further, for each of the light-emitting elements 3 and 4, the light-emitting layer 113 was formed on the hole-transport layer 112 in such a way that 4-[3-(triphenylene-2-yl)phenyl]dibenzothiophene (abbreviated as mDBTPTp-II) represented by the structural formula (v) and tris(2-phenylpyridinato)iridium(III) (abbreviated as Ir(ppy)₃) represented by the structural formula (vi) were evaporated to form a 10-nm-thick film such that the ratio of mDBTPTp-II to Ir(ppy)₃ was 1:0.08 (mass ratio) and then 4-[3-(triphenylene-2-yl)phenyl]dibenzothiophene (abbreviated as mDBTPTp-II) and tris(2-phenylpyridinato)iridium(III) (abbreviated as Ir(ppy)₃) were evaporated to form a 30-nm-thick film so that the ratio of mDBTPTp-II to Ir(ppy)₃ was 1:0.04 (mass ratio).

Next, on the light-emitting layer 113, Alq represented by the structural formula (Iv) was evaporated to a thickness of 10 nm, and then bathophenanthroline (abbreviated as BPhen) represented by the structural formula (iii) was evaporated to a thickness of 20 nm, so that the electron-transport layer 114 was formed. Further, lithium fluoride was evaporated to a thickness of 1 nm on the electron-transport layer 114, so that the electron-injection layer was formed. Lastly, a film of aluminum, was foamed to a thickness of 200 nm as a second electrode 104 which serves as a cathode, whereby each of the light-emitting elements 3 and 4 was fabricated. Note that in the above-described evaporation process, evaporation was all performed by a resistance heating method.

[Operation Characteristics of Light-Emitting Elements 3 and 4]

The light-emitting elements 3 and 4 obtained through the above-described steps were sealed in a glove box under a nitrogen atmosphere so as not to be exposed to atmospheric air. Then, the operation characteristics of the light-emitting elements 3 and 4 were measured. Note that the measurement was carried out at room temperature (in an atmosphere kept at 25° C.).

Figure 25:
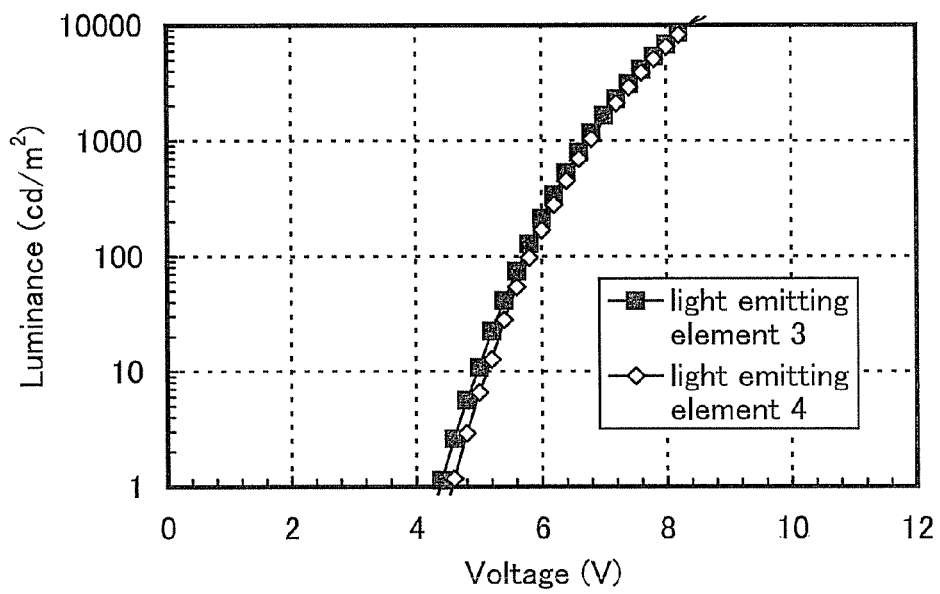
FIG. 25 shows luminance versus voltage characteristics of light-emitting elements 3 and 4.
Figure 26:
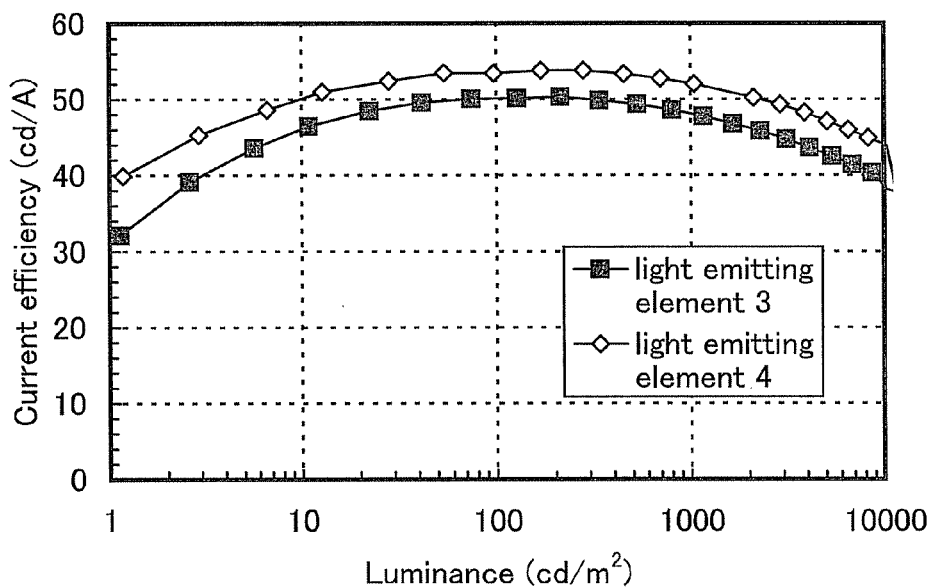
FIG. 26 shows current efficiency versus luminance characteristics of the light-emitting elements 3 and 4.
Figure 27:
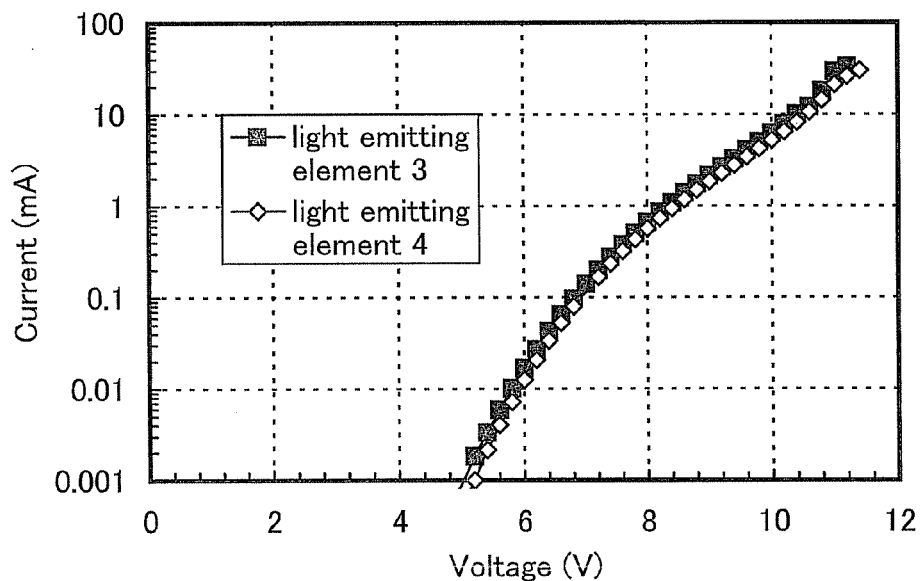
FIG. 27 shows current versus voltage characteristics of the light-emitting elements 3 and 4.

FIG. 25 shows luminance versus voltage characteristics of the light-emitting elements 3 and 4, FIG. 26 shows current efficiency versus luminance characteristics thereof, and FIG. 27 shows current versus voltage characteristics thereof.

FIG. 26 reveals that each of the light-emitting elements, in which the carbazole compound represented by the general formula (G1) is used as a material for the hole-transport layer in contact with the light-emitting layer for emitting green phosphorescence, has favorable emission efficiency versus luminance characteristics and high emission efficiency. This is because the carbazole compound represented by the general formula (G1) has a high T1 level, and thus transfer of excitation energy can be suppressed despite the adjacency to a light-emitting substance that emits green phosphorescence and has a high T1 level. In addition, FIG. 25 reveals that each of the light-emitting elements, in which the carbazole compound represented by the general formula (G1) is used as a material for the hole-transport layer adjacent to the light-emitting layer for emitting green phosphorescence, has favorable luminance versus voltage characteristics and can be driven with low voltage. This reveals that the carbazole compound represented by the general formula (G1) has an excellent carrier-transport property.

In addition, it was found that the hole-injection layer formed by co-evaporation of molybdenum oxide and the carbazole compound described in Embodiment 1 exhibited a good hole-injection property. This reveals that the composite material using the carbazole compound described in Embodiment 1 has a superior carrier-injection property.

Characteristics around 1000 cd/m$^2$ of the light-emitting elements 3 and 4 are shown below.

TABLE 7

| | Voltage (V) | Current (mA) | Chromaticity x | Chromaticity y | Y (Luminance (cd/m$^2$)) | Current Efficiency (cd/A) | Power Efficiency (lm/W) |
|---|---|---|---|---|---|---|---|
| Light emitting element 3 | 6.8 | 0.10 | 2.40 | 0.34 | 1200 | 48 | 22 |

TABLE 8

| | Voltage (V) | Current (mA) | Chromaticity x | Chromaticity y | Y (Luminance (cd/m$^2$)) | Current Efficiency (cd/A) | Power Efficiency (lm/W) |
|---|---|---|---|---|---|---|---|
| Light emitting element 4 | 6.8 | 0.08 | 2.00 | 0.33 | 1000 | 52 | 24 |

In addition, mDBTPPC-II in which the carbazole skeleton is bonded to the dibenzothiophene skeleton via arylene at a meta position provided a slightly more efficient element than DBTPPC-II in which the carbazole skeleton is bonded to the dibenzothiophene skeleton via arylene at a para position. It is thought that this is because mDBTPPC-II has a higher T1 level.

Figure 28:
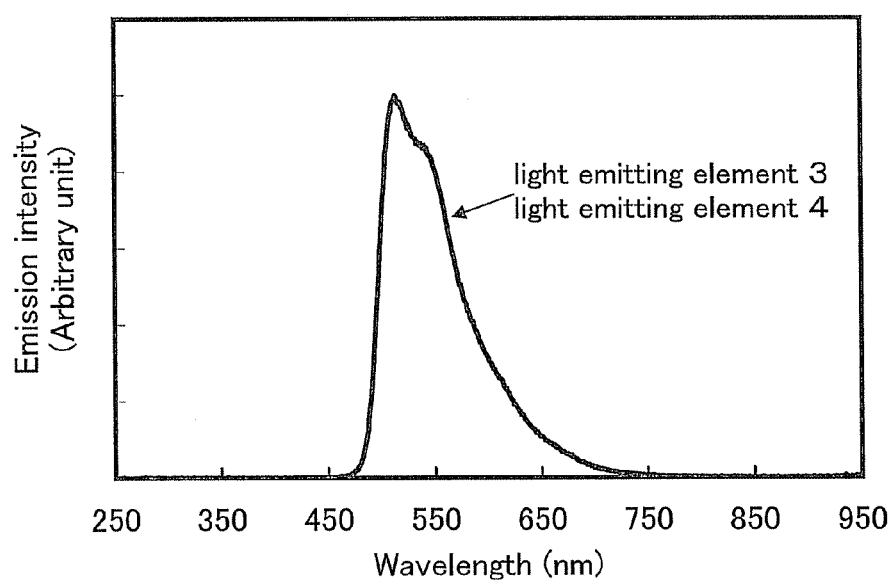
FIG. 28 shows emission spectra of the light-emitting elements 3 and 4.

FIG. 28 shows emission spectra when a current of 1 mA flowed in the fabricated light-emitting elements 3 and 4. In FIG. 28, the vertical axis represents emission intensity and the horizontal axis represents emission wavelength (nm). The emission intensity is shown as a value relative to the maximum emission intensity assumed to be 1. FIG. 28 reveals that the light-emitting elements 3 and 4 each emit green light originating from Ir(ppy)$_3$, which is the emission center substance.

Figure 29:
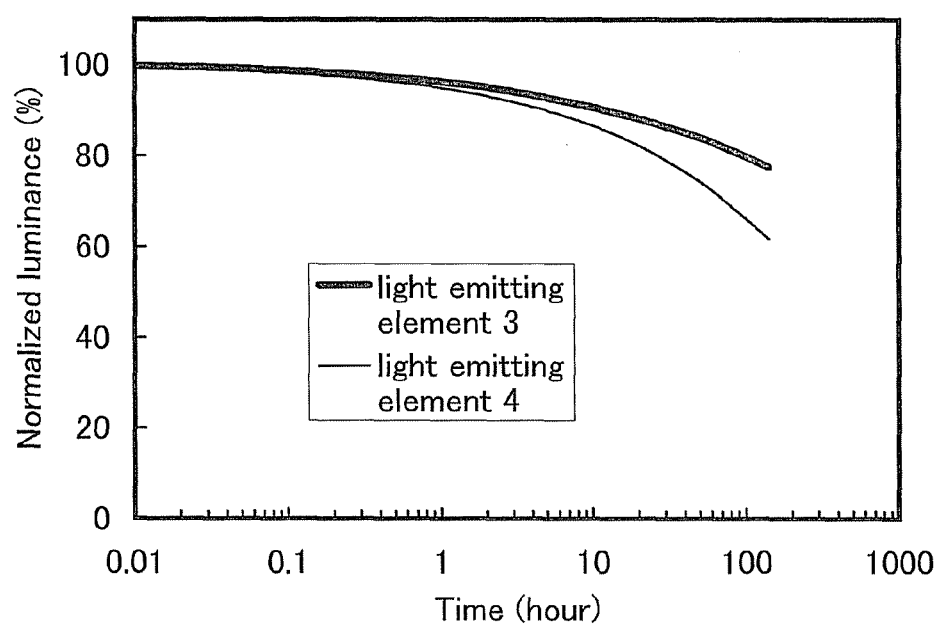
FIG. 29 shows normalized luminance versus time change characteristics of the light emitting elements 3 and 4.

Next, the initial luminance was set at 5000 cd/m$^2$, the element was driven under a condition where the current density was constant, and changes in luminance with respect to the driving time were examined. FIG. 29 shows normalized luminance versus time characteristics. From FIG. 29, it is found that each of the light-emitting elements 3 and 4 shows favorable characteristics and has high reliability.

In addition, DBTPPC-II in which the carbazole skeleton is bonded to the dibenzothiophene skeleton via arylene at a para position provided an element having slightly longer lifetime than mDBTPPC-II in which the carbazole skeleton is bonded to the dibenzothiophene skeleton via arylene at a meta position. It is thought that DBTPPC-II having a bond at the para position has a structure providing a higher reliability.

Example 8

In this example described is a light-emitting element in which 3-[4-(dibenzothiophen-4-yl)-phenyl]-9-phenyl-9H-carbazole (abbreviated as DBTPPC-II), which is represented by the structural formula (172)), which is one of the carbazole compounds represented by the general formula (G1), is used as a material for a hole-transport layer adjacent to a light-emitting layer using an emission center substance that emits blue phosphorescence.

The molecular structures of organic compounds used in this example are represented by the following structural formulae (iii), (vii), (viii), (ix), (x), and (172).

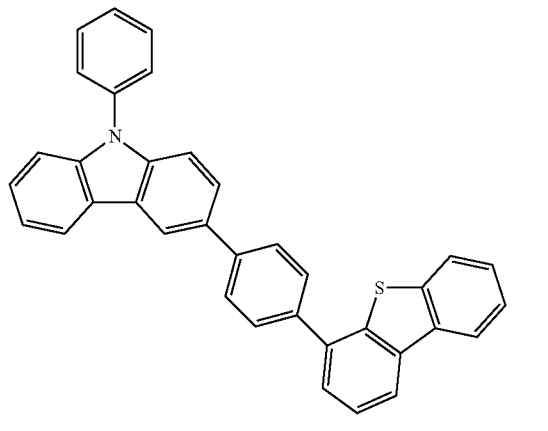

(172)

DBTPPC-II

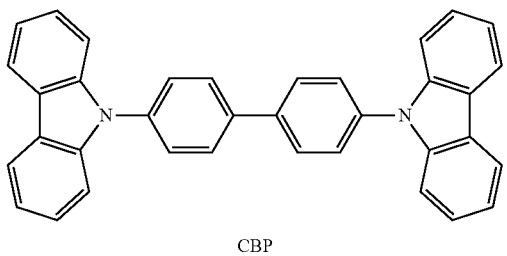

CBP (vii)

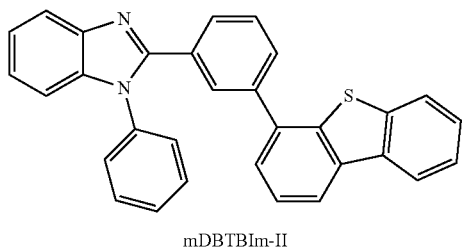

mDBTBIm-II (x)

mCP (viii)

BPhen (iii)

In FIG. 1A, the element structure in which an electron-injection layer is provided between the electron-transport layer 114 and the second electrode 104 was employed. The element structure of the light-emitting element 5 is shown below.

TABLE 9

| | First electrode | Hole injection layer | Hole transport layer | Light emitting layer | Electron transport layer | Electron injection layer | Second electrode |
|---|---|---|---|---|---|---|---|
| Light emitting element 5 | ITSO 110 nm | CBP:MoOx (=4:2) 50 nm | DBTPPC-II 10 nm | mCP:Ir(Mptz)3 (=1:0.08) 30 nm | mDBTBIm-II 10 nm | BPhen 15 nm | LiF 1 nm | Al 200 nm |

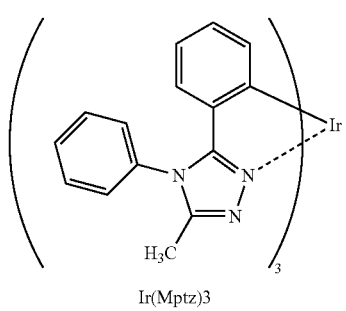

Ir(Mptz)3 (ix)

[Fabrication of Light-Emitting Element 5]

First, a glass substrate 101 over which indium tin oxide containing silicon (ITSO) with a thickness of 110 nm had been formed as a first electrode 102 was prepared. The surface of the ITSO film excluding an area of 2 mm×2 mm was provided with a polyimide film in the peripheral portion of the area, and thereby the area of 2 mm×2 mm was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate 101 was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 4,4'-di(N-carbazolyl)biphenyl (abbreviated as CBP) represented by the structural formula (vii) and molybdenum(VI) oxide such that the ratio of CBP:molybdenum(VI) oxide was 2:1 (mass ratio). The thickness thereof was 50 nm. Note that a co-evaporation method is an evaporation method in which a plurality of different substances are concurrently vaporized from respective different evaporation sources.

Next, DBTPPC-II represented by the structural formula (172) was evaporated to a thickness of 10 nm, so that a hole-transport layer 112 was formed.

Further, the light-emitting layer 113 was formed on the hole-transport layer 112 in such a way that 1,3-bis(N-carbazolyl)benzene (abbreviated as mCP) represented by the structural formula (viii) and tris(5-methyl-3,4-diphenyl-4H-1,2,4-triazolato)iridium(III) (abbreviated as [Ir(Mptz)$_3$])
represented by the structural formula (ix) were evaporated to form a 30-nm-thick film so that the ratio of mCP to [Ir(Mptz)$_3$] was 1:0.08 (mass ratio).

Then, the electron-transport layer 114 was formed on the light-emitting layer 113 in such a way that 2-[3-(dibenzothiophen-4-yl)phenyl]-1-phenyl-1H-benzimidazole (abbreviated as mDBTBIm-II) represented by the structural formula (x) was evaporated to form a 10-nm-thick film and bathophenanthroline (abbreviated as BPhen) represented by the structural formula (iii) was evaporated to form a 15-nm-thick film. After that, lithium fluoride was evaporated to a thickness of 1 nm on the electron-transport layer 114, so that the electron-injection layer was formed. Lastly, aluminum was formed with a thickness of 200 nm as the second electrode 104 which serves as a cathode, whereby the light-emitting element 5 was fabricated. Note that in the above-described evaporation process, evaporation was all performed by a resistance heating method.

[Operation Characteristics of Light-Emitting Element 5]

The thus obtained light-emitting element 5 was sealed in a glove box under a nitrogen atmosphere so as not to be exposed to air. Then, operation characteristics of the light-emitting element were measured. Note that the measurement was carried out at room temperature (in an atmosphere kept at 25° C.).

Figure 30:
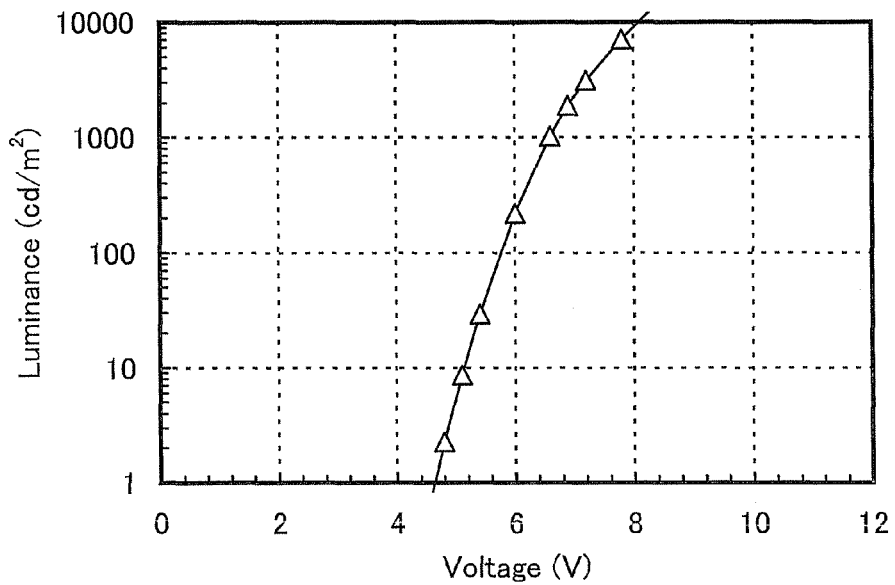
FIG. 30 shows luminance versus voltage characteristics of a light-emitting element 5.
Figure 31:
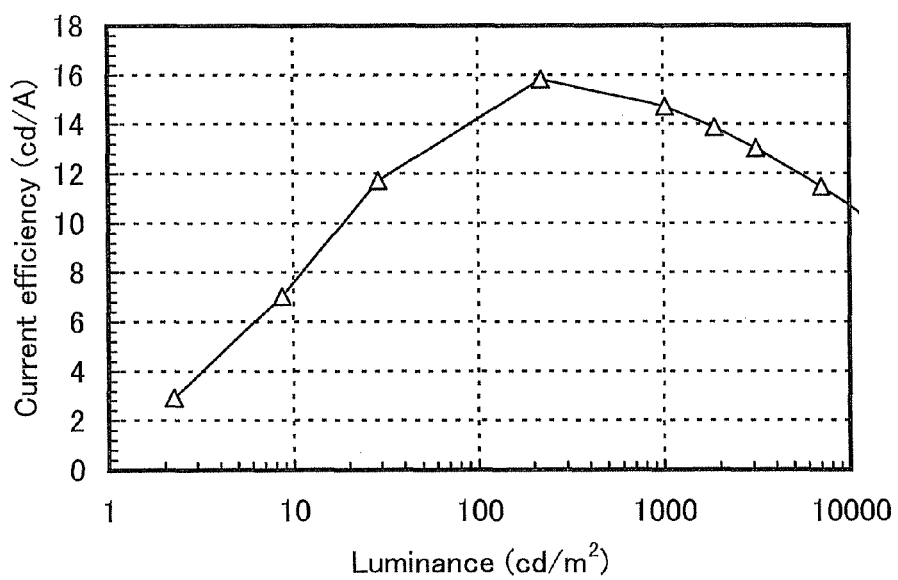
FIG. 31 shows current efficiency versus luminance characteristics of the light-emitting element 5.
Figure 32:
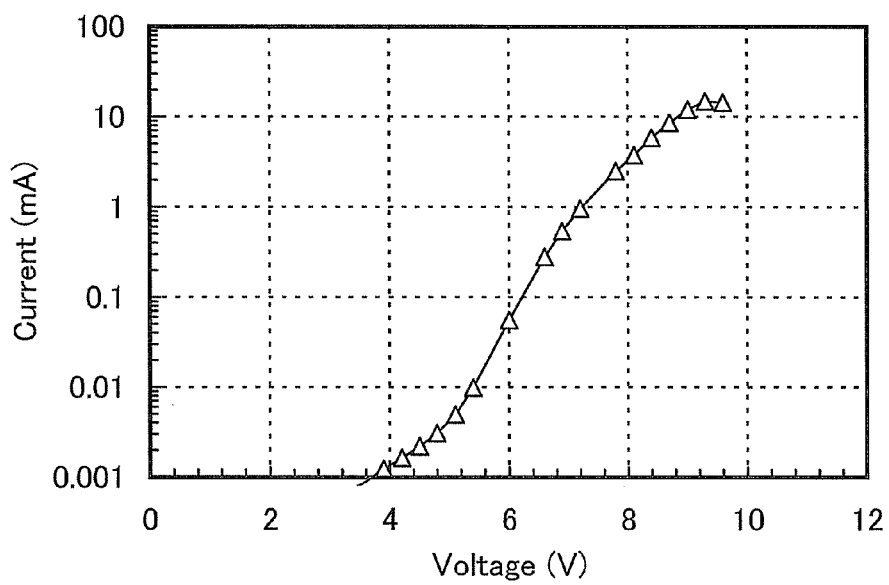
FIG. 32 shows current versus voltage characteristics of the light-emitting element 5.
Figure 33:
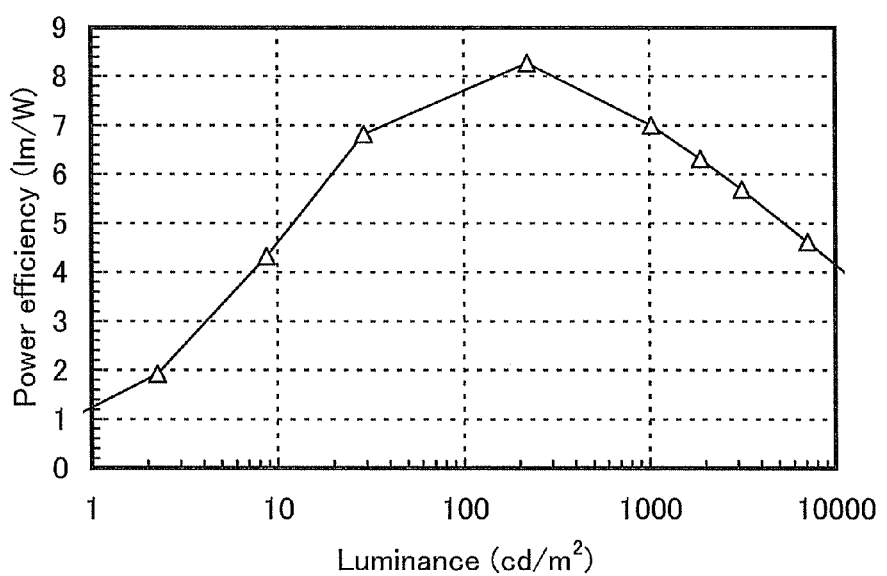
FIG. 33 shows power efficiency versus luminance characteristics of the light-emitting element 5.
Figure 34:
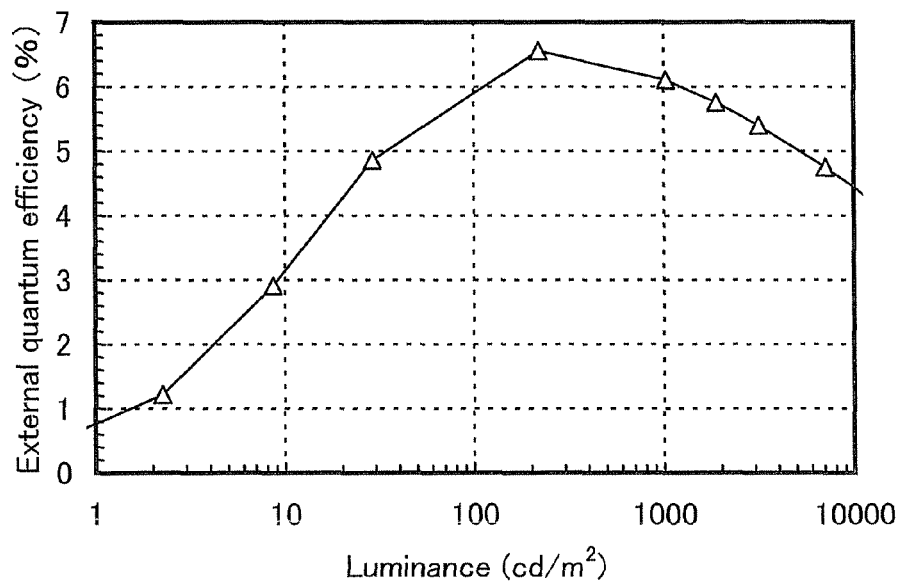
FIG. 34 shows external quantum efficiency versus luminance characteristics of the light-emitting element 5.

FIG. 30 shows luminance versus voltage characteristics of the light-emitting element 5, FIG. 31 shows current efficiency versus luminance characteristics thereof, FIG. 32 shows current versus voltage characteristics thereof, FIG. 33 shows power efficiency versus luminance characteristics thereof, and FIG. 34 shows external quantum efficiency versus luminance characteristics thereof.

FIG. 31 reveals that the light-emitting element, in which the carbazole compound represented by the general formula (G1) is used as a material for the hole-transport layer in contact with the light-emitting layer for emitting blue phosphorescence, has favorable emission efficiency versus luminance characteristics and high emission efficiency. This is because the carbazole compound represented by the general formula (G1) has a high T1 level, and thus transfer of excitation energy can be suppressed despite the adjacency to a light-emitting substance that emits blue phosphorescence and a high T1 level. In addition, FIG. 30 reveals that the light-emitting element, in which the carbazole compound represented by the general formula (G1) is used as a material for the hole-transport layer adjacent to the light-emitting layer for emitting blue phosphorescence, has favorable luminance versus voltage characteristics and can be driven with a low voltage. This reveals that the carbazole compound represented by the general formula (G1) has an excellent carrier-transport property. Further, FIG. 33 and FIG. 34 reveal that the light-emitting element 5 has excellent power efficiency versus luminance characteristics and excellent external quantum efficiency-luminance characteristics respectively.

Characteristics around 1000 cd/m$^2$ of the light-emitting element 5 are shown below.

TABLE 10

| | Voltage (V) | Current (mA) | Chromaticity x | Chromaticity y | Y (Luminance (cd/m$^2$)) | Current Efficiency (cd/A) | Power Efficiency (lm/W) | Quantum Efficiency (%) |
|---|---|---|---|---|---|---|---|---|
| Light emitting element 5 | 6.6 | 0.28 | 0.22 | 0.40 | 1000 | 15 | 7.0 | 6.1 |

Figure 35:
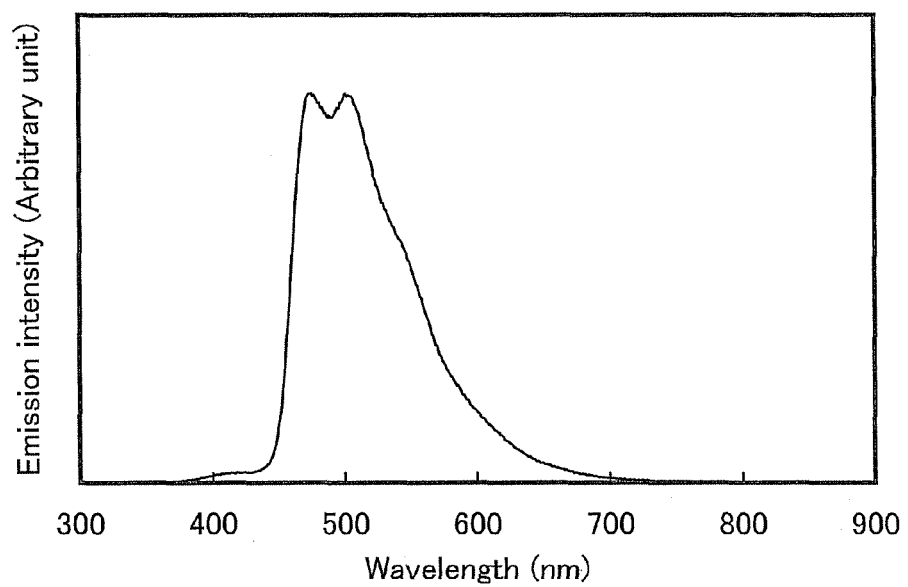
FIG. 35 shows an emission spectrum of the light-emitting element 5.

FIG. 35 shows an emission spectrum when a current of 1 mA flowed in the fabricated light-emitting element 5. The emission intensity is shown as a value relative to the maximum emission intensity assumed to be 1. FIG. 35 reveals that the light-emitting element 5 emits blue light originating from Ir(Mptz)$_3$, which is the emission center substance.

Example 9

In this example described is a light-emitting element in which 3,6-di-(dibenzothiophen-4-yl)-9-phenyl-9H-carbazole (abbreviated as DBT2PC-II, represented by the structural formula (150)), which is one of the carbazole compounds represented by the general formula (G1), is used as a material for a hole-transport layer adjacent to a light-emitting layer using an emission center substance that emits blue phosphorescence.

The molecular structures of organic compounds used in this example are represented by the structural formulae (iii), (vii), (viii), (ix), (x), and (150).

(150)

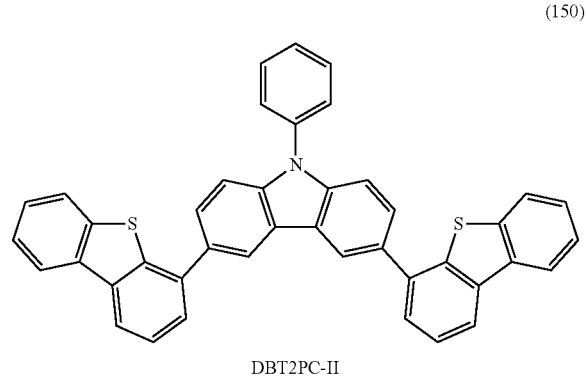

DBT2PC-II

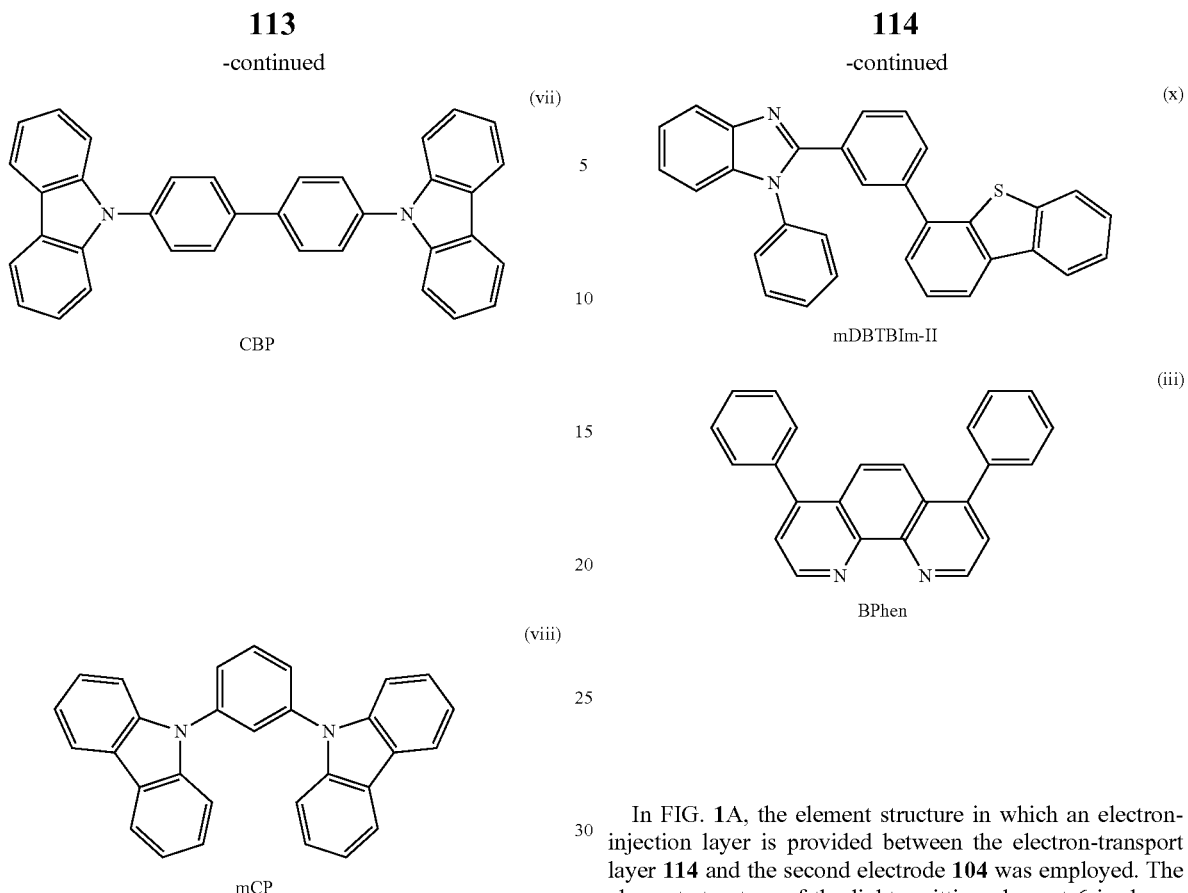

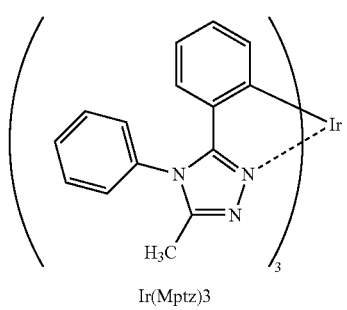

In FIG. 1A, the element structure in which an electron-injection layer is provided between the electron-transport layer 114 and the second electrode 104 was employed. The element structure of the light-emitting element 6 is shown below.

TABLE 11

| | First electrode | Hole injection layer | Hole transport layer | Light emitting layer | Electron transport layer | | Electron injection layer | Second electrode |
| --- | --- | --- | --- | --- | --- | --- | --- | --- |
| Light emitting element 6 | ITSO 110 nm | CBP:MoOx (=4:2) 50 nm | DBT2PC-II 10 nm | mCP:Ir(Mptz)3 (=1:0.08) 30 nm | mDBTBIm-II 10 nm | BPhen 15 nm | LiF 1 nm | Al 200 nm |

[Fabrication of Light-Emitting Element 6]

First, a glass substrate 101 over, which indium tin oxide containing silicon (ITSO) with a thickness of 110 nm had been formed as a first electrode 102 was prepared. The surface of the ITSO film excluding an area of 2 mm×2 mm was provided with a polyimide film in the peripheral portion of the area, and thereby the area of 2 mm×2 mm was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate 101 was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 4,4'-di(N-carbazolyl)biphenyl (abbreviated as CBP) represented by the structural formula (vii) and molybdenum(VI) oxide such that the ratio of CBP:molybdenum(VI) oxide was 2:1 (mass ratio). The thickness thereof was 50 nm. Note that a co-evaporation method is an evaporation method in which a plurality of different substances are concurrently vaporized from respective different evaporation sources.

Next, DBT2PC-II represented by the structural formula (150) was evaporated to a thickness of 10 nm, so that a hole-transport layer 112 was formed.

Further, the light-emitting layer 113 was formed on the hole-transport layer 112 in such a way that 1,3-bis(N-carbazolyl)benzene (abbreviated as mCP) represented by the structural formula (viii) and tris(5-methyl-3,4-diphenyl-4H-1,2,4-triazolato)iridium(III) (abbreviated as [Ir(Mptz)$_3$]) represented by the structural formula (ix) were evaporated to form a 30-nm-thick film such that the ratio of mCP to [Ir(Mptz)$_3$] was 1:0.08 (mass ratio).

because the carbazole compound represented by the general formula (G1) has a high T1 level, and thus transfer of excitation energy can be suppressed despite the adjacency to a light-emitting substance that emits blue phosphorescence and has a high T1 level. In addition, FIG. 36 reveals that the light-emitting element, in which the carbazole compound represented by the general formula (G1) is used as a material for the hole-transport layer adjacent to the light-emitting layer for emitting blue phosphorescence, has favorable luminance versus voltage characteristics and can be driven with low voltage. This reveals that the carbazole compound represented by the general formula (G1) has an excellent carrier-transport property. Further, FIG. 39 and FIG. 40 reveal that light-emitting element 6 has excellent power efficiency versus luminance characteristics and excellent external quantum efficiency versus luminance characteristics respectively.

Characteristics around 1000 cd/m$^2$ of the light-emitting element 6 are shown below.

TABLE 12

| | Voltage (V) | Current (mA) | Chromaticity x | Chromaticity y | Y (Luminance (cd/m$^2$)) | Current Efficiency (cd/A) | Power Efficiency (lm/W) | Quantum Efficiency (%) |
|---|---|---|---|---|---|---|---|---|
| Light emitting element 6 | 6.3 | 0.08 | 0.22 | 0.41 | 590 | 29 | 14 | 12 |

Then, the electron-transport layer 114 was formed on the light-emitting layer 113 in such a way that 2-[3-(dibenzothiophen-4-yl)phenyl]-1-phenyl-1H-benzimidazole (abbreviated as mDBTBIm-II) represented by the structural formula (x) was evaporated to form a 10-nm-thick film and bathophenanthroline (abbreviated as BPhen) represented by the structural formula (iii) was evaporated to form a 15-nm-thick film. After that, lithium fluoride was evaporated to a thickness of 1 nm on the electron-transport layer 114, so that the electron-injection layer was formed. Lastly, a film of aluminum was formed with a thickness of 200 nm as the second electrode 104 which serves as a cathode, whereby the light-emitting element 6 was fabricated. Note that in the above-described evaporation process, evaporation was all performed by a resistance heating method.

[Operation Characteristics of Light-Emitting Element 6]

The thus obtained light-emitting element 6 was sealed in a glove box under a nitrogen atmosphere so as not to be exposed to air. Then, operation characteristics of the light-emitting element were measured. Note that the measurement was carried out at room temperature (in an atmosphere kept at 25° C.).

Figure 36:
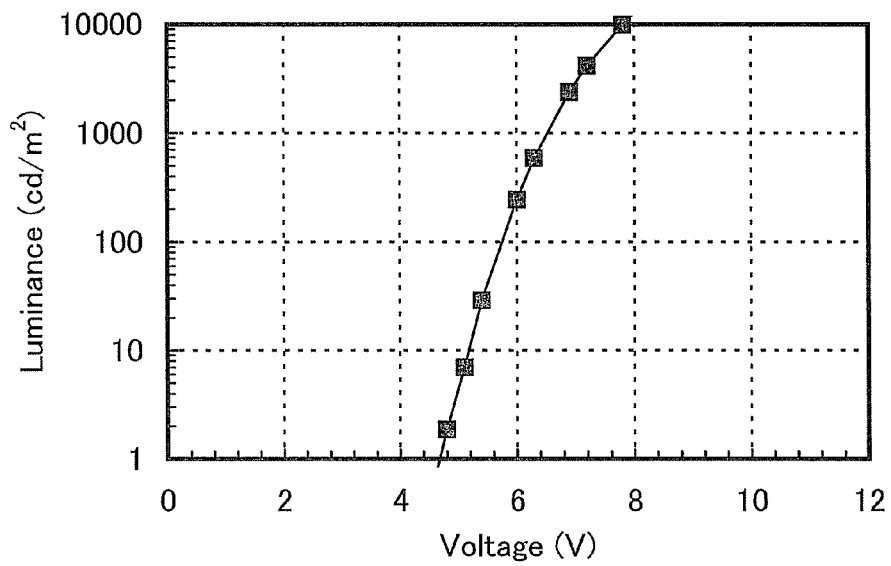
FIG. 36 shows luminance versus voltage characteristics of a light-emitting element 6.
Figure 37:
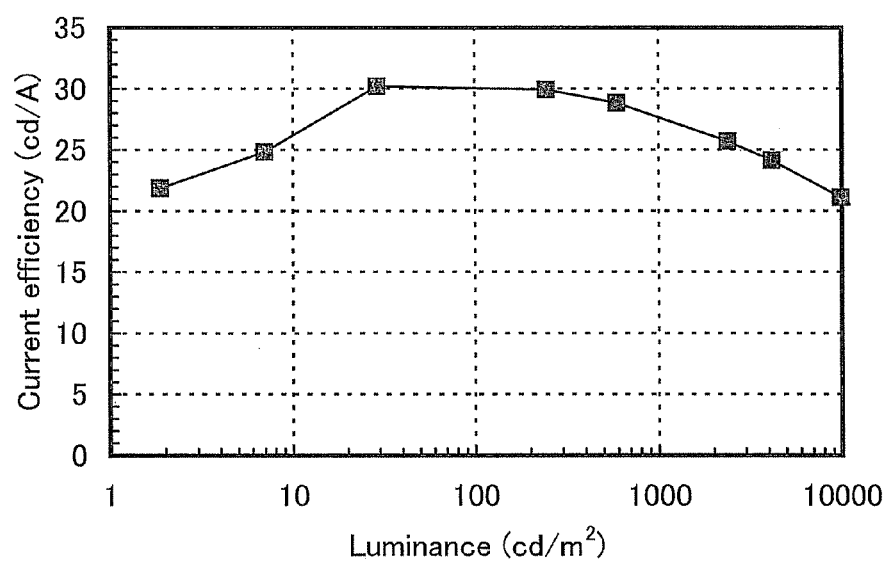
FIG. 37 shows current efficiency versus luminance characteristics of the light-emitting element 6.
Figure 38:
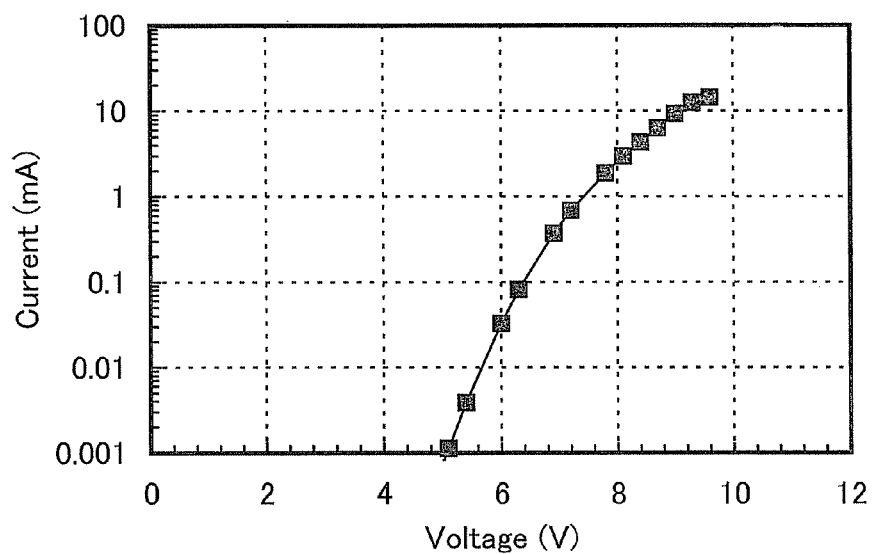
FIG. 38 shows current versus voltage characteristics of the light-emitting element 6.
Figure 39:
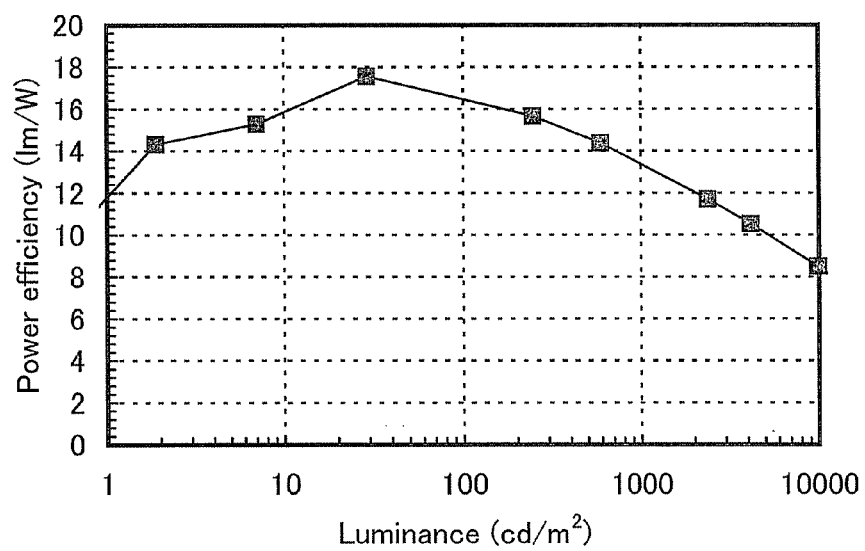
FIG. 39 shows power efficiency versus luminance characteristics of the light-emitting element 6.
Figure 40:
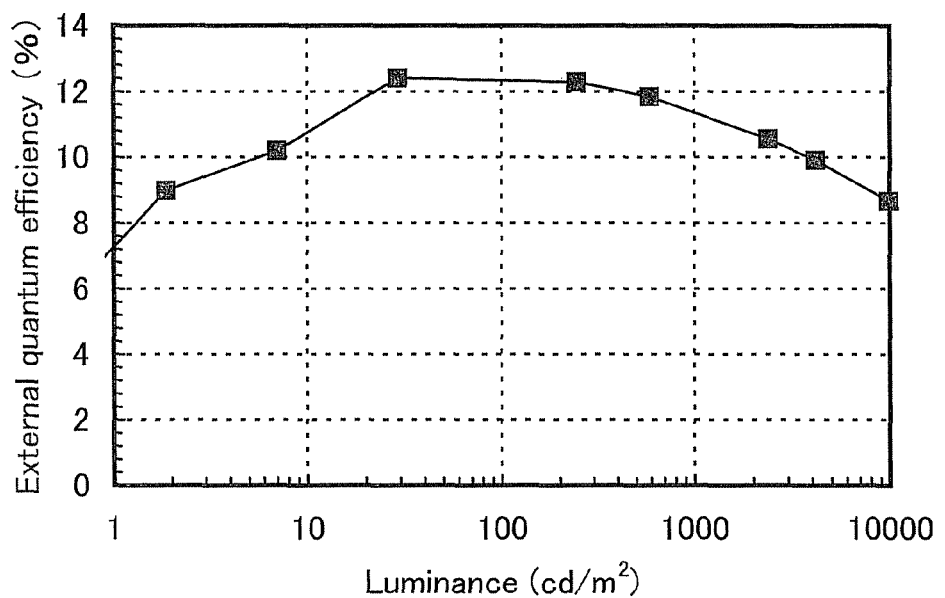
FIG. 40 shows external quantum efficiency versus luminance characteristics of the light-emitting element 6.

FIG. 36 shows luminance versus voltage characteristics of the light-emitting element 6, FIG. 37 shows current efficiency versus luminance characteristics thereof, FIG. 38 shows current versus voltage characteristics thereof, FIG. 39 shows power efficiency versus luminance characteristics thereof, and FIG. 40 shows external quantum efficiency-luminance characteristics thereof.

Figure 41:
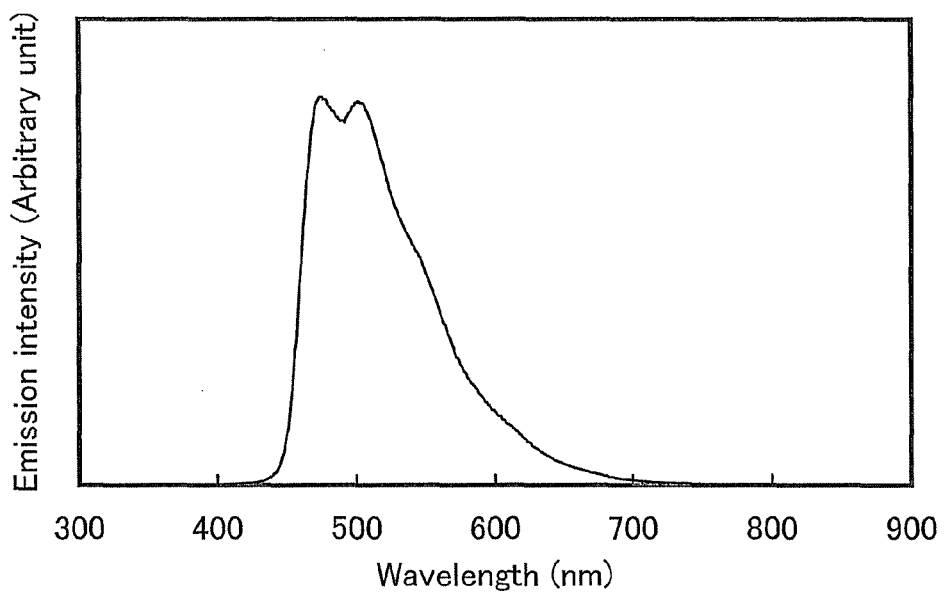
FIG. 41 is a graph showing an emission spectrum of the light-emitting element 6.

FIG. 37 reveals that the light-emitting element, in which the carbazole compound represented by the general formula (G1) is used as a material for the hole-transport layer in contact with the light-emitting layer for emitting blue phosphorescence, has favorable emission efficiency versus luminance characteristics and high emission efficiency. This is FIG. 41 shows an emission spectrum when a current of 1 mA flowed in the fabricated light-emitting element 6. In FIG. 41, the vertical axis represents emission intensity and the horizontal axis represents wavelength (nm). The emission intensity is shown as a value relative to the maximum emission intensity assumed to be 1. FIG. 41 reveals that the light-emitting element 6 emits blue light originating from Ir(Mptz)$_3$, which is the emission center substance.

In addition, the element in which the carbazole compound (DBT2PC-II), which is one embodiment of the present invention, was used for the hole-transport layer exhibited especially favorable emission efficiency. One of the reasons is that the 4-position of dibenzothiophene is directly bonded to the 3-position and the 6-position of the carbazole and thus especially high T1 level is obtained.

Example 10

In this example described is a light-emitting element in which 2,7-di-(dibenzothiophen-4-yl)-9-phenyl-9H-carbazole (abbreviated as 2,7DBT2PC-II, a structural formula (154)), which is one of the carbazole compounds represented by the general formula (G1), is used as a material for a hole-transport layer adjacent to a light-emitting layer using an emission center substance that emits blue phosphorescence.

The molecular structures of organic compounds used in this example are represented by the following structural formulae (iii), (vii), (viii), (ix), (x), and (154).

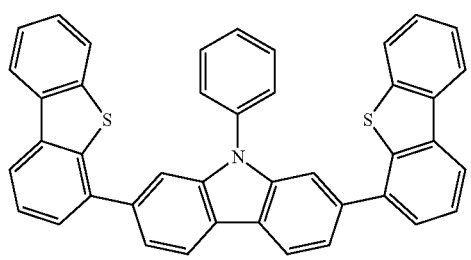

2,7DBT2PC-II (154)

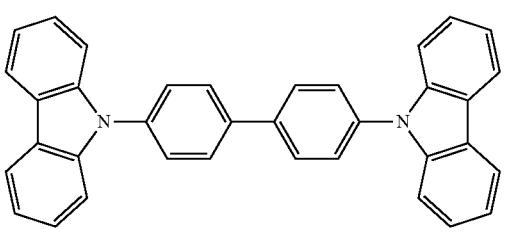

CBP (vii)

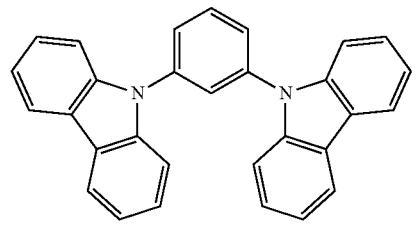

mCP (viii)

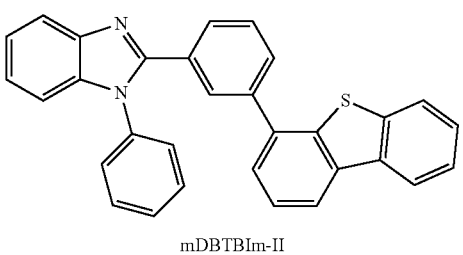

mDBTBIm-II (x)

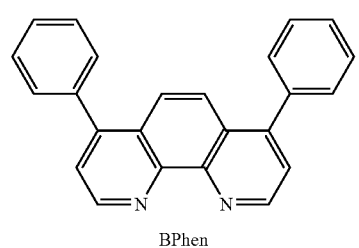

BPhen (iii)

In FIG. 1A, the element structure in which an electron-injection layer is provided between the electron-transport layer 114 and the second electrode 104 was employed. The element structure of the light-emitting element 7 is shown below.

TABLE 13

| | First electrode | Hole injection layer | Hole transport layer | Light emitting layer | Electron transport layer | Electron injection layer | Second electrode |
|---|---|---|---|---|---|---|---|
| Light emitting element 7 | ITSO 110 nm | CBP:MoOx (=4:2) 50 nm | 2,7DBT2PC-II 10 nm | mCP:Ir(Mptz)3 (=1:0.08) 30 nm | mDBTBIm-II 10 nm | BPhen 15 nm | LiF 1 nm | Al 200 nm |

-continued

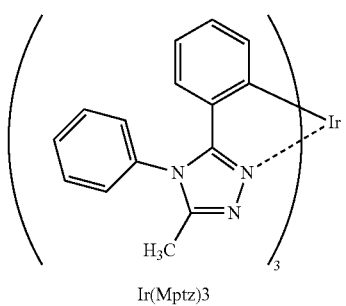

Ir(Mptz)3 (ix)

[Fabrication of Light-Emitting Element 7]

First, a glass substrate 101 over which indium tin oxide containing silicon (ITSO) with a thickness of 110 nm had been formed as a first electrode 102 was prepared. The surface of the ITSO film excluding an area of 2 mm×2 mm was provided with a polyimide film in the peripheral portion of the area, and thereby the area of 2 mm×2 mm was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate 101 was fixed on a holder provided in the vacuum evaporation apparatus such that the surface of the substrate 101 provided with ITSO faced downward.

After the pressure in the vacuum evaporation apparatus was reduced to 10⁻⁴ Pa, a hole-injection layer 111 was formed by co-evaporation of 4,4'-di(N-carbazolyl)biphenyl (abbreviated as CBP) represented by the structural formula (vii) and molybdenum(VI) oxide such that the ratio of CBP:molybdenum(VI) oxide was 2:1 (mass ratio). The thickness thereof was 50 nm. Note that a co-evaporation method is an evaporation method in which a plurality of different substances are concurrently vaporized from respective different evaporation sources.

Next, 2,7DBT2PC-II represented by the structural formula (154) was evaporated to a thickness of 10 nm, so that a hole-transport layer 112 was formed.

Further, the light-emitting layer 113 was formed on the hole-transport layer 112 in such a way that 1,3-bis(N-carbazolyl)benzene (abbreviated as mCP) represented by the structural formula (viii) and tris(5-methyl-3,4-diphenyl-4H-1,2,4-triazolato)iridium(III) (abbreviated as [Ir(Mptz)$_3$]) represented by the structural formula (ix) were evaporated to form a 30-nm-thick film so that the ratio of mCP to [Ir(Mptz)$_3$] was 1:0.08 (mass ratio).

Then, the electron-transport layer 114 was formed on the light-emitting layer 113 in such a way that 2-[3-(dibenzothiophen-4-yl)phenyl]-1-phenyl-1H-benzimidazole (abbreviated as mDBTBIm-II) represented by the structural formula (x) was evaporated to form a 10-nm-thick film and bathophenanthroline (abbreviated as BPhen) represented by the structural formula (iii) was evaporated to form a 15-nm-thick film. After that, lithium fluoride was evaporated to a thickness of 1 nm on the electron-transport layer 114, so that the electron-injection layer was formed. Lastly, aluminum was formed with a thickness of 200 nm as the second electrode 104 which serves as a cathode, whereby the light-emitting element 7 was fabricated. Note that in the above-described evaporation process, evaporation was all performed by a resistance heating method.

[Operation Characteristics of Light-Emitting Element 7]

The thus obtained light-emitting element 7 was sealed in a glove box under a nitrogen atmosphere so as not to be exposed to air. Then, operation characteristics of the light-emitting element were measured. Note that the measurement was carried out at room temperature (in an atmosphere kept at 25° C.).

Figure 42:
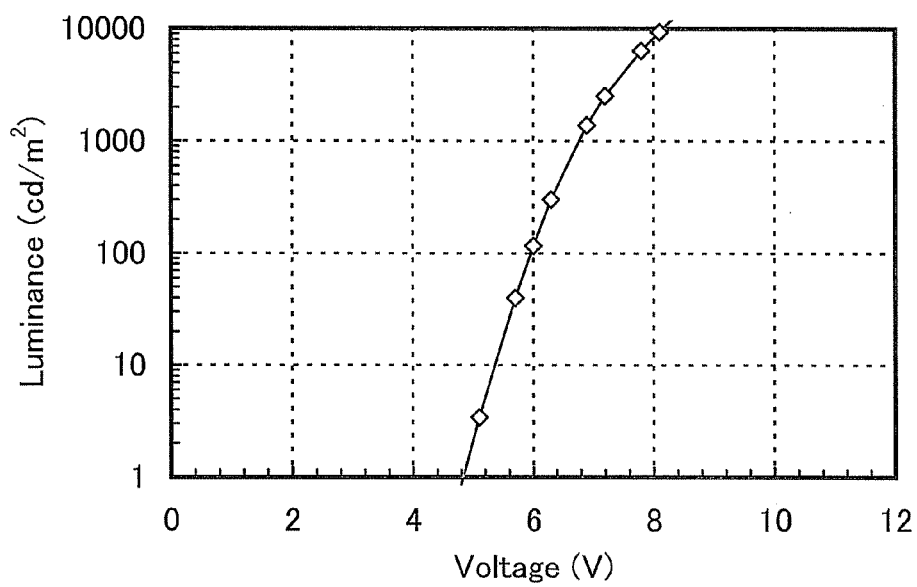
FIG. 42 shows luminance versus voltage characteristics of a light-emitting element 7.
Figure 43:
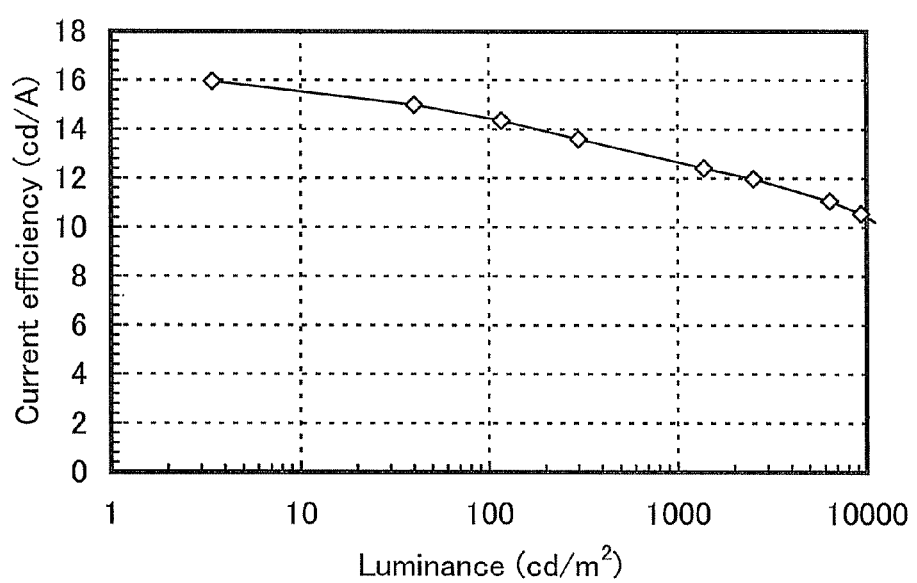
FIG. 43 shows current efficiency versus luminance characteristics of the light-emitting element 7.
Figure 44:
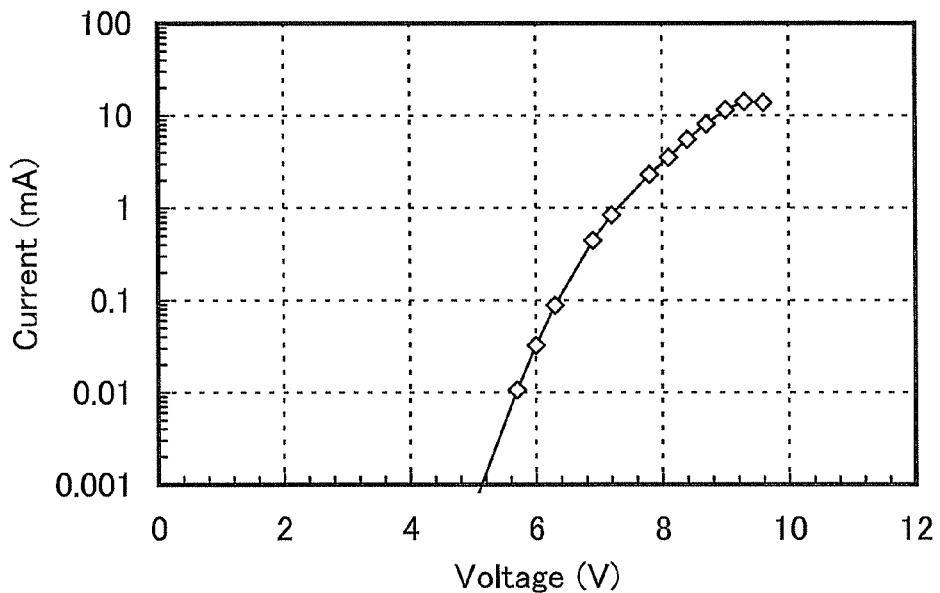
FIG. 44 shows current versus voltage characteristics of the light-emitting element 7.
Figure 45:
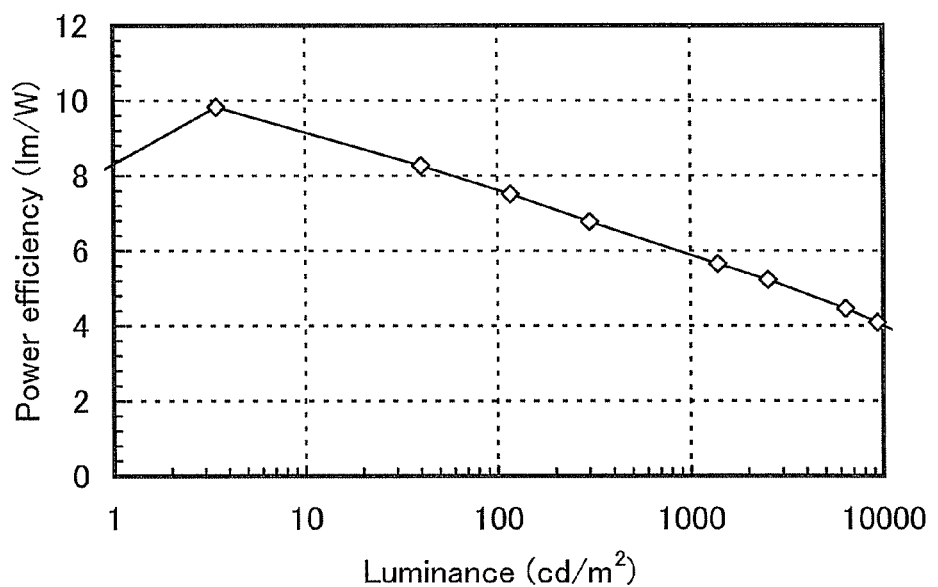
FIG. 45 shows power efficiency versus luminance characteristics of the light-emitting element 7.
Figure 46:
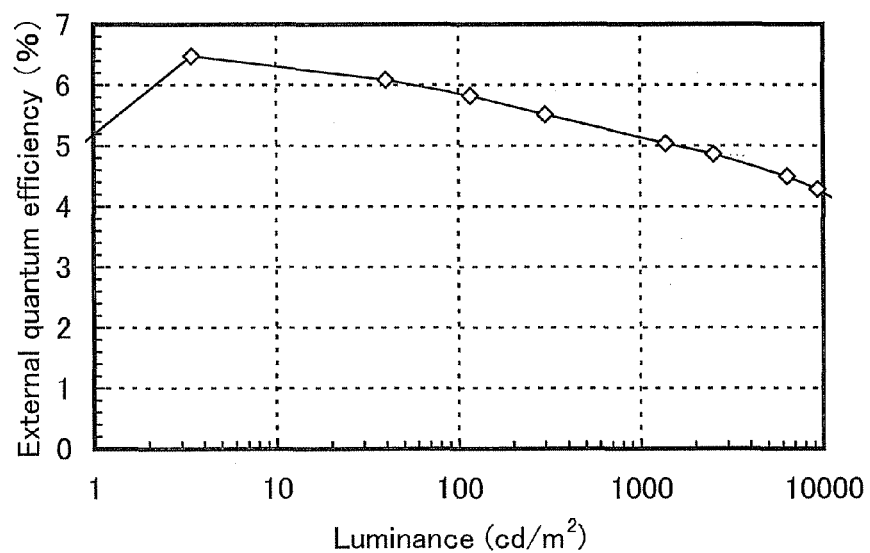
FIG. 46 shows external quantum efficiency versus luminance characteristics of the light-emitting element 7.

FIG. 42 shows luminance versus voltage characteristics of the light-emitting element 7, FIG. 43 shows current efficiency versus luminance characteristics thereof, FIG. 44 shows current versus voltage characteristics thereof, FIG. 45 shows power efficiency versus luminance characteristics thereof, and FIG. 46 shows external quantum efficiency-luminance characteristics thereof.

FIG. 43 reveals that the light-emitting element, in which the carbazole compound represented by the general formula (G1) is used as a material for the hole-transport layer in contact with the light-emitting layer for emitting blue phosphorescence, has favorable emission efficiency versus luminance characteristics and high emission efficiency. This is because the carbazole compound represented by the general formula (G1) has a high T1 level, and thus transfer of excitation energy can be suppressed despite the adjacency to a light-emitting substance that emits blue phosphorescence and has a high T1 level. In addition, FIG. 42 reveals that the light-emitting element, in which the carbazole compound represented by the general formula (G1) is used as a material for the hole-transport layer adjacent to the light-emitting layer for emitting blue phosphorescence, has favorable luminance versus voltage characteristics and can be driven with low voltage. This reveals that the carbazole compound represented by the general formula (G1) has an excellent carrier-transport property. Further, FIG. 45 and FIG. 46 reveal that light-emitting element 7 has excellent power efficiency versus luminance characteristics and excellent external quantum efficiency versus luminance characteristics respectively.

Characteristics around 1000 cd/m² of the light-emitting element 7 are shown below.

TABLE 14

| | Voltage (V) | Current (mA) | Chromaticity x | Chromaticity y | Y (Luminance (cd/m²)) | Current Efficiency (cd/A) | Power Efficiency (lm/W) | Quantum Efficiency (%) |
|---|---|---|---|---|---|---|---|---|
| Light emitting element 7 | 6.9 | 0.44 | 0.22 | 0.41 | 1400 | 12 | 5.7 | 5.0 |

Figure 47:
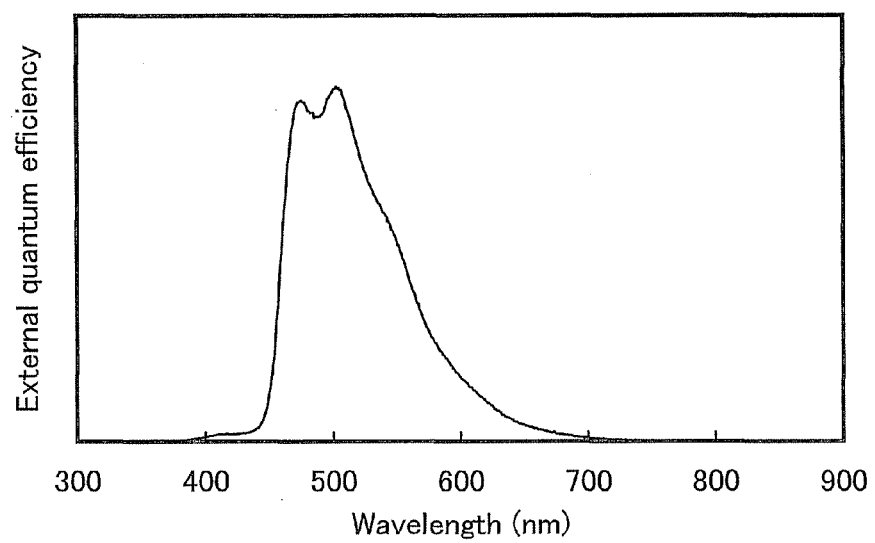
FIG. 47 shows an emission spectrum of the light-emitting element 7.

FIG. 47 shows an emission spectrum when a current of 1 mA flowed in the fabricated light-emitting element 7. The emission intensity is shown as a value relative to the maximum emission intensity assumed to be 1. FIG. 47 reveals that the light-emitting element 7 emits blue light originating from Ir(Mptz)$_3$, which is the emission center substance.

Example 11

Synthesis Example 5

In this example is described a method of synthesizing 3,6-di(dibenzofuran-4-yl)-9-phenyl-9H-carbazole (abbreviated as DBF2PC-II), which is one of the carbazole compounds described in Embodiment 1. A structure of DBF2PC-II is shown in the following structural formula (208).

(208)

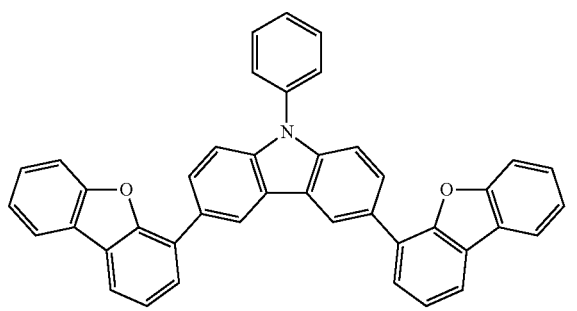

Synthesis Method of 3,6-di(dibenzofuran-4-yl)-9-phenyl-9H-carbazole (abbreviated as DBF2PC-II)

To a 200-mL three-neck flask were added 2.0 g (5.0 mmol) of 3,6-dibromo-9-phenyl-9H-carbazole, 3.2 g (11 mmol) of dibenzofuran-4-boronic acid, 10 mg (0.1 mmol) of palladium (II) acetate, 30 mg (0.1 mmol) of tris(o-tolyl)phosphine, 50 mL of toluene, 5 mL of ethanol, and 7.5 mL of a 2 mol/L aqueous potassium carbonate solution. This mixture was degassed while being stirred under reduced pressure, and then heated and stirred at 90° C. for 6.5 hours under a nitrogen stream to be reacted.

After the reaction, 250 mL of toluene was added to this reaction mixture and the mixture was heated. The mixture was filtered through Celite (produced by Wako Pure Chemical Industries, Ltd., Catalog No. 531-16855), alumina, and Florisil (produced by Wako Pure Chemical Industries, Ltd., Catalog No. 540-00135) in this order to give a filtrate. The resulting filtrate was purified by silica gel column chromatography (a developing solvent in which the toluene/hexane ratio was 1:3). The obtained fraction was concentrated, acetone, methanol, and water were added thereto, and the mixture was irradiated with ultrasonic waves. Then, acetone and methanol were added to the obtained precipitate and the mixture was irradiated with ultrasonic waves, filtrated, washed, and dried. Thereby, 2.8 g of a target substance, white powder, was obtained in 69% yield. A reaction scheme of the above synthesis method is illustrated in the following (E-1).

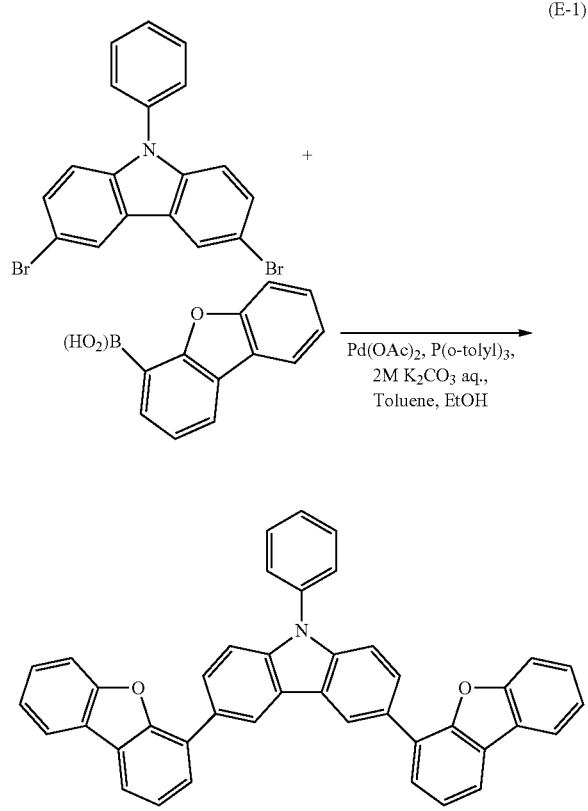

(E-1)

The Rf values of the white powder obtained through the reaction and 3,6-dibromo-9-phenyl-9H-carbazole were respectively 0.32 and 0.55, which were found by silica gel thin layer chromatography (TLC) (a developing solvent in which the ethyl acetate/hexane ratio was 1:10).

Figure 49A:
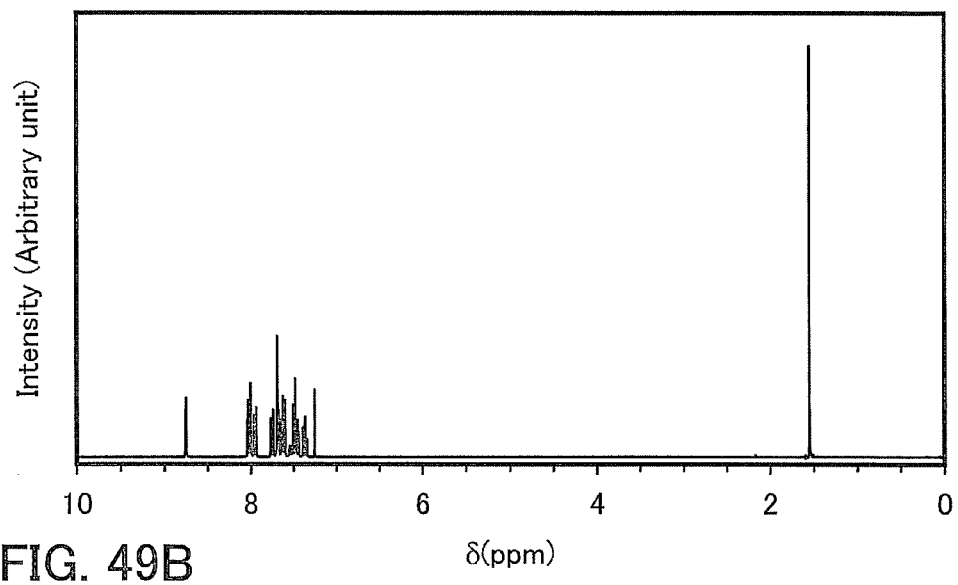
FIGS. 49A and 49B are $^1$H NMR charts of DBF2PC-II.
Figure 49B:
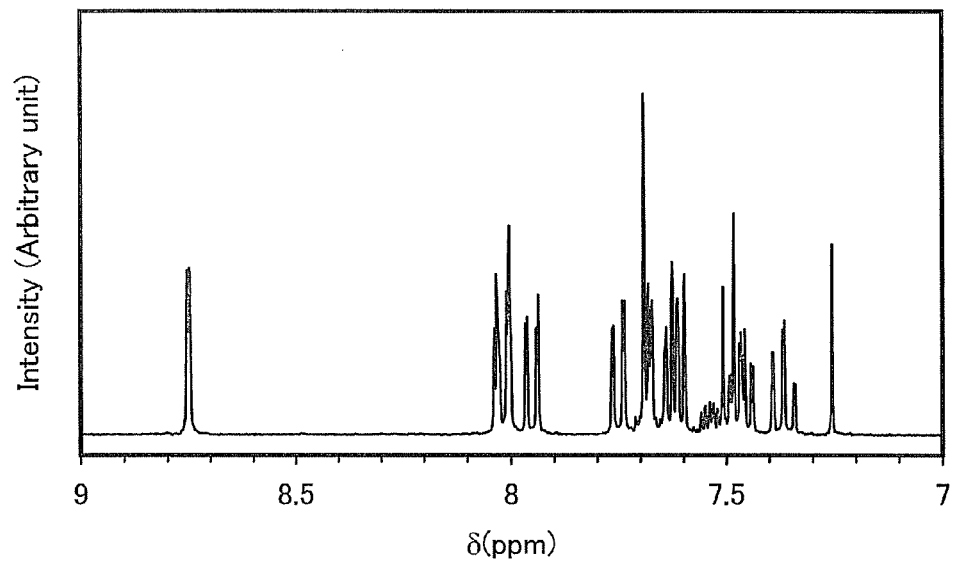

The white powder obtained by the step 1 was subjected to nuclear magnetic resonance (NMR) spectroscopy. The measurement data are shown below. FIGS. 49A and 49B show the $^1$H NMR charts. Note that FIG. 49B is an enlarged chart of FIG. 49A. By the measurement results, it was confirmed that the white powder obtained by the step 1 was DBF2PC-II, which is represented by the structural formula (208).

$^1$H NMR (CDCl$_3$, 300 M Hz): δ (ppm)=7.37 (dt, J=7.8 Hz, J=1.2 Hz, 2H), 7.44-7.56 (m, 5H), 7.60-7.69 (m, 8H), 7.75 (dd, J=7.2 Hz, J=1.5 Hz, 2H), 7.95 (dd, J=7.8 Hz, J=1.5 Hz, 2H), 8.00-8.04 (m, 4H), 8.75 (d, J=1.5 Hz, 2H).

Figure 50A:
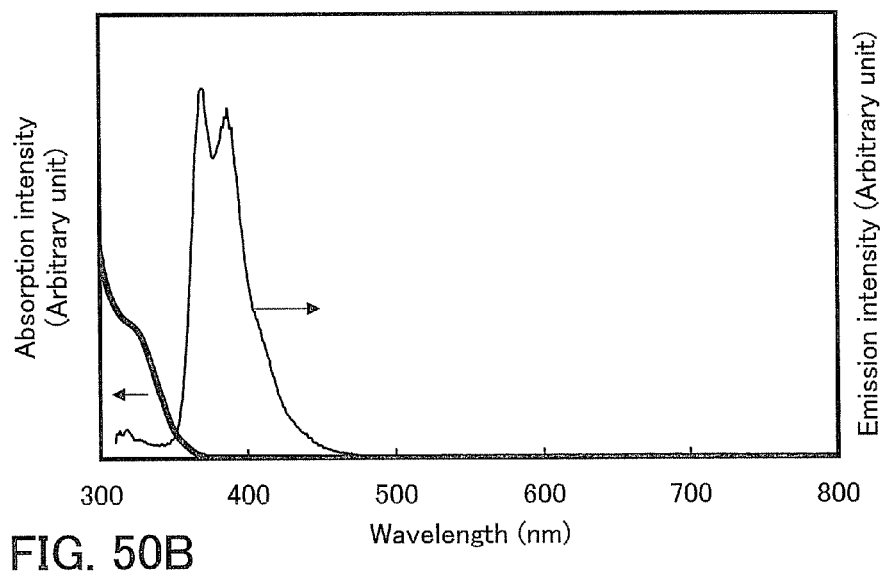
FIGS. 50A and 50B show an absorption spectrum and an emission spectrum of DBF2PC-II.
Figure 50B:
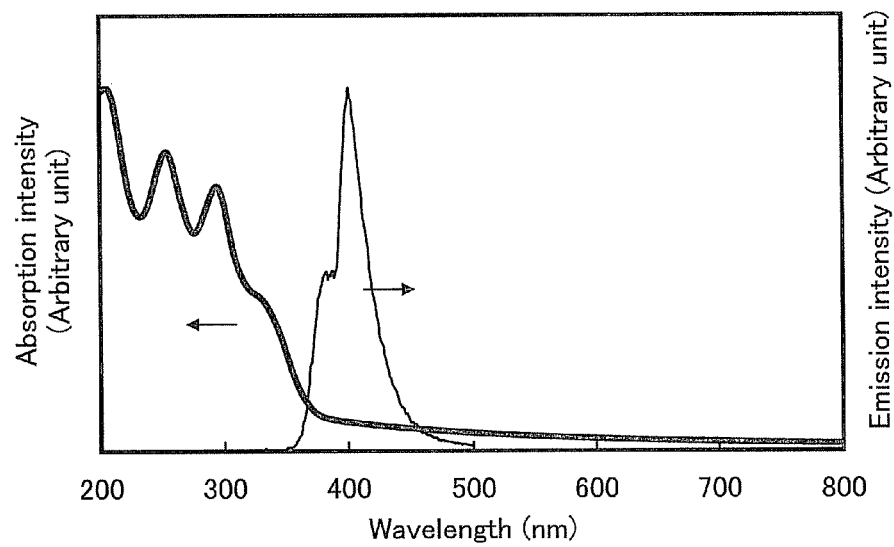

Further, an absorption spectrum and an emission spectrum of DBF2PC-II in a toluene solution of DBF2PC-II are shown in FIG. 50A, and an absorption spectrum and an emission spectrum of a thin film of DBF2PC-II are shown in FIG. 50B. The measurement of the spectra was performed using an ultraviolet-visible spectrophotometer (V-550, manufactured by JASCO Corporation). The spectra of the toluene solution were measured with a toluene solution of DBF2PC-II put in a quartz cell. The spectra of the thin film were measured with a sample prepared by evaporation of DBF2PC-II on a quartz substrate. Note that as the absorption spectrum of the toluene solution, the absorption spectrum obtained by subtraction of the absorption spectra of quartz and toluene from the measured spectra is shown in the graph, and as the absorption spectrum of the thin film, the absorption spectrum obtained by subtraction of that of quartz from the measured spectra is shown in the graph.

FIGS. 50A and 50B show that the maximum absorption wavelength of DBF2PC-II in the toluene solution of DBF2PC-II was around 320 nm, the maximum emission wavelengths thereof were around 370 nm and 387 nm (at an excitation wavelength of 290 nm), the maximum absorption wavelengths of the thin film of DBF2PC-II were around 325 nm, 294 nm, 253 nm, and 205 nm, and the maximum emission wavelengths thereof were around 401 nm and 382 nm (at an excitation wavelength of 325 nm).

The absorption spectra reveal that DBF2PC-II described in this example is a material that shows almost no absorption in the visible region. Further, the emission spectra reveal that the light emission is bluish purple.

Further, the ionization potential of DBF2PC-II in a thin film state was measured by a photoelectron spectrometer (AC-2, manufactured by Riken Keiki, Co., Ltd.) in air. The obtained value of the ionization potential was converted to a negative value, so that the HOMO level of DBF2PC-II was −5.67 eV. From the data of the absorption spectra of the thin film in FIGS. 50A and 50B, the absorption edge of DBF2PC-II, which was obtained from Tauc plot with an assumption of direct transition, was 3.40 eV. Therefore, the optical band gap of DBF2PC-II in the solid state was estimated at 3.40 eV; from the values of the HOMO level obtained above and this band gap, the LUMO level of DBF2PC-II was estimated at −2.27 eV. It was thus found that DBF2PC-II had a wide band gap of 3.40 eV in the solid state and also had a relatively deep HOMO level.

Further, thermophysical properties of DBF2PC-II were measured with a differential scanning calorimeter (DSC, manufactured by PerkinElmer, Inc., Pyris 1). First, a sample was heated from −10° C. up to 350° C. at a temperature rising rate of 40° C./min, and then it was cooled down to −10° C. at 40° C./min. After that, the sample was heated up to 290° C. at a temperature rising rate of 10° C./min, and thus a DSC chart was obtained. As can be seen from the DSC chart, a peak indicating the glass transition temperature of DBF2PC-II was observed, which showed the glass transition temperature (Tg) was 131° C. Thus, DBF2PC-II had a high glass transition point. Therefore, it was confirmed that DBF2PC-II of this synthesis example had high heat resistance.

Example 12

In this example described is a light-emitting element in which 3,6-di(dibenzofuran-4-yl)-9-phenyl-9H-carbazole (abbreviated as DBF2PC-II, the structural formula (208)), which is one of the carbazole compounds represented by the general formula (G1), is used as a material for a hole-transport layer adjacent to a light-emitting layer using an emission center substance that emits blue fluorescence.

The molecular structures of organic compounds used in this example are represented by the following structural formulae (208), (i), (iii) and (xi).

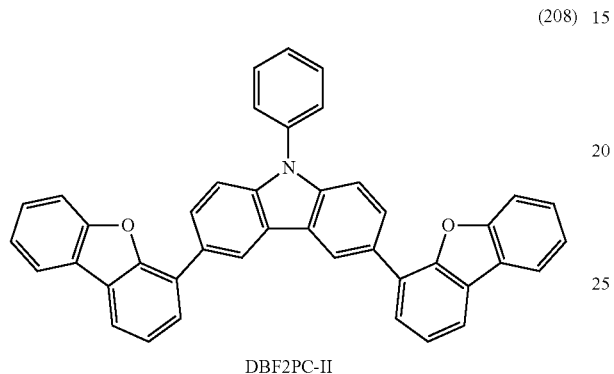

DBF2PC-II (208)

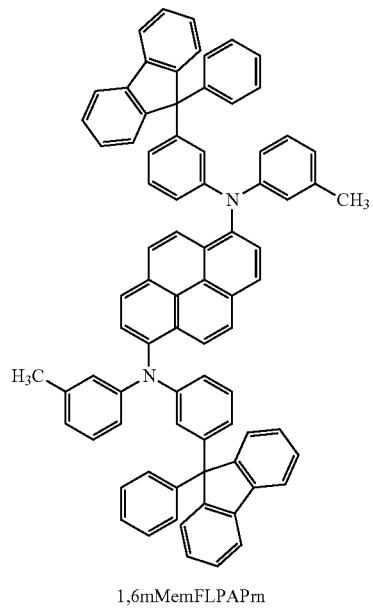

1,6mMemFLPAPrn (xi)

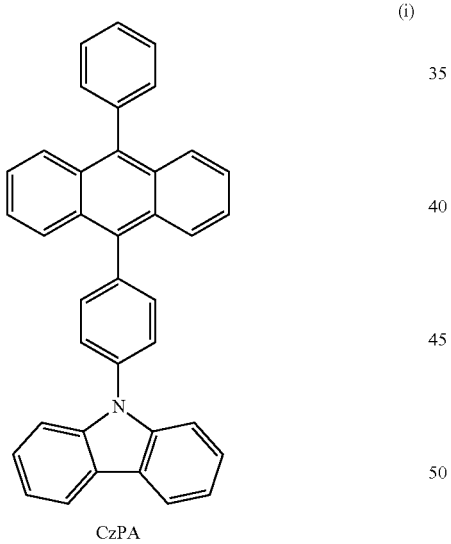

CzPA (i)

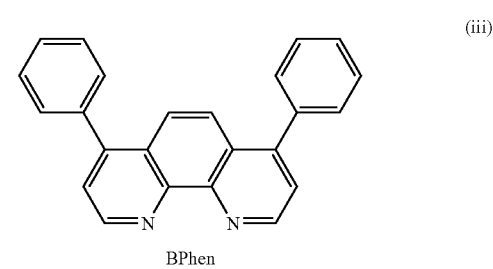 [SMILES: c1ccc(-c2ccnc3c2ccc2c(-c4ccccc4)ccnc23)cc1]

BPhen (iii)

In FIG. 1A, the element structure in which an electron-injection layer is provided between the electron-transport layer 114 and the second electrode 104 was employed. The element structure of the light-emitting element 8 is shown below.

TABLE 15

| | First electrode | Hole injection layer | Hole transport layer | Light emitting layer | Electron transport layer | | Electron injection layer | Second electrode |
|---|---|---|---|---|---|---|---|---|
| Light emitting element 8 | ITSO 110 nm | DBF2PC-II:MoOx (=4:2) 50 nm | DBF2PC-II 10 nm | CzPA:1,6mMmFLAPrn (=1:0.05) 30 nm | CzPA 10 nm | BPhen 15 nm | LiF 1 nm | Al 200 nm |

[Fabrication of Light-Emitting Element 8]

First, a glass substrate 101 over which indium tin oxide containing silicon (ITSO) with a thickness of 110 nm had been formed as a first electrode 102 was prepared. The surface of the ITSO film excluding an area of 2 mm×2 mm was provided with a polyimide film in the peripheral portion of the area, and thereby the area of 2 mm×2 mm was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate 101 was fixed on a holder provided in the vacuum evaporation apparatus such that the surface of the substrate 101 provided with ITSO faced downward.

After the pressure in the vacuum evaporation apparatus was reduced to $10^{-4}$ Pa, a hole-injection layer 111 was formed by co-evaporation of 3,6-di(dibenzofuran-4-yl)-9-phenyl-9H-carbazole (abbreviated as DBF2PC-II) represented by the structural formula (208) and molybdenum(VI) oxide such that the ratio of DBF2PC-II:molybdenum(VI) oxide was 2:1 (mass ratio). The thickness thereof was 50 nm. Note that a co-evaporation method is an evaporation method in which a plurality of different substances are concurrently vaporized from respective different evaporation sources.

Next, DBF2PC-II was evaporated to a thickness of 10 nm, so that a hole-transport layer 112 was formed.

Further, the light-emitting layer 113 was formed on the hole-transport layer 112 in such a way that 9-[4-(10-phenyl-9-anthryl)phenyl]-9H-carbazole (abbreviated as CzPA) represented by the structural formula (i) and N,N'-bis(3-methylphenyl)-N,N'-bis[3-(9-phenyl-9H-fluoren-9-yl)phenyl]-pyrene-1,6-diamine (abbreviated as 1,6mMemFLPAPrn) represented by the structural formula (xi) were evaporated to form a 30-nm-thick film so that the ratio of CzPA to 1,6mMemFLPAPrn was 1:0.05 (mass ratio).

Next, on the light-emitting layer 113, CzPA was evaporated to a thickness of 10 nm, and then bathophenanthroline (abbreviated as BPhen) represented by the structural formula (iii) was evaporated to a thickness of 15 nm, so that the electron-transport layer 114 was formed. Then, lithium fluoride was evaporated to a thickness of 1 nm on the electron-transport layer 114, so that the electron-injection layer was formed. Lastly, an aluminum film was formed to a thickness of 200 nm as the second electrode 104 functioning as a cathode, so that the light-emitting element 8 was fabricated. Note that in the above-described evaporation process, evaporation was all performed by a resistance heating method.

[Operation Characteristics of Light-Emitting Element 8]

The thus obtained light-emitting element 8 was sealed in a glove box under a nitrogen atmosphere so as not to be exposed to air. Then, operation characteristics of this light-emitting element were measured. Note that the measurement was carried out at room temperature (in an atmosphere kept at 25° C.).

Figure 51:
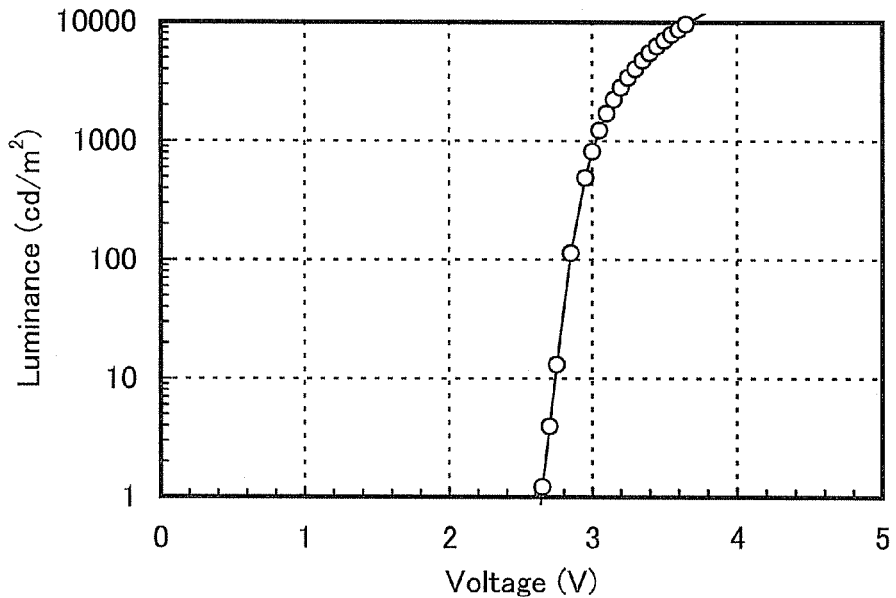
FIG. 51 shows luminance versus voltage characteristics of a light-emitting element 8.
Figure 52:
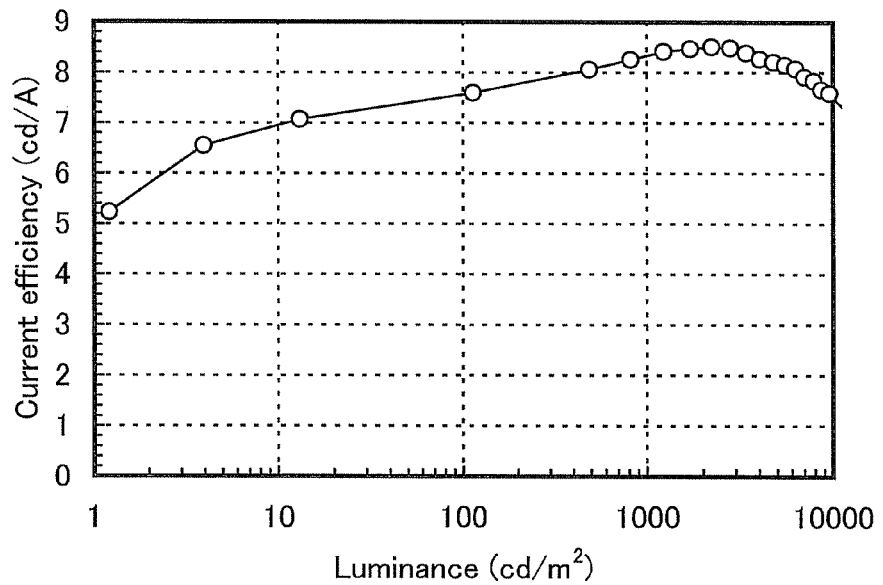
FIG. 52 shows current efficiency versus luminance characteristics of the light-emitting element 8.
Figure 53:
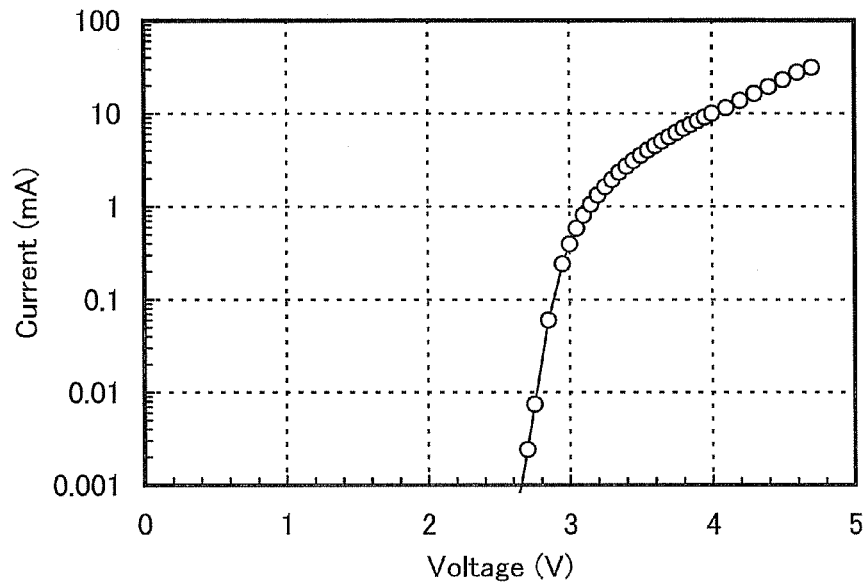
FIG. 53 shows current versus voltage characteristics of the light-emitting element 8.
Figure 54:
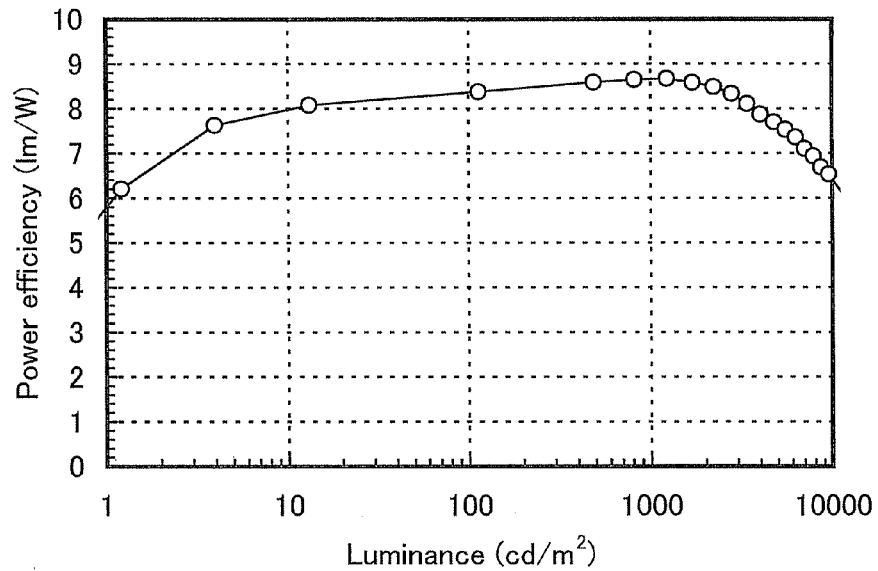
FIG. 54 shows power efficiency versus luminance characteristics of the light-emitting element 8.
Figure 55:
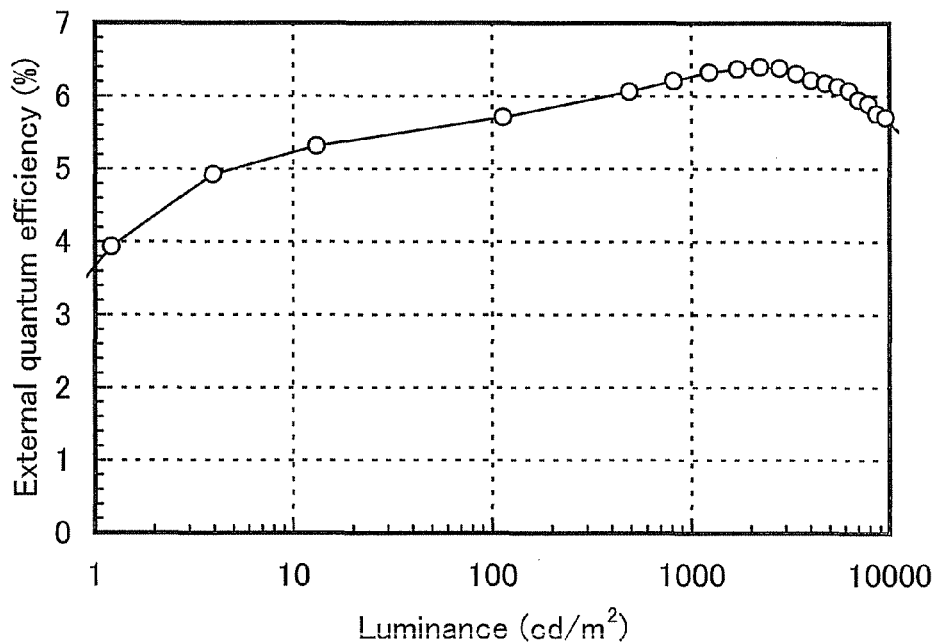
FIG. 55 shows external quantum efficiency versus luminance characteristics of the light-emitting element 8.

FIG. 51 shows luminance versus voltage characteristics of the light-emitting element 8, FIG. 52 shows current efficiency versus luminance characteristics thereof, FIG. 53 shows current versus voltage characteristics thereof, FIG. 54 shows power efficiency versus luminance characteristics thereof, and FIG. 55 shows external quantum efficiency versus luminance characteristics thereof.

FIG. 52 reveals that the light-emitting element, in which the carbazole compound represented by the general formula (G1) is used as a material for the hole-transport layer in contact with the light-emitting layer for emitting blue fluorescence, has favorable current efficiency versus luminance characteristics and high emission efficiency. This is because the carbazole compound represented by the general formula (G1) has a high T1 level, and thus transfer of excitation energy can be suppressed despite the adjacency to a light-emitting substance that emits blue fluorescence and has a wide energy gap. In addition, FIG. 51 reveals that the light-emitting element, in which the carbazole compound represented by the general formula (G1) is used as a material for the hole-transport layer adjacent to the light-emitting layer for emitting blue fluorescence, has favorable luminance versus voltage characteristics and can be driven with low voltage. This reveals that the carbazole compound represented by the general formula (G1) has an excellent carrier-transport property. Further, FIG. 54 and FIG. 55 reveal that light-emitting element 8 has excellent power efficiency versus luminance characteristics and excellent external quantum efficiency versus luminance characteristics respectively.

Characteristics around 1000 cd/m$^2$ of the light-emitting element 8 are shown below.

TABLE 16

| | Voltage (V) | Current (mA) | Chromaticity x | Chromaticity y | Y (Luminance (cd/m$^2$)) | Current Efficiency (cd/A) | Power Efficiency (lm/W) | Quantum Efficiency (%) |
|---|---|---|---|---|---|---|---|---|
| Light emitting element 8 | 3.0 | 0.4 | 0.14 | 0.19 | 816 | 8 | 8.6 | 6.2 |

Figure 56:
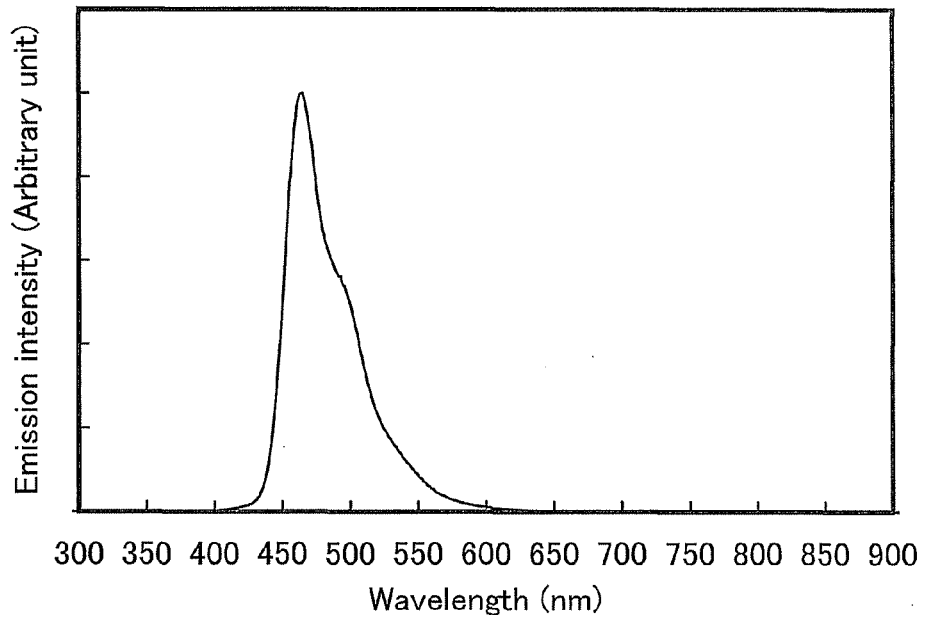
FIG. 56 shows an emission spectrum of the light-emitting element 8.

FIG. 56 shows an emission spectrum when a current of 1 mA flowed in the fabricated light-emitting element 8. The emission intensity is shown as a value relative to the maximum emission intensity assumed to be 1. FIG. 56 reveals that the light-emitting element 8 emits blue light originating from 1,6mMemFLPAPrn, which is the emission center substance.

Figure 57:
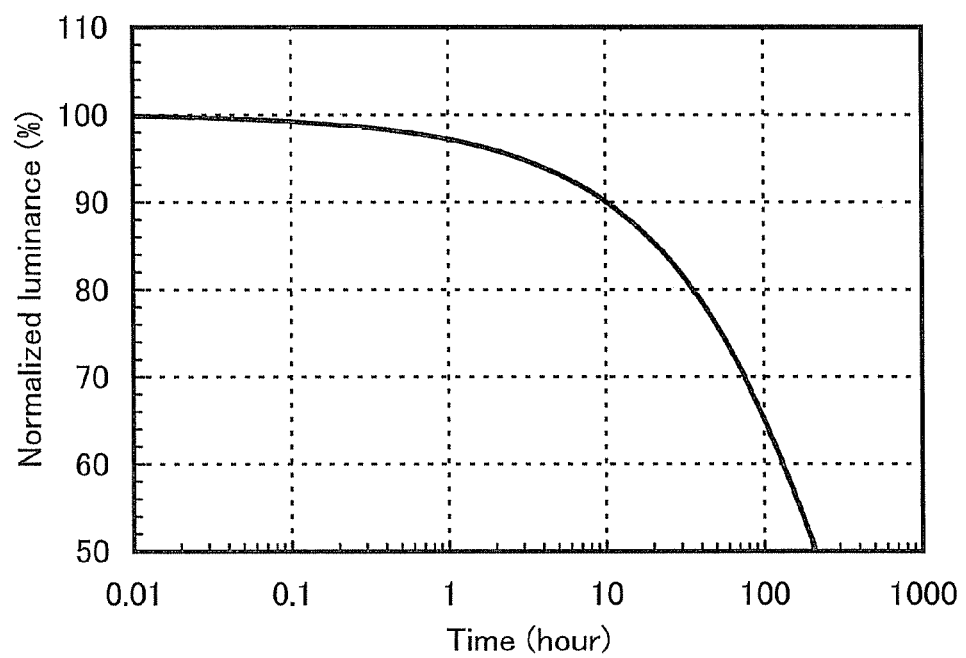
FIG. 57 shows normalized luminance versus time change characteristics of the light-emitting element 8.

Next, the initial luminance was set at 5000 cd/m$^2$, the element was driven under a condition where the current density was constant, and changes in luminance with respect to the driving time were examined. FIG. 57 shows normalized luminance versus time characteristics. From FIG. 57, it is found that the light-emitting element 8 shows favorable characteristics and has high reliability.

Reference Example 1

A method of synthesizing N,N'-bis[4-(9-phenyl-9H-fluoren-9-yl)phenyl]-N,N'-diphenyl-pyrene-1,6-diamine (abbreviated as 1,6FLPAPrn) (structural formula (vi)) used in Examples described above will be specifically described.

Step 1: synthesis method of 9-(4-bromophenyl)-9-phenylfluorene

In a 100-mL three-neck flask, 1.2 g (50 mmol) of magnesium was heated and stirred under reduced pressure for 30 minutes to be activated. After the flask was cooled to room temperature and is made to have a nitrogen atmosphere, several drops of dibromoethane were added, so that foam formation and heat generation were confirmed. After 12 g (50 mmol) of 2-bromobiphenyl dissolved in 10 mL of diethyl ether was slowly dropped into this mixture, the mixture was heated and stirred under reflux for 2.5 hours, whereby a Grignard reagent was prepared.

In a 500-mL three-neck flask, 10 g (40 mmol) of 4-bromobenzophenone and 100 mL of diethyl ether were put, and the air of the flask was replaced with nitrogen. After the Grignard reagent which was synthesized in advance was slowly dropped into this mixture, the mixture was stirred and heated under reflux for 9 hours After the reaction, this mixture was filtrated to obtain a residue. The obtained residue was dissolved in 150 mL of ethyl acetate, and 1M-hydrochloric acid was added to the mixture until the mixture became acid, and the mixture was then stirred for 2 hours. An organic layer of the mixture was washed with water and dried over magnesium sulfate. This mixture was filtered, and the obtained filtrate was concentrated to give an oily substance.

In a 500-mL recovery flask were put the obtained oily substance, 50 mL of glacial acetic acid, and 1.0 mL of hydrochloric acid. The mixture was heated and stirred under a nitrogen atmosphere at 130° C. for 1.5 hours to be reacted.

After the reaction, this reaction mixture was filtrated to give a residue. The residue was washed with water, a sodium hydroxide aqueous solution, water, and methanol in this order. Then, the mixture was dried to give 11 g of white powder in 69% yield, which was the target substance. The synthesis scheme of this Step 1 is illustrated below.

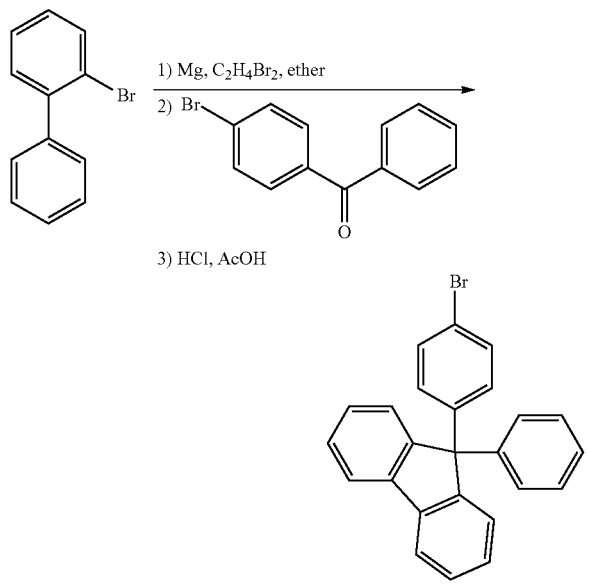

Step 2: Synthesis method of 4-(9-phenyl-9H-fluoren-9-yl)diphenylamine (abbreviated as FLPA)

In a 200 mL three-neck flask were put 5.8 g (14.6 mmol) of 9-(4-bromophenyl)-9-phenylfluorene, 1.7 mL (18.6 mmol) of aniline, and 4.2 g (44.0 mmol) of sodium tert-butoxide. The air in the flask was replaced with nitrogen. To this mixture were added 147.0 mL of toluene and 0.4 mL of a 10% hexane solution of tri(tert-butyl)phosphine. The temperature of this mixture was set to 60° C., and 66.1 mg (0.1 mmol) of bis(dibenzylideneacetone)palladium(0) was added to the mixture, followed by stirring for 3.5 hours. After the stirring, suction filtration through Florisil (produced by Wako Pure Chemical Industries, Ltd., Catalog No. 540-00135), Celite (produced by Wako Pure Chemical Industries, Ltd., Catalog No. 531-16855), and alumina was carried out to give a filtrate. The obtained filtrate was concentrated to give a solid, which was then purified by silica gel column chromatography (the developing solvent has a 2:1 ratio of hexane to toluene). The obtained fraction was concentrated to give 6.0 g of a white solid in 99% yield; which was the target substance. The synthesis scheme of Step 2 is shown below.

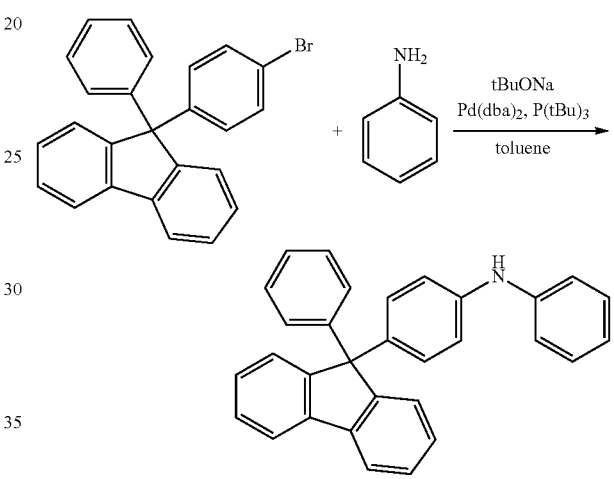

Step 3: Method of Synthesizing N,N'-bis[4-(9-phenyl-9H-fluoren-9-yl)phenyl]-N,N'-diphenyl-pyrene-1,6-diamine (abbreviated as 1,6FLPAPrn)

In a 50 mL three-neck flask were put 0.4 g (1.2 mmol) of 1,6-dibromopyrene, 1.0 g (2.4 mmol) of 4-(9-phenyl-9H-fluoren-9-yl)diphenylamine (abbreviated as FLPA) obtained in Step 2 of Example 1 and 0.3 g (3.6 mmol) of sodium tert-butoxide. The air in the flask was replaced with nitrogen. To this mixture were added 11.5 mL of toluene and 0.20 mL of a 10% hexane solution of tri(tert-butyl)phosphine. The temperature of this mixture was set to 70° C., and 31.1 mg (0.05 mmol) of bis(dibenzylideneacetone)palladium(0) was added to the mixture, followed by stirring for 4.0 hours. After the stirring, suction filtration through Florisil, Celite, and alumina was carried out to give a filtrate. The obtained filtrate was concentrated to give a solid, which was then purified by silica gel column chromatography (the developing solvent has a 2:1 ratio of hexane to toluene). The obtained fraction was concentrated to give a yellow solid. The obtained solid was washed with a mixed solvent of toluene and hexane, and then the mixture was suction-filtered to give a yellow solid. The obtained yellow solid was washed with a mixed solvent of chloroform and hexane, so that 0.8 g of a pale yellow powdered solid was obtained in 68% yield.

By a train sublimation method, 0.8 g of the obtained pale yellow solid was purified. Under a pressure of 2.7 Pa with a flow rate of argon at 5.0 mL/min, the sublimation purification was carried out at 360° C. After the sublimation purification, 0.4 g of the target substance was obtained in a yield of 56%. The synthesis scheme of the above Step 3 is shown below.

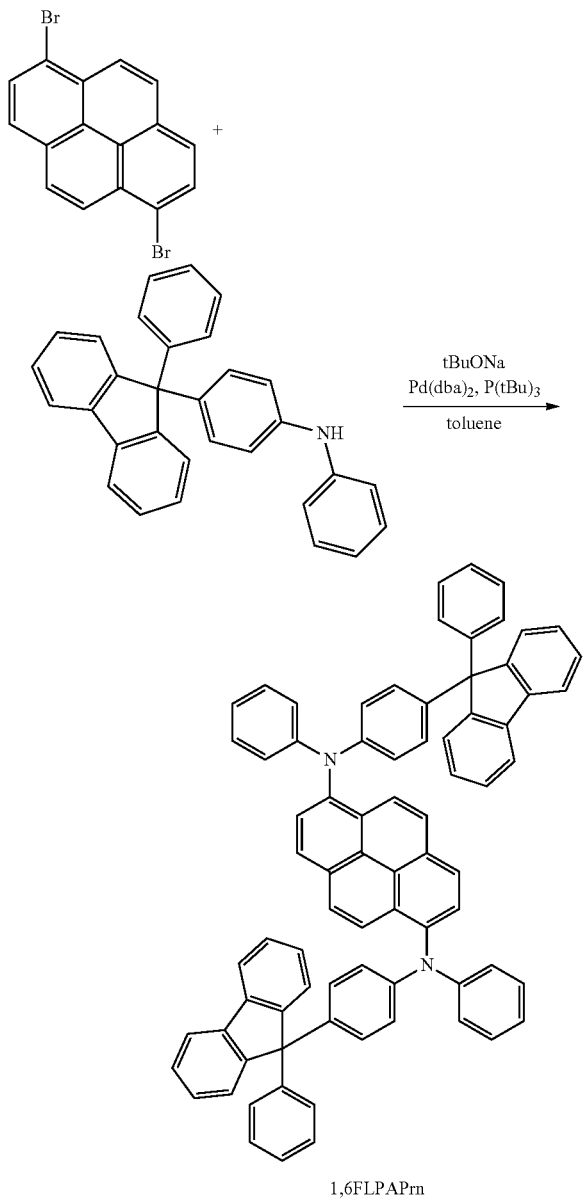

1,6FLPAPrn

A nuclear magnetic resonance (NMR) method and a mass spectrometry identified the obtained compound as N,N'-bis [4-(9-phenyl-9H-fluoren-9-yl)phenyl]-N,N'-diphenyl-pyrene-1,6-diamine (abbreviated as 1,6FLPAPrn). The $^1$H NMR data is given as follows.

$^1$H NMR (CDCl$_3$, 300 MHz): δ=6.88-6.91 (m, 6H), 7.00-7.03 (m, 8H), 7.13-7.40 (m, 26H), 7.73-7.80 (m, 6H), 7.87 (d, J=9.0 Hz, 2H), 8.06-8.09 (m, 4H).

Reference Example 2

A method of synthesizing tris(5-methyl-3,4-diphenyl-4H-1,2,4-triazolato)iridium(III) (abbreviated as [Ir(Mptz)$_3$], represented by the structural formula (ix)) used in Examples described above will be described specifically.

Step 1: Synthesis of 3-methyl-4,5-diphenyl-4H-1,2,4-triazole (abbreviated as HMptz)

First, 5.04 g of thioacetanilide, 5.44 g of benzoylhydrazine, and 50 mL of 1-butanol were put in a round-bottomed flask provided with a reflux pipe, and the air in the flask was replaced with argon. This reaction container was subjected to irradiation with a microwave (2.45 GHz, 100 W) for 2 hours and 45 minutes to be heated. Then, water was added to this solution and an organic layer was extracted with dichloromethane. The obtained organic layer was washed with water and dried with magnesium sulfate. After the drying, the solution was filtrated. The solvent of this solution was distilled off, and the resulting residue was purified by silica gel column chromatography which uses ethyl acetate as a developing solvent, so that 3-methyl-4,5-diphenyl-4H-1,2,4-triazole (abbreviated as HMptz) was obtained (pale yellow powder, yield: 18%). A scheme of the synthesis of Step 1 is shown below.

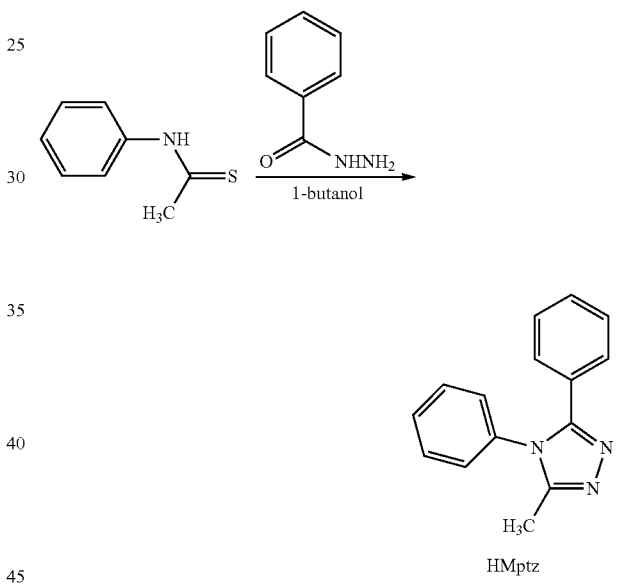

HMptz

Step 2: Synthesis of tris(5-methyl-3,4-diphenyl-4H-1,2,4-triazolato)iridium(III) (abbreviated as [Ir(Mptz)$_3$])

Next, 1.40 g of the ligand HMptz that was obtained in Step 1 described above, and 0.58 g of tris(acetylacetonato)iridium (III) were put in a reaction container with a three-way cock, and the air in the reaction container was replaced with argon. Then, the mixture was heated at 250° C. for 17 hours and 30 minutes to be reacted. The reactant was dissolved in dichloromethane, and the solution was filtrated. The solvent of the resulting filtrate was distilled off and purification was conducted by silica gel column chromatography using ethyl acetate as a developing solvent. Further, recrystallization was carried out with a mixed solvent of dichloromethane and hexane, so that the organometallic complex [Ir(Mptz)$_3$] which is one embodiment of the present invention was obtained (yellow powder, yield: 22%). A synthesis scheme of Step 2 is shown below.

131

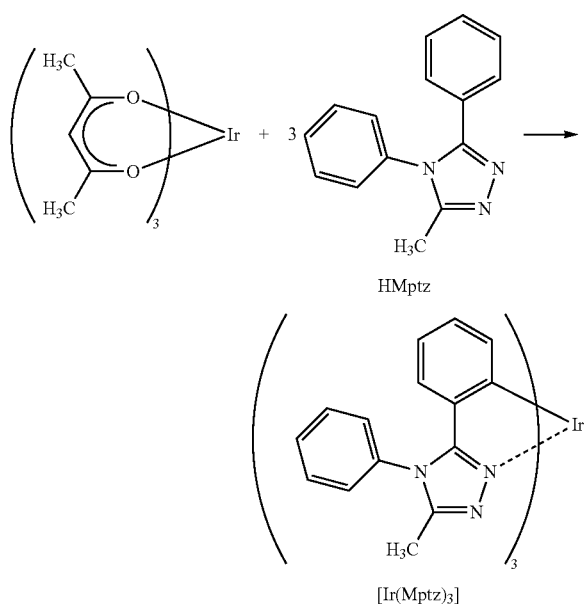

HMptz

[Ir(Mptz)₃]

An analysis result by nuclear magnetic resonance spectroscopy (¹H-NMR) of the yellow powder obtained in Step 2 described above is shown below. These results revealed that the organometallic complex [Ir(Mptz)₃] was obtained.

¹H-NMR. δ(CDCl₃): 2.17 (s, 9H), 6.38 (d, 3H), 6.54 (t, 3H), 6.72 (dt, 3H), 6.87 (dd, 3H), 7.34 (m, 3H), 7.51 (brm, 3H), 7.57 (m, 9H).

Reference Example 3

A method of synthesizing 2-[3-(dibenzothiophen-4-yl)phenyl]-1-phenyl-1H-benzimidazole (abbreviated as mDBT-BIm-II, represented by the structural formula (x)) used in Examples described above will be described specifically.

Synthesis of 2-[3-(dibenzothiophen-4-yl)phenyl]-1-phenyl-1H-benzimidazole (abbreviated as mDBT-BIm-II)

The synthesis scheme of 2-[3-(dibenzothiophen-4-yl)phenyl]-1-phenyl-1H-benzimidazole (abbreviated as mDBT-BIm-II) is shown below.

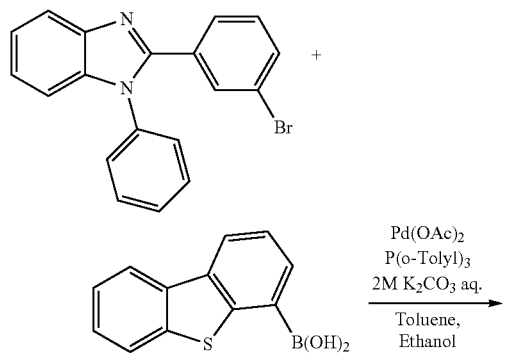

132

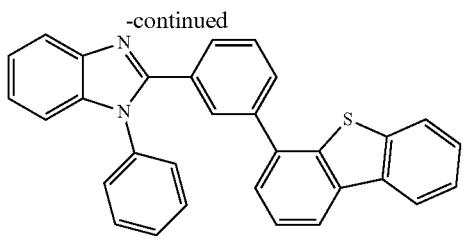
-continued

In a 50-mL three-neck flask were put 1.2 g (3.3 mmol) of 2-(3-bromophenyl)-1-phenyl-1H-benzimidazole, 0.8 g (3.3 mmol) of dibenzothiophene-4-boronic acid, and 50 mg (0.2 mmol) of tri(ortho-tolyl)phosphine. The air in the flask was replaced with nitrogen. To this mixture were added 3.3 mL of a 2.0 mmol/L aqueous solution of potassium carbonate, 12 mL of toluene, and 4 mL of ethanol. To this mixture were added 3.3 mL of a 2.0 mmol/L aqueous solution of potassium carbonate, 12 mL of toluene, and 4 mL of ethanol. Under reduced pressure, this mixture was stirred to be degassed. Then, 7.4 mg (33 μmol) of palladium(II) acetate was added to this mixture, and the mixture was stirred at 80° C. for 6 hours under a nitrogen stream.

After a predetermined time, the aqueous layer of the obtained mixture was extracted with toluene. The obtained extract was washed with a saturated saline together with the organic layer and then dried over magnesium sulfate. This mixture was separated by gravity filtration, and the filtrate was concentrated to give an oily substance. This oily substance was purified by silica gel column chromatography. The silica gel column chromatography was carried out using toluene as a developing solvent. The obtained fraction was concentrated to give an oily substance. This oily substance was purified by high performance liquid chromatography. The high performance liquid column chromatography was performed using chloroform as a developing solvent. The obtained fraction was concentrated to give an oily substance. This oily substance was recrystallized with a mixed solvent of toluene and hexane, so that 0.8 g of the target substance, pale yellow powder was obtained in 51% yield.

By a train sublimation method, 0.8 g of the obtained pale yellow powder was purified. In the purification, the pale yellow powder was heated at 215° C. under a pressure of 3.0 Pa with a flow rate of argon gas of 5 mL/min. After the sublimation purification, 0.6 g of the targent substance, white powder was obtained in 82% yield.

A nuclear magnetic resonance (NMR) method identified this compound as 2-[3-(dibenzothiophen-4-yl)phenyl]-1-phenyl-1H-benzimidazole (abbreviated as mDBTBIm-II).

¹H NMR data of the obtained compound is shown below.
¹H NMR (CDCl₃, 300 MHz): δ (ppm)=7.23-7.60 (m, 13H), 7.71-7.82 (m, 3H), 7.90-7.92 (m, 2H), 8.10-8.17 (m, 2H).

Reference Example 4

The materials used in the light-emitting element 8 in this example will be described in this reference example 4.

Synthesis Example of 1,6mMemFLPAPrn

In this example, an example is described in which N,N'-bis(3-methylphenyl)-N,N'-bis[3-(9-phenyl-9H-fluoren-9-yl)phenyl]-pyrene-1,6-diamine (abbreviated as 1,6mMemFL-PAPrn) used as the material of the light-emitting element 8 is synthesized.

Step 1: Synthesis method of 3-methylphenyl-3-(9-phenyl-9H-fluoren-9-yl)phenylamine (abbreviated as mMemFLPA)

In a 200 mL three-neck flask were put 3.2 g (8.1 mmol) of 9-(3-bromophenyl)-9-phenylfluorene and 2.3 g (24.1 mmol) of sodium tert-butoxide. The air in the flask was replaced with nitrogen. To this mixture were added 40.0 mL of toluene, 0.9 mL (8.3 mmol) of m-toluidine, and 0.2 mL of a 10% hexane solution of tri(tert-butyl)phosphine. The temperature of this mixture was set to 60° C., and 44.5 mg (0.1 mmol) of bis(dibenzylideneacetone)palladium(0) was added to the mixture. The temperature of the mixture was set to 80° C., followed by stirring for 2.0 hours. After the stirring, the mixture was suction-filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. The filtrate was concentrated to give a solid, which was then purified by silica gel column chromatography (the developing solvent has a 1:1 ratio of hexane to toluene) and recrystallized with a mixed solvent of toluene and hexane. Accordingly, 2.8 g of the targent substance, white solid was obtained in 82% yield. The synthesis scheme of this Step 1 is shown below.

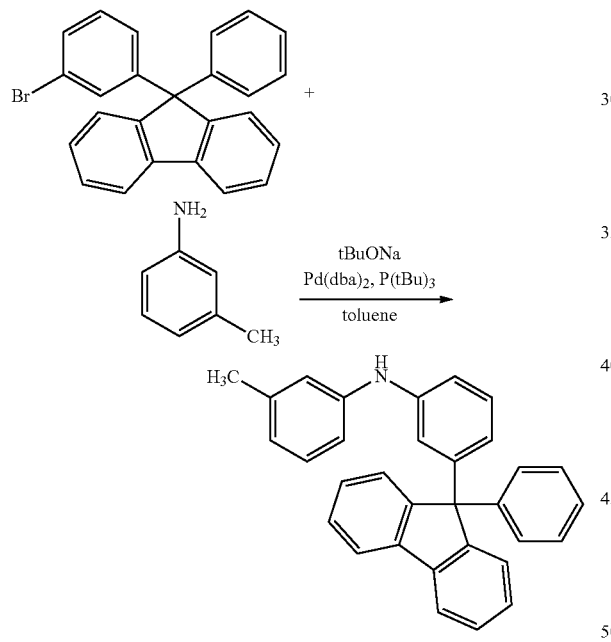

Step 2: Synthesis method of N,N'-bis(3-methylphenyl)-N,N'-bis[3-(9-phenyl-9H-fluoren-9-yl)phenyl]-pyrene-1,6-diamine (abbreviated as 1,6mMemFLPA-Prn)

In a 100 mL three-neck flask were put 0.6 g (1.7 mmol) of 1,6-dibromopyrene, 1.4 g (3.4 mmol) of 3-methylphenyl-3-(9-phenyl-9H-fluoren-9-yl)phenylamine, and 0.5 g (5.1 mmol) of sodium tert-butoxide. The air in the flask was replaced with nitrogen. To this mixture were added 21.0 mL of toluene and 0.2 mL of a 10% hexane solution of tri(tert-butyl)phosphine. The temperature of this mixture was set to 60° C., and 34.9 mg (0.1 mmol) of bis(dibenzylideneacetone)palladium(0) was added to the mixture, and this mixture was set to 80° C., followed by stirring for 3.0 hours. After the stirring, 400 mL of toluene was added to the mixture, and the mixture was heated. While the mixture was kept hot, it was suction-filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. The filtrate was concentrated to give a solid, which was then purified by silica gel column chromatography (the developing solvent has a 3:2 ratio of hexane to toluene) to give a yellow solid. Recrystallization of the obtained yellow solid from a mixed solvent of toluene and hexane gave 1.2 g of the target substance, yellow solid in 67% yield.

By a train sublimation method, 1.0 g of the obtained yellow solid was purified. In the purification, the yellow solid was heated at 317° C. under a pressure of 2.2 Pa with a flow rate of argon gas of 5.0 mL/min. After the sublimation purification, 1.0 g of the target substance, yellow solid, was obtained in a yield of 93%. The synthesis scheme of Step 2 is shown below.

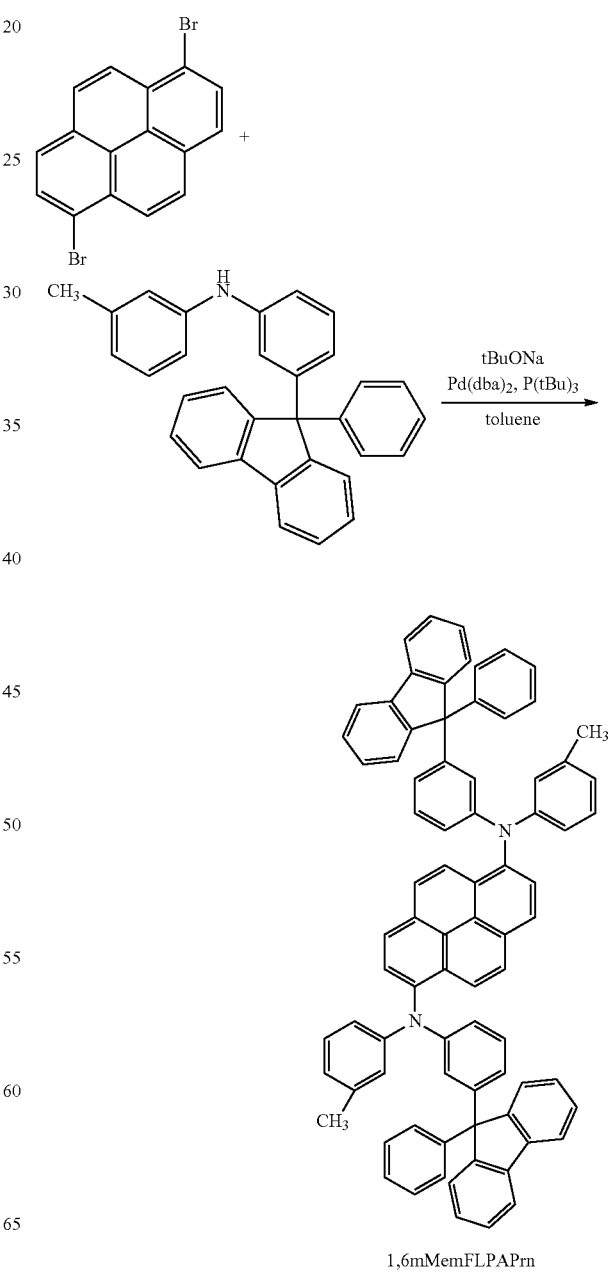

A nuclear magnetic resonance (NMR) method identified this compound as N,N'-bis(3-methylphenyl)-N,N'-bis[3-(9-phenyl-9H-fluoren-9-yl)phenyl]pyrene-1,6-diamine (abbreviated as 1,6mMemFLPAPrn), which was the targen substance.

$^1$H NMR data of the obtained compound is shown below.

$^1$H NMR (CDCl$_3$, 300 MHz): δ=2.21 (s, 6H), 6.67 (d, J=7.2 Hz, 2H), 6.74 (d, J=7.2 Hz, 2H), 7.17-7.23 (m, 34H), 7.62 (d, J=7.8 Hz, 4H), 7.74 (d, J=7.8 Hz, 2H), 7.86 (d, J=9.0 Hz, 2H), 8.04 (d, J=8.7 Hz, 4H)

This application is based on Japanese Patent Application serial No. 2010-232850 filed with the Japan Patent Office on Oct. 15, 2010, and Japanese Patent Application serial No. 2011-183202 filed with the Japan Patent Office on Aug. 25, 2011, the entire contents of which are hereby incorporated by reference.

What is claimed is:

1. A carbazole compound represented by a general formula (G1),

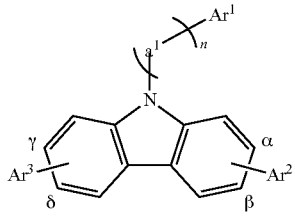

(G1)

wherein Ar$^1$ is any of a phenyl group, a biphenyl group, and a naphthyl group; Ar$^2$ is a group represented by a general formula (g1); Ar$^3$ is any of hydrogen, a group represented by a general formula (g2), and a group represented by a general formula (g3); n is 0 or 1; a$^1$ is a phenylene group or a biphenyldiyl group; a substitution site of Ar$^2$ is a carbon atom represented by either α or β, and a substitution site of Ar$^3$ is a carbon atom represented by either γ or δ; and Ar$^1$ and a$^1$ independently have no substituent or a first substituent, and the first substituent is an alkyl group having 1 to 6 carbon atoms or an aryl group having 1 to 13 carbon atoms;

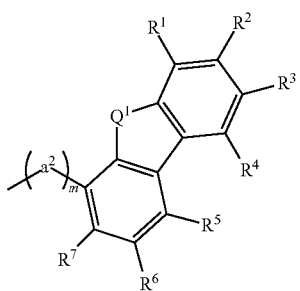

(g1)

wherein R$^1$ to R$^7$ are each independently any of hydrogen, an alkyl group having 1 to 6 carbon atoms, a phenyl group, a biphenyl group, and a naphthyl group; m is 0 or 1; a$^2$ is a phenylene group or a biphenyldiyl group; Q$^1$ is sulfur; R$^1$ to R$^7$ and a$^2$ independently have no substituent or a second substituent, and the second substituent is an alkyl group having 1 to 6 carbon atoms or an aryl group having 1 to 13 carbon atoms;

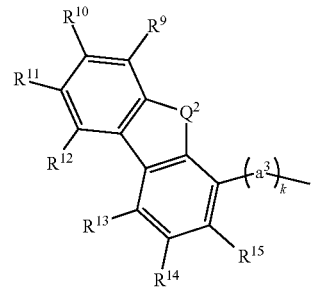

(g2)

wherein R$^9$ to R$^{15}$ are each independently any of hydrogen, an alkyl group having 1 to 6 carbon atoms, a phenyl group, a biphenyl group, and a naphthyl group; k is 0 or 1; a$^3$ is a phenylene group or a biphenyldiyl group; Q$^2$ is sulfur; and R$^9$ to R$^{15}$ and a$^3$ independently have no substituent or a third substituent, and the third substituent is an alkyl group having 1 to 6 carbon atoms or an aryl group having 1 to 13 carbon atoms; and

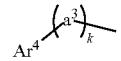

(g3)

wherein k is 0 or 1; a$^3$ is a pheneylene group or a biphenyldiyl group; Ar$^4$ is any of a phenyl group, a biphenyl group, and a naphthyl group; and Ar$^4$ and a$^3$ independently have no substituent or a fourth substituent, and the fourth substituent is an alkyl group having 1 to 6 carbon atoms or an aryl group having 1 to 13 carbon atoms.

2. The carbazole compound according to claim 1, represented by the general formula (G1),
wherein:
Ar$^3$ is a substituent represented by the general formula (g2) or a substituent represented by the general formula (g3);
when Ar$^2$ is bonded at the α position, Ar$^3$ is bonded at the γ position; or
when Ar$^2$ is bonded at the β position, Ar$^3$ is bonded at the δ position.

3. A carbazole compound represented by a general formula (G1),

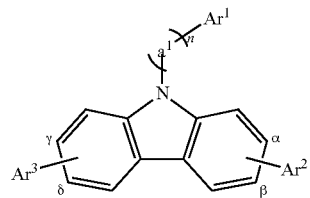

(G1)

wherein Ar$^1$ is any of a phenyl group, a biphenyl group, and a naphthyl group; Ar$^2$ is a group represented by a general formula (g4); Ar$^3$ is any of hydrogen, a group represented by a general formula (g5) and a group represented by the following general formula (g3); n is 0 or 1; a$^1$ is a phenylene group or a biphenyldiyl group; a substitution site of Ar$^2$ is a carbon atom represented by either α or β, and a substitution site of Ar$^3$ is a carbon atom represented by either γ or δ; and Ar¹ and a¹ independently have no substituent or a first substituent, and the first substituent is an alkyl group having 1 to 6 carbon atoms or an aryl group having 1 to 13 carbon atoms;

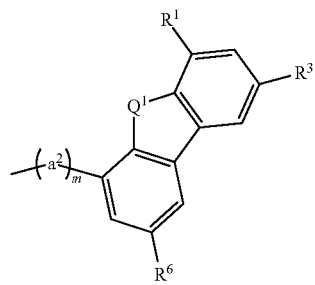

(g4)

wherein $R^1$, $R^3$, and $R^6$ are each independently any of hydrogen, an alkyl group having 1 to 6 carbon atoms, a phenyl group, a biphenyl group, and a naphthyl group; m is 0 or 1; $a^2$ is a phenylene group or a biphenyldiyl group; $Q^1$ is sulfur; and $R^3$, and $R^6$ and $a^2$ independently have no substituent or a second substituent, and the second substituent is an alkyl group having 1 to 6 carbon atoms or an aryl group having 1 to 13 carbon atoms;

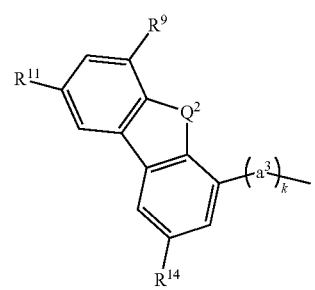

(g5)

wherein $R^9$, $R^{11}$, and $R^{14}$ are each independently any of hydrogen, an alkyl group having 1 to 6 carbon atoms, a phenyl group, a biphenyl group and a naphthyl group; k is 0 or 1; $a^3$ is a phenylene group or a biphenyldiyl group; $Q^2$ is sulfur or oxygen; and $R^9$, $R^{11}$, and $R^{14}$, and $a^3$ independently have no substituent or a third substituent, and the third substituent is an alkyl group having 1 to 6 carbon atoms or an aryl group having 1 to 13 carbon atoms; and

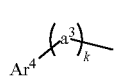

(g3)

wherein k is 0 or 1; $a^3$ is a pheneylene group or a biphenyldiyl group; $Ar^4$ is any of a phenyl group, a biphenyl group, and a naphthyl group; and $Ar^4$ and $a^3$ independently have no substituent or a fourth substituent, and the fourth substituent is an alkyl group having 1 to 6 carbon atoms or an aryl group having 1 to 13 carbon atoms.

4. The carbazole compound according to claim 3, represented by the general formula (G1), wherein:
$Ar^3$ is a substituent represented by the general formula (g3) or a substituent represented by the general formula (g5); when $Ar^2$ is bonded at the α position, $Ar^3$ is bonded at the γ position; or when $Ar^2$ is bonded at the β position, $Ar^3$ is bonded at the δ position.

5. A carbazole compound represented by a general formula (G1)

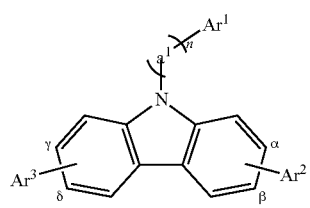

(G1)

wherein $Ar^1$ is any of a phenyl group, a biphenyl group, and a naphthyl group; $Ar^2$ is a group represented by a general formula (g4); $Ar^3$ is hydrogen or a group represented by a general formula (g5); n is 0 or 1; $a^1$ is a phenylene group or a biphenyldiyl group; a substitution site of $Ar^2$ is a carbon atom represented by either α or β; a substitution site of $Ar^3$ is a carbon atom represented by either γ or δ0.3; and $Ar^1$ and $a^1$ independently have no substituent or a first substituent, and the first substituent is an alkyl group having 1 to 6 carbon atoms or an aryl group having 1 to 13 carbon atoms;

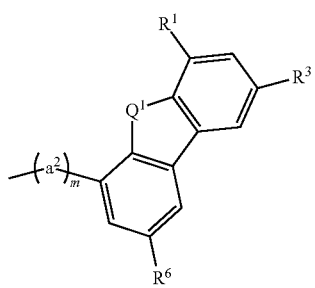

(g4)

wherein $R^1$, $R^3$, and $R^6$ are each independently any of hydrogen, an alkyl group having 1 to 6 carbon atoms, a phenyl group, a biphenyl group, and a naphthyl group; m is 0 or 1; $a^2$ is a phenylene group or a biphenyldiyl group; $Q^1$ is sulfur; and $R^1$, $R^3$, and $R^6$ and $a^2$ independently have no substituent or a second substituent, the second substituent is an alkyl group having 1 to 6 carbon atoms or an aryl group having 1 to 13 carbon atoms; and

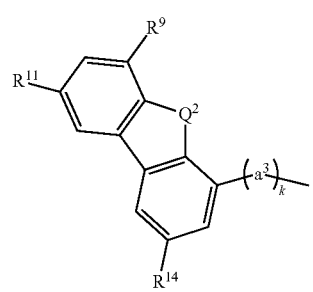

(g5)

wherein $R^9$, $R^{11}$, and $R^{14}$ are each independently any of hydrogen, an alkyl group having 1 to 6 carbon atoms, a phenyl group, a biphenyl group, and a naphthyl group; k is 0 or 1; $a^3$ is a phenylene group or a biphenyldiyl group; $Q^2$ is sulfur; and $R^9$, $R^{11}$, and $R^{14}$, and $a^3$ independently have no substituent or a third substituent, and the third substituent is an alkyl group having 1 to 6 carbon atoms or an aryl group having 1 to 13 carbon atoms.

6. The carbazole compound according to claim 5, represented by the general formula (G1), wherein:

Ar³ is a substituent represented by the general formula (g5);

when Ar² is bonded at the α position, Ar³ is bonded at the γ position; or when Ar² is bonded at the β position, Ar³ is bonded at the δ position.

7. A carbazole compound represented by a general formula (G1),

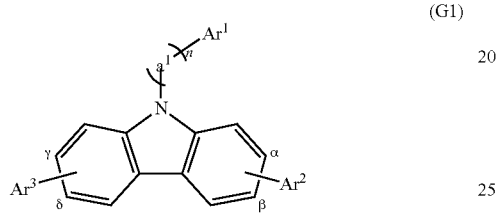

(G1)

wherein Ar¹ is any of a phenyl group, a biphenyl group, and a naphthyl group; Ar² is a group represented by a general formula (g6); Ar³ is hydrogen or a group represented by a general formula (g7); n is 0 or 1; $a^1$ is a phenylene group or a biphenyldiyl group; a substitution site of Ar² is a carbon atom represented by either α or β, and a substitution site of Ar³ is a carbon atom represented by either γ or δ; and Ar¹ and $a^1$ independently have no substituent or a first substituent, and the first substituent is an alkyl group having 1 to 6 carbon atoms or an aryl group having 1 to 13 carbon atoms;

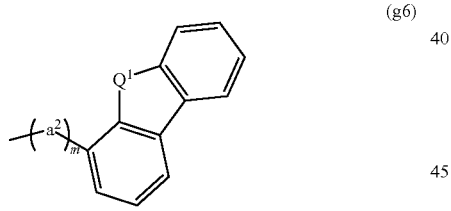

(g6)

wherein m is 0 or 1; $a^2$ is a phenylene group or a biphenyldiyl group; $Q^1$ is sulfur; and $a^2$ have no substituent or a second substituent, and the second substituent is an alkyl group having 1 to 6 carbon atoms or an aryl group having 1 to 13 carbon atoms; and

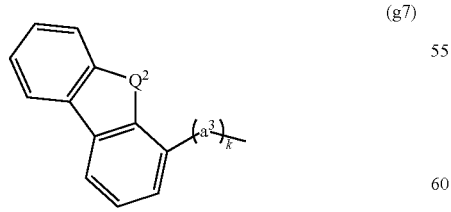

(g7)

wherein k is 0 or 1; $a^3$ is a phenylene group or a biphenyldiyl group; $Q^2$ is sulfur; and $a^3$ have no substituent or a third substituent, and, the third substituent is an alkyl group having 1 to 6 carbon atoms or an aryl group having 1 to 13 carbon atoms.

8. The carbazole compound according to claim 7, represented by the general formula (G1), wherein:

Ar³ is a substituent represented by the general formula (g7);

when Ar² is bonded at the α position, Ar³ is bonded at the γ position; or when Ar² is bonded at the β position, Ar³ is bonded at the δ position.

9. The carbazole compound according to any one of claims 1, 3, 5, or 7, wherein the groups, $a^1$, $a^2$, and $a^3$, are independently any of groups represented by structural formulae (a-1) to (a-7);

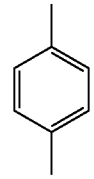

(α-1)

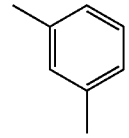

(α-2)

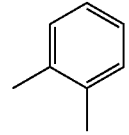

(α-3)

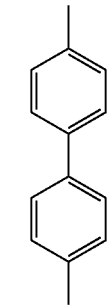

(α-4)

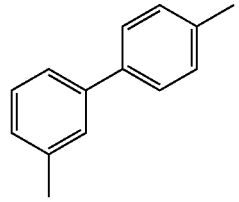

(α-5)

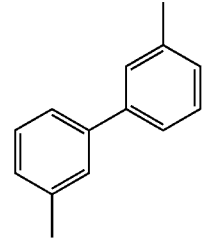

(α-6)

-continued
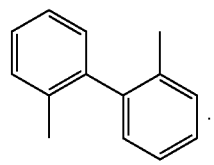 (α-7)
10. The carbazole compound according to claim 1, wherein the groups, $R^1$ to $R^7$ and $R^9$ to $R^{15}$, are independently any of groups represented by structural formulae (R-1) to (R-13);
 (R-1)
 (R-2)
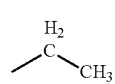 (R-3)
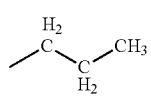 (R-4)
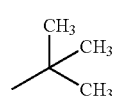 (R-5)
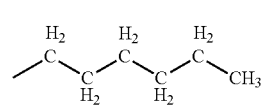 (R-6)
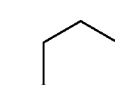 (R-7)
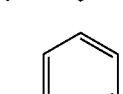 (R-8)
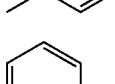 (R-9)
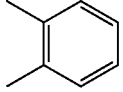 (R-10)
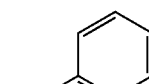 (R-11)
-continued
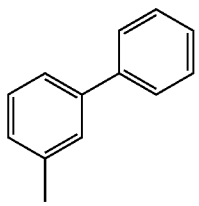 (R-12)
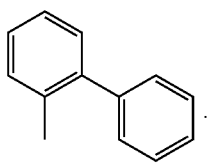 (R-13)
11. The carbazole compound according to claim 1 or 3, wherein the group, $Ar^4$, is any of groups represented by structural formulae (Ar-1) to (Ar-6);
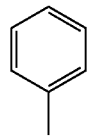 (Ar-1)
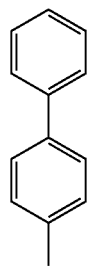 (Ar-2)
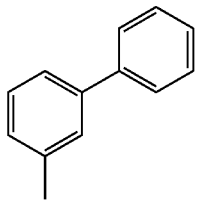 (Ar-3)
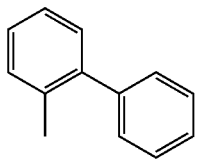 (Ar-4)
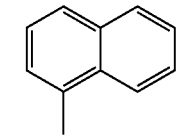 (Ar-5)

-continued

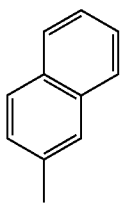
(Ar-6)

12. The carbazole compound according to any one of claims 1, 3, 5, or 7,

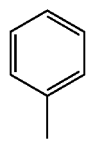
(Ar-1)

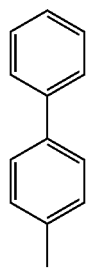
(Ar-2)

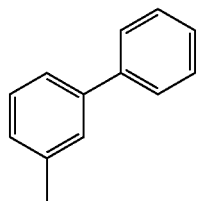
(Ar-3)

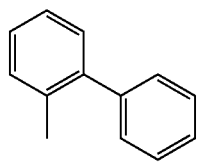
(Ar-4)

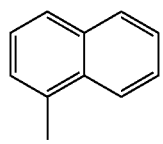
(Ar-5)

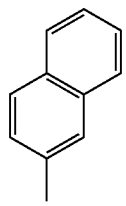
(Ar-6)

wherein the group, $Ar^1$, is any of groups represented by the following structural formulae (Ar-1) to (Ar-6).

13. The carbazole compound according to any one of claims 1, 3, 5, or 7, wherein n is 0.

14. The carbazole compound according to any one of claims 1, 3, 5, or 7, wherein the group represented by $Ar^1$ is a phenyl group.

15. The carbazole compound according to any one of claims 1, 3, 5, or 7, wherein m and k are both 0.

16. A carbazole compound represented by a structural formula (150)

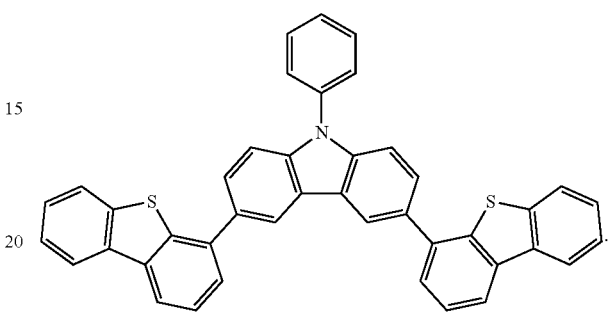
(150)

17. A carbazole compound represented by a structural formula (154)

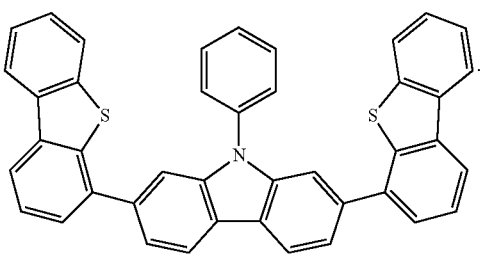
(154)

18. The carbazole compound according to any one of claims 1, 3, 5, or 7, wherein $Ar^3$ is hydrogen.

19. A carbazole compound represented by a structural formula (172)

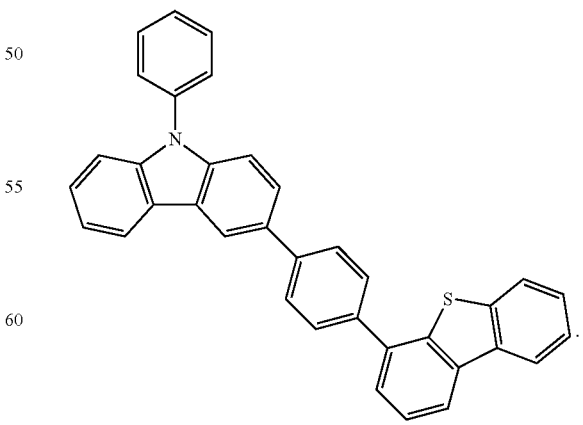
(172)

20. A carbazole compound represented by a structural formula (160)

(160)

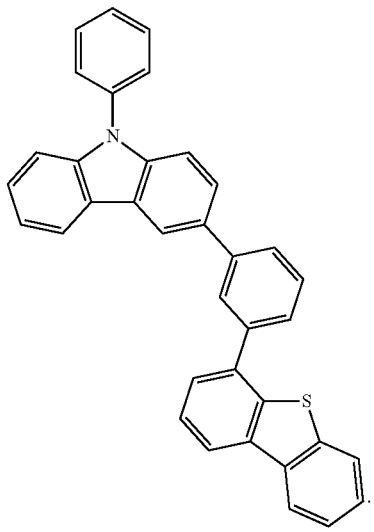

21. A material for a light-emitting element including the carbazole compound according to any one of claims 1, 3, 5, 7, 16, 17, 19, or 20.

22. An organic semiconductor material including the carbazole compound according to any one of claims 1, 3, 5, 7, 16, 17, 19, or 20.

23. A light-emitting element including a carbazole compound represented by a general formula (G1), wherein a layer containing an organic compound is interposed between a pair of electrodes,

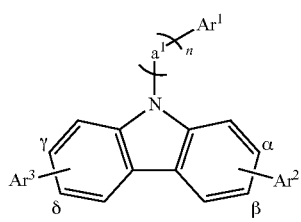
(G1)

wherein $Ar^1$ is any of a phenyl group, a biphenyl group, and a naphthyl group; $Ar^2$ is a group represented by a general formula (g1'); $Ar^3$ is any of hydrogen, a group represented by a general formula (g2) and a group represented by a general formula (g3); n is 0 or 1; $a^1$ is a phenylene group or a biphenyldiyl group; and a substitution site of $Ar^2$ is a carbon atom represented by either α or β, and a substitution site of $Ar^3$ is a carbon atom represented by either γ or δ and $Ar^1$ and $a^1$ independently have no substituent or a first substituent, and the first substituent is an alkyl group having 1 to 6 carbon atoms or an aryl group having 6 to 13 carbon atoms;

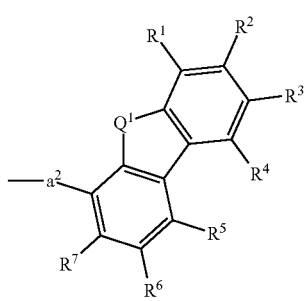
(g1')

wherein $R^1$ to $R^7$ are each independently hydrogen, an alkyl group having 1 to 6 carbon atoms, a phenyl group, a biphenyl group, and a naphthyl group; $a^2$ is a phenylene group or a biphenyldiyl group; $Q^1$ is sulfur; and $R^1$ to $R^7$ and $a^2$ independently have no substituent or a second substituent, the second substituent is an alkyl group having 1 to 6 carbon atoms or an aryl group having 6 to 13 carbon atoms;

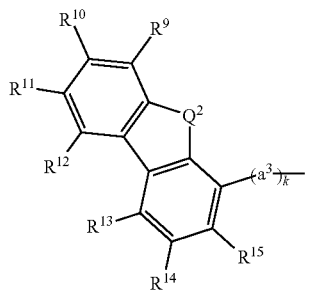
(g2)

wherein $R^9$ to $R^{15}$ are each independently any of hydrogen, an alkyl group having 1 to 6 carbon atoms, a phenyl group, a biphenyl group and a naphthyl group; k is 0 or 1, $a^3$ is a phenylene group or a biphenyldiyl group; $Q^2$ is sulfur; and $R^9$ to $R^{15}$ and $a^3$ independently have no substituent or a third substituent, and the third substituent is an alkyl group having 1 to 6 carbon atoms or an aryl group having 6 to 13 carbon atoms; and

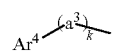
(g3)

wherein k is 0 or 1; $a^3$ is a pheneylene group or a biphenyldiyl group; $Ar^4$ is any of a phenyl group, a biphenyl group, and a naphthyl group; and $Ar^4$ and $a^3$ independently have no substituent or a fourth substituent, and the fourth substituent is an alkyl group having 1 to 6 carbon atoms or an aryl group having 6 to 13 carbon atoms.

24. A light-emitting element including a carbazole compound represented by a general formula (G1), wherein a layer containing an organic compound is interposed between a pair of electrodes,

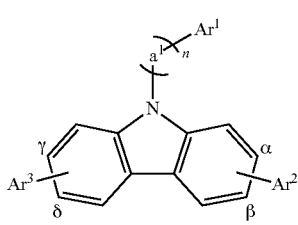
(G1)

wherein $Ar^1$ is any of a phenyl group, a biphenyl group, and a naphthyl group; $Ar^2$ is a group represented by a general formula (g4'); $Ar^3$ is any of hydrogen, a group represented by a general formula (g5) and a group represented by a general formula (g3); n is 0 or 1; $a^1$ is a phenylene group or a biphenyldiyl group; a substitution site of $Ar^2$ is a carbon atom represented by either α or β, and a substitution site of Ar³ is a carbon atom represented by either γ or δ; and Ar¹ and a¹ independently have no substituent or a first substituent, and the first substituent is an alkyl group having 1 to 6 carbon atoms or an aryl group having 6 to 13 carbon atoms;

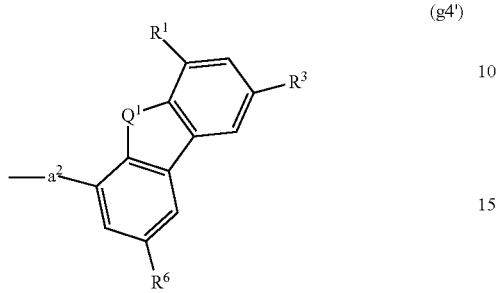

(g4')

wherein $R^1$, $R^3$, and $R^6$ are each independently hydrogen, an alkyl group having 1 to 6 carbon atoms, a phenyl group, a biphenyl group, and a naphthyl group; $a^2$ is a phenylene group or a biphenyldiyl group; $Q^1$ is sulfur; and $R^1$, $R^3$, and $R^6$ and $a^2$ independently have no substituent or a second substituent, the second substituent is an alkyl group having 1 to 6 carbon atoms or an aryl group having 6 to 13 carbon atoms;

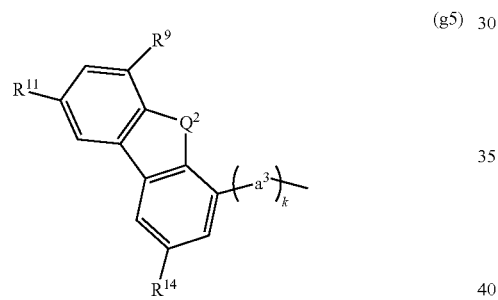

(g5)

wherein $R^9$, $R^{11}$, and $R^{14}$ are each independently any of hydrogen, an alkyl group having 1 to 6 carbon atoms, a phenyl group, a biphenyl group and a naphthyl group; k is 0 or 1; $a^3$ is a phenylene group or a biphenyldiyl group; $Q^2$ is sulfur; and $R^9$, $R^{11}$, and $R^{14}$, and $a^3$ independently have no substituent or a third substituent, and the third substituent is an alkyl group having 1 to 6 carbon atoms or an aryl group having 6 to 13 carbon atoms; and

(g3)

wherein k is 0 or 1; $a^3$ is a pheneylene group or a biphenyldiyl group; $Ar^4$ is any of a phenyl group, a biphenyl group, and a naphthyl group; and $Ar^4$ and $a^3$ independently have no substituent or a fourth substituent, and the fourth substituent is an alkyl group having 1 to 6 carbon atoms or an aryl group having 6 to 13 carbon atoms.

25. A light-emitting element including a carbazole compound represented by a general formula (G1), wherein a layer containing an organic compound is interposed between a pair of electrodes,

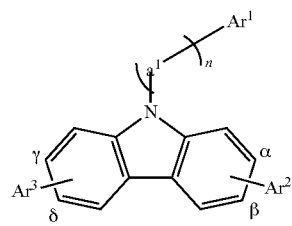

(G1)

wherein $Ar^1$ is any of a phenyl group, a biphenyl group, and a naphthyl group; $Ar^2$ is a group represented by a general formula (g4'); $Ar^3$ is hydrogen or a group represented by a general formula (g5); n is 0 or 1; $a^1$ is a phenylene group or a biphenyldiyl group; a substitution site of $Ar^2$ is a carbon atom represented by either α or β, and a substitution site of $Ar^3$ is a carbon atom represented by either γ or δ; and $Ar^1$ and $a^1$ independently have no substituent or a first substituent, and the first substituent is an alkyl group having 1 to 6 carbon atoms or an aryl group having 6 to 13 carbon atoms;

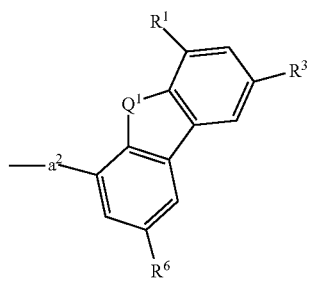

(g4')

wherein $R^1$, $R^3$, and $R^6$ are each independently any of hydrogen, an alkyl group having 1 to 6 carbon atoms, a phenyl group, a biphenyl group, and a naphthyl group; $a^2$ is a phenylene group or a biphenyldiyl group; $Q^1$ is sulfur; $R^1$, $R^3$, and $R^6$ and $a^2$ independently have no substituent or a second substituent, the second substituent is an alkyl group having 1 to 6 carbon atoms or an aryl group having 6 to 13 carbon atoms; and

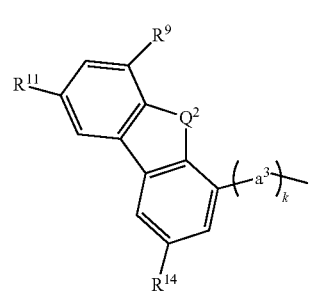

(g5)

wherein $R^9$, $R^{11}$, and $R^{14}$ are each independently any of hydrogen, an alkyl group having 1 to 6 carbon atoms, a phenyl group, a biphenyl group and a naphthyl group; k is 0 or 1; $a^3$ is a phenylene group or a biphenyldiyl group; $Q^2$ is sulfur or oxygen; and $R^9$, $R^{11}$, and $R^{14}$, and $a^3$ have no substituent or a third substituent, and the third substituent is an alkyl group having 1 to 6 carbon atoms or an aryl group having 6 to 13 carbon atoms.

26. A light-emitting element including a carbazole compound represented by a general formula (G1), wherein a layer containing an organic compound is interposed between a pair of electrodes,

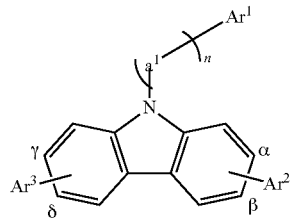

(G1)

wherein Ar¹ is any of a phenyl group, a biphenyl group, and a naphthyl group; Ar² is a group represented by a general formula (g6'); Ar³ is hydrogen or a group represented by a general formula (g7); n is 0 or 1; a¹ is a phenylene group or a biphenyldiyl group; a substitution site of Ar² is a carbon atom represented by either α or β, and a substitution site of Ar³ is a carbon atom represented by either γ or δ; and Ar¹ and a¹ independently have no substituent or a first substituent, and the first substituent is an alkyl group having 1 to 6 carbon atoms or an aryl group having 6 to 13 carbon atoms;

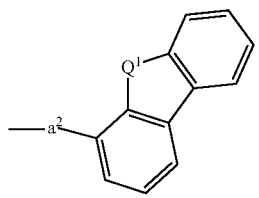

(g6')

wherein a² is a phenylene group or a biphenyldiyl group; Q¹ is sulfur or oxygen; and a² have no substituent or a second substituent, and the second substituent is an alkyl group having 1 to 6 carbon atoms or an aryl group having 6 to 13 carbon atoms; and

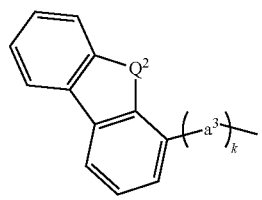

(g7)

wherein k is 0 or 1; a³ is a pheneylene group or a biphenyldiyl group; Q² is sulfur; and a³ have no substituent or a third substituent, and, the third substituent is an alkyl group having 1 to 6 carbon atoms or an aryl group having 6 to 13 carbon atoms.

27. The light-emitting element in which the layer containing the organic compound includes the carbazole compound represented by the general formula (G1), according to any one of claims 23 to 26, wherein:
when Ar³ is a substituent other than hydrogen, Ar² is bonded at the position α and Ar³ is bonded at the position γ, or the Ar² is bonded at the position β and Ar³ is bonded at the position δ.

28. The light-emitting element in which the layer containing the organic compound includes the carbazole compound, according to any one of claims 23 to 26,
wherein the groups, a¹, a², and a³, are independently any of groups represented by structural formulae (a-1) to (a-7);

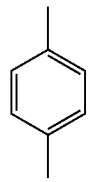

(α-1)

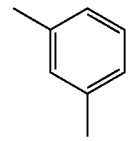

(α-2)

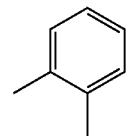

(α-3)

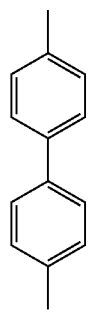

(α-4)

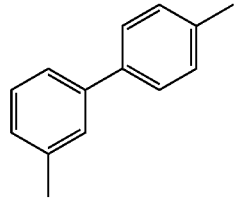

(α-5)

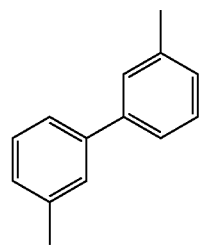

(α-6)

-continued

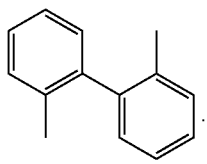
(α-7)

29. The light-emitting element in which the layer containing the organic compound includes the carbazole compound, according to claim 23,
  wherein the groups, $R^1$ to $R^7$ and $R^9$ to $R^{15}$, are independently any of groups represented by structural formulae (R-1) to (R-13);

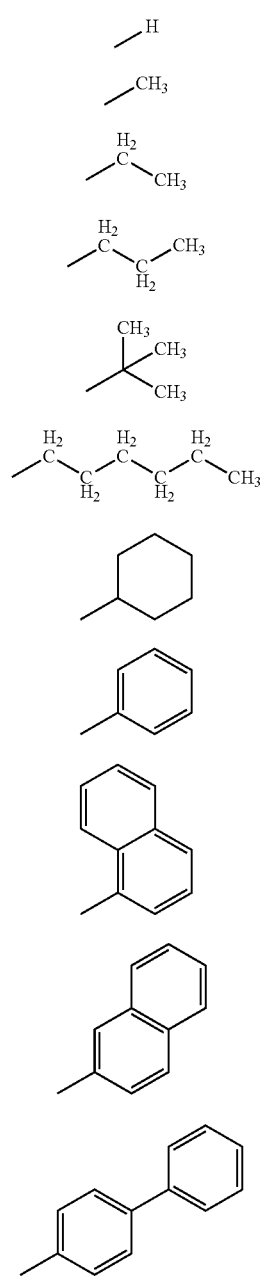

(R-1)
(R-2)
(R-3)
(R-4)
(R-5)
(R-6)
(R-7)
(R-8)
(R-9)
(R-10)
(R-11)

-continued

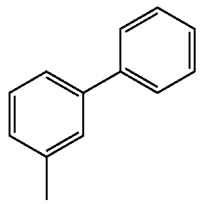
(R-12)

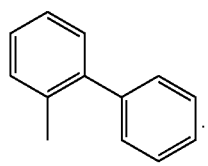
(R-13)

30. The light-emitting element in which the layer containing the organic compound includes the carbazole compound, according to claim 23 or claim 24,
  wherein the group, $Ar^4$, is any of groups represented by structural formulae (Ar-1) to (Ar-6);

(Ar-1)
(Ar-2)

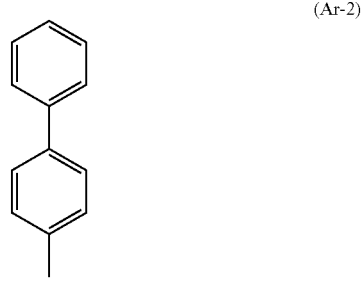
(Ar-3)
(Ar-4)

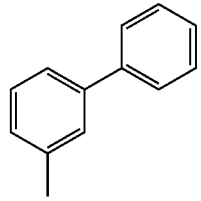
(Ar-3)

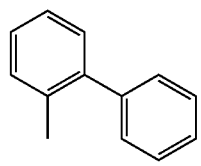
(Ar-4)

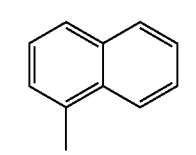
(Ar-5)

-continued

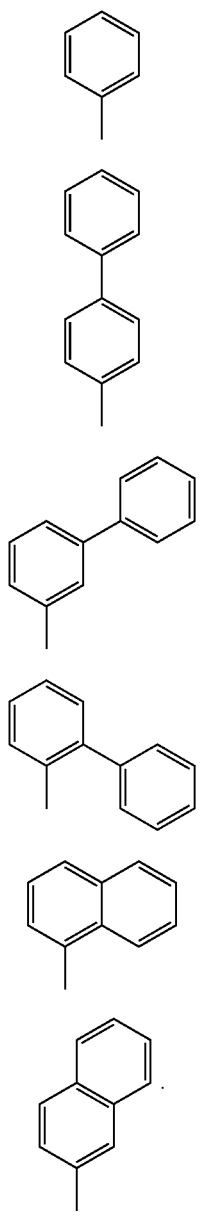

31. The light-emitting element in which the layer containing the organic compound includes the carbazole compound, according to any one of claims 23 to 26,
wherein the group, Ar¹ is any of groups represented by the structural formulae (Ar-1) to (Ar-6);

32. The light-emitting element in which the layer containing the organic compound includes the carbazole compound, according to any one of claims 23 to 26, wherein n is 0.

33. The light-emitting element in which the layer containing the organic compound includes the carbazole compound, according to any one of claims 23 to 26, wherein the group, Ar¹, is a phenyl group.

34. The light-emitting element in which the layer containing the organic compound includes the carbazole compound, according to any one of claims 23 to 26, wherein Ar$^a$ is hydrogen.

35. The light-emitting element according to any one of claims 23 to 26, wherein the layer containing the organic compound includes a carbazole compound represented by a structural formula (172)

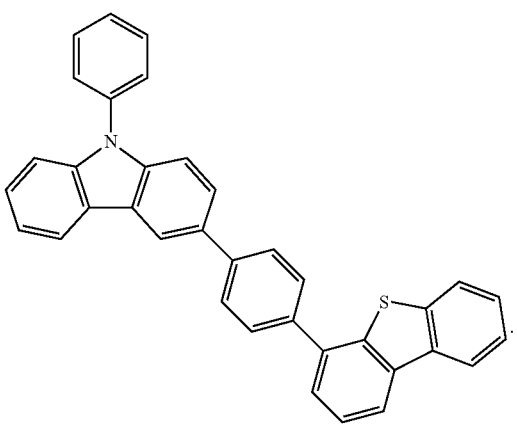

(172)

36. The light-emitting element according to any one of claims 23 to 26, wherein the layer containing the organic compound includes a carbazole compound represented by a structural formula (160)

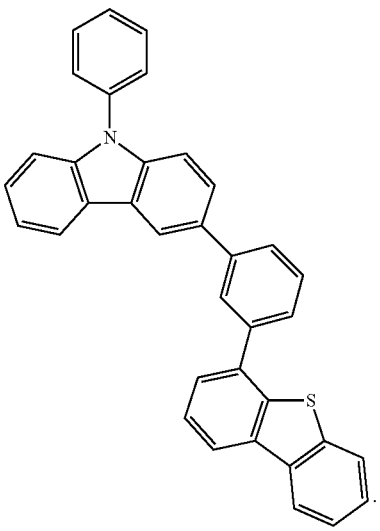

(160)

* * * * *

UNITED STATES PATENT AND TRADEMARK OFFICE
CERTIFICATE OF CORRECTION

PATENT NO. : 9,133,173 B2
APPLICATION NO. : 13/271406
DATED : September 15, 2015
INVENTOR(S) : Harue Osaka et al.

It is certified that error appears in the above-identified patent and that said Letters Patent is hereby corrected as shown below:

In the Specification:

Column 8, Line 55; Change "is, a" to --is a--.

Column 25, Line 33; Change "by, those" to --by those--.

Column 64, Lines 58 to 59; Change "synthesis scheme. [next line] (S-4) can be performed" to --synthesis scheme (S-4) can be performed--.

Column 68, Line 28; Change "phenyl-N-phenylamino}" to --phenyl-N'-phenylamino}--.

Column 69, Line 28; Change "[N,N,N'-triphenyl" to --[N,N',N'-triphenyl--.

Column 69, Line 31; Change "N,N,N'-triphenyl" to --[N,N',N'-triphenyl--.

Column 71, Line 42; Change "fowled" to --formed--.

Column 75, Line 19; Change "1,6FLPAPm)," to -- 1,6FLPAPrn),--.

Column 75, Line 55; Change "foimed" to --formed--.

Column 79, Line 17; Change "AM)" to --AlLi)--.

Column 85, Line 62; Change "913." to --9B.--.

Column 97, Line 45; Change "formula (I)" to --formula (i)--.

Column 97, Line 47; Change "1,6FLPAPm)" to --1,6FLPAPrn)--.

Column 97, Line 48; Change "formula (II)" to --formula (ii)--.

Column 97, Line 52; Change "formula (I)" to --formula (i)--.

Column 101, Line 52; Change "formula (Iv)" to --formula (iv)--.

Column 103, Line 8; Change "1,6FLPAPm," to --1,6FLPAPrn,--.

Column 106, Line 38; Change "formula (Iv)" to --formula (iv)--.

Column 106, Line 45; Change "aluminum, was foamed to" to --aluminum was formed to--.

Column 114, Line 47; Change "over, which" to --over which--.

Signed and Sealed this
Twenty-second Day of March, 2016

Michelle K. Lee
*Director of the United States Patent and Trademark Office*

CERTIFICATE OF CORRECTION (continued)
U.S. Pat. No. 9,133,173 B2

In the Specification:

Column 128, Line 16; Change "yield; which" to --yield, which--.

In the Claims:

Column 137, Line 48, Claim 3; Change "$Q_2$ is sulfur or oxygen; and" to --$Q_2$ is sulfur; and--.

Column 148, Line 66, Claim 25; Change "$Q_2$ is sulfur or oxygen; and" to --$Q_2$ is sulfur; and--.

Column 149, Line 44, Claim 26; Change "$Q^1$ is sulfur or oxygen; and" to --$Q^1$ is sulfur; and--.